US006308458B1

(12) United States Patent
Volrath et al.

(10) Patent No.: US 6,308,458 B1
(45) Date of Patent: *Oct. 30, 2001

(54) HERBICIDE-TOLERANT PLANTS AND METHODS OF CONTROLLING THE GROWTH OF UNDESIRED VEGETATION

(75) Inventors: Sandra L. Volrath, Durham; Marie A. Johnson, Wendell; Eric R. Ward; Peter B. Heifetz, both of Durham, all of NC (US)

(73) Assignee: Novartis Finance Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/497,698

(22) Filed: Feb. 3, 2000

Related U.S. Application Data

(60) Division of application No. 09/102,420, filed on Jun. 22, 1998, now Pat. No. 6,084,155, which is a continuation-in-part of application No. 09/059,164, filed on Apr. 13, 1998, which is a continuation-in-part of application No. 09/050,603, filed on Mar. 30, 1998, now Pat. No. 6,023,012, which is a continuation-in-part of application No. 08/808,931, filed on Feb. 28, 1997, now Pat. No. 5,939,602, which is a continuation-in-part of application No. 08/472,028, filed on Jun. 5, 1995, now Pat. No. 5,767,373.

(60) Provisional application No. 60/012,705, filed on Feb. 28, 1996, provisional application No. 60/013,612, filed on Feb. 28, 1996, provisional application No. 60/020,003, filed on Jun. 21, 1996, and provisional application No. 60/126,430, filed on Mar. 11, 1998.

(51) Int. Cl.$^7$ ................................ A01G 7/06; A01H 5/00
(52) U.S. Cl. ................................. 47/58.1; 800/300
(58) Field of Search ............................... 47/58.1; 800/300

(56) References Cited

U.S. PATENT DOCUMENTS

| 5,407,808 | 4/1995 | Halling et al. | 435/34 |
| 5,451,513 | 9/1995 | Maliga et al. | 800/278 |
| 5,530,191 | 6/1996 | Maliga et al. | 800/274 |
| 5,545,817 | 8/1996 | McBride et al. | 800/287 |
| 5,576,198 | 11/1996 | McBride et al. | 435/91.3 |
| 5,693,507 | 12/1997 | Daniell et al. | 435/470 |
| 5,767,373 | 6/1998 | Ward et al. | 800/300 |

FOREIGN PATENT DOCUMENTS

| 0 332 104 | 9/1989 | (EP) . |
| 0 360 750 | 9/1989 | (EP) . |
| 0 449 376 | 10/1991 | (EP) . |
| 0 478 502 A2 | 4/1992 | (EP) . |
| 0 479 359 | 4/1992 | (EP) . |
| 0 589 841 | 3/1994 | (EP) . |
| WO90/06748 | 6/1990 | (WO) . |
| WO91/16440 | 10/1991 | (WO) . |
| WO91/19418 | 12/1991 | (WO) . |
| WO92/01042 | 1/1992 | (WO) . |
| WO95/14099 | 5/1995 | (WO) . |
| WO95/16783 | 6/1995 | (WO) . |
| WO95/20668 | 8/1995 | (WO) . |
| WO95/25787 | 9/1995 | (WO) . |
| WO95/34659 | 12/1995 | (WO) . |
| WO96/04781 | 2/1996 | (WO) . |
| WO97/04088 | 2/1997 | (WO) . |
| WO97/04089 | 2/1997 | (WO) . |
| WO97/06250 | 2/1997 | (WO) . |
| WO97/32011 | 2/1997 | (WO) . |
| WO97/32977 | 9/1997 | (WO) . |

OTHER PUBLICATIONS

Al–Hazimi et al., J. Chem. Soc. Perkins Trans. 1: 265–276, 1987.

Camadro et al., The Journal of Biological Chemistry, 269 No. 51: 32085–32091, 1994.

Hallahan et al.,Plant Physiol. 100: 1211–1216, 1992.

Jacobs J.M. et al., Archives of Biochemistry and Biophysics, 280 No. 2: 369–375, 1990.

Allison et al. "Deletion of rpoB reveals a second distinct transcription system in plastids of higher plants" The EMBO Journal, 15:2802–2809 (1996).

Armbruster et al., "Herbicidal Action of Nitrophenyl Pyrazole Ether MON 12800: Immunolocalization, Ultrastructural, and Physiological Studies", Pestice Biochemistry and Physiology, 47: 21–35 (1993).

Aspegren et al., "Secretion of a heat–stable fungal beta–glucanase from transgenic suspension–cultured barley cells," Molecular Breeding, 1: 91–99 (1995).

Becerril et al., "Aciflourfen Effects on Intermediates of Chlorophyll Synthesis in Green Cucumber Cotyledon Tissues", Pesticide Biochemistry and Physiology, 35: 119–126 (1989).

Bilang et al., "Containing excitement over transplastomic plants," Nature Biotechnology, 16: 333–334 (1998).

Brenner et al., "Cloning of murine ferrocheletase", Proc. Natl. Acad. Sci. USA 88: 849–853 (1991).

Brenner et al., "A Fluorometric Assay for Measurement of Protoporphyrinogen Oxidase Activity in Mammalian Tissue", Clinica Chimica Acta, 100: 259–266 (1980).

Camadro et al., "A New Assay for Protoporphyrinogen Oxidase—Evidence for a Total Deficiency in that Activity in a Heme–less Mutant of *Saccharomyces cerevisiae*", Biochemical and Biophysical Research Communications, 106(3): 724–730 (1982).

(List continued on next page.)

*Primary Examiner*—Amy J. Nelson
*Assistant Examiner*—David H. Kruse
(74) *Attorney, Agent, or Firm*—J. Timothy Meigs; Edouard G. Lebel; Larry W. Stults

(57) ABSTRACT

The present invention relates to methods for controlling the growth of undesired vegetation comprising applying an effective amount of a protox-inhibiting herbicide to a population of transgenic plants or plant seed transformed with a DNA sequence coding for a modified protox enzyme that is tolerant to a protox-inhibiting herbicide or to the locus where a population of the transgenic plants or plant seeds is cultivated.

52 Claims, No Drawings

OTHER PUBLICATIONS

Camadro et al., "Cloning and Characterization of the Yeast HEM14 Gene Codoing for Protoporphyrinogen Oxidase, the Molecular Target of Diphenyl Ether–type Herbicides", The Journal of Biological Chemistry, 271(15): 9120–9128 (1996).

Camadro et al., "Molecular Properties of Yeast and Lettuce Protoporphyrinogen Oxidases", Abstract PAP Am Chem. Soc., 111. (1–2) (1993).

Camadro et al., "Photoaffinity labeling of protoporphyrinogen oxidase, the molecular target of diphenylether–type herbicides", Eur J of Biochem., 229: 669–674 (1995).

Cardin et al., "Characterization of Protoporphyrinogen Oxidase from *Rhodopseudomonas capsulata*", Abstracts of the Annual Meeting Am. Soc. Microbiol., Abstract #K–85, 207 (1986).

Che et al., "Localization of Target–Site of the Protoporphyrinogen Oxidase–Inhibiting Herbicide S–23142 in *Spinacia– oleracea* L.", Z. Naturforsch., 48(c): 350–355 (1993).

Clarke et al. "Identification and expression of the chloroplast clpP gene in the conifer *Pinus contorta*" Plant Molecular Biology, 26: 851–862 (1994).

Corrigall et al., "Inhibition of Mammalian Protoporphyrinogen Oxidase by Acifluorfen", Biochemistry and Molecular Biology International, 34(6): 1283–1289 (1994).

Crews et al., "Synthesis and Herbicidal Activity of bis–Aryloxybenzenes, a New Class of Protox Inhibitors", Abstracts of Papers American Chemical Society, Abstract #44. 209(1–2) (1995).

Dailey et al., "Expression of a Cloned Protoporphyrinogen Oxidase", The Journal of Biological Chemistry, 269(2):813–815 (1994).

Dailey T.A. et al., "Cloning, Sequence, and Expression of Mouse Protoporphyrinogen Oxidase", Archives of Biochemistry and Biophysics, 324(2): 379–384 (1995).

Dailey T.A. et al., "Human protoporphyrinogen oxidase: Expression, purification, and characterization of the cloned enzyme", Protein Science, 5: 98–105 (1996).

Daniell et al., "Containment of herbicide resistance through genetic engineering of the chloroplast genome," Nature Biotechnology, 16: 345–348 (1998).

Datta et al., "Transformation of the Tobacco Chloroplast Genome with the aroA Gene to Confer Glyphosate Tolerance," Supplement to Plant Physiology, 111(2): 790 (1996).

Derrick, Peter Michael, "An investigation into the mode of action of the herbicide M&B 39279", Dissertation Abstracts International, 50(10): 4283–B (1996).

Deybach et al., "The mitochondrial location of protoporphyrinogen oxidase", Eur. J. Biochem., 149(2): 431–436 (1985).

Duke et al., "Porphyric Pesticides Chemistry, Toxicology, and Pharmaceutical Applications", ACS Symposium Series 559, American Chemical Society, 1–318 (1994).

Duke et al., "Protoporphyrinogen Oxidase–Inhibiting Herbicides", Weed Science, 39: 465–473 (1991).

Duke et al., "Protoporphyrinogen Oxidase as the Optimal Herbicide Site in the Porphyrin Pathway", ACS SYMP. SER.—Porphyric Pesticides 191–204 (1994).

Duke et al., "Prospects for Herbicides Designed for Sites of Action in the Porphyrin Pathway Beyond Protoporphyrinogen Oxidase", Abstracts of Papers American Chemical Society, Abstract #129, 206(1–2) (1993).

Duke, S.O., "Pesticides that Act Through Prophyrin Accumulation", Abstracts of the 22nd Annual Meeting of the American Society for Photobiology, Abstract #SPM–B2, 59 (Spec. Issue) (1994).

Elder et al., "A Radiochemical Method for the Measurement of Coproporphyrinogen Oxidase and the Utilization of Substrates other than Coproporphyrinogen III by the Enzyme from Rat Liver", Biochem. J., 169: 205–214 (1978).

Ems et al. "Transcription, splicing and editing of plastid RNAs in the nonphotosynthetic plant *Epifagus virginiana*" Plant Molecular Biology, 29: 721–733 (1995).

EMBL Sequence Database Acc. No. M22063 Rel. 19 Apr. 22, 1989.

EMBL Sequence Database Acc. No. T43573, Rel. No. 42, Feb. 3, 1995.

Falbel et al., "Characterization of a Family of Chlorophyll–Deficient Wheat (Triticum) and Barley (*Hordeum vulgare*) Mutants with Defects in the Magnesium–Insertion Step of Chlorophyll Biosynthesis", Plant Physiology (Rockville), 104: 639–648 (1994).

Ferreira et al., "Organization of the Terminal Two Enzymes of the Heme Biosynthetic Pathway Orientation of Protoporphyrinogen Oxidase and Evidence for a Membrane Complex*", The Journal of Biolocial Chemistry, 263(8): 3835–3839 (1988).

Frustaci et al., "The *Escherichia–coli* vis A Gene Encodes Ferrochelatase, the Final Enzyme of the Heme Biosynthetic Pathway", Journal of Bacteriology, 175(7): 2154–2156 (1993).

Gollub et al., "Yeast Mutants Deficient in Heme Biosynthesis and a Heme Mutant Additionally Blocked in Cyclization of 2 3 Oxidosqualene*", The Journal of Biological Chemistry, 252(9): 2846–2854 (1977).

Guo et al., "High–performance liquid chromatographic assays for protoporphyrinogen oidase and ferrochelatase in human leukocytes", Journal of Chromatography Biomedical Applications, 566: 383–396 (1991).

Hansson et al., "*Bacillus subtilis* Hem Y Is a Peripheral Membrane Protein Essential for Protoheme IX Synthesis Which Can Oxidize Coproporphyrinogen III and Protoporphyrinogen IX", Journal of Bacteriology, 176(19): 5962–5970 (1994).

Hansson et al., "Cloning and Characterization of the *Bacillus subtilis* hemEHY Gene Cluster, Which Encodes Protoheme IX Biosynthetic Enzymes", J. Bacteriol. 174(24) 8081–8093 (1992).

Heifetz et al., "Chemical regulation of nuclear and plastid transgenes in plants," Supplement to Plant Physiology, 114(3): 308 (1997).

Huang et al. "The Chlamydomonas chloroplast clpP gene contains translated large insertion sequences and is essential for cell growth" Mol Gen Genet, 244: 151–159 (1994).

Ichinose et al., "Selection and Characterization of Protoporphyrinogen Oxidase Inhibiting Herbicide (S23142) Resistant Photomixotrophic Cultured Cells of *Nicotiana tabacum*", J. Plant Physiol., 146: 693–698 (1995).

Ihara et al., "Peroxidizing Phytotoxic Activity of 1,3, 4–Thiadiazolidine–2–thiones and 1,2,4–Triazolidine–3, 5–dithiones", Journal of Pesticide Science, 20: 41–47 (1995).

Iida et al., "Isomerization and Peroxidizing Phytotoxicity of Thiadiazolidine–thione Compounds", Z. Naturforsch., 50(c): 186–192 (1995).

International Search Report PCT/IB 95/00452.

Jacobs et al., "Effect of Diphenyl Ether Herbicides on Oxidation of Protoporphyrinogen to Protoporphyrin in Organellar and Plasma Membrane Enriched Fractions of Barley", Plant Physiol. (Bethesda), 97: 197–203 (1991).

Jacobs et al., "Oxidation of protoporphyrinogen to protoporphyrin, a step in chlorophyll and haem biosynthesis", Biochem J., 244: 219–224 (1987).

Jacobs et al., "Porphyrin Accumulation and Export by Isolated Barley (Hordeum–vulgare) Plastids. Effect of Diphenyl Ether Herbicides", Plant Physiol. (ROCKV), 101: 1181–1188 (1993).

Jacobs J. M. et al., "Terminal Enzymes of Heme Biosynthesis in the Plant Plasma Membrane", Archives of Biochemistry and Biophysics, 323(2): 274–278 (1995).

Jacobs J.M. et al., "Effects of Diphenyl Dther Herbicides on Porphyrin Accumulation by Cultured Hepatocytes", J. Biochem. Toxicology, 7(2): 87–95 (1992).

Jacobs J.M. et al., "Protoporphyrinogen Oxidation, and Enzymatic Step in Heme and Chlorophyll Synthesis: Partial Characterization of the Reaction in Plant Organelles and Comparison with Mammalian and Bacterial Systems1", Archives of Biochem and Biophys, 229(1): 312–319 (1984).

Jacobs N. et al., "Protoporphyrinogen oxidation in plants and rhizobia", Plant Physiol. (Bethesda), #1055 (4 Suppl.) (1989).

Jacobs N.J. et al., "Assay for Enzymatic Protoporphyrinogen Oxidation, a Late Step in Heme Synthesis", Enzyme (Basel), 28: 206–217 (1982).

Jacobs N.J. et al., "Characteristics of Purified Protoporphyrinogen Oxidase from Barley", Biochemical and Biophysical Research Communications, 161(2): 790–796 (1989).

Jacobs N.J. et al., "Mechanism of Protoporphyrin IX Accumulation in Plant Cells Treated with Herbicides Inhibiting Protoporphyrinogen Oxidase", Abstract PAP Am. Chem. Soc., Abstract #113, 206 (1–2) (1993).

Jacobs N.J. et al., "Microbial Oxidation of Protoporphyrinogen an Intermediate in Heme and Chlorophyll Biosynthesis", Archives of Biochemistry and Biophysics, 197(2): 396–403 (1979).

Jacobs N.J. et al., "Protoporphyrinogen Oxidation, a Step in Heme Synthesis in Soybean Root Nodules and Free–Living Rhizobia", Journal of Bacteriology, 171(1): 573–576 (1989).

Jansen et al., "Mode of Evolved Photooxidant Resistance to Herbicides and Xenobiotics", Z. Naturforsch Sect. Biosci., 45(c): 463–469 (1990).

Kataoka et al., "Isolation and Partial Characterization of Mutant Chlamydomas reinhardtii Resistant to Herbicide S–23142", J. Pesticide Sci., 15:499–451 (1990).

Klemm et al., "Protoporphyrinogen oxidation coupled to nitrite reduction with membranes from Desulfovibrio–gigas", FEMS Microbiology Letters, 61: 61–64 (1989).

Klemm et al., "Purification and Properties of Protoporphyrinogen Oxidase from an Anaerobic Bacterium, Desulfovibrio–gigas", Journal of Bacteriology, 169(11): 5209–5215 (1987).

Kohno et al., "Peroxidizing Phytotoxic Activity of Pyrazoles", Journal of Pesticide Science, 20: 137–143 (1995).

Kolarov et al., "Rat Liver Protoporphyrinogen IX Oxidase: Site of Synthesis and Factor Influencing its Activity", Biochemical and Biophysical Research Communications, 116(2): 383–387 (1983).

Komives et al., "Mechanisms of Plant Tolerance to Phytodynamic Herbicides", Abstract PAP Am. Chem. Soc., Abstract #128, 206(1–2) (1993).

Koop et al. "Integration of foreign sequences into the tobacco plastome via polyethylene glycol–mediated protoplast transformation" Planta, 199: 193–201 (1996).

Labbe–Bois R., "The Ferrochetelase from Saccharomyces–Cerevisiae. Sequence, Disruption, and Expression of its Structural Gene Hem15*", The Journal of Biological Chemistry, 265(13): 7278–7283 (1990).

Labbe et al., "Fluorometric assays for coproporphyrinogen oxidase and protoporphyrinogen oxidase", Analytical Biochemistry, 149: 248–260 (1985).

Lee et al., "Cellular Localization of Protoporphyrinogen–Oxidizing Activities of Etiolated Barley (Hordeum vulgare L.) Leaves", Plant Physiol., 102:881–889 (1993).

Lee et al., "Peroxidase Involvement in the Accumulation of Protoporphyrin IX in Acifluorfen–Methyl–Treated Plant Tissues", Plant Physiology (Rockville), 105(1 Suppl.): 125 (1994).

Lee H.J. et al., "Protoporphyrinogen IX–Oxidizing Activities Involved in the Mode of Action of Peroxidizing Herbicides", Journal of Agricultural and Food Chemistry, 42(11): 2610–2618 (1994).

Li et al., "An h.p.l.c. assay for protoporphyrinogen oxidase activity in rat liver", Biochem. J., 243: 863–866 (1987).

Lyga et al., "Synthesis, Mechanism of Action, and QSAR of Herbicidal 3–Substituted–2–aryl–4,5,6,7–tetrahydroindazoles", Pesticide Science, 42: 29–36 (1994).

Madsen et al., "A soybean coproporphyrinogen oxidase gene is highly expressed in root nodules", Plant Molecular Biology, 23: 35–43, (1993).

Martasek et al., "Homozygous hereditary coproporphyria caused by an arginine to tryptophan substitution in coproporphyrinogen oxidase and common intragenic polymorphisms", Human Molecular Genetics, 3(3): 477–480 (1994).

Martasek et al., "Molecular cloning, sequencing, and functional expression of a cDNA encoding human coproporphyrinogen oxidase", Proceedings of the National Academy of Sciences of the United States of America, 91: 3024–3028 (1994).

Matringe et al., "Characterization of [3H]acifluorfen binding to purified pea etioplasts, and evidence that protoporphyrinogen oxidase specifically binds acifluorfen", Eur. J. Biochem., 209: 861–868 (1992).

Matringe et al., "Localization within Chloroplasts of Protoporphyrinogen Oxidase, the Target Enzyme for Diphenylether–like Herbicides", The Journal of Biological Chemistry, 267(7):4646–4651 (1992).

Matringe et al., "Protoporphyrinogen oxidase as a molecular target for diphenyl ether herbicides", Biochem. J., 260:231–235 (1989).

Matringe et al., "Protoporphyrinogen oxidase inhibition by three peroxidizing herbicides: oxadiazon, LS 82–556 and M&B 39279", FEBS Letters, 245(1,2): 35–38 (1989).

Matsumoto et al., "A Rapid and Strong Inhibition of Protoporphyrinogen Oxidase from Several Plant Species by Oxyfluorfen", Pesticide Biochemistry and Physiology, 47: 113–118 (1993).

Matsumoto et al., "Variation in Crop Response to Protoporphyrinogen Oxidase Inhibitors", Abstract. PAP Am. Chem. Soc., Abstract #124, 206 (1–2) (1993).

McBride et al., "Controlled expression of plastid transgenes in plants based on a nuclear DNA–encoded and plastid–targeted T7 RNA polymerase," Proc.Natl. Acad. Sci., 91: 7301–7305 (1994).

Mullet, John E., "Dynamic Regulation of Chloroplast Transcription", Plant Physiology, 103: 309–313 (1993).

Nakayashiki et al., "Cloning and sequencing of a previously unidentified gene that is involved in the biosynthesis of heme in *Escherichia coli*", Gene (Amsterdam), 153: 67–70 (1995).

Nandihalli et al., "Correlation of Protoporphyrinogen Oxidase Inhibition by O–Phenyl Pyrrolidino– and Piperidino–Carbamates with their Herbicidal Effects", Pestic. Sci., 35: 227–235 (1992).

Nandihalli et al., "Enantioselectivity of Protoporphyrinogen Oxidase–Inhibiting Herbicides", Pesticide Science, 40: 265–277 (1994).

Nandihalli et al., "Relationships between Molecular Properties and Biological Activities of O–Phenyl Pyrrolidino– and Piperidinocarbamate Herbicides", J. Agri. Food Chem., 40(10): 1993–2000 (1992).

Nandihalli et al., "The Porphyrin Pathway as a H ervicide Target Site", Abstract #140 PAP Am. Chem. Soc., 203 (1992).

Nicolaus et al., "Binding Affinities of Peroxidizing Herbicides to Protoporphyrinogen Oxidase from Corn", Pesticide Biochemistry and Physiology, 51: 20–29 (1995).

Nicolaus et al., "Molecular Aspects of Herbicide Action on Protoporphyrinogen Oxidase", Z. Naturforsch, 48(c): 326–333 (1993).

Nishimura et al., "Cloning of a Human cDNA for Protoporphyrinogen Oxidase by Complementation in Vivo of a hemG Mutant of *Escherichia coli*", J. of Biological Chemistry, 270(14): 8076–8080 (1995).

O'Neill et al. "Chloroplast transformation in plants: polyethylene glycol (PEG) treatment of protoplasts is an alternative to biolistic delivery systems" The Plant Journal, 3(5): 729–738 (1993).

Oshio et al., "Isolation and Characterization of a *Chlamydomonas reinhardtii* Mutant Resistant to Photobleaching Herbicides", Z. Naturforsch. 48c: 339–344 (1993).

Pen et al., "Production of Active *Bacillus Licheniformis* Alpha–Amylase in Tobacco and its Application in Starch Liquefaction," Bio/Technology, 10(3): 292–296 (1992).

Pornprom et al., "Chracterization of Oxyfluorfen Tolerance in Selected Soybean Cell Line", Pesticide Biochemistry and Physiology 50: 107–114 (1994).

Pornprom et al., "Selection for Herbicide Tolerance in Soybean Using Cell Suspension Culture", Weed Research, 39(2): 102–108 (1994).

Prasad A.R.K. et al., "Generation of Resistance to the Diphenyl Ether Herbicide Acifluorfen by MEL Cells*", Biochemical and Biophysical Research Communications, 215(1): 186–191 (1995).

Proulx et al., "Characteristics of murine protoporphyrinogen oxidase", Protein Science, 1: 801–809 (1992).

Proulx et al., "In situ conversion of coproporphyrinogen to heme by murine mitochondria: Terminal steps of the heme biosynthetic pathway", Protein Science, 2: 1092–1098 (1993).

Reddy K.N., "Modulators of the Porphyrin Pathway Beyond Protox", Abstract PAP. Am. Chem. Soc., Abstract #127, 206(1–2) (1993).

Roberts et al., "Partial characterization and assignment of the gene for protoporphyrinogen oxidase and variegate porphyria to human chromosome 1q23", Human Molecular Genetics, 4(12): 2387–2390 (1995).

Sasarman et al., "Nucleotide sequence of the hemG gene involved in the protoporphyrinogen oxidase activity of *Escherichia coli* K12", Can. J. Microbiol., 39:1155–1161 (1993).

Sato et al., "Isomerization and Peroxidizing Phytotoxicity of Thiodiazolidine Herbicides", Z. Naturforsch., 49(c): 49–56 (1994).

Scalla et al., "Inhibitors of Protoporphyrinogen Oxidase as Herbicides: Diphenyl Ethers and Related Photobleaching Molecules", Reviews of Weed Science, 6: 103–132 (1994).

Shanklin et al. "The Stroma of Higher Plant Plastids Contain ClpP and ClpC, Functional Homologs of *Eschericha coli* ClpP and ClpA: An Archetypal Two–Component ATP–Dependent Protease" The Plant Cell, 7: 1713–1722 (1995).

Sherman et al., "Physiological Basis for Differential Sensitivities of Plant Species to Protoporphyrinogen Oxidase–Inhibiting Herbicides", Plant Physiol. 97: 280–287 (1991).

Sherman et al., "Pyrazole Phenyl Ether Herbicides Inhibit Protoporphyrinogen Oxidase", Pesticide Biochemistry and Physiology, 40: 236–245 (1991).

Sherman et al., "Tissue and Cellular Localization of Porphyrins in Cucumber Cotyledon Tissue with Inhibited Protoporphyrinogen Oxidase", Plant Physiol. (Bethesda), 93 (1Suppl.) (1990).

Shibata et al., "Isolation and Characterization of a *Chlamydomonas reinhardtii* Mutant Resistant to an Experimental Herbicide S–23142, Which Inhibits Chlorophyll Synthesis", Research in Photosynthesis, III:567–570 (1992).

Shimizu et al., "A Novel Isourazole Herbicide, Fluthiacet–Methyl, is a Potent Inhibitor of Protoporphyrinogen Oxidase after Isomerization by Glutathione S–Transferase", Plant and Cell Physiology, 36(4): 625–632 (1995).

Siepker et al., "Purification of bovine protoporphyrinogen oxidase: immunological cross–reactivity and structural relationship ferrochelatase", Biochimica et Biophysica Acta, 931: 349–358 (1987).

Smith et al., "Investigation of the subcellular location of the tetrapyrrole–biosynthesis enzyme coproporphyrinogen oxidase in higher pants", Biochem. J., 292: 503–508 (1993).

Staub et al., "Long Regions og Homologous DNA Are Incorporated into the Tobacco Plastid Genome by Transformation", The Plant Cell, 4: 39–45 (1992).

Struhl, "They new yeast genetics", Nature 305:3 91–397 (1983).

Svab et al. "High–frequency plastid transformation in tobacco by selection for a chimeric aadA gene" Proc. Natl. Acad. Sci. USA, 90: 913–917 (1993).

Taketani et al., "The Human Protoporphyrinogen Oxidase Gene (PPOX): Organization and Location to Chromosome 1", Genomics, 29: 698–703 (1995).

Tietjen K.G., "Quinone Activation of Protoporphyrinogen Oxidase of Barley Plastids", Pestic. Sci., 33: 467–471 (1991).

Tonkyn et al., "Differential expression of the partially duplicated chloroplast S10 ribosomal operon", Mol Gen Genet, 241: 141–152 (1993).

Troup et al., "Cloning and Characterization of the *Escherichia coli* hemN Gene Encoding the Oxygen–Independent Coproporphyrinogen III Oxidase", Journal of Bacteriology, 177(11): 3326–3331 (1995).

Troup et al., "Isolation of the hemF Operon Containing the Gene for the *Escherichia coli* Aerobic Coproporphyrinogen III Oxidase by In Vivo Complementation of a Yeast HEM13 Mutant", Journal of Bacteriology, 176(3): 673–680 (1994).

Varsano et al., "Competitive interaction of three peroxidizing herbicides with the binding of [3H]acifluorfen to corn etioplast membranes", FEBS, 272(1,2): 106–108 (1990).

Viljoen et al., "Protoporphyrinogen oxidase and ferrochelatase in porphyria variegata", European Journal of Clinical Investigation, 13: 283–287 (1983).

Wang et al., "New Assay Method for Protoporphyrinogen Oxidase Inhibitors Using Chloroplasts Isolated from *Spinacia oleracea* L", Bioscience Biotechnology and Biochemistry, 57(12): 2205–2206 (1993).

Wepplo et al., "Synthesis and Herbicidal Activity of 5–Aryloxybenzisoxazole–3–Acetate Esters", Abstr. Pap. Am. Chem. Soc., Abstract #16, 205(1–2) (1993).

Witkowski et al., "Inhibition of Plant Protoporphyrinogen Oxidase by the Herbicide Acifluorfen Methyl", Plant Physiol. (Bethesda), 90: 1239–1242 (1989).

Wright et al., "Herbicidal Activity of UCC–C4243 and Acifluorfen Is Due to Inhibition of Protoporphyrinogen Oxidase", Weed Science, 43: 47–54 (1995).

Xu et al., "An Oxygen–Dependent Coproporphyrinogen Oxidase Encoded by the hemF Gene of *Salmonella–typhimurium*", Journal of Bacteriology, 175(16): 4990–4999 (1993).

Xu et al., "The Genes Required for Heme Synthesis in *Salmonella–typhimurium* Include Those Encoding Alternative Functions for Aerobic and Anaerobic Coproporphyrinogen Oxidation", Journal of Bacteriology, 174(12): 3953–3963 (1992).

Yamato et al., "A Tobacco Soluble Protoporphyrinogen–oxidizing Enzyme Similar to Plant Peroxidases in Their Amino Acid Sequences and Immunochemical Reactivity", Bioscience Biotechnology and Biochemistry, 59(3): 558–559 (1995).

Yamato et al., "Purification and characterization of a protoporphyrinogen–oxidizing enzyme with peroxidase activity and light–dependent herbicide resistance in tobacco cultured cells", Pestic. Biochem. Physiol., 50: 72–82 (1994).

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 1719 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Arabidopsis thaliana (vii) IMMEDIATE SOURCE:
      (B) CLONE: pWDC-2 (NRRL B-21238)

(ix) FEATURE:
      (A) NAME/KEY: CDS
      (B) LOCATION: 31..1644
      (D) OTHER INFORMATION: /product= "Arabidopsis protox-1"

(xi) SEQUENCE DESCRIPTION: SEQ ID NO: 1:

```
TGACAAAATT CCGAATTCTC TGCGATTTCC ATG GAG TTA TCT CTT CTC CGT CCG        54
                                Met Glu Leu Ser Leu Leu Arg Pro
                                  1               5

ACG ACT CAA TCG CTT CTT CCG TCG TTT TCG AAG CCC AAT CTC CGA TTA        102
Thr Thr Gln Ser Leu Leu Pro Ser Phe Ser Lys Pro Asn Leu Arg Leu
    10                  15                  20

AAT GTT TAT AAG CCT CTT AGA CTC CGT TGT TCA GTG GCC GGT GGA CCA        150
Asn Val Tyr Lys Pro Leu Arg Leu Arg Cys Ser Val Ala Gly Gly Pro
25                  30                  35                  40

ACC GTC GGA TCT TCA AAA ATC GAA GGC GGA GGA GGC ACC ACC ATC ACG        198
Thr Val Gly Ser Ser Lys Ile Glu Gly Gly Gly Gly Thr Thr Ile Thr
                45                  50                  55
```

```
ACG GAT TGT GTG ATT GTC GGC GGA GGT ATT AGT GGT CTT TGC ATC GCT      246
Thr Asp Cys Val Ile Val Gly Gly Gly Ile Ser Gly Leu Cys Ile Ala
            60                  65                  70

CAG GCG CTT GCT ACT AAG CAT CCT GAT GCT GCT CCG AAT TTA ATT GTG      294
Gln Ala Leu Ala Thr Lys His Pro Asp Ala Ala Pro Asn Leu Ile Val
        75                  80                  85

ACC GAG GCT AAG GAT CGT GTT GGA GGC AAC ATT ATC ACT CGT GAA GAG      342
Thr Glu Ala Lys Asp Arg Val Gly Gly Asn Ile Ile Thr Arg Glu Glu
    90                  95                  100

AAT GGT TTT CTC TGG GAA GAA GGT CCC AAT AGT TTT CAA CCG TCT GAT      390
Asn Gly Phe Leu Trp Glu Glu Gly Pro Asn Ser Phe Gln Pro Ser Asp
105                 110                 115                 120

CCT ATG CTC ACT ATG GTG GTA GAT AGT GGT TTG AAG GAT GAT TTG GTG      438
Pro Met Leu Thr Met Val Val Asp Ser Gly Leu Lys Asp Asp Leu Val
                125                 130                 135

TTG GGA GAT CCT ACT GCG CCA AGG TTT GTG TTG TGG AAT GGG AAA TTG      486
Leu Gly Asp Pro Thr Ala Pro Arg Phe Val Leu Trp Asn Gly Lys Leu
            140                 145                 150

AGG CCG GTT CCA TCG AAG CTA ACA GAC TTA CCG TTC TTT GAT TTG ATG      534
Arg Pro Val Pro Ser Lys Leu Thr Asp Leu Pro Phe Phe Asp Leu Met
        155                 160                 165

AGT ATT GGT GGG AAG ATT AGA GCT GGT TTT GGT GCA CTT GGC ATT CGA      582
Ser Ile Gly Gly Lys Ile Arg Ala Gly Phe Gly Ala Leu Gly Ile Arg
    170                 175                 180

CCG TCA CCT CCA GGT CGT GAA GAA TCT GTG GAG GAG TTT GTA CGG CGT      630
Pro Ser Pro Pro Gly Arg Glu Glu Ser Val Glu Glu Phe Val Arg Arg
185                 190                 195                 200

AAC CTC GGT GAT GAG GTT TTT GAG CGC CTG ATT GAA CCG TTT TGT TCA      678
Asn Leu Gly Asp Glu Val Phe Glu Arg Leu Ile Glu Pro Phe Cys Ser
                205                 210                 215

GGT GTT TAT GCT GGT GAT CCT TCA AAA CTG AGC ATG AAA GCA GCG TTT      726
Gly Val Tyr Ala Gly Asp Pro Ser Lys Leu Ser Met Lys Ala Ala Phe
            220                 225                 230

GGG AAG GTT TGG AAA CTA GAG CAA AAT GGT GGA AGC ATA ATA GGT GGT      774
Gly Lys Val Trp Lys Leu Glu Gln Asn Gly Gly Ser Ile Ile Gly Gly
        235                 240                 245

ACT TTT AAG GCA ATT CAG GAG AGG AAA AAC GCT CCC AAG GCA GAA CGA      822
Thr Phe Lys Ala Ile Gln Glu Arg Lys Asn Ala Pro Lys Ala Glu Arg
    250                 255                 260

GAC CCG CGC CTG CCA AAA CCA CAG GGC CAA ACA GTT GGT TCT TTC AGG      870
Asp Pro Arg Leu Pro Lys Pro Gln Gly Gln Thr Val Gly Ser Phe Arg
265                 270                 275                 280

AAG GGA CTT CGA ATG TTG CCA GAA GCA ATA TCT GCA AGA TTA GGT AGC      918
Lys Gly Leu Arg Met Leu Pro Glu Ala Ile Ser Ala Arg Leu Gly Ser
                285                 290                 295

AAA GTT AAG TTG TCT TGG AAG CTC TCA GGT ATC ACT AAG CTG GAG AGC      966
Lys Val Lys Leu Ser Trp Lys Leu Ser Gly Ile Thr Lys Leu Glu Ser
            300                 305                 310

GGA GGA TAC AAC TTA ACA TAT GAG ACT CCA GAT GGT TTA GTT TCC GTG     1014
Gly Gly Tyr Asn Leu Thr Tyr Glu Thr Pro Asp Gly Leu Val Ser Val
        315                 320                 325

CAG AGC AAA AGT GTT GTA ATG ACG GTG CCA TCT CAT GTT GCA AGT GGT     1062
Gln Ser Lys Ser Val Val Met Thr Val Pro Ser His Val Ala Ser Gly
    330                 335                 340

CTC TTG CGC CCT CTT TCT GAA TCT GCT GCA AAT GCA CTC TCA AAA CTA     1110
Leu Leu Arg Pro Leu Ser Glu Ser Ala Ala Asn Ala Leu Ser Lys Leu
345                 350                 355                 360

TAT TAC CCA CCA GTT GCA GCA GTA TCT ATC TCG TAC CCG AAA GAA GCA     1158
Tyr Tyr Pro Pro Val Ala Ala Val Ser Ile Ser Tyr Pro Lys Glu Ala
                365                 370                 375
```

```
ATC CGA ACA GAA TGT TTG ATA GAT GGT GAA CTA AAG GGT TTT GGG CAA        1206
Ile Arg Thr Glu Cys Leu Ile Asp Gly Glu Leu Lys Gly Phe Gly Gln
            380                 385                 390

TTG CAT CCA CGC ACG CAA GGA GTT GAA ACA TTA GGA ACT ATC TAC AGC        1254
Leu His Pro Arg Thr Gln Gly Val Glu Thr Leu Gly Thr Ile Tyr Ser
            395                 400                 405

TCC TCA CTC TTT CCA AAT CGC GCA CCG CCC GGA AGA ATT TTG CTG TTG        1302
Ser Ser Leu Phe Pro Asn Arg Ala Pro Pro Gly Arg Ile Leu Leu Leu
            410                 415                 420

AAC TAC ATT GGC GGG TCT ACA AAC ACC GGA ATT CTG TCC AAG TCT GAA        1350
Asn Tyr Ile Gly Gly Ser Thr Asn Thr Gly Ile Leu Ser Lys Ser Glu
425                 430                 435                 440

GGT GAG TTA GTG GAA GCA GTT GAC AGA GAT TTG AGG AAA ATG CTA ATT        1398
Gly Glu Leu Val Glu Ala Val Asp Arg Asp Leu Arg Lys Met Leu Ile
                445                 450                 455

AAG CCT AAT TCG ACC GAT CCA CTT AAA TTA GGA GTT AGG GTA TGG CCT        1446
Lys Pro Asn Ser Thr Asp Pro Leu Lys Leu Gly Val Arg Val Trp Pro
            460                 465                 470

CAA GCC ATT CCT CAG TTT CTA GTT GGT CAC TTT GAT ATC CTT GAC ACG        1494
Gln Ala Ile Pro Gln Phe Leu Val Gly His Phe Asp Ile Leu Asp Thr
            475                 480                 485

GCT AAA TCA TCT CTA ACG TCT TCG GGC TAC GAA GGG CTA TTT TTG GGT        1542
Ala Lys Ser Ser Leu Thr Ser Ser Gly Tyr Glu Gly Leu Phe Leu Gly
            490                 495                 500

GGC AAT TAC GTC GCT GGT GTA GCC TTA GGC CGG TGT GTA GAA GGC GCA        1590
Gly Asn Tyr Val Ala Gly Val Ala Leu Gly Arg Cys Val Glu Gly Ala
505                 510                 515                 520

TAT GAA ACC GCG ATT GAG GTC AAC AAC TTC ATG TCA CGG TAC GCT TAC        1638
Tyr Glu Thr Ala Ile Glu Val Asn Asn Phe Met Ser Arg Tyr Ala Tyr
                525                 530                 535

AAG TAAATGTAAA ACATTAAATC TCCCAGCTTG CGTGAGTTTT ATTAAATATT            1691
Lys

TTGAGATATC CAAAAAAAAA AAAAAAA                                         1719

(2) INFORMATION FOR SEQ ID NO: 2:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Leu Ser Leu Leu Arg Pro Thr Thr Gln Ser Leu Leu Pro Ser
 1               5                  10                  15

Phe Ser Lys Pro Asn Leu Arg Leu Asn Val Tyr Lys Pro Leu Arg Leu
                20                  25                  30

Arg Cys Ser Val Ala Gly Pro Thr Val Gly Ser Ser Lys Ile Glu
            35                  40                  45

Gly Gly Gly Gly Thr Thr Ile Thr Thr Asp Cys Val Ile Val Gly Gly
        50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
                100                 105                 110
```

-continued

```
Pro Asn Ser Phe Gln Pro Ser Asp Pro Met Leu Thr Met Val Val Asp
    115                 120                 125
Ser Gly Leu Lys Asp Asp Leu Val Leu Gly Asp Pro Thr Ala Pro Arg
    130                 135                 140
Phe Val Leu Trp Asn Gly Lys Leu Arg Pro Val Pro Ser Lys Leu Thr
145                 150                 155                 160
Asp Leu Pro Phe Phe Asp Leu Met Ser Ile Gly Gly Lys Ile Arg Ala
                165                 170                 175
Gly Phe Gly Ala Leu Gly Ile Arg Pro Ser Pro Gly Arg Glu Glu
                180                 185                 190
Ser Val Glu Glu Phe Val Arg Arg Asn Leu Gly Asp Glu Val Phe Glu
                195                 200                 205
Arg Leu Ile Glu Pro Phe Cys Ser Gly Val Tyr Ala Gly Asp Pro Ser
                210                 215                 220
Lys Leu Ser Met Lys Ala Ala Phe Gly Lys Val Trp Lys Leu Glu Gln
225                 230                 235                 240
Asn Gly Gly Ser Ile Ile Gly Gly Thr Phe Lys Ala Ile Gln Glu Arg
                245                 250                 255
Lys Asn Ala Pro Lys Ala Glu Arg Asp Pro Arg Leu Pro Lys Pro Gln
                260                 265                 270
Gly Gln Thr Val Gly Ser Phe Arg Lys Gly Leu Arg Met Leu Pro Glu
                275                 280                 285
Ala Ile Ser Ala Arg Leu Gly Ser Lys Val Lys Leu Ser Trp Lys Leu
                290                 295                 300
Ser Gly Ile Thr Lys Leu Glu Ser Gly Gly Tyr Asn Leu Thr Tyr Glu
305                 310                 315                 320
Thr Pro Asp Gly Leu Val Ser Val Gln Ser Lys Ser Val Val Met Thr
                325                 330                 335
Val Pro Ser His Val Ala Ser Gly Leu Leu Arg Pro Leu Ser Glu Ser
                340                 345                 350
Ala Ala Asn Ala Leu Ser Lys Leu Tyr Tyr Pro Pro Val Ala Ala Val
                355                 360                 365
Ser Ile Ser Tyr Pro Lys Glu Ala Ile Arg Thr Glu Cys Leu Ile Asp
                370                 375                 380
Gly Glu Leu Lys Gly Phe Gly Gln Leu His Pro Arg Thr Gln Gly Val
385                 390                 395                 400
Glu Thr Leu Gly Thr Ile Tyr Ser Ser Ser Leu Phe Pro Asn Arg Ala
                405                 410                 415
Pro Pro Gly Arg Ile Leu Leu Leu Asn Tyr Ile Gly Gly Ser Thr Asn
                420                 425                 430
Thr Gly Ile Leu Ser Lys Ser Glu Gly Glu Leu Val Glu Ala Val Asp
                435                 440                 445
Arg Asp Leu Arg Lys Met Leu Ile Lys Pro Asn Ser Thr Asp Pro Leu
                450                 455                 460
Lys Leu Gly Val Arg Val Trp Pro Gln Ala Ile Pro Gln Phe Leu Val
465                 470                 475                 480
Gly His Phe Asp Ile Leu Asp Thr Ala Lys Ser Ser Leu Thr Ser Ser
                485                 490                 495
Gly Tyr Glu Gly Leu Phe Leu Gly Gly Asn Tyr Val Ala Gly Val Ala
                500                 505                 510
```

```
Leu Gly Arg Cys Val Glu Gly Ala Tyr Glu Thr Ala Ile Glu Val Asn
         515                 520                 525

Asn Phe Met Ser Arg Tyr Ala Tyr Lys
         530                 535

(2) INFORMATION FOR SEQ ID NO: 3:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pWDC-1 (NRRL B-21237)

(ix) FEATURE:
        (A) NAME/KEY: CDS
        (B) LOCATION: 70..1596
        (D) OTHER INFORMATION: /product= "Arabidopsis protox-2"

(xi) SEQUENCE DESCRIPTION: SEQ ID NO: 3:

TTTTTTACTT ATTTCCGTCA CTGCTTTCGA CTGGTCAGAG ATTTTGACTC TGAATTGTTG      60

CAGATAGCA ATG GCG TCT GGA GCA GTA GCA GAT CAT CAA ATT GAA GCG        108
          Met Ala Ser Gly Ala Val Ala Asp His Gln Ile Glu Ala
            1               5                  10

GTT TCA GGA AAA AGA GTC GCA GTC GTA GGT GCA GGT GTA AGT GGA CTT      156
Val Ser Gly Lys Arg Val Ala Val Val Gly Ala Gly Val Ser Gly Leu
 15                  20                  25

GCG GCG GCT TAC AAG TTG AAA TCG AGG GGT TTG AAT GTG ACT GTG TTT      204
Ala Ala Ala Tyr Lys Leu Lys Ser Arg Gly Leu Asn Val Thr Val Phe
 30                  35                  40                  45

GAA GCT GAT GGA AGA GTA GGT GGG AAG TTG AGA AGT GTT ATG CAA AAT      252
Glu Ala Asp Gly Arg Val Gly Gly Lys Leu Arg Ser Val Met Gln Asn
                 50                  55                  60

GGT TTG ATT TGG GAT GAA GGA GCA AAC ACC ATG ACT GAG GCT GAG CCA      300
Gly Leu Ile Trp Asp Glu Gly Ala Asn Thr Met Thr Glu Ala Glu Pro
         65                  70                  75

GAA GTT GGG AGT TTA CTT GAT GAT CTT GGG CTT CGT GAG AAA CAA CAA      348
Glu Val Gly Ser Leu Leu Asp Asp Leu Gly Leu Arg Glu Lys Gln Gln
     80                  85                  90

TTT CCA ATT TCA CAG AAA AAG CGG TAT ATT GTG CGG AAT GGT GTA CCT      396
Phe Pro Ile Ser Gln Lys Lys Arg Tyr Ile Val Arg Asn Gly Val Pro
 95                 100                 105

GTG ATG CTA CCT ACC AAT CCC ATA GAG CTG GTC ACA AGT AGT GTG CTC      444
Val Met Leu Pro Thr Asn Pro Ile Glu Leu Val Thr Ser Ser Val Leu
110                 115                 120                 125

TCT ACC CAA TCT AAG TTT CAA ATC TTG TTG GAA CCA TTT TTA TGG AAG      492
Ser Thr Gln Ser Lys Phe Gln Ile Leu Leu Glu Pro Phe Leu Trp Lys
                130                 135                 140

AAA AAG TCC TCA AAA GTC TCA GAT GCA TCT GCT GAA GAA AGT GTA AGC      540
Lys Lys Ser Ser Lys Val Ser Asp Ala Ser Ala Glu Glu Ser Val Ser
            145                 150                 155

GAG TTC TTT CAA CGC CAT TTT GGA CAA GAG GTT GTT GAC TAT CTC ATC      588
Glu Phe Phe Gln Arg His Phe Gly Gln Glu Val Val Asp Tyr Leu Ile
        160                 165                 170
```

-continued

```
GAC CCT TTT GTT GGT GGA ACA AGT GCT GCG GAC CCT GAT TCC CTT TCA        636
Asp Pro Phe Val Gly Gly Thr Ser Ala Ala Asp Pro Asp Ser Leu Ser
    175                 180                 185

ATG AAG CAT TCT TTC CCA GAT CTC TGG AAT GTA GAG AAA AGT TTT GGC        684
Met Lys His Ser Phe Pro Asp Leu Trp Asn Val Glu Lys Ser Phe Gly
190                 195                 200                 205

TCT ATT ATA GTC GGT GCA ATC AGA ACA AAG TTT GCT GCT AAA GGT GGT        732
Ser Ile Ile Val Gly Ala Ile Arg Thr Lys Phe Ala Ala Lys Gly Gly
                210                 215                 220

AAA AGT AGA GAC ACA AAG AGT TCT CCT GGC ACA AAA AAG GGT TCG CGT        780
Lys Ser Arg Asp Thr Lys Ser Ser Pro Gly Thr Lys Lys Gly Ser Arg
                225                 230                 235

GGG TCA TTC TCT TTT AAG GGG GGA ATG CAG ATT CTT CCT GAT ACG TTG        828
Gly Ser Phe Ser Phe Lys Gly Gly Met Gln Ile Leu Pro Asp Thr Leu
            240                 245                 250

TGC AAA AGT CTC TCA CAT GAT GAG ATC AAT TTA GAC TCC AAG GTA CTC        876
Cys Lys Ser Leu Ser His Asp Glu Ile Asn Leu Asp Ser Lys Val Leu
        255                 260                 265

TCT TTG TCT TAC AAT TCT GGA TCA AGA CAG GAG AAC TGG TCA TTA TCT        924
Ser Leu Ser Tyr Asn Ser Gly Ser Arg Gln Glu Asn Trp Ser Leu Ser
270                 275                 280                 285

TGT GTT TCG CAT AAT GAA ACG CAG AGA CAA AAC CCC CAT TAT GAT GCT        972
Cys Val Ser His Asn Glu Thr Gln Arg Gln Asn Pro His Tyr Asp Ala
                290                 295                 300

GTA ATT ATG ACG GCT CCT CTG TGC AAT GTG AAG GAG ATG AAG GTT ATG       1020
Val Ile Met Thr Ala Pro Leu Cys Asn Val Lys Glu Met Lys Val Met
                305                 310                 315

AAA GGA GGA CAA CCC TTT CAG CTA AAC TTT CTC CCC GAG ATT AAT TAC       1068
Lys Gly Gly Gln Pro Phe Gln Leu Asn Phe Leu Pro Glu Ile Asn Tyr
            320                 325                 330

ATG CCC CTC TCG GTT TTA ATC ACC ACA TTC ACA AAG GAG AAA GTA AAG       1116
Met Pro Leu Ser Val Leu Ile Thr Thr Phe Thr Lys Glu Lys Val Lys
        335                 340                 345

AGA CCT CTT GAA GGC TTT GGG GTA CTC ATT CCA TCT AAG GAG CAA AAG       1164
Arg Pro Leu Glu Gly Phe Gly Val Leu Ile Pro Ser Lys Glu Gln Lys
350                 355                 360                 365

CAT GGT TTC AAA ACT CTA GGT ACA CTT TTT TCA TCA ATG ATG TTT CCA       1212
His Gly Phe Lys Thr Leu Gly Thr Leu Phe Ser Ser Met Met Phe Pro
                370                 375                 380

GAT CGT TCC CCT AGT GAC GTT CAT CTA TAT ACA ACT TTT ATT GGT GGG       1260
Asp Arg Ser Pro Ser Asp Val His Leu Tyr Thr Thr Phe Ile Gly Gly
                385                 390                 395

AGT AGG AAC CAG GAA CTA GCC AAA GCT TCC ACT GAC GAA TTA AAA CAA       1308
Ser Arg Asn Gln Glu Leu Ala Lys Ala Ser Thr Asp Glu Leu Lys Gln
            400                 405                 410

GTT GTG ACT TCT GAC CTT CAG CGA CTG TTG GGG GTT GAA GGT GAA CCC       1356
Val Val Thr Ser Asp Leu Gln Arg Leu Leu Gly Val Glu Gly Glu Pro
        415                 420                 425

GTG TCT GTC AAC CAT TAC TAT TGG AGG AAA GCA TTC CCG TTG TAT GAC       1404
Val Ser Val Asn His Tyr Tyr Trp Arg Lys Ala Phe Pro Leu Tyr Asp
430                 435                 440                 445

AGC AGC TAT GAC TCA GTC ATG GAA GCA ATT GAC AAG ATG GAG AAT GAT       1452
Ser Ser Tyr Asp Ser Val Met Glu Ala Ile Asp Lys Met Glu Asn Asp
                450                 455                 460

CTA CCT GGG TTC TTC TAT GCA GGT AAT CAT CGA GGG GGG CTC TCT GTT       1500
Leu Pro Gly Phe Phe Tyr Ala Gly Asn His Arg Gly Gly Leu Ser Val
            465                 470                 475

GGG AAA TCA ATA GCA TCA GGT TGC AAA GCA GCT GAC CTT GTG ATC TCA       1548
Gly Lys Ser Ile Ala Ser Gly Cys Lys Ala Ala Asp Leu Val Ile Ser
        480                 485                 490
```

```
TAC CTG GAG TCT TGC TCA AAT GAC AAG AAA CCA AAT GAC AGC TTA TAA        1603
Tyr Leu Glu Ser Cys Ser Asn Asp Lys Lys Pro Asn Asp Ser Leu
    495                 500                 505

AAGGTTCGTC CCTTTTTATC ACTTACTTTG TAAACTTGTA AAATGCAACA AGCCGCCGTG      1663

CGATTAGCCA ACAACTCAGC AAAACCCAGA TTCTCATAAG GCTCACTAAT TCCAGAATAA      1723

ACTATTTATG TAAAA                                                      1738
```

(2) INFORMATION FOR SEQ ID NO: 4:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Ser Gly Ala Val Ala Asp His Gln Ile Glu Ala Val Ser Gly
 1               5                  10                  15

Lys Arg Val Ala Val Gly Ala Gly Val Ser Gly Leu Ala Ala Ala
            20                  25                  30

Tyr Lys Leu Lys Ser Arg Gly Leu Asn Val Thr Val Phe Glu Ala Asp
        35                  40                  45

Gly Arg Val Gly Gly Lys Leu Arg Ser Val Met Gln Asn Gly Leu Ile
    50                  55                  60

Trp Asp Glu Gly Ala Asn Thr Met Thr Glu Ala Glu Pro Glu Val Gly
 65                  70                  75                  80

Ser Leu Leu Asp Asp Leu Gly Leu Arg Glu Lys Gln Gln Phe Pro Ile
                85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
        115                 120                 125

Ser Lys Phe Gln Ile Leu Leu Glu Pro Phe Leu Trp Lys Lys Ser
130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
            180                 185                 190

Ser Phe Pro Asp Leu Trp Asn Val Glu Lys Ser Phe Gly Ser Ile Ile
        195                 200                 205

Val Gly Ala Ile Arg Thr Lys Phe Ala Ala Lys Gly Gly Lys Ser Arg
    210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                245                 250                 255

Leu Ser His Asp Glu Ile Asn Leu Asp Ser Lys Val Leu Ser Leu Ser
            260                 265                 270

Tyr Asn Ser Gly Ser Arg Gln Glu Asn Trp Ser Leu Ser Cys Val Ser
        275                 280                 285

His Asn Glu Thr Gln Arg Gln Asn Pro His Tyr Asp Ala Val Ile Met
    290                 295                 300
```

```
Thr Ala Pro Leu Cys Asn Val Lys Glu Met Lys Val Met Lys Gly Gly
305                 310                 315                 320

Gln Pro Phe Gln Leu Asn Phe Leu Pro Glu Ile Asn Tyr Met Pro Leu
            325                 330                 335

Ser Val Leu Ile Thr Thr Phe Thr Lys Glu Lys Val Lys Arg Pro Leu
            340                 345                 350

Glu Gly Phe Gly Val Leu Ile Pro Ser Lys Glu Gln Lys His Gly Phe
            355                 360                 365

Lys Thr Leu Gly Thr Leu Phe Ser Ser Met Met Phe Pro Asp Arg Ser
370                 375                 380

Pro Ser Asp Val His Leu Tyr Thr Thr Phe Ile Gly Gly Ser Arg Asn
385                 390                 395                 400

Gln Glu Leu Ala Lys Ala Ser Thr Asp Glu Leu Lys Gln Val Val Thr
            405                 410                 415

Ser Asp Leu Gln Arg Leu Leu Gly Val Glu Gly Glu Pro Val Ser Val
            420                 425                 430

Asn His Tyr Tyr Trp Arg Lys Ala Phe Pro Leu Tyr Asp Ser Ser Tyr
            435                 440                 445

Asp Ser Val Met Glu Ala Ile Asp Lys Met Glu Asn Asp Leu Pro Gly
450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
            485                 490                 495

Ser Cys Ser Asn Asp Lys Lys Pro Asn Asp Ser Leu
            500                 505

(2) INFORMATION FOR SEQ ID NO: 5:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Zea mays (maize)

(vii) IMMEDIATE SOURCE:
        (B) CLONE: pWDC-4 (NRRL B-21260)

(ix) FEATURE:
        (A) NAME/KEY: CDS
        (B) LOCATION: 1..1443
        (D) OTHER INFORMATION: /product= "Maize protox-1 cDNA (not
            full-length); first seven nucleotides removed vs. serial
            no. 60/012,705"

(xi) SEQUENCE DESCRIPTION: SEQ ID NO: 5:

GCG GAC TGC GTC GTG GTG GGC GGA GGC ATC AGT GGC CTC TGC ACC GCG      48
Ala Asp Cys Val Val Val Gly Gly Gly Ile Ser Gly Leu Cys Thr Ala
  1               5                  10                  15

CAG GCG CTG GCC ACG CGG CAC GGC GTC GGG GAC GTG CTT GTC ACG GAG      96
Gln Ala Leu Ala Thr Arg His Gly Val Gly Asp Val Leu Val Thr Glu
            20                  25                  30
```

-continued

```
GCC CGC GCC CGC CCC GGC GGC AAC ATT ACC ACC GTC GAG CGC CCC GAG        144
Ala Arg Ala Arg Pro Gly Gly Asn Ile Thr Thr Val Glu Arg Pro Glu
         35                  40                  45

GAA GGG TAC CTC TGG GAG GAG GGT CCC AAC AGC TTC CAG CCC TCC GAC        192
Glu Gly Tyr Leu Trp Glu Glu Gly Pro Asn Ser Phe Gln Pro Ser Asp
 50                  55                  60

CCC GTT CTC ACC ATG GCC GTG GAC AGC GGA CTG AAG GAT GAC TTG GTT        240
Pro Val Leu Thr Met Ala Val Asp Ser Gly Leu Lys Asp Asp Leu Val
 65                  70                  75                  80

TTT GGG GAC CCA AAC GCG CCG CGT TTC GTG CTG TGG GAG GGG AAG CTG        288
Phe Gly Asp Pro Asn Ala Pro Arg Phe Val Leu Trp Glu Gly Lys Leu
                 85                  90                  95

AGG CCC GTG CCA TCC AAG CCC GCC GAC CTC CCG TTC TTC GAT CTC ATG        336
Arg Pro Val Pro Ser Lys Pro Ala Asp Leu Pro Phe Phe Asp Leu Met
                100                 105                 110

AGC ATC CCA GGG AAG CTC AGG GCC GGT CTA GGC GCG CTT GGC ATC CGC        384
Ser Ile Pro Gly Lys Leu Arg Ala Gly Leu Gly Ala Leu Gly Ile Arg
                115                 120                 125

CCG CCT CCT CCA GGC CGC GAA GAG TCA GTG GAG GAG TTC GTG CGC CGC        432
Pro Pro Pro Pro Gly Arg Glu Glu Ser Val Glu Glu Phe Val Arg Arg
130                 135                 140

AAC CTC GGT GCT GAG GTC TTT GAG CGC CTC ATT GAG CCT TTC TGC TCA        480
Asn Leu Gly Ala Glu Val Phe Glu Arg Leu Ile Glu Pro Phe Cys Ser
145                 150                 155                 160

GGT GTC TAT GCT GGT GAT CCT TCT AAG CTC AGC ATG AAG GCT GCA TTT        528
Gly Val Tyr Ala Gly Asp Pro Ser Lys Leu Ser Met Lys Ala Ala Phe
                165                 170                 175

GGG AAG GTT TGG CGG TTG GAA GAA ACT GGA GGT AGT ATT ATT GGT GGA        576
Gly Lys Val Trp Arg Leu Glu Glu Thr Gly Gly Ser Ile Ile Gly Gly
                180                 185                 190

ACC ATC AAG ACA ATT CAG GAG AGG AGC AAG AAT CCA AAA CCA CCG AGG        624
Thr Ile Lys Thr Ile Gln Glu Arg Ser Lys Asn Pro Lys Pro Pro Arg
                195                 200                 205

GAT GCC CGC CTT CCG AAG CCA AAA GGG CAG ACA GTT GCA TCT TTC AGG        672
Asp Ala Arg Leu Pro Lys Pro Lys Gly Gln Thr Val Ala Ser Phe Arg
210                 215                 220

AAG GGT CTT GCC ATG CTT CCA AAT GCC ATT ACA TCC AGC TTG GGT AGT        720
Lys Gly Leu Ala Met Leu Pro Asn Ala Ile Thr Ser Ser Leu Gly Ser
225                 230                 235                 240

AAA GTC AAA CTA TCA TGG AAA CTC ACG AGC ATT ACA AAA TCA GAT GAC        768
Lys Val Lys Leu Ser Trp Lys Leu Thr Ser Ile Thr Lys Ser Asp Asp
                245                 250                 255

AAG GGA TAT GTT TTG GAG TAT GAA ACG CCA GAA GGG GTT GTT TCG GTG        816
Lys Gly Tyr Val Leu Glu Tyr Glu Thr Pro Glu Gly Val Val Ser Val
                260                 265                 270

CAG GCT AAA AGT GTT ATC ATG ACT ATT CCA TCA TAT GTT GCT AGC AAC        864
Gln Ala Lys Ser Val Ile Met Thr Ile Pro Ser Tyr Val Ala Ser Asn
                275                 280                 285

ATT TTG CGT CCA CTT TCA AGC GAT GCT GCA GAT GCT CTA TCA AGA TTC        912
Ile Leu Arg Pro Leu Ser Ser Asp Ala Ala Asp Ala Leu Ser Arg Phe
                290                 295                 300

TAT TAT CCA CCG GTT GCT GCT GTA ACT GTT TCG TAT CCA AAG GAA GCA        960
Tyr Tyr Pro Pro Val Ala Ala Val Thr Val Ser Tyr Pro Lys Glu Ala
305                 310                 315                 320

ATT AGA AAA GAA TGC TTA ATT GAT GGG GAA CTC CAG GGC TTT GGC CAG       1008
Ile Arg Lys Glu Cys Leu Ile Asp Gly Glu Leu Gln Gly Phe Gly Gln
                325                 330                 335

TTG CAT CCA CGT AGT CAA GGA GTT GAG ACA TTA GGA ACA ATA TAC AGT       1056
Leu His Pro Arg Ser Gln Gly Val Glu Thr Leu Gly Thr Ile Tyr Ser
                340                 345                 350
```

```
TCC TCA CTC TTT CCA AAT CGT GCT CCT GAC GGT AGG GTG TTA CTT CTA     1104
Ser Ser Leu Phe Pro Asn Arg Ala Pro Asp Gly Arg Val Leu Leu Leu
        355                 360                 365

AAC TAC ATA GGA GGT GCT ACA AAC ACA GGA ATT GTT TCC AAG ACT GAA     1152
Asn Tyr Ile Gly Gly Ala Thr Asn Thr Gly Ile Val Ser Lys Thr Glu
        370                 375                 380

AGT GAG CTG GTC GAA GCA GTT GAC CGT GAC CTC CGA AAA ATG CTT ATA     1200
Ser Glu Leu Val Glu Ala Val Asp Arg Asp Leu Arg Lys Met Leu Ile
385                 390                 395                 400

AAT TCT ACA GCA GTG GAC CCT TTA GTC CTT GGT GTT CGA GTT TGG CCA     1248
Asn Ser Thr Ala Val Asp Pro Leu Val Leu Gly Val Arg Val Trp Pro
                405                 410                 415

CAA GCC ATA CCT CAG TTC CTG GTA GGA CAT CTT GAT CTT CTG GAA GCC     1296
Gln Ala Ile Pro Gln Phe Leu Val Gly His Leu Asp Leu Leu Glu Ala
            420                 425                 430

GCA AAA GCT GCC CTG GAC CGA GGT GGC TAC GAT GGG CTG TTC CTA GGA     1344
Ala Lys Ala Ala Leu Asp Arg Gly Gly Tyr Asp Gly Leu Phe Leu Gly
                435                 440                 445

GGG AAC TAT GTT GCA GGA GTT GCC CTG GGC AGA TGC GTT GAG GGC GCG     1392
Gly Asn Tyr Val Ala Gly Val Ala Leu Gly Arg Cys Val Glu Gly Ala
450                 455                 460

TAT GAA AGT GCC TCG CAA ATA TCT GAC TTC TTG ACC AAG TAT GCC TAC     1440
Tyr Glu Ser Ala Ser Gln Ile Ser Asp Phe Leu Thr Lys Tyr Ala Tyr
465                 470                 475                 480

AAG TGATGAAAGA AGTGGAGCGC TACTTGTTAA TCGTTTATGT TGCATAGATG          1493
Lys

AGGTGCCTCC GGGAAAAAAA AAGCTTGAAT AGTATTTTTT ATTCTTATTT TGTAAATTGC   1553

ATTTCTGTTC TTTTTTCTAT CAGTAATTAG TTATATTTTA GTTCTGTAGG AGATTGTTCT   1613

GTTCACTGCC CTTCAAAAGA AATTTTATTT TTCATTCTTT TATGAGAGCT GTGCTACTTA   1673

AAAAAAAAAA AAAAAAAA                                                 1691

(2) INFORMATION FOR SEQ ID NO: 6:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO: 6:

Ala Asp Cys Val Val Gly Gly Ile Ser Gly Leu Cys Thr Ala
 1               5                  10                  15

Gln Ala Leu Ala Thr Arg His Gly Val Gly Asp Val Leu Val Thr Glu
                20                  25                  30

Ala Arg Ala Arg Pro Gly Gly Asn Ile Thr Thr Val Glu Arg Pro Glu
            35                  40                  45

Glu Gly Tyr Leu Trp Glu Glu Gly Pro Asn Ser Phe Gln Pro Ser Asp
        50                  55                  60

Pro Val Leu Thr Met Ala Val Asp Ser Gly Leu Lys Asp Asp Leu Val
65                  70                  75                  80

Phe Gly Asp Pro Asn Ala Pro Arg Phe Val Leu Trp Glu Gly Lys Leu
                85                  90                  95

Arg Pro Val Pro Ser Lys Pro Ala Asp Leu Pro Phe Phe Asp Leu Met
            100                 105                 110

Ser Ile Pro Gly Lys Leu Arg Ala Gly Leu Gly Ala Leu Gly Ile Arg
        115                 120                 125
```

```
Pro Pro Pro Pro Gly Arg Glu Glu Ser Val Glu Glu Phe Val Arg Arg
    130                 135                 140
Asn Leu Gly Ala Glu Val Phe Glu Arg Leu Ile Glu Pro Phe Cys Ser
145                 150                 155                 160
Gly Val Tyr Ala Gly Asp Pro Ser Lys Leu Ser Met Lys Ala Ala Phe
                165                 170                 175
Gly Lys Val Trp Arg Leu Glu Glu Thr Gly Ser Ile Ile Gly Gly
            180                 185                 190
Thr Ile Lys Thr Ile Gln Glu Arg Ser Lys Asn Pro Lys Pro Pro Arg
        195                 200                 205
Asp Ala Arg Leu Pro Lys Pro Lys Gly Gln Thr Val Ala Ser Phe Arg
    210                 215                 220
Lys Gly Leu Ala Met Leu Pro Asn Ala Ile Thr Ser Ser Leu Gly Ser
225                 230                 235                 240
Lys Val Lys Leu Ser Trp Lys Leu Thr Ser Ile Thr Lys Ser Asp Asp
                245                 250                 255
Lys Gly Tyr Val Leu Glu Tyr Glu Thr Pro Glu Gly Val Val Ser Val
                260                 265                 270
Gln Ala Lys Ser Val Ile Met Thr Ile Pro Ser Tyr Val Ala Ser Asn
            275                 280                 285
Ile Leu Arg Pro Leu Ser Ser Asp Ala Ala Asp Ala Leu Ser Arg Phe
    290                 295                 300
Tyr Tyr Pro Pro Val Ala Ala Val Thr Val Ser Tyr Pro Lys Glu Ala
305                 310                 315                 320
Ile Arg Lys Glu Cys Leu Ile Asp Gly Glu Leu Gln Gly Phe Gly Gln
                325                 330                 335
Leu His Pro Arg Ser Gln Gly Val Glu Thr Leu Gly Thr Ile Tyr Ser
                340                 345                 350
Ser Ser Leu Phe Pro Asn Arg Ala Pro Asp Gly Arg Val Leu Leu Leu
            355                 360                 365
Asn Tyr Ile Gly Gly Ala Thr Asn Thr Gly Ile Val Ser Lys Thr Glu
    370                 375                 380
Ser Glu Leu Val Glu Ala Val Asp Arg Asp Leu Arg Lys Met Leu Ile
385                 390                 395                 400
Asn Ser Thr Ala Val Asp Pro Leu Val Leu Gly Val Arg Val Trp Pro
                405                 410                 415
Gln Ala Ile Pro Gln Phe Leu Val Gly His Leu Asp Leu Leu Glu Ala
            420                 425                 430
Ala Lys Ala Ala Leu Asp Arg Gly Tyr Asp Gly Leu Phe Leu Gly
        435                 440                 445
Gly Asn Tyr Val Ala Gly Val Ala Leu Gly Arg Cys Val Glu Gly Ala
    450                 455                 460
Tyr Glu Ser Ala Ser Gln Ile Ser Asp Phe Leu Thr Lys Tyr Ala Tyr
465                 470                 475                 480
Lys (2) INFORMATION FOR SEQ ID NO: 7:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: cDNA
```

-continued

```
    (iii) HYPOTHETICAL: NO (iv) ANTI-SENSE: NO (vi) ORIGINAL SOURCE:
         (A) ORGANISM: Zea mays (maize)

(vii) IMMEDIATE SOURCE:
         (B) CLONE: pWDC-3 (NRRL B-21259)

(ix) FEATURE:
         (A) NAME/KEY: CDS
         (B) LOCATION: 64..1698
         (D) OTHER INFORMATION: /product= "Maize protox-2"

(xi) SEQUENCE DESCRIPTION: SEQ ID NO: 7:

CTCTCCTACC TCCACCTCCA CGACAACAAG CAAATCCCCA TCCAGTTCCA AACCCTAACT      60

CAA ATG CTC GCT TTG ACT GCC TCA GCC TCA TCC GCT TCG TCC CAT CCT     108
    Met Leu Ala Leu Thr Ala Ser Ala Ser Ser Ala Ser Ser His Pro
    1               5                  10                  15

TAT CGC CAC GCC TCC GCG CAC ACT CGT CGC CCC CGC CTA CGT GCG GTC     156
Tyr Arg His Ala Ser Ala His Thr Arg Arg Pro Arg Leu Arg Ala Val
                20                  25                  30

CTC GCG ATG GCG GGC TCC GAC GAC CCC CGT GCA GCG CCC GCC AGA TCG     204
Leu Ala Met Ala Gly Ser Asp Asp Pro Arg Ala Ala Pro Ala Arg Ser
            35                  40                  45

GTC GCC GTC GTC GGC GCC GGG GTC AGC GGG CTC GCG GCG GCG TAC AGG     252
Val Ala Val Val Gly Ala Gly Val Ser Gly Leu Ala Ala Ala Tyr Arg
        50                  55                  60

CTC AGA CAG AGC GGC GTG AAC GTA ACG GTG TTC GAA GCG GCC GAC AGG     300
Leu Arg Gln Ser Gly Val Asn Val Thr Val Phe Glu Ala Ala Asp Arg
    65                  70                  75

GCG GGA GGA AAG ATA CGG ACC AAT TCC GAG GGC GGG TTT GTC TGG GAT     348
Ala Gly Gly Lys Ile Arg Thr Asn Ser Glu Gly Gly Phe Val Trp Asp
80                  85                  90                  95

GAA GGA GCT AAC ACC ATG ACA GAA GGT GAA TGG GAG GCC AGT AGA CTG     396
Glu Gly Ala Asn Thr Met Thr Glu Gly Glu Trp Glu Ala Ser Arg Leu
                100                 105                 110

ATT GAT GAT CTT GGT CTA CAA GAC AAA CAG CAG TAT CCT AAC TCC CAA     444
Ile Asp Asp Leu Gly Leu Gln Asp Lys Gln Gln Tyr Pro Asn Ser Gln
            115                 120                 125

CAC AAG CGT TAC ATT GTC AAA GAT GGA GCA CCA GCA CTG ATT CCT TCG     492
His Lys Arg Tyr Ile Val Lys Asp Gly Ala Pro Ala Leu Ile Pro Ser
        130                 135                 140

GAT CCC ATT TCG CTA ATG AAA AGC AGT GTT CTT TCG ACA AAA TCA AAG     540
Asp Pro Ile Ser Leu Met Lys Ser Ser Val Leu Ser Thr Lys Ser Lys
    145                 150                 155

ATT GCG TTA TTT TTT GAA CCA TTT CTC TAC AAG AAA GCT AAC ACA AGA     588
Ile Ala Leu Phe Phe Glu Pro Phe Leu Tyr Lys Lys Ala Asn Thr Arg
160                 165                 170                 175

AAC TCT GGA AAA GTG TCT GAG GAG CAC TTG AGT GAG AGT GTT GGG AGC     636
Asn Ser Gly Lys Val Ser Glu Glu His Leu Ser Glu Ser Val Gly Ser
                180                 185                 190

TTC TGT GAA CGC CAC TTT GGA AGA GAA GTT GTT GAC TAT TTT GTT GAT     684
Phe Cys Glu Arg His Phe Gly Arg Glu Val Val Asp Tyr Phe Val Asp
            195                 200                 205

CCA TTT GTA GCT GGA ACA AGT GCA GGA GAT CCA GAG TCA CTA TCT ATT     732
Pro Phe Val Ala Gly Thr Ser Ala Gly Asp Pro Glu Ser Leu Ser Ile
        210                 215                 220

CGT CAT GCA TTC CCA GCA TTG TGG AAT TTG GAA AGA AAG TAT GGT TCA     780
Arg His Ala Phe Pro Ala Leu Trp Asn Leu Glu Arg Lys Tyr Gly Ser
    225                 230                 235
```

```
GTT ATT GTT GGT GCC ATC TTG TCT AAG CTA GCA GCT AAA GGT GAT CCA      828
Val Ile Val Gly Ala Ile Leu Ser Lys Leu Ala Ala Lys Gly Asp Pro
240                 245                 250                 255

GTA AAG ACA AGA CAT GAT TCA TCA GGG AAA AGA AGG AAT AGA CGA GTG      876
Val Lys Thr Arg His Asp Ser Ser Gly Lys Arg Arg Asn Arg Arg Val
                    260                 265                 270

TCG TTT TCA TTT CAT GGT GGA ATG CAG TCA CTA ATA AAT GCA CTT CAC      924
Ser Phe Ser Phe His Gly Gly Met Gln Ser Leu Ile Asn Ala Leu His
            275                 280                 285

AAT GAA GTT GGA GAT GAT AAT GTG AAG CTT GGT ACA GAA GTG TTG TCA      972
Asn Glu Val Gly Asp Asp Asn Val Lys Leu Gly Thr Glu Val Leu Ser
        290                 295                 300

TTG GCA TGT ACA TTT GAT GGA GTT CCT GCA CTA GGC AGG TGG TCA ATT     1020
Leu Ala Cys Thr Phe Asp Gly Val Pro Ala Leu Gly Arg Trp Ser Ile
305                 310                 315

TCT GTT GAT TCG AAG GAT AGC GGT GAC AAG GAC CTT GCT AGT AAC CAA     1068
Ser Val Asp Ser Lys Asp Ser Gly Asp Lys Asp Leu Ala Ser Asn Gln
320                 325                 330                 335

ACC TTT GAT GCT GTT ATA ATG ACA GCT CCA TTG TCA AAT GTC CGG AGG     1116
Thr Phe Asp Ala Val Ile Met Thr Ala Pro Leu Ser Asn Val Arg Arg
                    340                 345                 350

ATG AAG TTC ACC AAA GGT GGA GCT CCG GTT GTT CTT GAC TTT CTT CCT     1164
Met Lys Phe Thr Lys Gly Gly Ala Pro Val Val Leu Asp Phe Leu Pro
            355                 360                 365

AAG ATG GAT TAT CTA CCA CTA TCT CTC ATG GTG ACT GCT TTT AAG AAG     1212
Lys Met Asp Tyr Leu Pro Leu Ser Leu Met Val Thr Ala Phe Lys Lys
        370                 375                 380

GAT GAT GTC AAG AAA CCT CTG GAA GGA TTT GGG GTC TTA ATA CCT TAC     1260
Asp Asp Val Lys Lys Pro Leu Glu Gly Phe Gly Val Leu Ile Pro Tyr
385                 390                 395

AAG GAA CAG CAA AAA CAT GGT CTG AAA ACC CTT GGG ACT CTC TTT TCC     1308
Lys Glu Gln Gln Lys His Gly Leu Lys Thr Leu Gly Thr Leu Phe Ser
400                 405                 410                 415

TCA ATG ATG TTC CCA GAT CGA GCT CCT GAT GAC CAA TAT TTA TAT ACA     1356
Ser Met Met Phe Pro Asp Arg Ala Pro Asp Asp Gln Tyr Leu Tyr Thr
                    420                 425                 430

ACA TTT GTT GGG GGT AGC CAC AAT AGA GAT CTT GCT GGA GCT CCA ACG     1404
Thr Phe Val Gly Gly Ser His Asn Arg Asp Leu Ala Gly Ala Pro Thr
            435                 440                 445

TCT ATT CTG AAA CAA CTT GTG ACC TCT GAC CTT AAA AAA CTC TTG GGC     1452
Ser Ile Leu Lys Gln Leu Val Thr Ser Asp Leu Lys Lys Leu Leu Gly
        450                 455                 460

GTA GAG GGG CAA CCA ACT TTT GTC AAG CAT GTA TAC TGG GGA AAT GCT     1500
Val Glu Gly Gln Pro Thr Phe Val Lys His Val Tyr Trp Gly Asn Ala
465                 470                 475

TTT CCT TTG TAT GGC CAT GAT TAT AGT TCT GTA TTG GAA GCT ATA GAA     1548
Phe Pro Leu Tyr Gly His Asp Tyr Ser Ser Val Leu Glu Ala Ile Glu
480                 485                 490                 495

AAG ATG GAG AAA AAC CTT CCA GGG TTC TTC TAC GCA GGA AAT AGC AAG     1596
Lys Met Glu Lys Asn Leu Pro Gly Phe Phe Tyr Ala Gly Asn Ser Lys
                    500                 505                 510

GAT GGG CTT GCT GTT GGA AGT GTT ATA GCT TCA GGA AGC AAG GCT GCT     1644
Asp Gly Leu Ala Val Gly Ser Val Ile Ala Ser Gly Ser Lys Ala Ala
            515                 520                 525

GAC CTT GCA ATC TCA TAT CTT GAA TCT CAC ACC AAG CAT AAT AAT TCA     1692
Asp Leu Ala Ile Ser Tyr Leu Glu Ser His Thr Lys His Asn Asn Ser
        530                 535                 540

CAT TGAAAGTGTC TGACCTATCC TCTAGCAGTT GTCGACAAAT TTCTCCAGTT          1745
His
    545
```

```
CATGTACAGT AGAAACCGAT GCGTTGCAGT TTCAGAACAT CTTCACTTCT TCAGATATTA    1805

ACCCTTCGTT GAACATCCAC CAGAAAGGTA GTCACATGTG TAAGTGGGAA AATGAGGTTA    1865

AAAACTATTA TGGCGGCCGA AATGTTCCTT TTTGTTTTCC TCACAAGTGG CCTACGACAC    1925

TTGATGTTGG AAATACATTT AAATTTGTTG AATTGTTTGA GAACACATGC GTGACGTGTA    1985

ATATTTGCCT ATTGTGATTT TAGCAGTAGT CTTGGCCAGA TTATGCTTTA CGCCTTTAAA    2045

AAAAAAAAAA AAAAA                                                    2061
```

(2) INFORMATION FOR SEQ ID NO: 8:

(i) SEQUENCE CHARACTERISTICS:
        (A) LENGTH: 544 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Leu Ala Leu Thr Ala Ser Ala Ser Ser His Pro Tyr
 1               5                  10              15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Ala Tyr Arg Leu
    50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Phe Val Trp Asp Glu
                85                  90                  95

Gly Ala Asn Thr Met Thr Glu Gly Glu Trp Glu Ala Ser Arg Leu Ile
                100                 105                 110

Asp Asp Leu Gly Leu Gln Asp Lys Gln Gln Tyr Pro Asn Ser Gln His
            115                 120                 125

Lys Arg Tyr Ile Val Lys Asp Gly Ala Pro Ala Leu Ile Pro Ser Asp
    130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285
```

```
Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
        355                 360                 365

Met Asp Tyr Leu Pro Leu Ser Leu Met Val Thr Ala Phe Lys Lys Asp
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
            420                 425                 430

Phe Val Gly Gly Ser His Asn Arg Asp Leu Ala Gly Ala Pro Thr Ser
        435                 440                 445

Ile Leu Lys Gln Leu Val Thr Ser Asp Leu Lys Lys Leu Leu Gly Val
    450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Ser Lys Asp
            500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Ser His
    530                 535                 540
```

(2) INFORMATION FOR SEQ ID NO: 9:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Triticum aestivum (wheat)

(vii) IMMEDIATE SOURCE:
        (B) CLONE: pWDC-13 (NRRL B-21545)

(ix) FEATURE:
        (A) NAME/KEY: CDS
        (B) LOCATION: 3..1589
        (D) OTHER INFORMATION: /product= "wheat protox-1"

(xi) SEQUENCE DESCRIPTION: SEQ ID NO: 9:

```
GC GCA ACA ATG GCC ACC GCC ACC GTC GCG GCC GCG TCG CCG CTC CGC      47
   Ala Thr Met Ala Thr Ala Thr Val Ala Ala Ala Ser Pro Leu Arg
   1               5                  10                  15
```

-continued

```
GGC AGG GTC ACC GGG CGC CCA CAC CGC GTC CGC CCG CGT TGC GCT ACC        95
Gly Arg Val Thr Gly Arg Pro His Arg Val Arg Pro Arg Cys Ala Thr
             20                  25                  30

GCG AGC AGC GCG ACC GAG ACT CCG GCG GCG CCC GGC GTG CGG CTG TCC       143
Ala Ser Ser Ala Thr Glu Thr Pro Ala Ala Pro Gly Val Arg Leu Ser
             35                  40                  45

GCG GAA TGC GTC ATT GTG GGC GCC GGC ATC AGC GGC CTC TGC ACC GCG       191
Ala Glu Cys Val Ile Val Gly Ala Gly Ile Ser Gly Leu Cys Thr Ala
             50                  55                  60

CAG GCG CTG GCC ACC CGA TAC GGC GTC AGC GAC CTG CTC GTC ACG GAG       239
Gln Ala Leu Ala Thr Arg Tyr Gly Val Ser Asp Leu Leu Val Thr Glu
65                   70                  75

GCC CGC GAC CGC CCG GGC GGC AAC ATC ACC ACC GTC GAG CGT CCC GAC       287
Ala Arg Asp Arg Pro Gly Gly Asn Ile Thr Thr Val Glu Arg Pro Asp
80                   85                  90                  95

GAG GGG TAC CTG TGG GAG GAG GGA CCC AAC AGC TTC CAG CCC TCC GAC       335
Glu Gly Tyr Leu Trp Glu Glu Gly Pro Asn Ser Phe Gln Pro Ser Asp
                 100                 105                 110

CCG GTC CTC ACC ATG GCC GTG GAC AGC GGG CTC AAG GAT GAC TTG GTG       383
Pro Val Leu Thr Met Ala Val Asp Ser Gly Leu Lys Asp Asp Leu Val
             115                 120                 125

TTC GGG GAC CCC AAC GCG CCC CGG TTC GTG CTG TGG GAG GGG AAG CTG       431
Phe Gly Asp Pro Asn Ala Pro Arg Phe Val Leu Trp Glu Gly Lys Leu
             130                 135                 140

AGG CCG GTG CCG TCG AAG CCA GGC GAC CTG CCT TTC TTC AGC CTC ATG       479
Arg Pro Val Pro Ser Lys Pro Gly Asp Leu Pro Phe Phe Ser Leu Met
145                 150                 155

AGT ATC CCT GGG AAG CTC AGG GCC GGC CTT GGC GCG CTC GGC ATT CGC       527
Ser Ile Pro Gly Lys Leu Arg Ala Gly Leu Gly Ala Leu Gly Ile Arg
160                 165                 170                 175

CCA CCT CCT CCA GGG CGC GAG GAG TCG GTG GAG GAG TTT GTG CGC CGC       575
Pro Pro Pro Pro Gly Arg Glu Glu Ser Val Glu Glu Phe Val Arg Arg
                 180                 185                 190

AAC CTC GGT GCC GAG GTC TTT GAG CGC CTC ATC GAG CCT TTC TGC TCA       623
Asn Leu Gly Ala Glu Val Phe Glu Arg Leu Ile Glu Pro Phe Cys Ser
             195                 200                 205

GGT GTA TAT GCT GGT GAT CCT TCG AAG CTT AGT ATG AAG GCT GCA TTT       671
Gly Val Tyr Ala Gly Asp Pro Ser Lys Leu Ser Met Lys Ala Ala Phe
             210                 215                 220

GGG AAG GTC TGG AGG TTG GAG GAG ATT GGA GGT AGT ATT ATT GGT GGA       719
Gly Lys Val Trp Arg Leu Glu Glu Ile Gly Gly Ser Ile Ile Gly Gly
225                 230                 235

ACC ATC AAG GCG ATT CAG GAT AAA GGG AAG AAC CCC AAA CCG CCA AGG       767
Thr Ile Lys Ala Ile Gln Asp Lys Gly Lys Asn Pro Lys Pro Pro Arg
240                 245                 250                 255

GAT CCC CGA CTT CCG GCA CCA AAG GGA CAG ACG GTG GCA TCT TTC AGG       815
Asp Pro Arg Leu Pro Ala Pro Lys Gly Gln Thr Val Ala Ser Phe Arg
                 260                 265                 270

AAG GGT CTA GCC ATG CTC CCG AAT GCC ATC GCA TCT AGG CTG GGT AGT       863
Lys Gly Leu Ala Met Leu Pro Asn Ala Ile Ala Ser Arg Leu Gly Ser
             275                 280                 285

AAA GTC AAG CTG TCA TGG AAG CTT ACG AGC ATT ACA AAG GCG GAC AAC       911
Lys Val Lys Leu Ser Trp Lys Leu Thr Ser Ile Thr Lys Ala Asp Asn
             290                 295                 300

CAA GGA TAT GTA TTA GGT TAT GAA ACA CCA GAA GGA CTT GTT TCA GTG       959
Gln Gly Tyr Val Leu Gly Tyr Glu Thr Pro Glu Gly Leu Val Ser Val
305                 310                 315

CAG GCT AAA AGT GTT ATC ATG ACC ATC CCG TCA TAT GTT GCT AGT GAT      1007
Gln Ala Lys Ser Val Ile Met Thr Ile Pro Ser Tyr Val Ala Ser Asp
320                 325                 330                 335
```

```
ATC TTG CGC CCA CTT TCA ATT GAT GCA GCA GAT GCA CTC TCA AAA TTC    1055
Ile Leu Arg Pro Leu Ser Ile Asp Ala Ala Asp Ala Leu Ser Lys Phe
            340                 345                 350

TAT TAT CCG CCA GTT GCT GCT GTA ACT GTT TCA TAT CCA AAA GAA GCT    1103
Tyr Tyr Pro Pro Val Ala Ala Val Thr Val Ser Tyr Pro Lys Glu Ala
            355                 360                 365

ATT AGA AAA GAA TGC TTA ATT GAT GGG GAG CTC CAG GGT TTC GGC CAG    1151
Ile Arg Lys Glu Cys Leu Ile Asp Gly Glu Leu Gln Gly Phe Gly Gln
            370                 375                 380

TTG CAT CCA CGT AGC CAA GGA GTC GAG ACT TTA GGG ACA ATA TAT AGC    1199
Leu His Pro Arg Ser Gln Gly Val Glu Thr Leu Gly Thr Ile Tyr Ser
385                 390                 395

TCT TCT CTC TTT CCT AAT CGT GCT CCT GCT GGA AGA GTG TTA CTT CTG    1247
Ser Ser Leu Phe Pro Asn Arg Ala Pro Ala Gly Arg Val Leu Leu Leu
400                 405                 410                 415

AAC TAT ATC GGG GGT TCT ACA AAT ACA GGG ATC GTC TCC AAG ACT GAG    1295
Asn Tyr Ile Gly Gly Ser Thr Asn Thr Gly Ile Val Ser Lys Thr Glu
            420                 425                 430

AGT GAC TTA GTA GGA GCC GTT GAC CGT GAC CTC AGA AAA ATG TTG ATA    1343
Ser Asp Leu Val Gly Ala Val Asp Arg Asp Leu Arg Lys Met Leu Ile
            435                 440                 445

AAC CCT AGA GCA GCA GAC CCT TTA GCA TTA GGG GTT CGA GTG TGG CCA    1391
Asn Pro Arg Ala Ala Asp Pro Leu Ala Leu Gly Val Arg Val Trp Pro
            450                 455                 460

CAA GCA ATA CCA CAG TTT TTG ATT GGG CAC CTT GAT CGC CTT GCT GCT    1439
Gln Ala Ile Pro Gln Phe Leu Ile Gly His Leu Asp Arg Leu Ala Ala
465                 470                 475

GCA AAA TCT GCA CTG GGC CAA GGC GGC TAC GAC GGG TTG TTC CTA GGA    1487
Ala Lys Ser Ala Leu Gly Gln Gly Gly Tyr Asp Gly Leu Phe Leu Gly
480                 485                 490                 495

GGA AAC TAC GTC GCA GGA GTT GCC TTG GGC CGA TGC ATC GAG GGT GCG    1535
Gly Asn Tyr Val Ala Gly Val Ala Leu Gly Arg Cys Ile Glu Gly Ala
            500                 505                 510

TAC GAG AGT GCC TCA CAA GTA TCT GAC TTC TTG ACC AAG TAT GCC TAC    1583
Tyr Glu Ser Ala Ser Gln Val Ser Asp Phe Leu Thr Lys Tyr Ala Tyr
            515                 520                 525

AAG TGA TGGAAGTAGT GCATCTCTTC ATTTTGTTGC ATATACGAGG TGAGGCTAGG    1639
Lys

ATCGGTAAAA CATCATGAGA TTCTGTAGTG TTTCTTTAAT TGAAAAAACA AATTTTAGTG    1699

ATGCAATATG TGCTCTTTCC TGTAGTTCGA GCATGTACAT CGGTATGGGA TAAAGTAGAA    1759

TAAGCTATTC TGCAAAAGCA GTGATTTTTT TTGAAAAAAA AAAAAAAAA AA            1811

(2) INFORMATION FOR SEQ ID NO: 10:

(i) SEQUENCE CHARACTERISTICS:
        (A) LENGTH: 528 amino acids
        (B) TYPE: amino acid
        (D) TOPOLOGY: linear (ii) MOLECULE TYPE: protein (xi) SEQUENCE DESCRIPTION: SEQ ID NO: 10:

Ala Thr Met Ala Thr Ala Thr Val Ala Ala Ala Ser Pro Leu Arg Gly
 1               5                  10                  15

Arg Val Thr Gly Arg Pro His Arg Val Arg Pro Arg Cys Ala Thr Ala
            20                  25                  30

Ser Ser Ala Thr Glu Thr Pro Ala Ala Pro Gly Val Arg Leu Ser Ala
        35                  40                  45
```

```
Glu Cys Val Ile Val Gly Ala Gly Ile Ser Gly Leu Cys Thr Ala Gln
 50                  55                  60

Ala Leu Ala Thr Arg Tyr Gly Val Ser Asp Leu Leu Val Thr Glu Ala
 65                  70                  75                  80

Arg Asp Arg Pro Gly Gly Asn Ile Thr Thr Val Glu Arg Pro Asp Glu
                 85                  90                  95

Gly Tyr Leu Trp Glu Glu Gly Pro Asn Ser Phe Gln Pro Ser Asp Pro
                100                 105                 110

Val Leu Thr Met Ala Val Asp Ser Gly Leu Lys Asp Asp Leu Val Phe
            115                 120                 125

Gly Asp Pro Asn Ala Pro Arg Phe Val Leu Trp Glu Gly Lys Leu Arg
        130                 135                 140

Pro Val Pro Ser Lys Pro Gly Asp Leu Pro Phe Phe Ser Leu Met Ser
145                 150                 155                 160

Ile Pro Gly Lys Leu Arg Ala Gly Leu Gly Ala Leu Gly Ile Arg Pro
                165                 170                 175

Pro Pro Pro Gly Arg Glu Glu Ser Val Glu Glu Phe Val Arg Arg Asn
            180                 185                 190

Leu Gly Ala Glu Val Phe Glu Arg Leu Ile Glu Pro Phe Cys Ser Gly
        195                 200                 205

Val Tyr Ala Gly Asp Pro Ser Lys Leu Ser Met Lys Ala Ala Phe Gly
210                 215                 220

Lys Val Trp Arg Leu Glu Glu Ile Gly Gly Ser Ile Ile Gly Gly Thr
225                 230                 235                 240

Ile Lys Ala Ile Gln Asp Lys Gly Lys Asn Pro Lys Pro Pro Arg Asp
                245                 250                 255

Pro Arg Leu Pro Ala Pro Lys Gly Gln Thr Val Ala Ser Phe Arg Lys
            260                 265                 270

Gly Leu Ala Met Leu Pro Asn Ala Ile Ala Ser Arg Leu Gly Ser Lys
        275                 280                 285

Val Lys Leu Ser Trp Lys Leu Thr Ser Ile Thr Lys Ala Asp Asn Gln
290                 295                 300

Gly Tyr Val Leu Gly Tyr Glu Thr Pro Glu Gly Leu Val Ser Val Gln
305                 310                 315                 320

Ala Lys Ser Val Ile Met Thr Ile Pro Ser Tyr Val Ala Ser Asp Ile
                325                 330                 335

Leu Arg Pro Leu Ser Ile Asp Ala Ala Asp Ala Leu Ser Lys Phe Tyr
            340                 345                 350

Tyr Pro Pro Val Ala Ala Val Thr Val Ser Tyr Pro Lys Glu Ala Ile
        355                 360                 365

Arg Lys Glu Cys Leu Ile Asp Gly Glu Leu Gln Gly Phe Gly Gln Leu
370                 375                 380

His Pro Arg Ser Gln Gly Val Glu Thr Leu Gly Thr Ile Tyr Ser Ser
385                 390                 395                 400

Ser Leu Phe Pro Asn Arg Ala Pro Ala Gly Arg Val Leu Leu Leu Asn
                405                 410                 415

Tyr Ile Gly Gly Ser Thr Asn Thr Gly Ile Val Ser Lys Thr Glu Ser
            420                 425                 430

Asp Leu Val Gly Ala Val Asp Arg Asp Leu Arg Lys Met Leu Ile Asn
        435                 440                 445

Pro Arg Ala Ala Asp Pro Leu Ala Leu Gly Val Arg Val Trp Pro Gln
450                 455                 460
```

```
Ala Ile Pro Gln Phe Leu Ile Gly His Leu Asp Arg Leu Ala Ala Ala
465                 470                 475                 480

Lys Ser Ala Leu Gly Gln Gly Tyr Asp Gly Leu Phe Leu Gly Gly
            485                 490                 495

Asn Tyr Val Ala Gly Val Ala Leu Gly Arg Cys Ile Glu Gly Ala Tyr
                500                 505                 510

Glu Ser Ala Ser Gln Val Ser Asp Phe Leu Thr Lys Tyr Ala Tyr Lys
            515                 520                 525

(2) INFORMATION FOR SEQ ID NO: 11:

(i) SEQUENCE CHARACTERISTICS:
        (A) LENGTH: 1847 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: soybean (vii) IMMEDIATE SOURCE:
        (B) CLONE: pWDC-12 (NRRL B-21516)

(ix) FEATURE:
        (A) NAME/KEY: CDS
        (B) LOCATION: 55..1683
        (D) OTHER INFORMATION: /product= "soybean protox-1"

(xi) SEQUENCE DESCRIPTION: SEQ ID NO: 11:

CTTTAGCACA GTGTTGAAGA TAACGAACGA ATAGTGCCAT TACTGTAACC AACC ATG        57
                                                            Met
                                                            1

GTT TCC GTC TTC AAC GAG ATC CTA TTC CCG CCG AAC CAA ACC CTT CTT       105
Val Ser Val Phe Asn Glu Ile Leu Phe Pro Pro Asn Gln Thr Leu Leu
            5                   10                  15

CGC CCC TCC CTC CAT TCC CCA ACC TCT TTC TTC ACC TCT CCC ACT CGA       153
Arg Pro Ser Leu His Ser Pro Thr Ser Phe Phe Thr Ser Pro Thr Arg
        20                  25                  30

AAA TTC CCT CGC TCT CGC CCT AAC CCT ATT CTA CGC TGC TCC ATT GCG       201
Lys Phe Pro Arg Ser Arg Pro Asn Pro Ile Leu Arg Cys Ser Ile Ala
    35                  40                  45

GAG GAA TCC ACC GCG TCT CCG CCC AAA ACC AGA GAC TCC GCC CCC GTG       249
Glu Glu Ser Thr Ala Ser Pro Pro Lys Thr Arg Asp Ser Ala Pro Val
50                  55                  60                  65

GAC TGC GTC GTC GTC GGC GGA GGC GTC AGC GGC CTC TGC ATC GCC CAG       297
Asp Cys Val Val Val Gly Gly Gly Val Ser Gly Leu Cys Ile Ala Gln
                70                  75                  80

GCC CTC GCC ACC AAA CAC GCC AAT GCC AAC GTC GTC GTC ACG GAG GCC       345
Ala Leu Ala Thr Lys His Ala Asn Ala Asn Val Val Val Thr Glu Ala
            85                  90                  95

CGA GAC CGC GTC GGC GGC AAC ATC ACC ACG ATG GAG AGG GAC GGA TAC       393
Arg Asp Arg Val Gly Gly Asn Ile Thr Thr Met Glu Arg Asp Gly Tyr
        100                 105                 110

CTC TGG GAA GAA GGC CCC AAC AGC TTC CAG CCT TCT GAT CCA ATG CTC       441
Leu Trp Glu Glu Gly Pro Asn Ser Phe Gln Pro Ser Asp Pro Met Leu
    115                 120                 125

ACC ATG GTG GTG GAC AGT GGT TTA AAG GAT GAG CTT GTT TTG GGG GAT       489
Thr Met Val Val Asp Ser Gly Leu Lys Asp Glu Leu Val Leu Gly Asp
130                 135                 140                 145
```

```
CCT GAT GCA CCT CGG TTT GTG TTG TGG AAC AGG AAG TTG AGG CCG GTG      537
Pro Asp Ala Pro Arg Phe Val Leu Trp Asn Arg Lys Leu Arg Pro Val
            150                 155                 160

CCC GGG AAG CTG ACT GAT TTG CCT TTC TTT GAC TTG ATG AGC ATT GGT      585
Pro Gly Lys Leu Thr Asp Leu Pro Phe Phe Asp Leu Met Ser Ile Gly
        165                 170                 175

GGC AAA ATC AGG GCT GGC TTT GGT GCG CTT GGA ATT CGG CCT CCT CCT      633
Gly Lys Ile Arg Ala Gly Phe Gly Ala Leu Gly Ile Arg Pro Pro Pro
        180                 185                 190

CCA GGT CAT GAG GAA TCG GTT GAA GAG TTT GTT CGT CGG AAC CTT GGT      681
Pro Gly His Glu Glu Ser Val Glu Glu Phe Val Arg Arg Asn Leu Gly
        195                 200                 205

GAT GAG GTT TTT GAA CGG TTG ATA GAG CCT TTT TGT TCA GGG GTC TAT      729
Asp Glu Val Phe Glu Arg Leu Ile Glu Pro Phe Cys Ser Gly Val Tyr
210                 215                 220                 225

GCA GGC GAT CCT TCA AAA TTA AGT ATG AAA GCA GCA TTC GGG AAA GTT      777
Ala Gly Asp Pro Ser Lys Leu Ser Met Lys Ala Ala Phe Gly Lys Val
            230                 235                 240

TGG AAG CTG GAA AAA AAT GGT GGT AGC ATT ATT GGT GGA ACT TTC AAA      825
Trp Lys Leu Glu Lys Asn Gly Gly Ser Ile Ile Gly Gly Thr Phe Lys
            245                 250                 255

GCA ATA CAA GAG AGA AAT GGA GCT TCA AAA CCA CCT CGA GAT CCG CGT      873
Ala Ile Gln Glu Arg Asn Gly Ala Ser Lys Pro Pro Arg Asp Pro Arg
            260                 265                 270

CTG CCA AAA CCA AAA GGT CAG ACT GTT GGA TCT TTC CGG AAG GGA CTT      921
Leu Pro Lys Pro Lys Gly Gln Thr Val Gly Ser Phe Arg Lys Gly Leu
        275                 280                 285

ACC ATG TTG CCT GAT GCA ATT TCT GCC AGA CTA GGC AAC AAA GTA AAG      969
Thr Met Leu Pro Asp Ala Ile Ser Ala Arg Leu Gly Asn Lys Val Lys
290                 295                 300                 305

TTA TCT TGG AAG CTT TCA AGT ATT AGT AAA CTG GAT AGT GGA GAG TAC     1017
Leu Ser Trp Lys Leu Ser Ser Ile Ser Lys Leu Asp Ser Gly Glu Tyr
            310                 315                 320

AGT TTG ACA TAT GAA ACA CCA GAA GGA GTG GTT TCT TTG CAG TGC AAA     1065
Ser Leu Thr Tyr Glu Thr Pro Glu Gly Val Val Ser Leu Gln Cys Lys
            325                 330                 335

ACT GTT GTC CTG ACC ATT CCT TCC TAT GTT GCT AGT ACA TTG CTG CGT     1113
Thr Val Val Leu Thr Ile Pro Ser Tyr Val Ala Ser Thr Leu Leu Arg
            340                 345                 350

CCT CTG TCT GCT GCT GCT GCA GAT GCA CTT TCA AAG TTT TAT TAC CCT     1161
Pro Leu Ser Ala Ala Ala Ala Asp Ala Leu Ser Lys Phe Tyr Tyr Pro
        355                 360                 365

CCA GTT GCT GCA GTT TCC ATA TCC TAT CCA AAA GAA GCT ATT AGA TCA     1209
Pro Val Ala Ala Val Ser Ile Ser Tyr Pro Lys Glu Ala Ile Arg Ser
370                 375                 380                 385

GAA TGC TTG ATA GAT GGT GAG TTG AAG GGG TTT GGT CAA TTG CAT CCA     1257
Glu Cys Leu Ile Asp Gly Glu Leu Lys Gly Phe Gly Gln Leu His Pro
            390                 395                 400

CGT AGC CAA GGA GTG GAA ACA TTA GGA ACT ATA TAC AGC TCA TCA CTA     1305
Arg Ser Gln Gly Val Glu Thr Leu Gly Thr Ile Tyr Ser Ser Ser Leu
            405                 410                 415

TTC CCC AAC CGA GCA CCA CCT GGA AGG GTT CTA CTC TTG AAT TAC ATT     1353
Phe Pro Asn Arg Ala Pro Pro Gly Arg Val Leu Leu Leu Asn Tyr Ile
            420                 425                 430

GGA GGA GCA ACT AAT ACT GGA ATT TTA TCG AAG ACG GAC AGT GAA CTT     1401
Gly Gly Ala Thr Asn Thr Gly Ile Leu Ser Lys Thr Asp Ser Glu Leu
            435                 440                 445

GTG GAA ACA GTT GAT CGA GAT TTG AGG AAA ATC CTT ATA AAC CCA AAT     1449
Val Glu Thr Val Asp Arg Asp Leu Arg Lys Ile Leu Ile Asn Pro Asn
450                 455                 460                 465
```

```
GCC CAG GAT CCA TTT GTA GTG GGG GTG AGA CTG TGG CCT CAA GCT ATT      1497
Ala Gln Asp Pro Phe Val Val Gly Val Arg Leu Trp Pro Gln Ala Ile
                470                 475                 480

CCA CAG TTC TTA GTT GGC CAT CTT GAT CTT CTA GAT GTT GCT AAA GCT      1545
Pro Gln Phe Leu Val Gly His Leu Asp Leu Leu Asp Val Ala Lys Ala
            485                 490                 495

TCT ATC AGA AAT ACT GGG TTT GAA GGG CTC TTC CTT GGG GGT AAT TAT      1593
Ser Ile Arg Asn Thr Gly Phe Glu Gly Leu Phe Leu Gly Gly Asn Tyr
        500                 505                 510

GTG TCT GGT GTT GCC TTG GGA CGA TGC GTT GAG GGA GCC TAT GAG GTA      1641
Val Ser Gly Val Ala Leu Gly Arg Cys Val Glu Gly Ala Tyr Glu Val
    515                 520                 525

GCA GCT GAA GTA AAC GAT TTT CTC ACA AAT AGA GTG TAC AAA              1683
Ala Ala Glu Val Asn Asp Phe Leu Thr Asn Arg Val Tyr Lys
530                 535                 540

TAGTAGCAGT TTTTGTTTTT GTGGTGGAAT GGGTGATGGG ACTCTCGTGT TCCATTGAAT    1743

TATAATAATG TGAAAGTTTC TCAAATTCGT TCGATAGGTT TTTGGCGGCT TCTATTGCTG    1803

ATAATGTAAA ATCCTCTTTA AGTTTGAAAA AAAAAAAAAA AAAA                    1847

(2) INFORMATION FOR SEQ ID NO: 12:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO: 12:

Met Val Ser Val Phe Asn Glu Ile Leu Phe Pro Pro Asn Gln Thr Leu
1               5                   10                  15

Leu Arg Pro Ser Leu His Ser Pro Thr Ser Phe Phe Thr Ser Pro Thr
                20                  25                  30

Arg Lys Phe Pro Arg Ser Arg Pro Asn Pro Ile Leu Arg Cys Ser Ile
            35                  40                  45

Ala Glu Glu Ser Thr Ala Ser Pro Pro Lys Thr Arg Asp Ser Ala Pro
    50                  55                  60

Val Asp Cys Val Val Gly Gly Val Ser Gly Leu Cys Ile Ala
65                  70                  75                  80

Gln Ala Leu Ala Thr Lys His Ala Asn Ala Asn Val Val Thr Glu
                85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
    115                 120                 125

Leu Thr Met Val Val Asp Ser Gly Leu Lys Asp Glu Leu Val Leu Gly
130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
    195                 200                 205

Gly Asp Glu Val Phe Glu Arg Leu Ile Glu Pro Phe Cys Ser Gly Val
    210                 215                 220
```

```
Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
            245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
            275                 280                 285

Leu Thr Met Leu Pro Asp Ala Ile Ser Ala Arg Leu Gly Asn Lys Val
290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335

Lys Thr Val Val Leu Thr Ile Pro Ser Tyr Val Ala Ser Thr Leu Leu
            340                 345                 350

Arg Pro Leu Ser Ala Ala Ala Asp Ala Leu Ser Lys Phe Tyr Tyr
            355                 360                 365

Pro Pro Val Ala Ala Val Ser Ile Ser Tyr Pro Lys Glu Ala Ile Arg
370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Leu Asn Tyr
            420                 425                 430

Ile Gly Gly Ala Thr Asn Thr Gly Ile Leu Ser Lys Thr Asp Ser Glu
            435                 440                 445

Leu Val Glu Thr Val Asp Arg Asp Leu Arg Lys Ile Leu Ile Asn Pro
450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
            485                 490                 495

Ala Ser Ile Arg Asn Thr Gly Phe Glu Gly Leu Phe Leu Gly Gly Asn
            500                 505                 510

Tyr Val Ser Gly Val Ala Leu Gly Arg Cys Val Glu Gly Ala Tyr Glu
            515                 520                 525

Val Ala Ala Glu Val Asn Asp Phe Leu Thr Asn Arg Val Tyr Lys
530                 535                 540

(2) INFORMATION FOR SEQ ID NO: 13:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..583
        (D) OTHER INFORMATION: /function= "arabidopsis protox-1
            promoter"
```

(xi) SEQUENCE DESCRIPTION: SEQ ID NO: 13:

```
GAATTCCGAT CGAATTATAT AATTATCATA AATTTGAATA AGCATGTTGC CTTTTATTAA        60

AGAGGTTTAA TAAAGTTTGG TAATAATGGA CTTTGACTTC AAACTCGATT CTCATGTAAT       120

TAATTAATAT TTACATCAAA ATTTGGTCAC TAATATTACC AAATTAATAT ACTAAAATGT       180

TAATTCGCAA ATAAAACACT AATTCCAAAT AAAGGGTCAT TATGATAAAC ACGTATTGAA       240

CTTGATAAAG CAAAGCAAAA ATAATGGGTT TCAAGGTTTG GGTTATATAT GACAAAAAAA       300

AAAAAAGGTT TGGTTATATA TCTATTGGGC CTATAACCAT GTTATACAAA TTTGGGCCTA       360

ACTAAAATAA TAAAATAAAC GTAATGGTCC TTTTTATATT TGGGTCAAAC CCAACTCTAA       420

ACCCAAACCA AAGAAAAAGT ATACGGTACG GTACACAGAC TTATGGTGTG TGTGATTGCA       480

GGTGAATATT TCTCGTCGTC TTCTCCTTTC TTCTGAAGAA GATTACCCAA TCTGAAAAAA       540

ACCAAGAAGC TGACAAAATT CCGAATTCTC TGCGATTTCC ATG                         583
```

(2) INFORMATION FOR SEQ ID NO: 14:

(i) SEQUENCE CHARACTERISTICS:
        (A) LENGTH: 3848 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..3848
        (D) OTHER INFORMATION: /function= "maize protox-1 promoter"

(xi) SEQUENCE DESCRIPTION: SEQ ID NO: 14:

```
TCGATCTTTC TAGGCTGATC CCCAAATCTT CCTCCGAAGC CCCTGGCGCC TCTGCCCCTT        60

GGAGCTGGTG GCCTGAAAGA GCTTTGCTGT TGCCCCGAAG ATTGTGAGGT ATATTGTGAC       120

CTCTGAGACT GACTTCCTTT GTCGTCACTT TGAGTGGAGT TATGGATTGA CCTGACGTGC       180

CTCAGATGGA TTCTTCCTCC GAAGCCCCTG GTCATTTCGG AGAATCTGTA ATCTTATTCC       240

CTTCTTTGGC GAAAATCTGT CAGCTTGGAT GTACTCATCC ATCTTCTGAA GCAGCTTCTC       300

CAGAGTTTGT GGAGGCTTCC TGGCGAAATA TTGGGCTGTA GGTCCTGGAC GAAGACCCTT       360

GATCATGGCC TCAATGACAA TCTCATTGGG CACCGTAGGC GCTTGTGCCC TCAATCGCAA       420

GAACCTTCGT ACATATGCCT GAAGGTATTC TTCGTGATCT TGTGTGCATT GGAACAGAGC       480

CTGAGCTGTG ACCGACTTCG TTTGAAAGCC TTGGAAGCTA GTAACCAACA TGTGCTTAAG       540

CTTCTGCCAC GACGTGATAG TCCCTGGCCG AAGAGAAGAA TACCATGTTT GGGCTACATT       600

CCGGACTGCC ATGACGAAGG ACTTCGCCAT GACTACAGTG TTGACCCCAT ACGAAGATAT       660

AGTTGCTTCG TAGCTCATCA GAAACTGCTT TGGATCTGAG TGCCCATCAT ACATGGGGAG       720

CTGAGGTGGC TTGTATGATG GGGGCCATGG GGTAGCCTGC AGTTCTGCTG CCAAGGGAGA       780

AGCATCATCA AAAGTAAAGG CATCATGATT AAAATCATCA TACCATCCAT CCTCGTTGAA       840

TAAGCCTTCT TGACGAAGCT CCCTGTGTTG GGGCCTTCGA TCTTGTTCAT CTTGAACAAG       900

ATGACGCACT TCTTCAGTGG CTTCGTCGAT CTTTCTTTGG AGATCAGCCA GTCGCACCAT       960

CTTCTCCTTC TTTCTTTGTA CTTGTTGATG GATGATCTCC ATGTCCCTGA TCTCTTGGTC      1020

CAACTCCTCC TCTTGGAGTG TCAGACTGGT GGCTTTCCTC TTCTGGCTTC GAGCCTCTCG      1080

AAGAGAAAGA GTTTCTTGAT TTGGGTCCAG CGGCTGCAGT GCAGTGGTCC CTGGTGCTGA      1140
```

-continued

```
AGCTTTCTTC GGTGGCATGA CAAAGGTCAG TGCTTGCCGA AGGTGGTCGA AAAGGGTTCA    1200

CTAGAGGTGG GAGCCAATGT TGGGGACTTC TCAAGTGCTA TGAGTTAAGA ACAAGGCAAC    1260

ACAAAATGTT AAATATTAAT AGCTTTCATC TTTCGAAGCA TTATTTCCCT TTGGGTATAA    1320

TGATCTTCAG ACGAAAGAGT CCTTCATCAT TGCGATATAT GTTAATAGAA GGAGGAGCAT    1380

ATGAAATGTA AGAGACAACA TGAACAATCG TGTAGCATTG TTAATTCATC ATCATTTTAT    1440

TATTATGGAA AAATAGAAAC AATATTGAAT TACAAATGTA CCTTTGGCTT GACAGAAGAT    1500

AAAAGTACAA GCTTGACGCA CGAGCAAGTA CAAGTCAGTG TGAACAGTAC GGGGGTACTG    1560

TTCATCTATT TATAGGCACA GGACACAGCC TGTGAGAAAT TACAGTCATG CCCTTTACAT    1620

TTACTATTGA CTTATAGAAA AATCTATGAG GACTGGATAG CCTTTTCCCC TTTAAGTCGG    1680

TGCCTTTTTC CGCGATTAAG CCGAATCTCC CTTGCGCATA GCTTCGGAGC ATCGGCAACC    1740

TTCGTCACGA TCATGCCCTT CTCATTGTGT ATGCTTTTAA TCCTGAATTC GAAGGTACCT    1800

GTCCATAAAC CATACTTGGA AGACATTGTT AAATTATGTT TTTGAGGACC TTCGGAGGAC    1860

GAAGGCCCCC AACAGTCGTG TTTTTGAGGA CCTTCGGAAG ATGAAGGCCC CAACAAGAC    1920

CTATCCATAA AACCAACCTA TCCACAAAAC CGACCCCATT CACCCTTCAT TTGCCTCACC    1980

AACAACCCTA ATTAGGTTGT TGGTTTAAAT TTTTTAGGGT CAATTTGGTC ATCACCATCC    2040

ACTGTCACTC CACAAACTCA ATATCAATAA ACAGACTCAA TCACCCAAAC TGACCATACC    2100

CATAAAACCG CCCCACCCTT CTAGCGCCTC GCCAGAAACC AGAAACCCTG ATTCAGAGTT    2160

CAAACTTAAA ACGACCATAA CTTTCACCTT GGAACTCGAA TCAGGTCCAT TTTTTTCCAA    2220

ATCACACAAA ATTAAATTTC GCATCCGATA ATCAAGCCAT CTCTTCACTA TGGTTTTAAG    2280

TGTTGCTCAC ACTAGTGTAT TTATGGACTA ATCACCTGTG TATCTCATAC AATAACATAT    2340

CAGTACATCT AAGTTGTTAC TCAATTACCA AAACCGAATT ATAGCCTTCG AAAAAGGTTA    2400

TCGACTAGTC ACTCAATTAC CAAAACTAAA CTTTAGACTT TCATGTATGA CATCCAACAT    2460

GACACTGTAC TGGACTAAAC CACCTTTCAA GCTACACAAG GAGCAAAAAT AACTAATTTT    2520

CGTAGTTGTA GGAGCTAAAG TATATGTCCA ACAATAGT TAAGGGAAGC CCCCAAGGAC     2580

TTAAAAGTCC TTTTACCTCT TGAAACTTTT GTCGTGGTCT ACTTTTTCAC TTTAAACTTC    2640

AAAATTTGAC ATTTTATCAC CCCTTAACTC TTAAAACCAT TTAAATTACA TTCTTACTAG    2700

ATTATAGATG ATTTTGTTGT GAAAAGTTTT TAAGACATGT TTACACATTG ATTAAAATCA    2760

TTTGTTCAAT TTCCTAGAGT TAAATCTAAT CTTATTAAAA CTATTAGAGA TACTTTCACG    2820

AGCTCTAAAT ATTTTTATTT TTTCATTATG GAATTTGTT AGAATTCTTA TAGACCTTTT     2880

TTTGTGGTTT AAAAGCCTTG CCATGTTTTT AACAAGTTTT TTTTCTATTT TTTGAAATTT    2940

TCTTGGAAAC CACTTCTAAC CCGGTAGAAG ATTTATTTTG CTACACTTAT ATCTACAACA    3000

AAATCAACTT ATGAAATTGT CTTGGAAACT ACCTCTAACC CGGTAGAATG AATTTGAATG    3060

AAAATTAAAC CAACTTACGG AATCGCCCAA CATATGTCGA TTAAAGTGGA TATGGATACA    3120

TATGAAGAAG CCCTAGAGAT AATCTAAATG GTTTCGAAAT TGAGGGTTAT TTTTTGAAGT    3180

TTGATGGGAA GATAAGACCA TAACGGTAGT TCACAGAGAT AAAAGGGTTA TTTTTTTCAG    3240

AAATATTTGT GCTGCAATTG ATCCTGTGCC TCAAATTCAG CCTGCAACCA AGGCCAGGTT    3300

CTAGAGCGAA CAAGGCCCAC GTCACCCGTG GCCCGTCAGG CGAAGCAGGT CTTGTGCAGA    3360

CTTTGAGAGG GATTGGATAT CAACGGAACC AATCACGCAC GGCAATGCGA TTCCCAGCCC    3420

ACCTGTAACG TTCCAGTGGG CCATCCTTAA CTCCAAGCCC AACGGCCCTA CCCCATCTCG    3480

TCGTGTCATC CACTCCGCCG CACAGGCGCT CAGCTCCGCA ACGCCGCCGG AAATGGTCGC    3540
```

| | |
|---|---|
| CGCCACAGCC ACCGCCATGG CCACCGCTGC ATCGCCGCTA CTCAACGGGA CCCGAATACC | 3600 |
| TGCGCGGCTC CGCCATCGAG GACTCAGCGT GCGCTGCGCT GCTGTGGCGG GCGGCGCGGC | 3660 |
| CGAGGCACCG GCATCCACCG GCGCGCGGCT GTCCGCGGAC TGCGTTGTGG TGGGCGGAGG | 3720 |
| CATCAGTGGC CTCTGCACCG CGCAGGCGCT GGCCACGCGG CACGGCGTCG GGACGTGCT | 3780 |
| TGTCACGGAG GCCCGCGCCC GCCCCGGCGG CAACATTACC ACCGTCGAGC GCCCCGAGGA | 3840 |
| AGGGTACC | 3848 |

(2) INFORMATION FOR SEQ ID NO: 15:

(i) SEQUENCE CHARACTERISTICS:
        (A) LENGTH: 1826 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Gossypium hirsutum (cotton)

(vii) IMMEDIATE SOURCE:
        (B) CLONE: pWDC-15 (NRRL B-21594)

(ix) FEATURE:
        (A) NAME/KEY: misc_feature
        (B) LOCATION: 31..1647
        (D) OTHER INFORMATION: /product= "Cotton protox-1 coding
            sequence"

(xi) SEQUENCE DESCRIPTION: SEQ ID NO: 15:

| | |
|---|---|
| CCTCTCGCTC GCCTGGCCCC ACCACCAATC ATGACGGCTC TAATCGACCT TTCTCTTCTC | 60 |
| CGTTCCTCGC CCTCCGTTTC CCCTTTCTCC ATACCCCACC ACCAGCATCC GCCCCGCTTT | 120 |
| CGTAAACCTT TCAAGCTCCG ATGCTCCCTC GCCGAGGGTC CCACGATTTC CTCATCTAAA | 180 |
| ATCGACGGGG GAGAATCATC CATCGCGGAT TGCGTCATCG TTGGAGGTGG TATCAGTGGA | 240 |
| CTTTGCATTG CTCAAGCTCT CGCCACCAAG CACCGTGACG TCGCTTCCAA TGTGATTGTG | 300 |
| ACGGAGGCCA GAGACCGTGT TGGTGGCAAC ATCACTACCG TTGAGAGAGA TGGATATCTG | 360 |
| TGGGAAGAAG GCCCCAACAG TTTTCAGCCC TCCGATCCTA TTCTAACCAT GGCCGTGGAT | 420 |
| AGTGGATTGA AGGACGATTT GGTTTTAGGT GACCCTAATG CACCGCGATT TGTACTATGG | 480 |
| GAGGGAAAAC TAAGGCCTGT GCCCTCCAAG CCAACCGACT TGCCGTTTTT TGATTTGATG | 540 |
| AGCATTGCTG GAAAACTTAG GGCTGGGTTC GGGGCTATTG GCATTCGGCC TCCCCCTCCG | 600 |
| GGTTATGAAG AATCGGTGGA GGAGTTTGTG CGCCGTAATC TTGGTGCTGA GGTTTTTGAA | 660 |
| CGCTTTATTG AACCATTTTG TTCAGGTGTT TATGCAGGGG ATCCTTCAAA ATTAAGCATG | 720 |
| AAAGCAGCAT TGGAAGAGT ATGGAAGCTA GAAGAGATTG GTGGCAGCAT CATTGGTGGC | 780 |
| ACTTTCAAGA CAATCCAGGA GAGAAATAAG ACACCTAAGC CACCCAGAGA CCCGCGTCTG | 840 |
| CCAAAACCGA AGGGCCAAAC AGTTGGATCT TTTAGGAAGG GACTTACCAT GCTGCCTGAG | 900 |
| GCAATTGCTA ACAGTTTGGG TAGCAATGTA AAATTATCTT GGAAGCTTTC CAGTATTACC | 960 |
| AAATTGGGCA ATGGAGGGTA TAACTTGACA TTTGAAACAC CTGAAGGAAT GGTATCTCTT | 1020 |
| CAGAGTAGAA GTGTTGTAAT GACCATTCCA TCCCATGTTG CCAGTAACTT GTTGCATCCT | 1080 |
| CTCTCGGCTG CTGCTGCAGA TGCATTATCC CAATTTTATT ATCCTCCAGT TGCATCAGTC | 1140 |

-continued

```
ACAGTCTCCT ATCCAAAAGA AGCCATTCGA AAAGAATGTT TGATTGATGG TGAACTTAAG    1200

GGGTTTGGCC AGTTGCACCC ACGCAGCCAA GGAATTGAAA CTTTAGGGAC GATATACAGT    1260

TCATCACTTT TCCCCAATCG AGCTCCATCT GGCAGGGTGT TGCTCTTGAA CTACATAGGA    1320

GGAGCTACCA ACACTGGAAT TTTGTCCAAG ACTGAAGGGG AACTTGTAGA AGCAGTTGAT    1380

CGTGATTTGA GAAAAATGCT TATAAATCCT AATGCAAAGG ATCCTCTTGT TTTGGGTGTA    1440

AGAGTATGGC CAAAAGCCAT TCCACAGTTC TTGGTTGGTC ATTTGGATCT CCTTGATAGT    1500

GCAAAAATGG CTCTCAGGGA TTCTGGGTTT CATGGACTGT TTCTTGGGGG CAACTATGTA    1560

TCTGGTGTGG CATTAGGACG GTGTGTGGAA GGTGCTTACG AGGTTGCAGC TGAAGTGAAG    1620

GAATTCCTGT CACAATATGC ATACAAATAA TATTGAAATT CTTGTCAGGC TGCAAATGTA    1680

GAAGTCAGTT ATTGGATAGT ATCTCTTTAG CTAAAAAATT GGGTAGGGTT TTTTTTGTTA    1740

GTTCCTTGAC CACTTTTTGG GGTTTTCATT AGAACTTCAT ATTTGTATAT CATGTTGCAA    1800

TATCAAAAAA AAAAAAAAAA AAAAAA                                        1826
```

(2) INFORMATION FOR SEQ ID NO: 16:

(i) SEQUENCE CHARACTERISTICS:
        (A) LENGTH: 539 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 16:

```
Met Thr Ala Leu Ile Asp Leu Ser Leu Leu Arg Ser Pro Ser Val
 1               5                  10                  15

Ser Pro Phe Ser Ile Pro His His Gln His Pro Pro Arg Phe Arg Lys
            20                  25                  30

Pro Phe Lys Leu Arg Cys Ser Leu Ala Glu Gly Pro Thr Ile Ser Ser
            35                  40                  45

Ser Lys Ile Asp Gly Gly Glu Ser Ser Ile Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
            115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Gly Tyr
            180                 185                 190

Glu Glu Ser Val Glu Glu Phe Val Arg Arg Asn Leu Gly Ala Glu Val
            195                 200                 205

Phe Glu Arg Phe Ile Glu Pro Phe Cys Ser Gly Val Tyr Ala Gly Asp
    210                 215                 220
```

```
Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
            245                 250                 255

Glu Arg Asn Lys Thr Pro Lys Pro Arg Asp Pro Arg Leu Pro Lys
            260             265                 270

Pro Lys Gly Gln Thr Val Gly Ser Phe Arg Lys Gly Leu Thr Met Leu
            275                 280                 285

Pro Glu Ala Ile Ala Asn Ser Leu Gly Ser Asn Val Lys Leu Ser Trp
            290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
                340                 345                 350

Ala Ala Ala Ala Asp Ala Leu Ser Gln Phe Tyr Tyr Pro Pro Val Ala
            355                 360                 365

Ser Val Thr Val Ser Tyr Pro Lys Glu Ala Ile Arg Lys Glu Cys Leu
            370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Leu Phe Pro Asn
                405                 410                 415

Arg Ala Pro Ser Gly Arg Val Leu Leu Leu Asn Tyr Ile Gly Gly Ala
            420                 425                 430

Thr Asn Thr Gly Ile Leu Ser Lys Thr Glu Gly Glu Leu Val Glu Ala
            435                 440                 445

Val Asp Arg Asp Leu Arg Lys Met Leu Ile Asn Pro Asn Ala Lys Asp
            450                 455                 460

Pro Leu Val Leu Gly Val Arg Val Trp Pro Lys Ala Ile Pro Gln Phe
465                 470                 475                 480

Leu Val Gly His Leu Asp Leu Leu Asp Ser Ala Lys Met Ala Leu Arg
                485                 490                 495

Asp Ser Gly Phe His Gly Leu Phe Leu Gly Gly Asn Tyr Val Ser Gly
                500                 505                 510

Val Ala Leu Gly Arg Cys Val Glu Gly Ala Tyr Glu Val Ala Ala Glu
            515                 520                 525

Val Lys Glu Phe Leu Ser Gln Tyr Ala Tyr Lys
530                 535
```

(2) INFORMATION FOR SEQ ID NO: 17:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Beta vulgaris (Sugar Beet)

(vii) IMMEDIATE SOURCE:
          (B) CLONE: pWDC-16 (NRRL B-21595N)

(ix) FEATURE:
         (A) NAME/KEY: misc_feature
         (B) LOCATION: 1..1680
         (D) OTHER INFORMATION: /product= "Sugar Beet protox-1 coding
             sequence"

(xi) SEQUENCE DESCRIPTION: SEQ ID NO: 17:

```
ATGAAATCAA TGGCGTTATC AAACTGCATT CCACAGACAC AGTGCATGCC ATTGCGCAGC     60

AGCGGGCATT ACAGGGGTAA TTGTATCATG TTGTCAATTC CATGTAGTTT AATTGGAAGa    120

CGAGGTTATT ATTCACATAA GAAGAGGAGG ATGAGCATGA GTTGCAGCAC AAGCTCAGGC    180

TCAAAGTCAG CGGTTAAAGA AGCAGGATCA GGATCAGGTG CAGGAGGATT GCTAGACTGC    240

GTAATCGTTG GAGGTGGAAT TAGCGGGCTT TGCATCGCGC AGGCTCTTTG TACAAAACAC    300

TCCTCTTCCT CTTTATCCCC AAATTTTATA GTTACAGAGG CCAAAGACAG AGTTGGCGGC    360

AACATCGTCA CTGTGGAGGC CGATGGCTAT ATCTGGGAGG AGGGACCCAA TAGCTTCCAG    420

CCTTCCGACG CGGTGCTCAC CATGGCGGTC GACAGTGGCT TGAAAGATGA GTTGGTGCTC    480

GGAGATCCCA ATGCTCCTCG CTTTGTGCTA TGGAATGACA AATTAAGGCC CGTACCTTCC    540

AGTCTCACCG ACCTCCCTTT CTTCGACCTC ATGACCATTC CGGGCAAGAT TAGGGCTGCT    600

CTTGGTGCTC TCGGATTTCG CCCTTCTCCT CCACCTCATG AGGAATCGTG TGAACACTTT    660

GTGCGTCGTA ATCTCGGAGA TGAGGTCTTT GAACGCTTGA TTGAACCCTT TGTTCAGGT    720

GTGTATGCCG GTGATCCTGC CAAGCTGAGT ATGAAAGCTG CTTTTGGGAA GGTCTGGAAG    780

TTGGAGCAAA AGGGTGGCAG CATAATTGGT GGCACTCTCA AAGCTATACA GGAAAGAGGG    840

AGTAATCCTA AGCCGCCCCG TGACCAGCGC CTCCCTAAAC CAAAGGGTCA GACTGTTGGA    900

TCCTTTAGAA AGGGACTCGT TATGTTGCCT ACCGCCATTT CTGCTCGACT TGGCAGTAGA    960

GTGAAACTAT CTTGGACCCT TTCTAGTATC GTAAAGTCAC TCAATGGAGA ATATAGTCTG   1020

ACTTATGATA CCCCAGATGG CTTGGTTTCT GTAAGAACCA AAAGTGTTGT GATGACTGTT   1080

CCATCATATG TTGCAAGTAG GCTTCTTCGT CCACTTTCAG ACTCTGCTGC AGATTCTCTT   1140

TCAAAATTTT ACTATCCACC AGTTGCAGCA GTGTCACTTT CCTATCCTAA AGAAGCGATC   1200

AGATCAGAAT GCTTGATTAA TGGTGAACTT CAAGGTTTCG GCAACTACA TCCCCGCAGT    1260

CAGGGTGTGG AAACCTTGGG AACAATTTAT AGTTCGTCTC TTTTCCCTGG TCGAGCACCA   1320

CCTGGTAGGA TCTTGATCTT GAGCTACATC GGAGGTGCTA AAAATCCTGG CATATTAAAC   1380

AAGTCGAAAG ATGAACTTGC CAAGACAGTT GACAAGGACC TGAGAAGAAT GCTTATAAAT   1440

CCTGATGCAA AACTTCCTCG TGTACTGGGT GTGAGAGTAT GGCCTCAAGC AATACCCCAG   1500

TTTTCTATTG GCACTTTGA TCTGCTCGAT GCTGCAAAAG CTGCTCTGAC AGATACAGGG   1560

GTCAAAGGAC TGTTTCTTGG TGGCAACTAT GTTTCAGGTG TTGCCTTGGG GCGGTGTATA   1620

GAGGGTGCTT ATGAGTCTGC AGCTGAGGTA GTAGATTTCC TCTCACAGTA CTCAGACAAA   1680

TAGAGCTTCA GCATCCTGTG TAATTCAACA CAGGCCTTTT TGTATCTGTT GTGCGCGCAT   1740

GTAGTCTGGT CGTGGTGCTA GGATTGATTA GTTGCTCTGC TGTGTGATCC ACAAGAATTT   1800

TGATGGAATT TTTCCAGATG TGGGCATTAT ATGTTGCTGT CTTATAAATC CTTAATTTGT   1860

ACGTTTAGTG AATTACACCG CATTTGATGA CTAAAAAAAA AAAAAAAAAA              1910
```

(2) INFORMATION FOR SEQ ID NO: 18:

(i) SEQUENCE CHARACTERISTICS:
        (A) LENGTH: 560 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 18:

```
Met Lys Ser Met Ala Leu Ser Asn Cys Ile Pro Gln Thr Gln Cys Met
  1               5                  10                  15

Pro Leu Arg Ser Ser Gly His Tyr Arg Gly Asn Cys Ile Met Leu Ser
             20                  25                  30

Ile Pro Cys Ser Leu Ile Gly Arg Gly Tyr Tyr Ser His Lys Lys
         35                  40                  45

Arg Arg Met Ser Met Ser Cys Ser Thr Ser Ser Gly Ser Lys Ser Ala
 50                  55                  60

Val Lys Glu Ala Gly Ser Gly Ser Gly Ala Gly Gly Leu Leu Asp Cys
 65                  70                  75                  80

Val Ile Val Gly Gly Gly Ile Ser Gly Leu Cys Ile Ala Gln Ala Leu
                 85                  90                  95

Cys Thr Lys His Ser Ser Ser Leu Ser Pro Asn Phe Ile Val Thr
                100                 105                 110

Glu Ala Lys Asp Arg Val Gly Gly Asn Ile Val Thr Val Glu Ala Asp
            115                 120                 125

Gly Tyr Ile Trp Glu Glu Gly Pro Asn Ser Phe Gln Pro Ser Asp Ala
        130                 135                 140

Val Leu Thr Met Ala Val Asp Ser Gly Leu Lys Asp Glu Leu Val Leu
145                 150                 155                 160

Gly Asp Pro Asn Ala Pro Arg Phe Val Leu Trp Asn Asp Lys Leu Arg
                165                 170                 175

Pro Val Pro Ser Ser Leu Thr Asp Leu Pro Phe Phe Asp Leu Met Thr
            180                 185                 190

Ile Pro Gly Lys Ile Arg Ala Ala Leu Gly Ala Leu Gly Phe Arg Pro
        195                 200                 205

Ser Pro Pro Pro His Glu Glu Ser Val Glu His Phe Val Arg Arg Asn
210                 215                 220

Leu Gly Asp Glu Val Phe Glu Arg Leu Ile Glu Pro Phe Cys Ser Gly
225                 230                 235                 240

Val Tyr Ala Gly Asp Pro Ala Lys Leu Ser Met Lys Ala Ala Phe Glr
                245                 250                 255

Lys Val Trp Lys Leu Glu Gln Lys Gly Gly Ser Ile Ile Gly Gly Thr
            260                 265                 270

Leu Lys Ala Ile Gln Glu Arg Gly Ser Asn Pro Lys Pro Pro Arg Asp
        275                 280                 285

Gln Arg Leu Pro Lys Pro Lys Gly Gln Thr Val Gly Ser Phe Arg Lys
    290                 295                 300

Gly Leu Val Met Leu Pro Thr Ala Ile Ser Ala Arg Leu Gly Ser Arg
305                 310                 315                 320

Val Lys Leu Ser Trp Thr Leu Ser Ser Ile Val Lys Ser Leu Asn Gly
                325                 330                 335

Glu Tyr Ser Leu Thr Tyr Asp Thr Pro Asp Gly Leu Val Ser Val Arg
            340                 345                 350
```

—continued

```
Thr Lys Ser Val Val Met Thr Val Pro Ser Tyr Val Ala Ser Arg Leu
    355                 360                 365

Leu Arg Pro Leu Ser Asp Ser Ala Ala Asp Ser Leu Ser Lys Phe Tyr
    370                 375                 380

Tyr Pro Pro Val Ala Ala Val Ser Leu Ser Tyr Pro Lys Glu Ala Ile
385                 390                 395                 400

Arg Ser Glu Cys Leu Ile Asn Gly Glu Leu Gln Gly Phe Gly Gln Leu
                405                 410                 415

His Pro Arg Ser Gln Gly Val Glu Thr Leu Gly Thr Ile Tyr Ser Ser
                420                 425                 430

Ser Leu Phe Pro Gly Arg Ala Pro Pro Gly Arg Ile Leu Ile Leu Ser
            435                 440                 445

Tyr Ile Gly Gly Ala Lys Asn Pro Gly Ile Leu Asn Lys Ser Lys Asp
    450                 455                 460

Glu Leu Ala Lys Thr Val Asp Lys Asp Leu Arg Arg Met Leu Ile Asn
465                 470                 475                 480

Pro Asp Ala Lys Leu Pro Arg Val Leu Gly Val Arg Val Trp Pro Gln
                485                 490                 495

Ala Ile Pro Gln Phe Ser Ile Gly His Phe Asp Leu Leu Asp Ala Ala
                500                 505                 510

Lys Ala Ala Leu Thr Asp Thr Gly Val Lys Gly Leu Phe Leu Gly Gly
            515                 520                 525

Asn Tyr Val Ser Gly Val Ala Leu Gly Arg Cys Ile Glu Gly Ala Tyr
    530                 535                 540

Glu Ser Ala Ala Glu Val Val Asp Phe Leu Ser Gln Tyr Ser Asp Lys
545                 550                 555                 560
```

(2) INFORMATION FOR SEQ ID NO: 19:

(i) SEQUENCE CHARACTERISTICS:
        (A) LENGTH: 1784 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Brassica napus (oilseed rape)

(vii) IMMEDIATE SOURCE:
        (B) CLONE: pWDC-17 (NRRL B-21615)

(ix) FEATURE:
        (A) NAME/KEY: misc_feature
        (B) LOCATION: 47..1654
        (D) OTHER INFORMATION: /product= "Oilseed rape protox-1 coding
           sequence"

(xi) SEQUENCE DESCRIPTION: SEQ ID NO: 19:

```
GGGCCCCCCC CAAAATTGAG GATTCTCCTT CTCGCGGGCG ATCGCCATGG ATTTATCTCT      60

TCTCCGTCCG CAGCCATTCC TATCGCCATT CTCAAATCCA TTTCCTCGGT CGCGTCCCTA     120

CAAGCCTCTC AACCTCCGTT GCTCCGTATC CGGTGGATCC GTCGTCGGCT CTTCTACAAT     180

CGAAGGCGGA GGAGGAGGTA AAACCGTCAC GGCGGACTGC GTGATCGTCG GCGGAGGAAT     240

CAGCGGCCTG TGCATTGCGC AAGCGCTCGT GACGAAGCAC CCAGACGCTG CAAAGAATGT     300

GATGGTGACG GAGGCGAAGG ACCGTGTGGG AGGGAATATC ATCACGCGAG AGGAGCAAGG     360
```

-continued

```
GTTTCTATGG GAAGAAGGTC CCAATAGCTT TCAGCCGTCT GATCCTATGC TCACTATGGT      420

GGTAGATAGT GGTTTGAAAG ATGATCTAGT CTTGGGAGAT CCTACTGCTC CGAGGTTTGT      480

GTTGTGGAAT GGGAAGCTGA GGCCGGTTCC GTCGAAGCTA ACTGACTTGC CTTTCTTTGA      540

CTTGATGAGT ATTGGAGGGA AGATTAGAGC TGGGTTTGGT GCCATTGGTA TTCGACCTTC      600

ACCTCCGGGT CGTGAGGAAT CAGTGGAAGA GTTTGTAAGG CGTAATCTTG GTGATGAGGT      660

TTTTGAGCGC TTGATTGAAC CCTTTTGCTC AGGTGTTTAT GCGGGAGATC CTGCGAAACT      720

GAGTATGAAA GCAGCTTTTG GGAAGGTTTG GAAGCTAGAG GAGAATGGTG GGAGCATCAT      780

TGGTGGTGCT TTTAAGGCAA TTCAAGCGAA AAATAAAGCT CCCAAGACAA CCCGAGATCC      840

GCGTCTGCCA AAGCCAAAGG GCCAAACTGT TGGTTCTTTC AGGAAAGGAC TCACAATGCT      900

GCCAGAGGCA ATCTCCGCAA GGTTGGGTGA CAAGGTGAAA GTTTCTTGGA AGCTCTCAAG      960

TATCACTAAG CTGGCCAGCG GAGAATATAG CTTAACTTAC GAAACTCCGG AGGGTATAGT     1020

CACTGTACAG AGCAAAAGTG TAGTGATGAC TGTGCCATCT CATGTTGCTA GTAGTCTCTT     1080

GCGCCCTCTC TCTGATTCTG CAGCTGAAGC GCTCTCAAAA CTCTACTATC CGCCAGTTGC     1140

AGCCGTATCC ATCTCATACG CGAAAGAAGC AATCCGAAGC GAATGCTTAA TAGATGGTGA     1200

ACTAAAAGGG TTCGGCCAGT TGCATCCACG CACGCAAAAA GTGGAAACTC TTGGAACAAT     1260

ATACAGTTCA TCGCTCTTTC CCAACCGAGC ACCGCCTGGA AGAGTATTGC TATTGAACTA     1320

CATCGGTGGA GCTACCAACA CTGGGATCTT ATCAAAGTCG GAAGGTGAGT TAGTGGAAGC     1380

AGTAGATAGA GACTTGAGGA AGATGCTGAT AAAGCCAAGC TCGACCGATC CACTTGTACT     1440

TGGAGTAAAA TTATGGCCTC AAGCCATTCC TCAGTTTCTG ATAGGTCACA TTGATTTGGT     1500

AGACGCAGCG AAAGCATCGC TCTCGTCATC TGGTCATGAG GGCTTATTCT TGGGTGGAAA     1560

TTACGTTGCC GGTGTAGCAT GGGTCGGTG TGTGGAAGGT GCTTATGAAA CTGCAACCCA     1620

AGTGAATGAT TTCATGTCAA GGTATGCTTA CAAGTAATGT AACGCAGCAA CGATTTGATA     1680

CTAAGTAGTA GATTTTGCAG TTTTGACTTT AAGAACACTC TGTTTGTGAA AAATTCAAGT     1740

CTGTGATTGA GTAAATTTAT GTATTATTAC TAAAAAAAAA AAAA                     1784
```

(2) INFORMATION FOR SEQ ID NO: 20:

(i) SEQUENCE CHARACTERISTICS:
        (A) LENGTH: 536 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 20:

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
            20                  25                  30

Ser Val Ser Gly Gly Ser Val Val Gly Ser Ser Thr Ile Glu Gly Gly
        35                  40                  45

Gly Gly Gly Lys Thr Val Thr Ala Asp Cys Val Ile Val Gly Gly Gly
    50                  55                  60

Ile Ser Gly Leu Cys Ile Ala Gln Ala Leu Val Thr Lys His Pro Asp
65                  70                  75                  80

Ala Ala Lys Asn Val Met Val Thr Glu Ala Lys Asp Arg Val Gly Gly
                85                  90                  95
```

-continued

```
Asn Ile Ile Thr Arg Glu Glu Gln Gly Phe Leu Trp Glu Glu Gly Pro
                100                 105                 110
Asn Ser Phe Gln Pro Ser Asp Pro Met Leu Thr Met Val Val Asp Ser
            115                 120                 125
Gly Leu Lys Asp Asp Leu Val Leu Gly Asp Pro Thr Ala Pro Arg Phe
        130                 135                 140
Val Leu Trp Asn Gly Lys Leu Arg Pro Val Pro Ser Lys Leu Thr Asp
145                 150                 155                 160
Leu Pro Phe Phe Asp Leu Met Ser Ile Gly Gly Lys Ile Arg Ala Gly
                165                 170                 175
Phe Gly Ala Ile Gly Ile Arg Pro Ser Pro Gly Arg Glu Glu Ser
            180                 185                 190
Val Glu Glu Phe Val Arg Arg Asn Leu Gly Asp Glu Val Phe Glu Arg
            195                 200                 205
Leu Ile Glu Pro Phe Cys Ser Gly Val Tyr Ala Gly Asp Pro Ala Lys
        210                 215                 220
Leu Ser Met Lys Ala Ala Phe Gly Lys Val Trp Lys Leu Glu Glu Asn
225                 230                 235                 240
Gly Gly Ser Ile Ile Gly Gly Ala Phe Lys Ala Ile Gln Ala Lys Asn
                245                 250                 255
Lys Ala Pro Lys Thr Thr Arg Asp Pro Arg Leu Pro Lys Pro Lys Gly
            260                 265                 270
Gln Thr Val Gly Ser Phe Arg Lys Gly Leu Thr Met Leu Pro Glu Ala
        275                 280                 285
Ile Ser Ala Arg Leu Gly Asp Lys Val Lys Val Ser Trp Lys Leu Ser
290                 295                 300
Ser Ile Thr Lys Leu Ala Ser Gly Glu Tyr Ser Leu Thr Tyr Glu Thr
305                 310                 315                 320
Pro Glu Gly Ile Val Thr Val Gln Ser Lys Ser Val Val Met Thr Val
                325                 330                 335
Pro Ser His Val Ala Ser Ser Leu Leu Arg Pro Leu Ser Asp Ser Ala
            340                 345                 350
Ala Glu Ala Leu Ser Lys Leu Tyr Tyr Pro Pro Val Ala Ala Val Ser
        355                 360                 365
Ile Ser Tyr Ala Lys Glu Ala Ile Arg Ser Glu Cys Leu Ile Asp Gly
        370                 375                 380
Glu Leu Lys Gly Phe Gly Gln Leu His Pro Arg Thr Gln Lys Val Glu
385                 390                 395                 400
Thr Leu Gly Thr Ile Tyr Ser Ser Ser Leu Phe Pro Asn Arg Ala Pro
                405                 410                 415
Pro Gly Arg Val Leu Leu Asn Tyr Ile Gly Gly Ala Thr Asn Thr
            420                 425                 430
Gly Ile Leu Ser Lys Ser Glu Gly Glu Leu Val Glu Ala Val Asp Arg
        435                 440                 445
Asp Leu Arg Lys Met Leu Ile Lys Pro Ser Ser Thr Asp Pro Leu Val
    450                 455                 460
Leu Gly Val Lys Leu Trp Pro Gln Ala Ile Pro Gln Phe Leu Ile Gly
465                 470                 475                 480
His Ile Asp Leu Val Asp Ala Ala Lys Ala Ser Leu Ser Ser Ser Gly
                485                 490                 495
His Glu Gly Leu Phe Leu Gly Gly Asn Tyr Val Ala Gly Val Ala Leu
            500                 505                 510
```

```
Gly Arg Cys Val Glu Gly Ala Tyr Glu Thr Ala Thr Gln Val Asn Asp
    515                 520                 525

Phe Met Ser Arg Tyr Ala Tyr Lys
    530                 535
```

(2) INFORMATION FOR SEQ ID NO: 21:

(i) SEQUENCE CHARACTERISTICS:
        (A) LENGTH: 1224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryza sative (rice)

(vii) IMMEDIATE SOURCE:
        (B) CLONE: pWDC-18 (NRRL B-21648)

(ix) FEATURE:
        (A) NAME/KEY: misc_feature
        (B) LOCATION: 1..936
        (D) OTHER INFORMATION: /product= "Rice protox-1 partial coding
            sequence"

(xi) SEQUENCE DESCRIPTION: SEQ ID NO: 21:

```
CGGGCTTTGA AGGCTGCATT TGGGAAGGTG TGGAGGCTGG AGGATACTGG AGGTAGCATT      60

ATTGGTGGAA CCATCAAGAC AATCCAGGAG AGGGGGAAAA ACCCCAAACC GCCGAGGGAT     120

CCCCGCCTTC AACGCCAAA GGGGCAGACA GTTGCATCTT TCAGGAAGGG TCTGACTATG     180

CTCCCGGATG CTATTACATC TAGGTTGGGT AGCAAAGTCA AACTTTCATG GAAGTTGACA     240

AGCATTACAA AGTCAGACAA CAAAGGATAT GCATTAGTGT ATGAAACACC AGAAGGGGTG     300

GTCTCGGTGC AAGCTAAAAC TGTTGTCATG ACCATCCCAT CATATGTTGC TAGTGATATC     360

TTGCGGCCAC TTTCAAGTGA TGCAGCAGAT GCTCTGTCAA TATTCTATTA TCCACCAGTT     420

GCTGCTGTAA CTGTTTCATA TCCAAAAGAA GCAATTAGAA AAGAATGCTT AATTGACGGA     480

GAGCTCCAGG GTTTCGGCCA GCTGCATCCG CGTAGTCAGG GAGTTGAGAC TTTAGGAACA     540

ATATATAGCT CATCACTCTT TCCAAATCGT GCTCCAGCTG AAGGGTGTT ACTTCTGAAC     600

TACATAGGAG GTTCTACAAA TACAGGGATT GTTTCCAAGA CTGAAAGTGA GCTGGTAGAA     660

GCAGTTGACC GTGACCTCAG GAAGATGCTG ATAAATCCTA GAGCAGTGGA CCCTTTGGTC     720

CTTGGCGTCC GGGTATGGCC ACAAGCCATA CCACAGTTCC TCATTGGCCA TCTTGATCAT     780

CTTGAGGCTG CAAAATCTGC CCTGGGCAAA GGTGGGTATG ATGGATTGTT CCTCGGAGGG     840

AACTATGTTG CAGGAGTTGC CCTGGGCCGA TGCGTTGAAG GTGCATATGA GAGTGCCTCA     900

CAAATATCTG ACTACTTGAC CAAGTACGCC TACAAGTGAT CAAAGTTGGC CTGCTCCTTT     960

TGGCACATAG ATGTGAGGCT TCTAGCAGCA AAAATTTCAT GGGCATCTTT TTATCCTGAT    1020

TCTAATTAGT TAGAATTTAG AATTGTAGAG GAATGTTCCA TTTGCAGTTC ATAATAGTTG    1080

TTCAGATTTC AGCCATTCAA TTTGTGCAGC CATTTACTAT ATGTAGTATG ATCTTGTAAG    1140

TACTACTAAG AACAAATCAA TTATATTTTC CTGCAAGTGA CATCTTAATC GTCAGCAAAT    1200

CCAGTTACTA GTAAAAAAAA AAAA                                          1224
```

(2) INFORMATION FOR SEQ ID NO: 22:

(i) SEQUENCE CHARACTERISTICS:
        (A) LENGTH: 312 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 22:

```
Arg Ala Leu Lys Ala Ala Phe Gly Lys Val Trp Arg Leu Glu Asp Thr
  1               5                  10                  15

Gly Gly Ser Ile Ile Gly Gly Thr Ile Lys Thr Ile Gln Glu Arg Gly
                 20                  25                  30

Lys Asn Pro Lys Pro Pro Arg Asp Pro Arg Leu Pro Thr Pro Lys Gly
                 35                  40                  45

Gln Thr Val Ala Ser Phe Arg Lys Gly Leu Thr Met Leu Pro Asp Ala
 50                  55                  60

Ile Thr Ser Arg Leu Gly Ser Lys Val Lys Leu Ser Trp Lys Leu Thr
 65                  70                  75                  80

Ser Ile Thr Lys Ser Asp Asn Lys Gly Tyr Ala Leu Val Tyr Glu Thr
                 85                  90                  95

Pro Glu Gly Val Val Ser Val Gln Ala Lys Thr Val Val Met Thr Ile
                100                 105                 110

Pro Ser Tyr Val Ala Ser Asp Ile Leu Arg Pro Leu Ser Ser Asp Ala
                115                 120                 125

Ala Asp Ala Leu Ser Ile Phe Tyr Tyr Pro Pro Val Ala Ala Val Thr
130                 135                 140

Val Ser Tyr Pro Lys Glu Ala Ile Arg Lys Glu Cys Leu Ile Asp Gly
145                 150                 155                 160

Glu Leu Gln Gly Phe Gly Gln Leu His Pro Arg Ser Gln Gly Val Glu
                165                 170                 175

Thr Leu Gly Thr Ile Tyr Ser Ser Ser Leu Phe Pro Asn Arg Ala Pro
                180                 185                 190

Ala Gly Arg Val Leu Leu Leu Asn Tyr Ile Gly Gly Ser Thr Asn Thr
                195                 200                 205

Gly Ile Val Ser Lys Thr Glu Ser Glu Leu Val Glu Ala Val Asp Arg
                210                 215                 220

Asp Leu Arg Lys Met Leu Ile Asn Pro Arg Ala Val Asp Pro Leu Val
225                 230                 235                 240

Leu Gly Val Arg Val Trp Pro Gln Ala Ile Pro Gln Phe Leu Ile Gly
                245                 250                 255

His Leu Asp His Leu Glu Ala Ala Lys Ser Ala Leu Gly Lys Gly Gly
                260                 265                 270

Tyr Asp Gly Leu Phe Leu Gly Gly Asn Tyr Val Ala Gly Val Ala Leu
                275                 280                 285

Gly Arg Cys Val Glu Gly Ala Tyr Glu Ser Ala Ser Gln Ile Ser Asp
                290                 295                 300

Tyr Leu Thr Lys Tyr Ala Tyr Lys
305                 310
```

(2) INFORMATION FOR SEQ ID NO: 23:

(i) SEQUENCE CHARACTERISTICS:
        (A) LENGTH: 1590 base pairs
        (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Sorghum bicolor (sorghum)

(vii) IMMEDIATE SOURCE:
        (B) CLONE: pWDC-19 (NRRL B-21649)

(ix) FEATURE:
        (A) NAME/KEY: misc_feature
        (B) LOCATION: 1..1320
        (D) OTHER INFORMATION: /product= "Sorghum protox-1 partial
            coding sequence"

(xi) SEQUENCE DESCRIPTION: SEQ ID NO: 23:

```
TCCACCGTCG AGCGCCCCGA GGAAGGGTAC CTCTGGGAGG AGGGTCCCAA CAGCTTCCAG      60

CCATCCGACC CCGTTCTCTC CATGGCCGTG GACAGCGGGC TGAAGGATGA CCTGGTTTTT     120

GGGGACCCCA ACGCGCCACG GTTCGTGCTG TGGGAGGGGA AGCTGAGGCC CGTGCCATCC     180

AAGCCCGCCG ACCTCCCGTT CTTCGATCTC ATGAGCATCC CTGGCAAGCT CAGGGCCGGT     240

CTCGGCGCGC TTGGCATCCG CCCGCCTGCT CCAGGCCGCG AGGAGTCAGT GGAGGAGTTT     300

GTGCGCCGCA ACCTCGGTGC TGAGGTCTTT GAGCGCCTAA TTGAGCCTTT CTGCTCAGGT     360

GTCTATGCTG GCGATCCTTC CAAGCTCAGT ATGAAGGCTG CATTTGGGAA GGTGTGGCGG     420

TTAGAAGAAG CTGGAGGTAG TATTATTGGT GGAACCATCA AGACGATTCA GGAGAGGGGC     480

AAGAATCCAA AACCACCGAG GGATCCCCGC CTTCCGAAGC CAAAAGGGCA GACAGTTGCA     540

TCTTTCAGGA AGGGTCTTGC CATGCTTCCA AATGCCATCA CATCCAGCTT GGGTAGTAAA     600

GTCAAACTAT CATGGAAACT CACGAGCATG ACAAAATCAG ATGGCAAGGG GTATGTTTTG     660

GAGTATGAAA CACCAGAAGG GGTTGTTTTG GTGCAGGCTA AAAGTGTTAT CATGACCATT     720

CCATCATATG TTGCTAGCGA CATTTTGCGT CCACTTTCAG GTGATGCTGC AGATGTTCTA     780

TCAAGATTCT ATTATCCACC AGTTGCTGCT GTAACGGTTT CGTATCCAAA GGAAGCAATT     840

AGAAAAGAAT GCTTAATTGA TGGGGAACTC CAGGGTTTTG GCCAGTTGCA TCCACGTAGT     900

CAAGGAGTTG AGACATTAGG AACAATATAC AGCTCATCAC TCTTTCCAAA TCGTGCTCCT     960

GCTGGTAGGG TGTTACTTCT AAACTACATA GGAGGTGCTA CAAACACAGG AATTGTTTCC    1020

AAGACTGAAA GTGAGCTGGT AGAAGCAGTT GACCGTGACC TCCGAAAAAT GCTTATAAAT    1080

CCTACAGCAG TGGACCCTTT AGTCCTTGGT GTCCGAGTTT GGCCACAAGC CATACCTCAG    1140

TTCCTGGTAG GACATCTTGA TCTTCTGGAG CCGCAAAAT  CTGCCCTGGA CCAAGGTGGC    1200

TATAATGGGC TGTTCCTAGG AGGGAACTAT GTTGCAGGAG TTGCCCTGGG CAGATGCATT    1260

GAGGGCGCAT ATGAGAGTGC CGCGCAAATA TATGACTTCT TGACCAAGTA CGCCTACAAG    1320

TGATGGAAGA AGTGGAGCGC TGCTTGTTAA TTGTTATGTT GCATAGATGA GGTGAGACCA    1380

GGAGTAGTAA AAGGCGTCAC GAGTATTTTT CATTCTTATT TTGTAAATTG CACTTCTGTT    1440

TTTTTTTCCT GTCAGTAATT AGTTAGATTT TAGTTATGTA GGAGATTGTT GTGTTCACTG    1500

CCCTACAAAA GAATTTTTAT TTTGCATTCG TTTATGAGAG CTGTGCAGAC TTATGTAACG    1560

TTTTACTGTA AGTATCAACA AAATCAAATA                                     1590
```

(2) INFORMATION FOR SEQ ID NO: 24:

(i) SEQUENCE CHARACTERISTICS:
        (A) LENGTH: 440 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 24:

```
Ser Thr Val Glu Arg Pro Glu Gly Tyr Leu Trp Glu Gly Pro
  1               5                  10                  15

Asn Ser Phe Gln Pro Ser Asp Pro Val Leu Ser Met Ala Val Asp Ser
                 20                  25                  30

Gly Leu Lys Asp Asp Leu Val Phe Gly Asp Pro Asn Ala Pro Arg Phe
             35                  40                  45

Val Leu Trp Glu Gly Lys Leu Arg Pro Val Pro Ser Lys Pro Ala Asp
 50                  55                  60

Leu Pro Phe Phe Asp Leu Met Ser Ile Pro Gly Lys Leu Arg Ala Gly
 65                  70                  75                  80

Leu Gly Ala Leu Gly Ile Arg Pro Pro Ala Pro Gly Arg Glu Glu Ser
                 85                  90                  95

Val Glu Glu Phe Val Arg Arg Asn Leu Gly Ala Glu Val Phe Glu Arg
                100                 105                 110

Leu Ile Glu Pro Phe Cys Ser Gly Val Tyr Ala Gly Asp Pro Ser Lys
             115                 120                 125

Leu Ser Met Lys Ala Ala Phe Gly Lys Val Trp Arg Leu Glu Glu Ala
             130                 135                 140

Gly Gly Ser Ile Ile Gly Gly Thr Ile Lys Thr Ile Gln Glu Arg Gly
145                 150                 155                 160

Lys Asn Pro Lys Pro Pro Arg Asp Pro Arg Leu Pro Lys Pro Lys Gly
                 165                 170                 175

Gln Thr Val Ala Ser Phe Arg Lys Gly Leu Ala Met Leu Pro Asn Ala
                 180                 185                 190

Ile Thr Ser Ser Leu Gly Ser Lys Val Lys Leu Ser Trp Lys Leu Thr
             195                 200                 205

Ser Met Thr Lys Ser Asp Gly Lys Gly Tyr Val Leu Glu Tyr Glu Thr
             210                 215                 220

Pro Glu Gly Val Val Leu Val Gln Ala Lys Ser Val Ile Met Thr Ile
225                 230                 235                 240

Pro Ser Tyr Val Ala Ser Asp Ile Leu Arg Pro Leu Ser Gly Asp Ala
                 245                 250                 255

Ala Asp Val Leu Ser Arg Phe Tyr Tyr Pro Pro Val Ala Ala Val Thr
                 260                 265                 270

Val Ser Tyr Pro Lys Glu Ala Ile Arg Lys Glu Cys Leu Ile Asp Gly
             275                 280                 285

Glu Leu Gln Gly Phe Gly Gln Leu His Pro Arg Ser Gln Gly Val Glu
             290                 295                 300

Thr Leu Gly Thr Ile Tyr Ser Ser Leu Phe Pro Asn Arg Ala Pro
305                 310                 315                 320

Ala Gly Arg Val Leu Leu Leu Asn Tyr Ile Gly Gly Ala Thr Asn Thr
                 325                 330                 335

Gly Ile Val Ser Lys Thr Glu Ser Glu Leu Val Glu Ala Val Asp Arg
                 340                 345                 350
```

```
Asp Leu Arg Lys Met Leu Ile Asn Pro Thr Ala Val Asp Pro Leu Val
            355                 360                 365

Leu Gly Val Arg Val Trp Pro Gln Ala Ile Pro Gln Phe Leu Val Gly
        370                 375                 380

His Leu Asp Leu Leu Glu Ala Ala Lys Ser Ala Leu Asp Gln Gly Gly
385                 390                 395                 400

Tyr Asn Gly Leu Phe Leu Gly Gly Asn Tyr Val Ala Gly Val Ala Leu
                405                 410                 415

Gly Arg Cys Ile Glu Gly Ala Tyr Glu Ser Ala Ala Gln Ile Tyr Asp
                420                 425                 430

Phe Leu Thr Lys Tyr Ala Tyr Lys
            435                 440
```

(2) INFORMATION FOR SEQ ID NO: 25:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "maize protox-1 intron (xi) SEQUENCE DESCRIPTION: SEQ ID NO: 25:

```
GTACGCTCCT CGCTGGCGCC GCAGCGTCTT CTTCTCAGAC TCATGCGCAG CCATGGAATT    60

GAGATGCTGA ATGGATTTTA TACGCGCGCG CAG                                 93
```

(2) INFORMATION FOR SEQ ID NO: 26:

(i) SEQUENCE CHARACTERISTICS:
        (A) LENGTH: 2606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Beta vulgaris (sugar beet)

(vii) IMMEDIATE SOURCE:
        (B) CLONE: pWDC-20 (NRRL B-21650)

(ix) FEATURE:
        (A) NAME/KEY: misc_feature
        (B) LOCATION: 2601..2606
        (D) OTHER INFORMATION: /note= "SalI site"

(ix) FEATURE:
        (A) NAME/KEY: misc_feature
        (B) LOCATION: complement (1..538)
        (D) OTHER INFORMATION: /note= "partial cDNA of sugar beet
           protox-1"

(ix) FEATURE:
        (A) NAME/KEY: misc_feature
        (B) LOCATION: 539..2606
        (D) OTHER INFORMATION: /note= "sugar beet protox-1 promoter
           region(partial sequence of the [] 3 kb PstI-SalI fragment
           subcloned from pWDC-2

(xi) SEQUENCE DESCRIPTION: SEQ ID NO: 26:

```
CTGCAGGGGG AGGGAAAGAG AGACCGCGAC GGTGAGGGAG GGGAGACCGC GACGGTGAGG      60
GAGGGGAGAA CGCGACGGTG AGGGAGGGGA GAACGCGATG GTGAGGGAGG GGAGAACGCG     120
ACGCGCAGGG GAGGGGGATA ACTCGACGGT GCAGGGAGGT GAGGGGGACG ACGTGACGGC     180
GCAGGGGAGG GGGGAACCGT CGCGGGAAGG GGAAGACCGG GGGGCCGACA AGGTGGTGTT     240
ACTGGGGTAG GGAGAGGCGG CGTGGAGAAT AGTAACAGAG GGAGGAGTGG TGGTGCTAGG     300
GTGGAAGAAG GGTAAGAAAG AGGAAGAAAG AGAATTAACA TTATCTTAAC CAAACACCAC     360
TCTAAATCTA AGGGTTTTCT TTTCCTTTCC TCTCCTCTCC CTTTCTTGAT TCCATTCCCY     420
TTACCCCGTT GCAACCAAAC GCCCCCTTAT TATGGACCGG AGGAAGTATG TAGAGATGGT     480
CACAAAACTA CTTAAGCTGG TAACTTATAA ATATACTGGG TATTAAATGA ATTAAGTGGC     540
CACAAAATGA CTATAAATTA CTTCGTAATC TTTAGGAACT ATGTTGGTCA CGAAATAACA     600
TAAAACTGGT TATTTAATGG CTTTATGTAG GTACTGCATT CATAAATATA TTTCTAACAT     660
AATCGTGGTA TGTAGGTGTT TTATAACACA AGGATTAGGT TTACACCAAT GTCATTTTCA     720
TTAGAATGTA GTTAGAATCA CTTTGGAACT TTGAAGAGTG ATGACACATT TTTATTATGC     780
TTTTATGAAA TGTCTTTGTG GTTTTTATGA TAGTATTGAG TTTAAGGCAA GTTGGAAGTA     840
TATGATGGAG AAGTACAGTA TATAGGTGAC AATTGGTTTG CTTGTTTCTA TGAGTTGAAA     900
GATAAGTAGT ACACGACACT GAGCAATGAC CTCTTCTTAG TTGTAATTTT GTCTTCTCGA     960
CGTAGTGAAA GTACAAACAA GATTATGGCT TTCAAGCTTC CAAGATAACG AGATTGTATG    1020
AATTTTGTGG TGTATTTCAC ATCATTGTTT TACGTTGGAG ACAAACTAAA ACCAATGATG    1080
AGTTTGTGGA TTCGAGATTT GCCCCTAAGT CTTATTTACC CATGGCAAGC ATGCTGAAAC    1140
ATGTTAGTCA AACTTACACA GCTACAATGT TTAGGGATTT TGAGCAAAAA ATTTGGGTAT    1200
TCTTTGGGTA CCATTATGTG AGTTGTTGAC TATGGATTAA ACAAAATCAC TATATAAAGT    1260
CTGGAATGAG AAGCATCCGC AATTGACACA CCATGTTACT TTGATTGTTT CAACAAGTTT    1320
ATTAGATGTA TTTTGTAGGAA TTTTGAAGAG GCGGAGATGT TGTGTTATAA TTGCTTTGGG    1380
GGTGCTTCAC ATGCACTCTG TTAGTGAGAC ATCTTCAGCT TATATTTTAA GGCGGTTAGT    1440
GAGTATGATT TTTTTTTTTC AAACTTTTCG ATTTCCATGT AATTAAAAAA GGTGTTTGAT    1500
AAATACATGT TAAGATAGCC AAGAAAGGC AACTTTCAAA CAAATAAAAA AAATTAAGTC     1560
GCTTAATCAT TTTTCCAAGT ACTTTTTACT TTTAACACCA CTTATTACTG AATCTATAGC    1620
CGTTAAGAAT GCATTTTCAC GCTCATACAT GCAAATCAAG AACCTCCTCA TTGAAGGAGA    1680
TAATTTAGTC CTCATAAACC CCGTTAAAGA CATTTTTAGC ATCCAGAGAA ATTTCGATTC    1740
AGTTAAAATT GCATATATAA CCAGAGAAAC AAATTCAGAT GTTAGTCAGT CCAGCTACAT    1800
AGGTCAATGC CTGAGAGTTT AAAAGAATCC GTATCCTTAA GCATAAGTAG GTATTGAGGT    1860
GAGTTACAAA GGTAAGTTAC CGGTTACGCA CCACCTCCAC CAAACAAGTA TGGTTAGAAG    1920
ATACATGTAA TCGTTTATTT AGAGTACTAT TTATAAAAAA CTTTTTAACT AGAAACAGTT    1980
GTTTCATTTT GATATAAGGT TAATTAGAAT TCCCGAGCAA GCAAGAAGGG GATATAGAGG    2040
ATAAGGAGGG CGAGAGAGCG AGAGAGAGAT GAAATCAATG GCGTTATCAA ACTGCATTCC    2100
ACAGACACAG TGCATGCCAT TGCACAGCAG CGGGCATTAC AGGGGCAATT GTATCATGTT    2160
GTCAATTCCA TGTAGTTTAA TTGGAAGACG AGGTTATTAT TCACATAAGA AGAGGAGGAT    2220
GAGCATGAGT TGCAGCACAA GCTCAGGCTC AAAGTCAGCG GTTAAAGAAG CAGGATCAGG    2280
ATCAGGATCA GGAGCAGGAG GATTGCTAGA CTGCGTAATC GTTGGAGGTG GAATTAGCGG    2340
```

```
GCTTTGCATC GCGCAGGCTC TTTGTACAAA ACAGTCCTCT TTATCCCCAA ATTTTATAGT        2400

GACAGAGGCC AAAGACAGAG TTGGCGGCAA CATCGTCACT GTGGAGGCCG ATGGCTATAT        2460

CTGGGAGGAG GGACCCAATA GCTTCCAGCC TTCCGACGCG GTGCTCACCA TGGCGGTAAT        2520

TCTGTCTCTT CATTATTCAT AATCATAATT CAATTCAATT CAATTCCTAA CGTGGAATGT        2580

GGAATGTGGC ATGTGCGTAG GTCGAC                                            2606
```

(2) INFORMATION FOR SEQ ID NO: 27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Pclp_P1a - plastid clpP (iii) HYPOTHETICAL: NO (iv) ANTI-SENSE: NO (ix) FEATURE:
        (A) NAME/KEY: misc_feature
        (B) LOCATION: 4..9
        (D) OTHER INFORMATION: /note= "EcoRI restriction site"

(xi) SEQUENCE DESCRIPTION: SEQ ID NO: 27:

```
GCGGAATTCA TACTTATTTA TCATTAGAAA G                                        31
```

(2) INFORMATION FOR SEQ ID NO: 28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Pclp_P1b - plastid clpP (iii) HYPOTHETICAL: NO (iv) ANTI-SENSE: NO (ix) FEATURE:
        (A) NAME/KEY: misc_feature
        (B) LOCATION: 4..9
        (D) OTHER INFORMATION: /note= "XbaI restriction site"

(xi) SEQUENCE DESCRIPTION: SEQ ID NO: 28:

```
GCGTCTAGAA AGAACTAAAT ACTATATTTC AC                                       32
```

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Pclp_P2b - plastid clpP (iii) HYPOTHETICAL: NO (iv) ANTI-SENSE: NO

```
    (ix) FEATURE:
         (A) NAME/KEY: misc_feature
         (B) LOCATION: 4..9
         (D) OTHER INFORMATION: /note= "NcoI restriction site"

(xi) SEQUENCE DESCRIPTION: SEQ ID NO: 29:

GCGCCATGGT AAATGAAAGA AAGAACTAAA                                            30

(2) INFORMATION FOR SEQ ID NO: 30:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Trps16_P1a - plastid rps16"

(iii) HYPOTHETICAL: NO (iv) ANTI-SENSE: NO (ix) FEATURE:
         (A) NAME/KEY: misc_feature
         (B) LOCATION: 4..9
         (D) OTHER INFORMATION: /note= "XbaI restriction site"

(xi) SEQUENCE DESCRIPTION: SEQ ID NO: 30:

GCGTCTAGAT CAACCGAAAT TCAATTAAGG                                            30

(2) INFORMATION FOR SEQ ID NO: 31:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Trps16_p1b - plastid rps16"

(iii) HYPOTHETICAL: NO (iv) ANTI-SENSE: NO (ix) FEATURE:
         (A) NAME/KEY: misc_feature
         (B) LOCATION: 4..9
         (D) OTHER INFORMATION: /note= "HindIII restriction site"

(xi) SEQUENCE DESCRIPTION: SEQ ID NO: 31:

CGCAAGCTTC AATGGAAGCA ATGATAA                                               27

(2) INFORMATION FOR SEQ ID NO: 32:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "minpsb_U - plastid psbA"

(iii) HYPOTHETICAL: NO (xi) SEQUENCE DESCRIPTION: SEQ ID NO: 32:

GGGAGTCCCT GATGATTAAA TAAACCAAGA TTTTAC                                     36
```

(2) INFORMATION FOR SEQ ID NO: 33:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "minpsb_L - plastid psbA (iii) HYPOTHETICAL: NO (iv) ANTI-SENSE: NO (xi) SEQUENCE DESCRIPTION: SEQ ID NO: 33:

CATGGTAAAA TCTTGGTTTA TTTAATCATC AGGGACTCCC                    40

(2) INFORMATION FOR SEQ ID NO: 34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "APRTXP1a - top strand PCR (iii) HYPOTHETICAL: NO (iv) ANTI-SENSE: NO (ix) FEATURE:
        (A) NAME/KEY: misc_feature
        (B) LOCATION: 5..10
        (D) OTHER INFORMATION: /note= "NcoI restriction site/ATG start
            codon"

(xi) SEQUENCE DESCRIPTION: SEQ ID NO: 34:

GGGACCATGG ATTGTGTGAT TGTCGGCGGA GG                            32

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "APRTXP1b - bottom strand PCR (iii) HYPOTHETICAL: NO (iv) ANTI-SENSE: NO (xi) SEQUENCE DESCRIPTION: SEQ ID NO: 35:

CTCCGCTCTC CAGCTTAGTG ATAC                                      24

(2) INFORMATION FOR SEQ ID NO: 36:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: sugar cane -continued (ix) FEATURE:
    (A) NAME/KEY: misc_feature
    (B) LOCATION: 1..308
    (D) OTHER INFORMATION: /product= "Sugar cane protox-1 partial
        coding sequence"

(xi) SEQUENCE DESCRIPTION: SEQ ID NO: 36:

| | | |
|---|---|---|
| TTTCCAAGAC TGAAAGTGAG CTGGTAGAAG CAGTTGACCG TGACCTCCGG AAAATGCTTA | 60 |
| TAAATCCTAC AGCAGTGGAC CCTTTAGTCC TTGGTGTCCG AGTTTGGCCA CAAGCCATAC | 120 |
| CTCAGTTCCT GGTAGGACAT CTTGATCTTC TGGAGGCCGC AAAATCTGCC CTGGACCGAG | 180 |
| GTGGCTACGA TGGGCTGTTC CTAGGAGGGA ACTATGTTGC AGGAGTTGCC CTAGGCAGAT | 240 |
| GCGTTGAGGG CGCGTATGAG AGTGCCTCGC AAATATATGA CTTCTTGACC AAGTATGCCT | 300 |
| ACAAGTGATG AAAGAAGTGG AGTGCTGCTT GTTAATTGTT ATGTTGCATA GATGAGGTGA | 360 |
| GACCAGGAGT AGTAAAAGCG TTACGAGTAT TTTTCATTCT TATTTTGTAA ATTGCACTTC | 420 |
| TGGTTTTTTC CTGTCAGTAA TTAGTTAGAT TTTAGTTCTG TAGGAGATTG TTCTGTTCAC | 480 |
| TGCCCTACAA AAGAATTTTT ATTTTGCATT CGTTTATGAG AGCTGTGCAG ACTTATGTAG | 540 |
| CGTTTTTCTG TAAGTACCAA CAAAATCAAA TACTATTCTG TAAGAGCTAA CAGAATGTGC | 600 |
| AACTGAGATT GCCTTGGATG AAAAAAAAAA AAA | 633 |

(2) INFORMATION FOR SEQ ID NO: 37:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

Ser Lys Thr Glu Ser Glu Leu Val Glu Ala Val Asp Arg Asp Leu Arg
1               5                   10                  15

Lys Met Leu Ile Asn Pro Thr Ala Val Asp Pro Leu Val Leu Gly Val
            20                  25                  30

Arg Val Trp Pro Gln Ala Ile Pro Gln Phe Leu Val Gly His Leu Asp
        35                  40                  45

Leu Leu Glu Ala Ala Lys Ser Ala Leu Asp Arg Gly Gly Tyr Asp Gly
    50                  55                  60

Leu Phe Leu Gly Gly Asn Tyr Val Ala Gly Val Ala Leu Gly Arg Cys
65                  70                  75                  80

Val Glu Gly Ala Tyr Glu Ser Ala Ser Gln Ile Tyr Asp Phe Leu Thr
                85                  90                  95

Lys Tyr Ala Tyr Lys
            100

(2) INFORMATION FOR SEQ ID NO: 38:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO: 38:

Ala Pro Xaa Phe
1

(2) INFORMATION FOR SEQ ID NO: 39:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (xi) SEQUENCE DESCRIPTION: SEQ ID NO: 39:

Tyr Ile Gly Gly Xaa
1               5

(2) INFORMATION FOR SEQ ID NO: 40:

(i) SEQUENCE CHARACTERISTICS:
           (A) LENGTH: 4 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (xi) SEQUENCE DESCRIPTION: SEQ ID NO: 40:

Ile Gly Gly Xaa
1

(2) INFORMATION FOR SEQ ID NO: 41:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (xi) SEQUENCE DESCRIPTION: SEQ ID NO: 41:

Ser Trp Xaa Leu Xaa
1               5

(2) INFORMATION FOR SEQ ID NO: 42:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (xi) SEQUENCE DESCRIPTION: SEQ ID NO: 42:

Gly Xaa Xaa Gly Leu
1               5

```
-continued (2) INFORMATION FOR SEQ ID NO: 43:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (xi) SEQUENCE DESCRIPTION: SEQ ID NO: 43:

Tyr Val Xaa Gly
```

HERBICIDE-TOLERANT PLANTS AND METHODS OF CONTROLLING THE GROWTH OF UNDESIRED VEGETATION

This application is a divisional application of U.S. application Ser. No. 09/102,420, filed Jun. 22, 1998, now U.S. Pat. No. 6,084,155, issued Jul. 4, 2000, which is a continuation-in-part of U.S. application Ser. No. 09/059,164, filed Apr. 13, 1998, which is a continuation-in-part of U.S. application Ser. No. 09/050,603, filed Mar. 30, 1998, now U.S. Pat. No. 6,023,012, issued Feb. 8, 2000, which is a continuation-in-part of U.S. application Ser. No. 08/808,931, filed Feb. 28, 1997, now U.S. Pat. No. 5,939,602, issued Aug. 17, 1999, which is a continuation-in-part of U.S. application Ser. No. 08/472,028, filed Jun. 6, 1995, now U.S. Pat. No. 5,767,373, issued Jun. 16, 1998. Said U.S. application Ser. No. 08/808,931 also claims the benefit of U.S. Provisional Application No. 60/012,705, filed on Feb. 28, 1996, U.S. Provisional Application No. 60/013,612, filed on Feb. 28, 1996, and U.S. Provisional Application No. 60/020,003, filed on Jun. 21, 1996. Said U.S. application Ser. No. 09/059,164 also claims the benefit of U.S. Provisional Application No. 60/126,430, filed Mar. 11, 1998. All of the aforementioned applications are incorporated herein by reference.

FIELD OF THE INVENTION

The present invention relates to DNA molecules encoding herbicide-tolerant forms of the enzyme protoporphyrinogen oxidase ("protox"). The invention further relates to herbicide-tolerant plants as well as methods for tissue culture selection and herbicide application based on these herbicide-tolerant forms of protox.

BACKGROUND OF THE INVENTION

I. The Protox Enzyme and its Involvement in the Chlorophyll/Heme Biosynthetic Pathway The biosynthetic pathways that lead to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalyses (see, e.g. Lehninger, *Biochemistry*, Worth Publishers, New York (1975)), and is therefore a necessary component for all aerobic organisms.

The last common step in chlorophyll and heme biosynthesis is the oxidation of protoporphyrinogen IX to protoporphyrin IX. Protoporphyrinogen oxidase (referred to herein as "protox") is the enzyme that catalyzes this last oxidation step (Matringe et al., *Biochem. J.* 260: 231 (1989)).

The protox enzyme has been purified either partially or completely from a number of organisms including the yeast *Saccharomyces cerevisiae* (Labbe-Bois and Labbe, In *Biosynthesis of Heme and Chlorophyll*, E. H. Dailey, ed. McGraw Hill: New York, pp. 235–285 (1990)), barley etioplasts (Jacobs and Jacobs, *Biochem. J.* 244: 219 (1987)), and mouse liver (Dailey and Karr, *Biochem.* 26: 2697 (1987)). Genes encoding protox have been isolated from two prokaryotic organisms, *Escherichia coli* (Sasarman et al., *Can. J. Microbiol.* 39: 1155 (1993)) and *Bacillus subtilis* (Dailey et al., *J. Biol. Chem.* 269: 813 (1994)). These genes share no sequence similarity; neither do their predicted protein products share any amino acid sequence identity. The *E. coli* protein is approximately 21 kDa, and associates with the cell membrane. The *B. subtilis* protein is 51 kDa, and is a soluble, cytoplasmic activity.

Protox encoding genes have now also been isolated from humans (see Nishimura et al., *J. Biol. Chem.* 270(14): 8076–8080 (1995) and plants (International application no. PCT/IB95/00452 filed Jun. 8, 1995, published Dec. 21, 1995 as WO 95/34659).

II. The Protox Gene as a Herbicide Target

The use of herbicides to control undesirable vegetation such as weeds or plants in crops has become an almost universal practice. The relevant market exceeds a billion dollars annually. Despite this extensive use, weed control remains a significant and costly problem for farmers.

Effective use of herbicides requires sound management. For instance, time and method of application and stage of weed plant development are critical to getting good weed control with herbicides. Since various weed species are resistant to herbicides, the production of effective herbicides becomes increasingly important. Novel herbicides can now be discovered using high-throughput screens that implement recombinant DNA technology. Metabolic enzymes essential to plant growth and development can be recombinantly produced though standard molecular biological techniques and utilized as herbicide targets in screens for novel inhibitors of the enzymes' activity. The novel inhibitors discovered through such screens may then be used as herbicides to control undesirable vegetation.

Unfortunately, herbicides that exhibit greater potency, broader weed spectrum and more rapid degradation in soil can also have greater crop phytotoxicity. One solution applied to this problem has been to develop crops that are resistant or tolerant to herbicides. Crop hybrids or varieties resistant to the herbicides allow for the use of the herbicides without attendant risk of damage to the crop. Development of resistance can allow application of a herbicide to a crop where its use was previously precluded or limited (e.g. to pre-emergence use) due to sensitivity of the crop to the herbicide. For example, U.S. Pat. No. 4,761,373, incorporated herein by reference, is directed to plants resistant to various imidazolinone or sulfonamide herbicides. The resistance is conferred by an altered acetohydroxyacid synthase (AHAS) enzyme. U.S. Pat. No. 4,975,374, incorporated herein by reference, relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659, incorporated herein by reference, is directed to plants that express a mutant acetolactate synthase (ALS) that renders the plants resistant to inhibition by sulfonylurea herbicides. U.S. Pat. No. 5,162,602, incorporated herein by reference, discloses plants tolerant to inhibition by cyclohexanedione and aryloxyphenoxypropanoic acid herbicides. The tolerance is conferred by an altered acetyl coenzyme A carboxylase(ACCase). U.S. Pat. No. 5,554,798, incorporated herein by reference, discloses transgenic glyphosate resistant maize plants, which tolerance is conferred by an altered 5-enolpyruvyl-3-phosphoshikimate (EPSP) synthase gene.

The protox enzyme serves as the target for a variety of herbicidal compounds. The herbicides that inhibit protox include many different structural classes of molecules (Duke et al., *Weed Sci.* 39: 465 (1991); Nandihalli et al., *Pesticide Biochem. Physiol.* 43: 193 (1992); Matringe et al., *FEBS Lett.* 245: 35 (1989); Yanase and Andoh, *Pesticide Biochem. Physiol.* 35: 70 (1989)). These herbicidal compounds include the diphenylethers {e.g. acifluorfen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g.

oxidiazon, 3-[2,4-dichloro-5-(1-methylethoxy)phenyl]-5-(1, 1-dimethylethyl)-1,3,4-oxadiazol-2-(3H)-one), cyclic imides (e.g. S-23142,N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82–556), and phenopylate and its O-phenylpyrrolidino- and piperidinocarbamate analogs. Many of these compounds competitively inhibit the normal reaction catalyzed by the enzyme, apparently acting as substrate analogs.

Typically, the inhibitory effect on protox is determined by measuring fluorescence at about 622 to 635 nm, after excitation at about 395 to 410 nM (see, e.g. Jacobs and Jacobs, *Enzyme* 28: 206 (1982); Sherman et al., *Plant Physiol.* 97: 280 (1991)). This assay is based on the fact that protoporphyrin IX is a fluorescent pigment, and protoporphyrinogen IX is nonfluorescent.

The predicted mode of action of protox-inhibiting herbicides involves the accumulation of protoporphyrinogen IX in the chloroplast. This accumulation is thought to lead to leakage of protoporphyrinogen IX into the cytosol where it is oxidized by a peroxidase activity to protoporphyrin IX. When exposed to light, protoporphyrin IX can cause formation of singlet oxygen in the cytosol. This singlet oxygen can in turn lead to the formation of other reactive oxygen species, which can cause lipid peroxidation and membrane disruption leading to rapid cell death (Lee et al., *Plant Physiol.* 102: 881 (1993)).

Not all protox enzymes are sensitive to herbicides that inhibit plant protox enzymes. Both of the protox enzymes encoded by genes isolated from *Escherichia coli* (Sasarman et al., *Can. J. Microbiol.* 39: 1155 (1993)) and *Bacillus subtilis* (Dailey et al., *J. Biol. Chem.* 269: 813 (1994)) are resistant to these herbicidal inhibitors. In addition, mutants of the unicellular alga *Chlamydomonas reinhardtii* resistant to the phenylimide herbicide S-23142 have been reported (Kataoka et al., *J. Pesticide Sci.* 15: 449 (1990); Shibata et al., In *Research in Photosynthesis*, Vol. III, N. Murata, ed. Kluwer:Netherlands. pp. 567–570 (1992)). At least one of these mutants appears to have an altered protox activity that is resistant not only to the herbicidal inhibitor on which the mutant was selected, but also to other classes of protox inhibitors (Oshio et al., *Z. Naturforsch.* 48c: 339 (1993); Sato et al., In *ACS Symposium on Porphyric Pesticides*, S. Duke, ed. ACS Press: Washington, D.C. (1994)). A mutant tobacco cell line has also been reported that is resistant to the inhibitor S-21432 (Che et al., *Z. Naturforsch.* 48c: 350 (1993).

III. Plastid Transformation and Expression

Plastid transformation, in which genes are inserted by homologous recombination into some or all of the several thousand copies of the circular plastid genome present in each plant cell, takes advantage of the enormous copy number advantage over nuclear-expressed genes to permit expression levels that may exceed 10% of the total soluble plant protein. In addition, plastid transformation is desirable because in most plants plastid-encoded traits are not pollen transmissible; hence, potential risks of inadvertent transgene escape to wild relatives of transgenic plants is obviated. Plastid transformation technology is extensively described in U.S. Pat. Nos. 5,451,513, 5,545,817, 5,545,818, and 5,576,198; in PCT Application Nos. WO 95/16783 and WO 97/32977; and in McBride et al., *Proc. Natl. Acad. Sci. USA* 91: 7301–7305 (1994), all of which are incorporated herein by reference. Plastid transformation via biolistics was achieved initially in the unicellular green alga *Chlamydomonas reinhardtii* (Boynton et al. (1988) *Science* 240: 1534–1537, incorporated herein by reference) and this approach, using selection for cis-acting antibiotic resistance loci (spectinomycin/streptomycin resistance) or complementation of non-photosynthetic mutant phenotypes, was soon extended to *Nicotiana tabacum* (Svab et al. (1990) *Proc. Natl. Acad. Sci. USA* 87: 8526–8530, incorporated herein by reference).

The basic technique for tobacco chloroplast transformation involves the particle bombardment of leaf tissue or PEG-mediated uptake of plasmid DNA in protoplasts with regions of cloned plastid DNA flanking a selectable antibiotic resistance marker. The 1 to 1.5 kb flanking regions, termed "targeting sequences," facilitate homologous recombination with the plastid genome and thus allow the replacement or modification of specific regions of the 156 kb tobacco plastid genome. Initially, point mutations in the chloroplast 16S rDNA and rps12 genes conferring resistance to spectinomycin and/or streptomycin were utilized as selectable markers for transformation (Svab, Z., Hajdukiewicz, P., and Maliga, P. (1990) *Proc. Natl. Acad. Sci. USA* 87, 8526–8530; Staub, J. M., and Maliga, P. (1992) *Plant Cell* 4, 39–45, incorporated herein by reference). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P., *EMBO J.* 12: 601–606 (1993), incorporated herein by reference). Substantial increases in transformation frequency were obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917, incorporated herein by reference). Previously, this marker had been used successfully for high-frequency transformation of the plastid genome of the green alga *Chlamydomonas reinhardtii* (Goldschmidt-Clermont, M. (1991) *Nucl. Acids Res.* 19, 4083–4089, incorporated herein by reference). Recently, plastid transformation of protoplasts from tobacco and the moss *Physcomitrella patens* has been attained using polyethylene glycol (PEG) mediated DNA uptake (O'Neill et al. (1993) *Plant J.* 3: 729–738; Koop et al. (1996) *Planta* 199: 193–201, both of which are incorporated herein by reference).

SUMMARY OF THE INVENTION

The present invention provides DNA molecules isolated from wheat, soybean, cotton, sugar beet, oilseed rape, rice, sorghum, and sugar cane encoding enzymes having protoporphyrinogen oxidase (protox) activity and chimeric genes comprising such DNA. Sequences of such DNA molecules are set forth in SEQ ID NOs:9 (wheat), 11 (soybean), 15 (cotton), 17 (sugar beet), 19 (oilseed rape), 21 (rice), 23 (sorghum), and 36 (sugar cane).

The present invention also provides modified forms of plant protoporphyrinogen oxidase (protox) enzymes that are resistant to compounds that inhibit unmodified naturally occurring plant protox enzymes, and DNA molecules coding for such inhibitor-resistant plant protox enzymes. Thus, in one aspect the present invention provides a DNA molecule encoding a plant protox enzyme that is capable of being incorporated into a DNA construct used to transform a plant containing wild-type, herbicide-sensitive protox, wherein the DNA molecule has at least one point mutation relative to a wild-type DNA molecule encoding plant protox such that upon transformation with the DNA construct the plant contains the DNA molecule, which renders the plant resistant to the application of a herbicide that inhibits naturally occurring plant protox. The present invention includes chimeric genes and modified forms of naturally occurring protox genes that can express the inhibitor-resistant plant protox enzymes in plants.

Genes encoding inhibitor-resistant plant protox enzymes can be used to confer resistance to protox-inhibitory herbicides in whole plants and as a selectable marker in plant cell transformation methods. Accordingly, the present invention also includes plants, including the descendants thereof, plant tissues and plant seeds containing plant expressible genes encoding these modified protox enzymes. These plants, plant tissues and plant seeds are resistant to protox-inhibitors at levels that normally are inhibitory to the naturally occurring protox activity in the plant. Plants encompassed by the invention especially include those that would be potential targets for protox inhibiting herbicides, particularly agronomically important crops such as maize and other cereal crops such as barley, wheat, sorghum, rye, oats, turf and forage grasses, millet and rice. Also comprised are other crop plants such as sugar cane, soybean, cotton, sugar beet, oilseed rape and tobacco.

The present invention accordingly provides a method for selecting plant cells transformed with a DNA molecule of the invention that encodes a herbicide-tolerant form of plant protox. The method comprises introducing the DNA molecule into plant cells whose growth is sensitive to inhibition by herbicides to which the protox encoded by the DNA molecule is resistant, thus forming a transformed plant cell. The transformed plant cell whose growth is resistant to the selected herbicide is identified by selection at a herbicide concentration that inhibits the growth of untransfonned plant cells.

The present invention is directed further to methods for the production of plants, including plant material, such as for example plant tissues, protoplasts, cells, calli, organs, plant seeds, embryos, pollen, egg cells, zygotes, together with any other propagating material and plant parts, such as for example flowers, stems, fruits, leaves, roots originating in transgenic plants or their progeny previously transformed by means of the process of the invention, which produce an inhibitor-resistant form of the plant protox enzyme provided herein. Such plants may be stably transformed with a structural gene encoding the resistant protox, or prepared by direct selection techniques whereby herbicide resistant lines are isolated, characterized and developed.

In another aspect, the present invention is directed to a method for controlling unwanted vegetation growing at a locus where a herbicide-tolerant, agronomically useful plant, which is transformed with a DNA molecule according to the present invention that encodes a herbicide-tolerant form of plant protox, has been cultivated. The method comprises applying to the locus to be protected an effective amount of herbicide that inhibits naturally occurring protox activity.

The present invention is further directed to probes and methods for detecting the presence of genes encoding inhibitor-resistant forms of the plant protox enzyme and quantitating levels of inhibitor-resistant protox transcripts in plant tissue. These methods may be used to identify or screen for plants or plant tissue containing and/or expressing a gene encoding an inhibitor-resistant form of the plant protox enzyme.

The present invention also relates to plastid transformation and to the expression of DNA molecules in a plant plastid. In a preferred embodiment, a native plant protox enzyme or a modified plant protox enzyme is expressed in plant plastids to obtain herbicide resistant plants.

In a further embodiment, the present invention is directed to a chimeric gene comprising: (a) a DNA molecule isolated from a plant, which in its native state encodes a polypeptide that comprises a plastid transit peptide, and a mature enzyme that is natively targeted to a plastid of the plant by the plastid transit peptide, wherein the DNA molecule is modified such that it does not encode a functional plastid transit peptide; and (b) a promoter capable of expressing the DNA molecule in a plastid, wherein the promoter is operatively linked to the DNA molecule. The DNA molecule may be modified in that at least a portion of the native plastid transit peptide coding sequence is absent from the DNA molecule. Alternatively, the DNA molecule may be modified in that one or more nucleotides of the native plastid transit peptide coding sequence are mutated, thereby rendering an encoded plastid transit peptide nonfunctional. The present invention also relates to plants homoplasmic for chloroplast genomes containing such chimeric genes. In a preferred embodiment, the DNA molecule encodes an enzyme that is naturally inhibited by a herbicidal compound. In this case, such plants are resistant to a herbicide that naturally inhibits the enzyme encoded by a DNA molecule according to the present invention.

The present invention is also directed to plants made resistant to a herbicide by transforming their plastid genome with a DNA molecule according to the present invention and to methods for obtaining such plants. In a preferred embodiment, the DNA molecule encodes an enzyme that is naturally inhibited by a herbicidal compound. In a more preferred embodiment, the DNA molecule encodes an enzyme having protoporphyrinogen oxidase (protox) activity, which is modified so that it that confers resistance to protox inhibitors. A further embodiment of the present invention is directed to a method for controlling the growth of undesired vegetation, which comprises applying to a population of the above-described plants an effective amount of an inhibitor of the enzyme.

The present invention also provides a novel method for selecting a transplastomic plant cell, comprising the steps of: introducing the above-described chimeric gene into the plastome of a plant cell; expressing the encoded enzyme in the plastids of the plant cell; and selecting a cell that is resistant to a herbicidal compound that naturally inhibits the activity of the enzyme, whereby the resistant cell comprises transformed plastids. In a preferred embodiment, the enzyme is naturally inhibited by a herbicidal compound and the transgenic plant is able to grow on an amount of the herbicidal compound that naturally inhibits the activity of the enzyme. In a further preferred embodiment, the enzyme has protoporphyrinogen oxidase (protox) activity and is modified so that it that confers resistance to protox inhibitors.

BRIEF DESCRIPTION OF THE SEQUENCES IN THE SEQUENCE LISTING

SEQ ID NO:1: DNA coding sequence for an *Arabidopsis thaliana* protox-1 protein.

SEQ ID NO:2: Arabidopsis protox-1 amino acid sequence encoded by SEQ ID NO:1.

SEQ ID NO:3: DNA coding sequence for an *Arabidopsis thaliana* protox-2 protein.

SEQ ID NO:4: Arabidopsis protox-2 amino acid sequence encoded by SEQ ID NO:3.

SEQ ID NO:5: DNA coding sequence for a maize protox-1 protein.

SEQ ID NO:6: Maize protox-1 amino acid sequence encoded by SEQ ID NO:5.

SEQ ID NO:7: DNA coding sequence for a maize protox-2 protein.

SEQ ID NO:8: Maize protox-2 amino acid sequence encoded by SEQ ID NO:7.

SEQ ID NO:9: Partial DNA coding sequence for a wheat protox-1 protein.

SEQ ID NO:10: Partial wheat protox-1 amino acid sequence encoded by SEQ ID NO:9.

SEQ ID NO:11: DNA coding sequence for a soybean protox-1 protein.

SEQ ID NO:12: Soybean protox-1 protein encoded by SEQ ID NO:11.

SEQ ID NO:13: Promoter sequence from *Arabidopsis thaliana* protox-1 gene.

SEQ ID NO:14: Promoter sequence from maize protox-1 gene.

SEQ ID NO:15: DNA coding sequence for a cotton protox-1 protein.

SEQ ID NO:16: Cotton protox-1 amino acid sequence encoded by SEQ ID NO:15.

SEQ ID NO:17: DNA coding sequence for a sugar beet protox-1 protein.

SEQ ID NO:18: Sugar beet protox-1 amino acid sequence encoded by SEQ ID NO:17.

SEQ ID NO:19: DNA coding sequence for an oilseed rape protox-1 protein.

SEQ ID NO:20: Oilseed rape protox-1 amino acid sequence encoded by SEQ ID NO:19.

SEQ ID NO:21: Partial DNA coding sequence for a rice protox-1 protein.

SEQ ID NO:22: Partial rice protox-1 amino acid sequence encoded by SEQ ID NO:21.

SEQ ID NO:23: Partial DNA coding sequence for a sorghum protox-1 protein.

SEQ ID NO:24: Partial sorghum protox-1 amino acid sequence encoded by SEQ ID NO:23.

SEQ ID NO:25: Maize protox-1 intron sequence.

SEQ ID NO:26: Promoter sequence from sugar beet protox-1 gene.

SEQ ID NO:27: Pclp_P1a—plastid clpP gene promoter top strand PCR primer.

SEQ ID NO:28: Pclp_P1b—plastid clpP gene promoter bottom strand PCR primer.

SEQ ID NO:29: Pclp_P2b—plastid clpP gene promoter bottom strand PCR primer.

SEQ ID NO:30: Trps16_P1a—plastid rps16 gene top strand PCR primer.

SEQ ID NO:31: Trps16_p1b—plastid rps16 gene bottom strand PCR primer.

SEQ ID NO:32: minpsb_U—plastid psbA gene top strand primer.

SEQ ID NO:33: minpsb_L—plastid psbA gene bottom strand primer.

SEQ ID NO:34: APRTXP1a—top strand PCR primer.

SEQ ID NO:35: APRTXP1b—bottom strand PCR primer.

SEQ ID NO:36: Partial DNA coding sequence for a sugar cane protox-1 protein.

SEQ ID NO:37: Partial sugar cane protox-1 amino acid sequence encoded by SEQ ID NO:36.

SEQ ID NO:38: Sub-sequence #1 ($AP\Delta_1F$).

SEQ ID NO:39: Sub-sequence #8 ($YIGG\Delta_8$).

SEQ ID NO:40: Sub-sequence #12 ($IGG\Delta_{12}$).

SEQ ID NO:41: Sub-sequence #13 ($SWXL\Delta_{13}$).

SEQ ID NO:42: Sub-sequence #15 ($G\Delta_{15}XGL$).

SEQ ID NO:43: Sub-sequence #17 ($YV\Delta_{17}G$).

DEPOSITS

The following vector molecules have been deposited with Agricultural Research Service, Patent Culture Collection (NRRL), Northern Regional Research Center, 1815 North University Street, Peoria, Ill. 61604, U.S.A on the dates indicated below:

Wheat protox-1a, in the pBluescript SK vector, was deposited Mar. 19, 1996, as pWDC-13 (NRRL #B21545).

Soybean protox-1, in the pBluescript SK vector, was deposited Dec. 15, 1995 as pWDC-12 (NRRL #B-21516).

Cotton protox-1, in the pBluescript SK vector, was deposited Jul. 1, 1996 as pWDC-15 (NRRL #B-21594).

Sugar beet protox-1, in the pBluescript SK vector, was deposited Jul. 29, 1996, as pWDC-16 (NRRL #B-21595N).

Oilseed rape protox-1, in the pBluescript SK vector, was deposited Aug. 23, 1996, as pWDC-17 (NRRL #B-21615).

Rice protox-1, in the pBluescript SK vector, was deposited Dec. 6, 1996, as pWDC-18 (NRRL #B-21648).

Sorghum protox-1, in the pBluescript SK vector, was deposited Dec. 6, 1996, as pWDC-19 (NRRL #B-21649).

Resistant mutant pAraC-2Cys, in the pMut-1 plasmid, was deposited on Nov. 14, 1994 under the designation pWDC-7 with the Agricultural Research Culture Collection and given the deposit designation NRRL #21339N.

AraPT1Pro containing the Arabidopsis protox-1 promoter was deposited Dec. 15, 1995, as pWDC-11 (NRRL #B-21515).

A plasmid containing the maize protox-1 promoter fused to the remainder of the maize protox-1 coding sequence was deposited Mar. 19, 1996 as pWDC-14 (NRRL #B-21546).

A plasmid containing the sugar beet protox-1 promoter was deposited Dec. 6, 1996, as pWDC-20 (NRRL #B-21650).

DEFINITIONS

For clarity, certain terms used in the specification are defined and presented as follows:

Associated With/Operatively Linked: refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: a recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding DNA Sequence: a DNA sequence that is translated in an organism to produce a protein.

Corresponding To: in the context of the present invention, "corresponding to" means that when the amino acid sequences of various protox enzymes are aligned with each other, such as in Table 1A, the amino acids that "correspond to" certain enumerated positions in Table 1A are those that align with these positions in Table 1A, but that are not necessarily in these exact numerical positions relative to the particular protox enzyme's amino acid sequence. Likewise, when the amino acid sequence of a particular protox enzyme (for example, the soybean protox enzyme) is aligned with the amino acid sequence of a reference protox enzyme (for example, the Arabidopsis protox-1 sequence given in SEQ ID NO:2), the amino acids in the soybean protox sequence that "correspond to" certain enumerated positions of SEQ ID NO:2 are those that align with these positions of SEQ ID NO:2, but are not necessarily in these exact numerical positions of the soybean protox enzyme's amino acid sequence.

Herbicide: a chemical substance used to kill or suppress the growth of plants, plant cells, plant seeds, or plant tissues.

Heterologous DNA Sequence: a DNA sequence not naturally associated with a host cell into which it is introduced, including non-naturally occurring multiple copies of a naturally occurring DNA sequence.

Homologous DNA Sequence: a DNA sequence naturally associated with a host cell into which it is introduced.

Homoplasmic: refers to a plant, plant tissue or plant cell, wherein all of the plastids are genetically identical. In different tissues or stages of development, the plastids may take different forms, e.g., chloroplasts, proplastids, etioplasts, amyloplasts, chromoplasts, and so forth.

Inhibitor: a chemical substance that inactivates the enzymatic activity of a protein such as a biosynthetic enzyme, receptor, signal transduction protein, structural gene product, or transport protein that is essential to the growth or survival of the plant. In the context of the instant invention, an inhibitor is a chemical substance that inactivates the enzymatic activity of protox. The term "herbicide" is used herein to define an inhibitor when applied to plants, plant cells, plant seeds, or plant tissues.

Isolated: in the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a transgenic host cell.

Minimal Promoter: promoter elements, particularly a TATA element, that are inactive or that have greatly reduced promoter activity in the absence of upstream activation. In the presence of a suitable transcrption factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Nucleic Acid Molecule: a linear segment of single- or double-stranded DNA or RNA that can be isolated from any source. In the context of the present invention, the nucleic acid molecule is preferably a segment of DNA.

Plant: refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units.

Plastome: the genome of a plastid.

Protox-1: chloroplast protox.

Protox-2: mitochondrial protox.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Substantially Similar: with respect to nucleic acids, a nucleic acid molecule that has at least 60 percent sequence identity with a reference nucleic acid molecule. In a preferred embodiment, a substantially similar DNA sequence is at least 80% identical to a reference DNA sequence; in a more preferred embodiment, a substantially similar DNA sequence is at least 90% identical to a reference DNA sequence; and in a most preferred embodiment, a substantially similar DNA sequence is at least 95% identical to a reference DNA sequence. A substantially similar nucleotide sequence typically hybridizes to a reference nucleic acid molecule, or fragments thereof, under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C. With respect to proteins or peptides, a substantially similar amino acid sequence is an amino acid sequence that is at least 90% identical to the amino acid sequence of a reference protein or peptide and has substantially the same activity as the reference protein or peptide.

Tolerance/Resistance: the ability to continue normal growth or function when exposed to an inhibitor or herbicide.

Transformation: a process for introducing heterologous DNA into a cell, tissue, or plant. Transformed cells, tissues, or plants are understood to encompass not only the end product of a transformation process, but also transgenic progeny thereof.

Transit Peptide: a signal polypeptide that is translated in conjunction with a protein encoded by a DNA molecule, forming a polypeptide precursor. In the process of transport to a selected site within the cell, a chloroplast for example, the transit peptide can be cleaved from the remainder of the polypeptide precursor to provide an active or mature protein.

Transformed: refers to an organism such as a plant into which a heterologous DNA molecule has been introduced. The DNA molecule can be stably integrated into the genome of the plant, wherein the genome of the plant encompasses the nuclear genome, the plastid genome and the mitochondrial genome. In a transformed plant, the DNA molecule can also be present as an extrachromosomal molecule. Such an extrachromosomal molecule can be auto-replicating. A "non-transformed" plant refers to a wild-type organism, i.e., a plant, which does not contain the heterologous DNA molecule.

Transplastome: a transformed plastid genome.

Nucleotides are indicated by their bases by the following standard abbreviations: adenine (A), cytosine (C), thymine (T), and guanine (G). Amino acids are likewise indicated by the following standard abbreviations: alanine (ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore (Xaa; X) represents any amino acid.

DETAILED DESCRIPTION OF THE INVENTION

I. Plant Protox Coding Sequences

In one aspect, the present invention is directed to an isolated DNA molecule that encodes protoporphyrinogen oxidase (referred to herein as "protox"), the enzyme that catalyzes the oxidation of protoporphyrinogen IX to protoporphyrin IX, from wheat, soybean, cotton, sugar beet, oilseed rape, rice, sorghum, and sugar cane. The partial DNA coding sequence and corresponding amino acid sequence for a wheat protox enzyme are provided as SEQ ID NOs:9 and 10, respectively. The DNA coding sequence and corresponding amino acid sequence for a soybean protox enzyme are provided as SEQ ID NOs:11 and 12, respectively. The DNA coding sequence and corresponding amino acid sequence for a cotton protox enzyme are provided as SEQ ID NOs:15 and 16, respectively. The DNA coding sequence and corresponding amino acid sequence for a sugar beet protox enzyme are provided as SEQ ID NOs:17 and 18, respectively. The DNA coding sequence and corresponding amino acid sequence for an oilseed rape protox enzyme are provided as SEQ ID NOs:19 and 20, respectively. The partial DNA coding sequence and corresponding amino acid sequence for a rice protox enzyme are provided as SEQ ID NOs:21 and 22, respectively. The partial DNA coding sequence and corresponding amino acid sequence for a sorghum protox enzyme are provided as SEQ ID NOs:23 and 24, respectively. The partial DNA coding sequence and corresponding amino acid sequence for a sugar cane protox enzyme are provided as SEQ ID NOs:36 and 37, respectively.

The DNA coding sequences and corresponding amino acid sequences for protox enzymes from *Arabidopsis thaliana* and maize are provided herein as SEQ ID NOs:1–4 (Arabidopsis) and SEQ ID NOs:5–8 (maize).

The invention therefore is directed to a DNA molecule encoding a protoporphyrinogen oxidase (protox) comprising a eukaryotic protox selected from the group consisting of a wheat protox enzyme, a soybean protox enzyme, a cotton protox enzyme, a sugar beet protox enzyme, an oilseed rape protox enzyme, a rice protox enzyme, a sorghum protox enzyme, and a sugar cane protox enzyme.

Preferred within the scope of the invention are isolated DNA molecules encoding the protoporphyrinogen oxidase (protox) enzyme from dicotyledonous plants, but especially from soybean plants, cotton plants, sugar beet plants and oilseed rape plants, such as those given in SEQ ID NOS: 11, 15, 17 and 19. More preferred are isolated DNA molecules encoding the protoporphyrinogen oxidase (protox) enzyme from soybean, such as given in SEQ ID NO:11, and sugar beet, such as given in SEQ ID NO:17.

Also preferred are isolated DNA molecules encoding the protoporphyrinogen oxidase (protox) enzyme from monocotyledonous plants, but especially from wheat plants, rice plants, sorghum plants, and sugar cane plants, such as those given in SEQ ID NOS: 9, 21, 23, and 36. More preferred are isolated DNA molecules encoding the protoporphyrinogen oxidase (protox) enzyme from wheat such as given in SEQ ID NO:9.

In another aspect, the present invention is directed to isolated DNA molecules encoding the protoporphyrinogen oxidase (protox) enzyme protein from a dicotyledonous plant, wherein the protein comprises the amino acid sequence selected from the group consisting of SEQ ID NOs: 12, 16, 18 and 20. Further comprised are isolated DNA molecules encoding the protoporphyrinogen oxidase (protox) enzyme protein from a monocotyledonous plant, wherein the protein comprises the amino acid sequence selected from the group consisting of SEQ ID NOs: 10, 22, 24, and 37. More preferred is an isolated DNA molecule encoding the protoporphyrinogen oxidase (protox) enzyme wherein the protein comprises the amino acid sequence from wheat such as given in SEQ ID NO:10. More preferred is an isolated DNA molecule encoding the protoporphyrinogen oxidase (protox) enzyme wherein the protein comprises the amino acid sequence from soybean, such as given in SEQ ID NO:12 and sugar beet, such as given in SEQ ID NO:18.

Using the information provided by the present invention, the DNA coding sequence for the protoporphyrinogen oxidase (protox) enzyme from any eukaryotic organism may be obtained using standard methods.

In another aspect, the present invention is directed to an isolated DNA molecule that encodes a wheat protox enzyme and that comprises a nucleotide sequence that hybridizes to the coding sequence shown in SEQ ID NO:9 under the following hybridization and wash conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

In yet another aspect, the present invention is directed to an isolated DNA molecule that encodes a soybean protox enzyme and that comprises a nucleotide sequence that hybridizes to the coding sequence shown in SEQ ID NO:11 under the following hybridization and wash conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

In still another aspect, the present invention is directed to an isolated DNA molecule that encodes a cotton protox enzyme and that comprises a nucleotide sequence that hybridizes to the coding sequence shown in SEQ ID NO:15 under the following hybridization and wash conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

In another aspect, the present invention is directed to an isolated DNA molecule that encodes a sugar beet protox enzyme and that comprises a nucleotide sequence that hybridizes to the coding sequence shown in SEQ ID NO:17 under the following hybridization and wash conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

In another aspect, the present invention is directed to an isolated DNA molecule that encodes an oilseed rape protox enzyme and that comprises a nucleotide sequence that hybridizes to the coding sequence shown in SEQ ID NO:19 under the following hybridization and wash conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

In another aspect, the present invention is directed to an isolated DNA molecule that encodes a rice protox enzyme and that comprises a nucleotide sequence that hybridizes to the coding sequence shown in SEQ ID NO:21 under the following hybridization and wash conditions:
  (a) hybridization in 7% sodium dodecyl sulfate (SDS), 0.5 M NaPO4 pH 7.0, 1 mM EDTA at 50° C.; and
  (b) wash in 2×SSC, 1% SDS at 50° C.

In another aspect, the present invention is directed to an isolated DNA molecule that encodes a sorghum protox enzyme and that comprises a nucleotide sequence that hybridizes to the coding sequence shown in SEQ ID NO:23 under the following hybridization and wash conditions:
  (a) hybridization in 7% sodium dodecyl sulfate (SDS), 0.5 M NaPO4 pH 7.0, 1 mM EDTA at 50° C.; and
  (b) wash in 2×SSC, 1% SDS at 50° C.

In another aspect, the present invention is directed to an isolated DNA molecule that encodes a sugar cane protox enzyme and that comprises a nucleotide sequence that hybridizes to the coding sequence shown in SEQ ID NO:36 under the following hybridization and wash conditions:
  (a) hybridization in 7% sodium dodecyl sulfate (SDS), 0.5 M NaPO4 pH 7.0, 1 mM EDTA at 50° C.; and
  (b) wash in 2×SSC, 1% SDS at 50° C.

The isolated eukaryotic protox sequences taught by the present invention may be manipulated according to standard genetic engineering techniques to suit any desired purpose. For example, the entire protox sequence or portions thereof may be used as probes capable of specifically hybridizing to protox coding sequences and messenger RNA's. To achieve specific hybridization under a variety of conditions, such probes include sequences that are unique among protox coding sequences and are preferably at least 10 nucleotides in length, and most preferably at least 20 nucleotides in length. Such probes may be used to amplify and analyze protox coding sequences from a chosen organism via the well known process of polymerase chain reaction (PCR). This technique may be useful to isolate additional protox coding sequences from a desired organism or as a diagnostic assay to determine the presence of protox coding sequences in an organism.

Factors that affect the stability of hybrids determine the stringency of the hybridization. One such factor is the melting temperature $T_m$, which can be easily calculated according to the formula provided in DNA PROBES, George H. Keller and Mark M. Manak, Macmillan Publishers Ltd, 1993, Section one: Molecular Hybridization Technology; page 8 ff. The preferred hybridization temperature is in the range of about 25° C. below the calculated melting temperature $T_m$ and preferably in the range of about 12–15° C. below the calculated melting temperature $T_m$ and in the case of oligonucleotides in the range of about 5–10° C. below the melting temperature $T_m$.

Comprised by the present invention are DNA molecules that hybridize to a DNA molecule according to the invention as defined hereinbefore, but preferably to an oligonucleotide probe obtainable from the DNA molecule comprising a contiguous portion of the sequence of the protoporphyrinogen oxidase (protox) enzyme at least 10 nucleotides in length, under moderately stringent conditions.

The invention further embodies the use of a nucleotide probe capable of specifically hybridizing to a plant protox gene or mRNA of at least 10 nucleotides length in a polymerase chain reaction (PCR).

In a further embodiment, the present invention provides probes capable of specifically hybridizing to a eukaryotic DNA sequence encoding a protoporphyrinogen oxidase activity or to the respective mRNA and methods for detecting the DNA sequences in eukaryotic organisms using the probes according to the invention.

Protox specific hybridization probes may also be used to map the location of the native eukaryotic protox gene(s) in the genome of a chosen organism using standard techniques based on the selective hybridization of the probe to genomic protox sequences. These techniques include, but are not limited to, identification of DNA polymorphisms identified or contained within the protox probe sequence, and use of such polymorphisms to follow segregation of the protox gene relative to other markers of known map position in a mapping population derived from self fertilization of a hybrid of two polymorphic parental lines (see e.g. Helentjaris et al., *Plant Mol. Biol.* 5: 109 (1985). Sommer et al. *Biotechniques* 12: 82 (1992); D'Ovidio et al., *Plant Mol. Biol.* 15: 169 (1990)). While any eukaryotic protox sequence is contemplated to be useful as a probe for mapping protox genes from any eukaryotic organism, preferred probes are those protox sequences from organisms more closely related to the chosen organism, and most preferred probes are those protox sequences from the chosen organism. Mapping of protox genes in this manner is contemplated to be particularly useful in plants for breeding purposes. For instance, by knowing the genetic map position of a mutant protox gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of protox-linked flanking chromosomal DNA still present in the recurrent parent after each round of back-crossing.

Protox specific hybridization probes may also be used to quantitate levels of protox mRNA in an organism using standard techniques such as Northern blot analysis. This technique may be useful as a diagnostic assay to detect altered levels of protox expression that may be associated with particular adverse conditions such as autosomal dominant disorder in humans characterized by both neuropsychiatric symptoms and skin lesions, which are associated with decreased levels of protox activity (Brenner and Bloomer, *New Engl. J. Med.* 302: 765 (1980)).

A further embodiment of the invention is a method of producing a DNA molecule comprising a DNA portion encoding a protein having protoporphyrinogen oxidase (protox) enzyme activity comprising:
  (a) preparing a nucleotide probe capable of specifically hybridizing to a plant protox gene or mRNA, wherein the probe comprises a contiguous portion of the coding sequence for a protox protein from a plant of at least 10 nucleotides length;
  (b) probing for other protox coding sequences in populations of cloned genomic DNA fragments or cDNA fragments from a chosen organism using the nucleotide probe prepared according to step (a); and
  (c) isolating and multiplying a DNA molecule comprising a DNA portion encoding a protein having protoporphyrinogen oxidase (protox) enzyme activity.

A further embodiment of the invention is a method of isolating a DNA molecule from any plant comprising a DNA portion encoding a protein having protoporphyrinogen oxidase (protox) enzyme activity.
  (a) preparing a nucleotide probe capable of specifically hybridizing to a plant protox gene or mRNA, wherein the probe comprises a contiguous portion of the coding sequence for a protox protein from a plant of at least 10 nucleotides length;
  (b) probing for other protox coding sequences in populations of cloned genomic DNA fragments or cDNA fragments from a chosen organism using the nucleotide probe prepared according to step (a); and (c) isolating a DNA molecule comprising a DNA portion encoding a protein having protoporphyrinogen oxidase (protox) enzyme activity.

The invention further comprises a method of producing an essentially pure DNA sequence coding for a protein exhibiting protoporphyrinogen oxidase (protox) enzyme activity, which method comprises:

(a) preparing a genomic or a cDNA library from a suitable source organism using an appropriate cloning vector;

(b) hybridizing the library with a probe molecule; and (c) identifying positive hybridizations of the probe to the DNA clones from the library that is clones potentially containing the nucleotide sequence corresponding to the amino acid sequence for protoporphyrinogen oxidase (protox).

The invention further comprises a method of producing an essentially pure DNA sequence coding for a protein exhibiting protoporphyrinogen oxidase (protox) enzyme activity, which method comprises:

(a) preparing total DNA from a genomic or a cDNA library;

(b) using the DNA of step (a) as a template for PCR reaction with primers representing low degeneracy portions of the amino acid sequence of protoporphyrinogen oxidase (protox).

A further object of the invention is an assay to identify inhibitors of protoporphyrinogen oxidase (protox) enzyme activity that comprises:

(a) incubating a first sample of protoporphyrinogen oxidase (protox) and its substrate;

(b) measuring an uninhibited reactivity of the protoporphyrinogen oxidase (protox) from step (a);

(c) incubating a first sample of protoporphyrinogen oxidase (protox) and its substrate in the presence of a second sample comprising an inhibitor compound;

(d) measuring an inhibited reactivity of the protoporphyrinogen oxidase (protox) enzyme from step (c); and (e) comparing the inhibited reactivity to the uninhibited reactivity of protoporphyrinogen oxidase (protox) enzyme.

A further object of the invention is an assay to identify inhibitor-resistant protoporphyrinogen oxidase (protox) mutants that comprises:

(a) incubating a first sample of protoporphyrinogen oxidase (protox) enzyme and its substrate in the presence of a second sample comprising a protoporphyrinogen oxidase (protox) enzyme inhibitor;

(b) measuring an unmutated reactivity of the protoporphyrinogen oxidase (protox) enzyme from step (a);

(c) incubating a first sample of a mutated protoporphyrinogen oxidase (protox) enzyme and its substrate in the presence of a second sample comprising protoporphyrinogen oxidase (protox) enzyme inhibitor;

(d) measuring a mutated reactivity of the mutated protoporphyrinogen oxidase (protox) enzyme from step (c); and (e) comparing the mutated reactivity to the unmutated reactivity of the protoporphyrinogen oxidase (protox) enzyme.

A further object of the invention is a protox enzyme inhibitor obtained by a method according to the invention.

For recombinant production of the enzyme in a host organism, the protox coding sequence may be inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pV111392/Sf21 cells (Invitrogen, La Jolla, Calif.).

Recombinantly produced eukaryotic protox enzyme is useful for a variety of purposes. For example, it may be used to supply protox enzymatic activity in vitro. It may also be used in an in vitro assay to screen known herbicidal chemicals whose target has not been identified to determine if they inhibit protox. Such an in vitro assay may also be used as a more general screen to identify chemicals that inhibit protox activity and that are therefore herbicide candidates. Recombinantly produced eukaryotic protox enzyme may also be used in an assay to identify inhibitor-resistant protox mutants (see International application no. PCT/IB95/00452 filed Jun. 8, 1995, published Dec. 21, 1995 as WO 95/34659, incorporated by reference herein in its entirety). Alternatively, recombinantly produced protox enzyme may be used to further characterize its association with known inhibitors in order to rationally design new inhibitory herbicides as well as herbicide tolerant forms of the enzyme.

II. Inhibitor Resistant Plant Protox Enzymes

In another aspect, the present invention teaches modifications that can be made to the amino acid sequence of any eukaryotic protoporphyrinogen oxidase (referred to herein as "protox") enzyme to yield an inhibitor-resistant form of this enzyme. Preferably, the eukaryotic protox enzyme is a plant protox enzyme. The present invention is directed to inhibitor-resistant protox enzymes having the modifications taught herein, to DNA molecules encoding these modified enzymes, and to chimeric genes capable of expressing these modified enzymes in plants.

The present invention is thus directed to an isolated DNA molecule encoding a modified eukaryotic protoporphyrinogen oxidase (protox) having at least one amino acid modification, wherein the amino acid modification has the property of conferring resistance to a protox inhibitor, that is wherein the modified protox is tolerant to an inhibitor in amounts that inhibit the naturally occurring eukaryotic protox. As used herein "inhibit" refers to a reduction in enzymatic activity observed in the presence of a subject compound compared to the level of activity observed in the absence of the subject compound, wherein the percent level of reduction is preferably at least 10%, more preferably at least 50%, and most preferably at least 90%.

Preferred is a DNA molecule encoding a modified eukaryotic protoporphyrinogen oxidase (protox) that is a plant protox, wherein the modified protox is tolerant to a herbicide in amounts that inhibit the naturally occurring protox activity. Even more preferred is a protox selected from the group consisting of an Arabidopsis protox enzyme, a maize protox enzyme, a wheat protox enzyme, a soybean protox enzyme, a cotton protox enzyme, a sugar beet protox enzyme, an oilseed rape protox enzyme, a rice protox enzyme, a sorghum protox enzyme, and a sugar cane protox enzyme having at least one amino acid modification, wherein the modified protox is tolerant to a herbicide in amounts that inhibit the naturally occurring protox activity.

As used herein, the expression "substantially conserved amino acid sequences" refers to regions of amino acid homology between polypeptides comprising protox enzymes from different sources. In the present invention, seventeen substantially conserved amino acid sub-sequences, designated 1–17 respectively, are shown in Table 1B. One skilled in the art could align the amino acid sequences of protox enzymes from different sources, as has been done in Table 1A, to identify the sub-sequences therein that make up the substantially conserved amino acid sequences defined herein. Stated another way, a given sub-sequence from one source "corresponds to" a homologous subsequence from a different source. The skilled person could then determine whether the identified subsequences have the characteristics disclosed and claimed in the present application.

Therefore, a preferred embodiment of the present invention is directed to a nucleic acid molecule comprising a nucleotide sequence isolated from a plant that encodes an enzyme having protoporphyrinogen oxidase (protox) activity, wherein the nucleic acid molecule is capable of being incorporated into a nucleic acid construct used to transform a plant containing wild-type, herbicide-sensitive protox, wherein the nucleotide sequence has at least one point mutation relative to a wild-type nucleotide sequence encoding plant protox, such that upon transformation with the nucleic acid construct the plant is rendered herbicide-tolerant.

More particularly, a preferred embodiment of the present invention is directed to a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises at least one of the following amino acid sub-sequences:

(a) $AP\Delta_1F$, wherein $\Delta_1$ is an amino acid other than arginine;

(b) $F\Delta_2S$, wherein $\Delta_2$ is an amino acid other than cysteine;

(c) $Y\Delta_3G$, wherein $\Delta_3$ is an amino acid other than alanine;

(d) $A\Delta_4D$, wherein $\Delta_4$ is an amino acid other than glycine;

(e) $Y\Delta_5P$, wherein $\Delta_5$ is an amino acid other than proline;

(f) $P\Delta_6A$, wherein $\Delta_6$ is an amino acid other than valine;

(g) $\Delta_7IG$, wherein $\Delta_7$ is an amino acid other than tyrosine;

(h) $YIGG\Delta_8$, wherein $\Delta_8$ is an amino acid other than alanine or serine;

(i) $A\Delta_9P$, wherein $\Delta_9$ is an amino acid other than isoleucine; and (j) $G\Delta_{10}A$, wherein $\Delta_{10}$ is an amino acid other than valine (Table 1B; sub-sequences 1–10).

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $AP\Delta_1F$, wherein $\Delta_1$ is an amino acid other than arginine. Most preferably, $\Delta_1$ is cysteine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $F\Delta_2S$, wherein $\Delta_2$ is an amino acid other than cysteine. Most preferably, $\Delta_2$ is phenylalanine, leucine, or lysine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $Y\Delta_3G$, wherein $\Delta_3$ is an amino acid other than alanine. Most preferably, $\Delta_3$ is valine, threonine, leucine, cysteine, or isoleucine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $A\Delta_4D$, wherein $\Delta_4$ is an amino acid other than glycine. Most preferably, $\Delta_4$ is serine or leucine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $\Delta_5$ is an amino acid other than proline. Most preferably, $\Delta_5$ is serine or histidine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $P\Delta_6A$, wherein $\Delta_6$ is an amino acid other than valine. Most preferably, $\Delta_6$ is leucine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid subsequence $\Delta_7IG$, wherein $\Delta_7$ is an amino acid other than tyrosine. Most preferably, $\Delta_7$ is cysteine, isoleucine, leucine, threonine, methionine, valine, alanine, or arginine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence $F\Delta_2S$, wherein $\Delta_8$ is an amino acid other than alanine or serine. Most preferably, $\Delta_8$ is proline.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid subsequence AΔ₉P, wherein Δ₉ is an amino acid other than isoleucine. Most preferably, Δ₉ is threonine, histidine, glycine, or asparagine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence GΔ₁₀A, wherein Δ₁₀ is an amino acid other than valine. Most preferably, Δ₁₀ is alanine.

Another preferred embodiment of the present invention is directed to a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises at least one of the following amino acid sub-sequences:

(a) APΔ₁F, wherein Δ₁ is an amino acid other than arginine;

(b) FΔ₂S, wherein Δ₂ is an amino acid other than cysteine;

(c) YΔ₃G, wherein Δ₃ is an amino acid other than alanine;

(d) AΔ₄D, wherein Δ₄ is an amino acid other than glycine;

(e) YΔ₅P, wherein Δ₅ is an amino acid other than proline;

(f) PΔ₆A, wherein Δ₆ is an amino acid other than valine;

(g) Δ₇IG, wherein Δ₇ is an amino acid other than tyrosine;

(h) YIGGΔ₈, wherein Δ₈ is an amino acid other than alanine or serine;

(i) AΔ₉P, wherein Δ₉ is an amino acid other than isoleucine; and (j) GΔ₁₀A, wherein Δ₁₀ is an amino acid other than valine (Table 1B; sub-sequences 1–10), and wherein the modified enzyme further comprises at least one additional amino acid sub-sequence selected from the group consisting of:

(k) QΔ₁₁S, wherein Δ₁₁ is an amino acid other than proline;

(l) IGGΔ₁₂, wherein Δ₁₂ is an amino acid other than threonine;

(m) SWXLΔ₁₃, wherein Δ₁₃ is an amino acid other than serine;

(n) LΔ₁₄Y, wherein Δ₁₄ is an amino acid other than asparagine; and (o) GΔ₁₅XGL, wherein Δ₁₅ is an amino acid other than tyrosine.

Preferred is a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises the amino acid sub-sequence YΔ₃G, wherein Δ₃ is an amino acid other than alanine, or the amino acid sub-sequence Δ₇IG, wherein Δ₇ is an amino acid other than tyrosine, and wherein the modified enzyme further comprises at least one additional amino acid sub-sequence selected from the group consisting of:

(k) QΔ₁₁S, wherein Δ₁₁ is an amino acid other than proline;

(l) IGGΔ₁₂, wherein Δ₁₂ is an amino acid other than threonine;

(m) SWXLΔ₁₃, wherein Δ₁₃ is an amino acid other than serine;

(n) LΔ₁₄Y, wherein Δ₁₄ is an amino acid other than asparagine; and (o) GΔ₁₅XGL, wherein Δ₁₅ is an amino acid other than tyrosine.

Preferably, Δ₁₁ is leucine, Δ₁₂ is isoleucine or alanine, Δ₁₃ is leucine, Δ₁₄ is serine, and Δ₁₅ is cysteine.

Another preferred embodiment of the present invention is directed to a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the modified enzyme comprises: the amino acid sub-sequence Δ₇IG, wherein Δ₇ is an amino acid other than tyrosine; the amino acid sub-sequences IGGΔ₁₂, wherein Δ₁₂ is an amino acid other than threonine; and the amino acid sub-sequence SWXLΔ₁₃, wherein Δ₁₃ is an amino acid other than serine. Most preferably, Δ₇ is isoleucine, Δ₁₂ is isoleucine, and Δ₁₃ is leucine.

Yet another preferred embodiment of the present invention is directed to a nucleic acid molecule comprising a nucleotide sequence isolated from a plant that encodes a modified enzyme having protoporphyrinogen oxidase (protox) activity, wherein the modified enzyme is resistant to an inhibitor of a naturally occurring protox enzyme, wherein the nucleotide sequence is further characterized in that at least one of the following conditions is met:

(a) the nucleic acid sequence has a sequence that encodes amino acid sub-sequence APΔ₁F, wherein Δ₁ is an amino acid other than arginine;

(b) the nucleic acid sequence has a sequence that encodes amino acid sub-sequence FΔ₂S, wherein Δ₂ is an amino acid other than cysteine;

(c) the nucleic acid sequence has a sequence that encodes amino acid sub-sequence YΔ₃G, wherein Δ₃ is an amino acid other than alanine;

(d) the nucleic acid sequence has a sequence that encodes amino acid sub-sequence AΔ₄D, wherein Δ₄ is an amino acid other than glycine;

(e) the nucleic acid sequence has a sequence that encodes amino acid sub-sequence YΔ₅P, wherein Δ₅ is an amino acid other than proline;

(f) the nucleic acid sequence has a sequence that encodes amino acid sub-sequence PΔ₆A, wherein Δ₆ is an amino acid other than valine;

(g) the nucleic acid sequence has a sequence that encodes amino acid sub-sequence Δ₇IG, wherein Δ₇ is an amino acid other than tyrosine;

(h) the nucleic acid sequence has a sequence that encodes amino acid sub-sequence YIGGΔ₈, wherein Δ₈ is an amino acid other than alanine or serine;

(i) the nucleic acid sequence has a sequence that encodes amino acid sub-sequence AΔ₉P, wherein Δ₉ is an amino acid other than isoleucine;

(j) the nucleic acid sequence has a sequence that encodes amino acid sub-sequence GΔ₁₀A, wherein Δ₁₀ is an amino acid other than valine;

(k) the nucleic acid sequence has a sequence that encodes amino acid sub-sequence YΔ₃G, wherein Δ₃ is an amino acid other than alanine, and the nucleic acid sequence also has a sequence that encodes one of the group consisting of:

(1) sub-sequence QΔ₁₁S, wherein Δ₁₁ is an amino acid other than proline, (2) sub-sequence IGGΔ₁₂, wherein Δ₁₂ is an amino acid other than threonine, (3) sub-sequence SWXLΔ₁₃, wherein Δ₁₃ is an amino acid other than serine, (4) sub-sequence LΔ$_{14}$Y, wherein Δ$_{14}$ is an amino acid other than asparagine, and
(5) sub-sequence GΔ$_{15}$XGL, wherein Δ$_{15}$ is an amino acid other than tyrosine;
(l) the nucleic acid sequence has a sequence that encodes amino acid sub-sequence Δ$_7$1G, wherein Δ$_7$ is an amino acid other than tyrosine, and the nucleic acid sequence also has a sequence that encodes one of the group consisting of:
(1) sub-sequence QΔ$_{11}$S, wherein Δ$_{11}$ is an amino acid other than proline,
(2) sub-sequence IGGΔ$_{12}$, wherein Δ$_{12}$ is an amino acid other than threonine,
(3) sub-sequence SWXLΔ$_{13}$, wherein Δ$_{13}$ is an amino acid other than serine,
(4) sub-sequence LΔ$_{14}$Y, wherein Δ$_{14}$ is an amino acid other than asparagine, and
(5) sub-sequence GΔ$_{15}$XGL, wherein Δ$_{15}$ is an amino acid other than tyrosine; and
(m) the nucleic has a sequence that encodes amino acid sub-sequence TΔ$_{16}$G, wherein Δ$_{16}$ is an amino acid other than leucine, and the nucleic acid sequence also has a sequence that encodes amino acid sub-sequence YVΔ$_{17}$G, wherein Δ$_{16}$ is an amino acid other than alanine.

Preferably, said nucleic acid sequence has a sequence that encodes amino acid sub-sequence TΔ$_{16}$G, wherein Δ$_{16}$ is an amino acid other than leucine, and said nucleic acid sequence also has a sequence that encodes amino acid sub-sequence YVΔ$_{17}$G, wherein Δ$_{16}$ is an amino acid other than alanine.

Also preferred is a DNA molecule encoding a modified protoporphyrinogen oxidase (protox) comprising a plant protox wherein the arginine occurring at the position corresponding to amino acid 88 of SEQ ID NO:6 is replaced with another amino acid, wherein the modified protox is tolerant to a herbicide in amounts that inhibit the naturally occurring protox activity. Particularly preferred is the DNA molecule wherein the arginine is replaced with a cysteine.

Also preferred is a DNA molecule encoding a modified protoporphyrinogen oxidase (protox) comprising a plant protox wherein the cysteine occurring at the position corresponding to amino acid 159 of SEQ ID NO:6 is replaced with another amino acid, wherein the modified protox is tolerant to a herbicide in amounts that inhibit the naturally occurring protox activity. Particularly preferred is the DNA molecule wherein the cysteine is replaced with a phenylalanine or lysine, most preferred, wherein the cysteine is replaced with a phenylalanine.

Also preferred is a DNA encoding a modified protoporphyrinogen oxidase (protox) comprising a plant protox wherein the isoleucine occurring at the position corresponding to amino acid 419 of SEQ ID NO:6 is replaced with another amino acid, wherein the modified protox is tolerant to a herbicide in amounts that inhibit the naturally occurring protox activity. Particularly preferred is a DNA molecule, wherein the isoleucine is replaced with a threonine, histidine, glycine or asparagine most preferred, wherein the isoleucine is replaced with a threonine.

Also preferred is a DNA molecule encoding a modified protoporphyrinogen oxidase (protox) comprising a plant protox wherein the alanine occurring at the position corresponding to amino acid 164 of SEQ ID NO:6 is replaced with another amino acid, wherein the modified protox is tolerant to a herbicide in amounts that inhibit the naturally occurring protox activity. Particularly preferred is a DNA molecule wherein the alanine is replaced with a threonine, leucine or valine.

Also preferred is a DNA molecule encoding a modified protoporphyrinogen oxidase (protox) comprising a plant protox wherein the glycine occurring at the position corresponding to amino acid 165 of SEQ ID NO:6 is replaced with another amino acid, wherein the modified protox is tolerant to a herbicide in amounts that inhibit the naturally occurring protox activity. Particularly preferred is a DNA molecule wherein the glycine is replaced with a serine or leucine.

Also preferred is a DNA molecule encoding a modified protoporphyrinogen oxidase (protox) comprising a plant protox wherein the tyrosine occurring at the position corresponding to amino acid 370 of SEQ ID NO:6 is replaced with another amino acid, wherein the modified protox is tolerant to a herbicide in amounts that inhibit the naturally occurring protox activity. Particularly preferred is a DNA molecule wherein the tyrosine is replaced with a isoleucine or methionine.

Also preferred is a DNA molecule encoding a modified protoporphyrinogen oxidase (protox) comprising a plant protox wherein the valine occurring at the position corresponding to amino acid 356 of SEQ ID NO:10 is replaced with another amino acid, wherein the modified protox is tolerant to a herbicide in amounts that inhibit the naturally occurring protox activity. Particularly preferred is a DNA molecule wherein the valine is replaced with a leucine.

Also preferred is a DNA molecule encoding a modified protoporphyrinogen oxidase (protox) comprising a plant protox wherein the serine occurring at the position corresponding to amino acid 421 of SEQ ID NO:10 is replaced with another amino acid, wherein the modified protox is tolerant to a herbicide in amounts that inhibit the naturally occurring protox activity. Particularly preferred is a DNA molecule wherein the serine is replaced with a proline.

Also preferred is a DNA molecule encoding a modified protoporphyrinogen oxidase (protox) comprising a plant protox wherein the valine occurring at the position corresponding to amino acid 502 of SEQ ID NO:10 is replaced with another amino acid, wherein the modified protox is tolerant to a herbicide in amounts that inhibit the naturally occurring protox activity. Particularly preferred is a DNA molecule wherein the valine is replaced with a alanine.

Also preferred is a DNA molecule encoding a modified protoporphyrinogen oxidase (protox) comprising a plant protox wherein the alanine occurring at the position corresponding to amino acid 211 of SEQ ID NO:10 is replaced with another amino acid, wherein the modified protox is tolerant to a herbicide in amounts that inhibit the naturally occurring protox activity. Particularly preferred is a DNA molecule wherein the alanine is replaced with a valine or threonine.

Also preferred is a DNA molecule encoding a modified protoporphyrinogen oxidase (protox) comprising a plant protox wherein the glycine occurring at the position corresponding to amino acid 212 of SEQ ID NO:10 is replaced with another amino acid, wherein the modified protox is tolerant to a herbicide in amounts that inhibit the naturally occurring protox activity. Particularly preferred is a DNA molecule wherein the glycine is replaced with a serine.

Also preferred is a DNA encoding a modified protoporphyrinogen oxidase (protox) comprising a plant protox wherein the isoleucine occurring at the position corresponding to amino acid 466 of SEQ ID NO:10 is replaced with another amino acid, wherein the modified protox is tolerant to a herbicide in amounts that inhibit the naturally occurring protox activity. Particularly preferred is a DNA molecule wherein the isoleucine is replaced with a threonine.

Also preferred is a DNA molecule encoding a modified protoporphyrinogen ox idase (protox) comprising a plant protox wherein the proline occurring at the position corresponding to amino acid 369 of SEQ ID NO:12 is replaced with another amino acid, wherein the modified protox is tolerant to a herbicide in amounts that inhibit the naturally occurring protox activity. Particularly preferred is a DNA molecule wherein the proline is replaced with a serine or histidine.

Also preferred is a DNA molecule encoding a modified protoporphyrinogen oxidase (protox) comprising a plant protox wherein the alanine occurring at the position corresponding to amino acid 226 of SEQ ID NO:12 is replaced with another amino acid, wherein the modified protox is tolerant to a herbicide in amounts that inhibit the naturally occurring protox activity. Particularly preferred is a DNA molecule, wherein the alanine is replaced with a threonine or leucine.

Also preferred is a DNA molecule encoding a modified protoporphyrinogen oxidase (protox) comprising a plant protox wherein the valine occurring at the position corresponding to amino acid 517 of SEQ ID NO:12 is replaced with another amino acid, wherein the modified protox is tolerant to a herbicide in amounts that inhibit the naturally occurring protox activity. Particularly preferred is a DNA molecule wherein the valine is replaced with a alanine.

Also preferred is a DNA molecule encoding a modified protoporphyrinogen oxidase (protox) comprising a plant protox wherein the tyrosine occurring at the position corresponding to amino acid 432 of SEQ ID NO:12 is replaced with another amino acid, wherein the modified protox is tolerant to a herbicide in amounts that inhibit the naturally occurring protox activity. Particularly preferred is a DNA molecule wherein the tyrosine is replaced with a leucine or isoleucine.

Also preferred is a DNA molecule encoding a modified protoporphyrinogen oxidase (protox) comprising a plant protox wherein the proline occurring at the position corresponding to amino acid 365 of SEQ ID NO:16 is replaced with another amino acid, wherein the modified protox is tolerant to a herbicide in amounts that inhibit the naturally occurring protox activity. Particularly preferred is a DNA molecule wherein the proline is replaced with a serine.

Also preferred is a DNA molecule encoding a modified protoporphyrinogen oxidase (protox) comprising a plant protox wherein the tyrosine occurring at the position corresponding to amino acid 428 of SEQ ID NO:16 is replaced with another amino acid, wherein the modified protox is tolerant to a herbicide in amounts that inhibit the naturally occurring protox activity. Particularly preferred is a DNA molecule wherein the tyrosine is replaced with a cysteine or arginine.

Also preferred is a DNA encoding a modified protoporphyrinogen oxidase (protox) comprising a plant protox wherein the tyrosine occurring at the position corresponding to amino acid 449 of SEQ ID NO:18 is replaced with another amino acid, wherein the modified protox is tolerant to a herbicide in amounts that inhibit the naturally occurring protox activity. Particularly preferred is a DNA molecule wherein the tyrosine is replaced with a cysteine, leucine, isoleucine, valine or methionine.

The present invention is further directed to a DNA molecule encoding a modified protoporphyrinogen oxidase (protox) comprising a plant protox having a first amino acid substitution and a second amino acid substitution; the first amino acid substitution having the property of conferring resistance to a protox inhibitor; and the second amino acid substitution having the property of enhancing the resistance conferred by the first amino acid substitution. Preferred is a DNA molecule encoding a modified protoporphyrinogen oxidase (protox) comprising a plant protox, wherein the plant is selected from the group consisting of maize, wheat, soybean, cotton, sugar beet, oilseed rape, rice, sorghum, sugar cane, and Arabidopsis. More preferred is a DNA molecule encoding a modified protoporphyrinogen oxidase (protox) comprising a plant protox, wherein the plant is selected from the group consisting of maize, wheat, soybean, sugar beet, and Arabidopsis.

Preferred is a DNA molecule wherein the second amino acid substitution occurs at a position selected from the group consisting of:

(a) the position corresponding to the serine at amino acid 305 of SEQ ID NO:2;

(b) the position corresponding to the threonine at amino acid 249 of SEQ ID NO:2;

(c) the position corresponding to the proline at amino acid 118 of SEQ ID NO:2;

(d) the position corresponding to the asparagine at amino acid 425 of SEQ ID NO:2; and (e) the position corresponding to the tyrosine at amino acid 498 of SEQ ID NO:2.

Also preferred is a DNA molecule wherein the first amino acid substitution occurs at a position selected from the group consisting of:

(a) the position corresponding to the arginine at amino acid 88 of SEQ ID NO:6;

(b) the position corresponding to the alanine at amino acid 164 of SEQ ID NO:6;

(c) the position corresponding to the glycine at amino acid 165 of SEQ ID NO:6;

(d) the position corresponding to the tyrosine at amino acid 370 of SEQ ID NO:6;

(e) the position corresponding to the cysteine at amino acid 159 of SEQ ID NO:6;

(f) the position corresponding to the isoleucine at amino acid 419 of SEQ ID NO:6.

(g) the position corresponding to the valine at amino acid 356 of SEQ ID NO:10;

(h) the position corresponding to the serine at amino acid 421 of SEQ ID NO:10;

(i) the position corresponding to the valine at amino acid 502 of SEQ ID NO:10;

(j) the position corresponding to the alanine at amino acid 211 of SEQ ID NO:10;

(k) the position corresponding to the glycine at amino acid 212 of SEQ ID NO:10;

(l) the position corresponding to the isoleucine at amino acid 466 of SEQ ID NO:10;

(m) the position corresponding to the proline at amino acid 369 of SEQ ID NO:12;

(n) the position corresponding to the alanine at amino acid 226 of SEQ ID NO:12;

(o) the position corresponding to the tyrosine at amino acid 432 of SEQ ID NO:12;

(p) the position corresponding to the valine at amino acid 517 of SEQ ID NO:12;

(q) the position corresponding to the tyrosine at amino acid 428 of SEQ ID NO:16;

(r) the position corresponding to the proline at amino acid 365 of SEQ ID NO:16; and (s) the position corresponding to the tyrosine at amino acid 449 of SEQ ID NO:18.

Particularly preferred is a DNA molecule encoding a modified protoporphyrinogen oxidase (protox) comprising a plant protox wherein the plant protox comprises an amino acid sequence selected from the group consisting of SEQ ID NOs: 2, 4, 6, 8, 10, 12, 16, 18, 20, 22, and 37. Most preferred is a DNA molecule encoding a modified protoporphyrinogen oxidase (protox) comprising a plant protox, wherein the plant protox comprises an amino acid sequence selected from the group consisting of SEQ ID NOs: 2, 4, 6, 8, 10, 12, and 18.

More preferred is a DNA molecule, wherein the first amino acid substitution occurs at a position selected from the group consisting of:
(a) the position corresponding to the arginine at amino acid 88 of SEQ ID NO:6;
(b) the position corresponding to the alanine at amino acid 164 of SEQ ID NO:6;
(c) the position corresponding to the glycine at amino acid 165 of SEQ ID NO:6;
(d) the position corresponding to the tyrosine at amino acid 370 of SEQ ID NO:6;
(e) the position corresponding to the cysteine at amino acid 159 of SEQ ID NO:6; and
(f) the position corresponding to the isoleucine at amino acid 419 of SEQ ID NO:6.

More preferred is a DNA molecule wherein the second amino acid substitution occurs at the position corresponding to the serine at amino acid 305 of SEQ ID NO:2 and the first amino acid substitution occurs at a position selected from the group consisting of:
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein the serine occurring at the position corresponding to amino acid 305 of SEQ ID NO:2 is replaced with leucine.

More preferred is a DNA molecule wherein the second amino acid substitution occurs at the position corresponding to the threonine at amino acid 249 of SEQ ID NO:2 and the first amino acid substitution occurs at a position selected from the group consisting of:
(a) the position corresponding to the alanine at amino acid 164 of SEQ ID NO:6; and
(b) the position corresponding to the tyrosine at amino acid 370 of SEQ ID NO:6.

Particularly preferred is a DNA wherein the threonine occurring at the position corresponding to amino acid 249 of SEQ ID NO:2 is replaced with an amino acid selected from the group consisting of isoleucine and alanine.

More preferred is a DNA molecule wherein the second amino acid substitution occurs at the position corresponding to the proline at amino acid 118 of SEQ ID NO:2 and the first amino acid substitution occurs at a position selected from the group consisting of:
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein the proline occurring at the position corresponding to amino acid 118 of SEQ ID NO:2 is replaced with a leucine.

More preferred is a DNA molecule wherein the second amino acid substitution occurs at the position corresponding to the asparagine at amino acid 425 of SEQ ID NO:2 and the first amino acid substitution occurs at a position selected from the group consisting of:
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein the asparagine occurring at the position corresponding to amino acid 425 of SEQ ID NO:2 is replaced with a serine.

More preferred is a DNA molecule wherein the second amino acid substitution occurs the position corresponding to the tyrosine at amino acid 498 of SEQ ID NO:2 and the first amino acid substitution occurs at a position selected from the group consisting of:
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein the tyrosine occurring at the position corresponding to amino acid 498 of SEQ ID NO:2 is replaced with a cysteine.

More preferred is a DNA molecule wherein the tyrosine occurring at the position corresponding to amino acid 370 of SEQ ID NO:6 is replaced with an amino acid selected from the group consisting of cysteine, isoleucine, leucine, threonine, valine and methionine.

Particularly preferred is a DNA molecule wherein the tyrosine occurring at the position corresponding to amino acid 370 of SEQ ID NO:6 is replaced with an amino acid selected from the group consisting of cysteine, isoleucine, leucine, threonine and methionine.

More preferred is a DNA molecule wherein the alanine occurring at the position corresponding to residue 164 of SEQ ID NO:6 is replaced with an amino acid selected from the group consisting of valine, threonine, leucine, cysteine and tyrosine.

More preferred is a DNA molecule wherein the glycine occurring at the position corresponding to residue 165 of SEQ ID NO:6 is replaced with an amino acid selected from the group consisting of serine and leucine.

Particularly preferred is a DNA molecule wherein the glycine occurring at the position corresponding to residue 165 of SEQ ID NO:6 is replaced with a serine.

Particularly preferred is a DNA molecule wherein the arginine occurring at the position corresponding to residue 88 of SEQ ID NO:6 is replaced with a cysteine.

More preferred is a DNA molecule wherein the cysteine occurring at the position corresponding to residue 159 of SEQ ID NO:6 is replaced with an amino acid selected from the group consisting of phenylalanine and lysine.

Particularly preferred is a DNA molecule wherein the cysteine occurring at the position corresponding to residue 159 of SEQ ID NO:6 is replaced with a phenylalanine.

More preferred is a DNA molecule wherein the isoleucine occurring at the position corresponding to residue 419 of SEQ ID NO:6 is replaced with an amino acid selected from the group consisting of threonine, histidine, glycine and asparagine.

Particularly preferred is a DNA molecule wherein the isoleucine occurring at the position corresponding to residue 419 of SEQ ID NO:6 is replaced with a threonine.

More preferred is a DNA molecule wherein the valine occurring at the position corresponding to residue 356 of SEQ ID NO:10 is replaced with a leucine.

More preferred is a DNA molecule wherein the serine occurring at the position corresponding to residue 421 of SEQ ID NO:10 is replaced with a proline.

More preferred is a DNA molecule wherein the valine occurring at the position corresponding to residue 502 of SEQ ID NO:10 is replaced with a alanine.

More preferred is a DNA molecule wherein the isoleucine occurring at the position corresponding to residue 466 of SEQ ID NO:10 is replaced with a threonine.

More preferred is a DNA molecule wherein the glycine occurring at the position corresponding to residue 212 of SEQ ID NO:10 is replaced with a serine.

More preferred is a DNA molecule wherein the alanine occurring at the position corresponding to residue 211 of SEQ ID NO:10 is replaced with a valine or threonine.

More preferred is a DNA molecule wherein the proline occurring at the position corresponding to residue 369 of SEQ ID NO:12 is replaced with a serine or a histidine.

More preferred is a DNA molecule wherein the alanine occurring at the position corresponding to residue 226 of SEQ ID NO:12 is replaced with a leucine or threonine.

More preferred is a DNA molecule wherein the tyrosine occurring at the position corresponding to residue 432 of SEQ ID NO:12 is replaced with a leucine or isoleucine.

More preferred is a DNA molecule wherein the valine occurring at the position corresponding to residue 517 of SEQ ID NO:12 is replaced with a alanine.

More preferred is a DNA molecule wherein the tyrosine occurring at the position corresponding to residue 428 of SEQ ID NO:16 is replaced with cysteine or arginine.

More preferred is a DNA molecule wherein the proline occurring at the position corresponding to residue 365 of SEQ ID NO:16 is replaced with serine.

More preferred is a DNA molecule wherein the proline occurring at the position corresponding to residue 449 of SEQ ID NO:18 is replaced with an amino acid selected from the group consisting of leucine, isoleucine, valine and methionine.

The present invention is still further directed to a DNA molecule encoding a modified protoporphyrinogen oxidase (protox) comprising a plant protox having a double amino acid substitution, wherein both amino acid substitutions are required for there to be resistance to a protox inhibitor. Preferred is a DNA molecule encoding a modified protoporphyrinogen oxidase (protox) comprising a plant protox, wherein the plant is selected from the group consisting of maize, wheat, soybean, cotton, sugar beet, oilseed rape, rice, sorghum, sugar cane, and Arabidopsis. More preferred is a DNA molecule encoding a modified protoporphyrinogen oxidase (protox) comprising a plant protox, wherein the plant is maize.

Preferred is a DNA molecule having a double amino acid substitution, wherein one amino acid substitution occurs at the position corresponding to the leucine at amino acid 347 of SEQ ID NO:6, and wherein the second amino acid substitution occurs at the position corresponding to the alanine at amino acid 453 of SEQ ID NO:6.

Particularly preferred is a DNA molecule having a double amino acid substitution, wherein a leucine occurring at the position corresponding to amino acid 347 of SEQ ID NO:6 is replaced with a serine, and wherein an alanine occurring at the position corresponding to amino acid 453 of SEQ ID NO:6 is replaced with a threonine.

The present invention is directed to expression cassettes and recombinant vectors comprising the expression cassettes comprising essentially a promoter, but especially a promoter that is active in a plant, operatively linked to a DNA molecule encoding the protoporphyrinogen oxidase (protox) enzyme from a eukaryotic organism according to the invention. The expression cassette according to the invention may in addition further comprise a signal sequence operatively linked to the DNA molecule, wherein the signal sequence is capable of targeting the protein encoded by the DNA molecule into the chloroplast or the mitochondria.

The invention relates to a chimeric gene, which comprises an expression cassette comprising essentially a promoter, but especially a promoter that is active in a plant, operatively linked to a heterologous DNA molecule encoding a protoporphyrinogen oxidase (protox) enzyme from a eukaryotic organism according to the invention. Preferred is a chimeric gene, wherein the DNA molecule encodes an protoporphyrinogen oxidase (protox) enzyme from a plant selected from the group consisting of Arabidopsis, sugar cane, soybean, barley, cotton, tobacco, sugar beet, oilseed rape, maize, wheat, sorghum, rye, oats, turf and forage grasses, millet, forage and rice. More preferred is a chimeric gene, wherein the DNA molecule encodes an protoporphyrinogen oxidase (protox) enzyme from a plant selected from the group consisting of soybean, cotton, tobacco, sugar beet, oilseed rape, maize, wheat, sorghum, rye, oats, turf grass, and rice. Particularly preferred is a chimeric gene, wherein the DNA molecule encodes an protoporphyrinogen oxidase (protox) enzyme from a plant selected from the group consisting of wheat, soybean, cotton, sugar beet, oilseed rape, rice and sorghum. Most preferred is a chimeric gene, wherein the DNA molecule encodes an protoporphyrinogen oxidase (protox) enzyme from a plant selected from the group consisting of soybean, sugar beet, and wheat.

More preferred is a chimeric gene comprising a promoter active in a plant operatively linked to a heterologous DNA molecule encoding a protoporphyrinogen oxidase (protox) selected from the group consisting of a wheat protox comprising the sequence set forth in SEQ ID NO:10, a soybean protox comprising the sequence set forth in SEQ ID NO:12, cotton protox comprising the sequence set forth in SEQ ID NO:16, a sugar beet protox comprising the sequence set forth in SEQ ID NO:18, an oilseed rape protox comprising the sequence set forth in SEQ ID NO:20, a rice protox comprising the sequence set forth in SEQ ID NO:22, a sorghum protox comprising the sequence set forth in SEQ ID NO:24, and a sugar cane protox comprising the sequence set forth in SEQ ID NO:37. More preferred is a chimeric gene, wherein the protoporphyrinogen oxidase.(protox) is selected from the group consisting of a wheat protox comprising the sequence set forth in SEQ ID NO:10, a soybean protox comprising the sequence set forth in SEQ ID NO:12, and a sugar beet protox comprising the sequence set forth in SEQ ID NO:18.

Particularly preferred is a chimeric gene, wherein the DNA molecule encodes a protein from an Arabidopsis species having protox-1 activity or protox-2 activity, preferably wherein the protein comprises the amino acid sequence set forth in SEQ ID NO:2 or SEQ ID NO:4.

Particularly preferred is a chimeric gene, wherein the DNA molecule encodes a protein from maize having protox-1 activity or protox-2 activity, preferably wherein the protein comprises the amino acid sequence set forth in set forth in SEQ ID NO:6 or SEQ ID NO:8.

Particularly preferred is a chimeric gene, wherein the DNA molecule encodes a protein from wheat having protox-1 activity preferably wherein the protein comprises the amino acid sequence set forth in SEQ ID NO:10.

Particularly preferred is a chimeric gene, wherein the DNA molecule encodes a protein from soybean having protox-1 activity, preferably wherein the protein comprises the amino acid sequence set forth in SEQ ID NO:12.

Particularly preferred is a chimeric gene, wherein the DNA molecule encodes a protein from cotton having protox-1 activity, preferably wherein the protein comprises the amino acid sequence set forth in SEQ ID NO:16.

Particularly preferred is a chimeric gene, wherein the DNA molecule encodes a protein from sugar beet having protox-1 activity, preferably wherein the protein comprises the amino acid sequence set forth in SEQ ID NO:18.

Particularly preferred is a chimeric gene, wherein the DNA molecule encodes a protein from oilseed rape having protox-1 activity, preferably wherein the protein comprises the amino acid sequence set forth in SEQ ID NO:20.

Particularly preferred is a chimeric gene, wherein the DNA molecule encodes a protein from rice having protox-1 activity, preferably wherein the protein comprises the amino acid sequence set forth in SEQ ID NO:22.

Particularly preferred is a chimeric gene, wherein the DNA molecule encodes a protein from sorghum having protox-1 activity, preferably wherein the protein comprises the amino acid sequence set forth in SEQ ID NO:24.

Particularly preferred is a chimeric gene, wherein the DNA molecule encodes a protein from sugar cane having protox-1 activity, preferably wherein the protein comprises the amino acid sequence set forth in SEQ ID NO:37.

The invention also embodies a chimeric gene, which comprises an expression cassette comprising essentially a promoter, but especially a promoter that is active in a plant, operatively linked to the DNA molecule encoding an protoporphyrinogen oxidase (protox) enzyme from a eukaryotic organism according to the invention, which is resistant to herbicides at levels that inhibit the corresponding unmodified version of the enzyme. Preferred is a chimeric gene, wherein the DNA molecule encodes an protoporphyrinogen oxidase (protox) enzyme from a plant selected from the group consisting of Arabidopsis, sugar cane, soybean, barley, cotton, tobacco, sugar beet, oilseed rape, maize, wheat, sorghum, rye, oats, turf and forage grasses, millet, forage and rice. More preferred is a chimeric gene, wherein the DNA molecule encodes an protoporphyrinogen oxidase (protox) enzyme from a plant selected from the group consisting of soybean, cotton, tobacco, sugar beet, oilseed rape, maize, wheat, sorghum, rye, oats, turf grass, and rice. Particularly preferred is a chimeric gene, wherein the DNA molecule encodes an protoporphyrinogen oxidase (protox) enzyme from a plant selected from the group consisting of Arabidopsis, soybean, cotton, sugar beet, oilseed rape, maize, wheat, sorghum, and rice.

Encompassed by the present invention is a chimeric gene comprising a promoter that is active in a plant operatively linked to the DNA molecule encoding a modified protoporphyrinogen oxidase (protox) comprising a eukaryotic protox having at least one amino acid modification, wherein the amino acid modification has the property of conferring resistance to a protox inhibitor.

Also encompassed by the present invention is a chimeric gene comprising a promoter that is active in a plant operatively linked to the DNA molecule encoding a modified protoporphyrinogen oxidase (protox) comprising a plant protox having a first amino acid substitution and a second amino acid substitution; the first amino acid substitution having the property of conferring resistance to a protox inhibitor; and the second amino acid substitution having the property of enhancing the resistance conferred by the first amino acid substitution. Preferred is the chimeric gene additionally comprising a signal sequence operatively linked to the DNA molecule, wherein the signal sequence is capable of targeting the protein encoded by the DNA molecule into the chloroplast or in the mitochondria.

The chimeric gene according to the invention may in addition further comprise a signal sequence operatively linked to the DNA molecule, wherein the signal sequence is capable of targeting the protein encoded by the DNA molecule into the chloroplast. The chimeric gene according to the invention may in addition further comprise a signal sequence operatively linked to the DNA molecule, wherein the signal sequence is capable of targeting the protein encoded by the DNA molecule into the mitochondria.

Also encompassed by the present invention is any of the DNA sequences mentioned herein before, which is stably integrated into a host genome.

The invention further relates to a recombinant DNA molecule comprising a plant protoporphyrinogen oxidase (protox) or a functionally equivalent derivative thereof.

The invention further relates to a recombinant DNA vector comprising the recombinant DNA molecule of the invention.

A further object of the invention is a recombinant vector comprising the chimeric gene according to the invention, wherein the vector is capable of being stably transformed into a host cell.

A further object of the invention is a recombinant vector comprising the chimeric gene according to the invention, wherein the vector is capable of being stably transformed into a plant, plant seeds, plant tissue or plant cell. Preferred is a recombinant vector comprising the chimeric gene according to the invention, wherein the vector is capable of being stably transformed into a plant. The plant, plant seeds, plant tissue or plant cell stably transformed with the vector is capable of expressing the DNA molecule encoding a protoporphyrinogen oxidase (protox). Preferred is a recombinant vector, wherein the plant, plant seeds, plant tissue or plant cell stably transformed with the the vector is capable of expressing the DNA molecule encoding a protoporphyrinogen oxidase (protox) from a plant that is resistant to herbicides at levels that inhibit the corresponding unmodified version of the enzyme.

Preferred is a recombinant vector comprising the chimeric gene comprising a promoter active in a plant operatively linked to a heterologous DNA molecule encoding a protoporphyrinogen oxidase (protox) selected from the group consisting of a wheat protox comprising the sequence set forth in SEQ ID NO:10, a soybean protox comprising the sequence set forth in SEQ ID NO:12, cotton protox comprising the sequence set forth in SEQ ID NO:16, a sugar beet protox comprising the sequence set forth in SEQ ID NO:18, an oilseed rape protox comprising the sequence set forth in SEQ ID NO:20, a rice protox comprising the sequence set forth in SEQ ID NO:22, a sorghum protox comprising the sequence set forth in SEQ ID NO:24, and a sugar cane protox comprising the sequence set forth in SEQ ID NO:37, wherein the vector is capable of being stably transformed into a host cell.

Also preferred is recombinant vector comprising the chimeric gene comprising a promoter that is active in a plant operatively linked to the DNA molecule encoding a modified protoporphyrinogen oxidase (protox) comprising a plant protox having a first amino acid substitution and a second amino acid substitution; the first amino acid substitution having the property of conferring resistance to a protox inhibitor; and the second amino acid substitution having the property of enhancing the resistance conferred by the first amino acid substitution, wherein the vector is capable of being stably transformed into a plant cell.

Also encompassed by the present invention is a host cell stably transformed with the vector according to the invention, wherein the host cell is capable of expressing the DNA molecule. Preferred is a host cell selected from the group consisting of a plant cell, a bacterial cell, a yeast cell, and an insect cell.

The present invention is further directed to plants and the progeny thereof, plant tissue and plant seeds tolerant to herbicides that inhibit the naturally occurring protox activity in these plants, wherein the tolerance is conferred by a gene expressing a modified inhibitor-resistant protox enzyme as taught herein. Representative plants include any plants to which these herbicides may be applied for their normally intended purpose. Preferred are agronomically important crops, i.e., angiosperms and gymnosperms such as Arabidopsis, sugar cane, soybean, barley, cotton, tobacco, sugar beet, oilseed rape, maize, wheat, sorghum, rye, oats, tomato, potato, turf and forage grasses, millet, forage, and rice and the like. More preferred are agronomically important crops, i.e., angiosperms and gynmosperms such as Arabidopsis, cotton, soybean, oilseed rape, sugar beet, maize, rice, wheat, barley, oats, rye, sorghum, millet, turf, forage, turf grasses. Particularly preferred are agronomically important crops, i.e., angiosperms and gymnosperms such as Arabidopsis, soybean, cotton, sugar beet, oilseed rape, maize, wheat, sorghum, and rice.

Preferred is a plant comprising the DNA molecule encoding a modified protoporphyrinogen oxidase (protox) comprising a plant protox having a first amino acid substitution and a second amino acid substitution; the first amino acid substitution having the property of conferring resistance to a protox inhibitor; and the second amino acid substitution having the property of enhancing the resistance conferred by the first amino acid substitution, wherein the DNA molecule is expressed in the plant and confers upon the plant tolerance to a herbicide in amounts that inhibit naturally occurring protox activity. Preferred is a plant, wherein the DNA molecule replaces a corresponding naturally occurring protox coding sequence. Comprised by the present invention is a plant and the progeny thereof comprising the chimeric gene according to the invention, wherein the chimeric gene confers upon the plant tolerance to a herbicide in amounts that inhibit naturally occurring protox activity.

Encompassed by the present invention are transgenic plant tissue, including plants and the progeny thereof, seeds, and cultured tissue, stably transformed with at least one chimeric gene according to the invention. Preferred is transgenic plant tissue, including plants, seeds, and cultured tissue, stably transformed with at least one chimeric gene that comprises an expression cassette comprising essentially a promoter, but especially a promoter that is active in a plant, operatively linked to the DNA molecule encoding an protoporphyrinogen oxidase (protox) enzyme that is resistant to herbicides at levels that inhibit the corresponding unmodified version of the enzyme in the plant tissue.

The present invention is further directed to plants, plant tissue, plant seeds, and plant cells tolerant to herbicides that inhibit the naturally occurring protox activity in these plants, wherein the tolerance is conferred by increasing expression of wild-type herbicide-sensitive protox. This results in a level of a protox enzyme in the plant cell at least sufficient to overcome growth inhibition caused by the herbicide. The level of expressed enzyme generally is at least two times, preferably at least five times, and more preferably at least ten times the natively expressed amount. Increased expression may be due to multiple copies of a wild-type protox gene; multiple occurrences of the coding sequence within the gene (i.e. gene amplification) or a mutation in the non-coding, regulatory sequence of the endogenous gene in the plant cell.

Plants having such altered gene activity can be obtained by direct selection in plants by methods known in the art (see, e.g. U.S. Pat. No. 5,162,602, and U.S. Pat. No. 4,761,373, and references cited therein). These plants also may be obtained by genetic engineering techniques known in the art. Increased expression of a herbicide-sensitive protox gene can also be accomplished by stably transforming a plant cell with a recombinant or chimeric DNA molecule comprising a promoter capable of driving expression of an associated structural gene in a plant cell operatively linked to a homologous or heterologous structural gene encoding the protox enzyme.

The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., *Bio Techniques* 4:320–334 (1986)), electroporation (Riggs et al, *Proc. Natl. Acad. Sci. USA* 83:5602–5606 (1986), Agrobacterium mediated transformation (Hinchee et al., *Biotechnology* 6:915–921 (1988)), direct gene transfer (Paszkowski et al., *EMBO J.* 3:2717–2722 (1984)), ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)), protoplast transfonnation/regeneration methods (see U.S. Pat. No. 5,350,689 issued sep. 27, 1994 to Ciba-Geigy Corp.), and pollen transformation (see U.S. Pat. No. 5,629,183). Also see, Weissinger et al., *Annual Rev. Genet.* 22:421–477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA*, 85:4305–4309 (1988)(maize); Klein et al., *Bio/Technology* 6:559–563 (1988)(maize); Klein et al., *Plant Physiol.* 91:440–444 (1988)(maize); Fromm et al., *Bio/Technology* 8:833–839 (1990); Gordon-Kamm et al., *Plant Cell* 2:603–618 (1990) (maize); and U.S. Pat. Nos. 5,591,616 and 5,679,558 (rice).

Comprised within the scope of the present invention are transgenic plants, in particular transgenic fertile plants transformed by means of the aforedescribed processes and their asexual and/or sexual progeny, which still are resistant or at least tolerant to inhibition by a herbicide at levels that normally are inhibitory to the naturally occurring protox activity in the plant. Progeny plants also include plants with a different genetic background than the parent plant, which plants result from a backcrossing program and still comprise in their genome the herbicide resistance trait according to the invention. Very especially preferred are hybrid plants that are resistant or at least tolerant to inhibition by a herbicide at levels that normally are inhibitory to the naturally occurring protox activity in the plant.

The transgenic plant according to the invention may be a dicotyledonous or a monocotyledonous plant. Preferred are monocotyledonous plants of the Graminaceae family involving Lolium, Zea, Triticum, Triticale, Sorghum, Saccharum, Bromus, Oryzae, Avena, Hordeum, Secale and Setaria plants. More preferred are transgenic maize, wheat, barley, sorghum, rye, oats, sugar cane, turf and forage grasses, millet and rice. Especially preferred are maize, wheat, sorghum, rye, oats, turf grasses and rice.

Among the dicotyledonous plants Arabidopsis, soybean, cotton, sugar beet, oilseed rape, tobacco, tomato, potato, and sunflower are more preferred herein. Especially preferred are soybean, cotton, tobacco, sugar beet, tomato, potato, and oilseed rape.

The expression 'progeny' is understood to embrace both, "asexually" and "sexually" generated progeny of transgenic plants. This definition is also meant to include all mutants and variants obtainable by means of known processes, such as for example cell fusion or mutant selection and that still exhibit the characteristic properties of the initial transformed plant, together with all crossing and fusion products of the transformed plant material. This also includes progeny plants that result from a backcrossing program, as long as the progeny plants still contain the herbicide resistant trait according to the invention.

Another object of the invention concerns the proliferation material of transgenic plants. The proliferation material of transgenic plants is defined relative to the invention as any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants.

Parts of plants, such as for example flowers, stems, fruits, leaves, roots originating in transgenic plants or their progeny previously transformed by means of the process of the invention and therefore consisting at least in part of transgenic cells, are also an object of the present invention.

A further object of the invention is a method of producing plants, protoplasts, cells, calli, tissues, organs, seeds, embryos, pollen, egg cells, zygotes, together with any other propagating material, parts of plants, such as for example flowers, stems, fruits, leaves, roots originating in transgenic plants or their progeny previously transformed by means of the process of the invention, which therefore produce an inhibitor resistant form of a plant protox enzyme by transforming the plant, plant parts with the DNA according to the invention. Preferred is a method of producing a host cell comprising an isolated DNA molecule encoding a protein from a eukaryote having protoporphyrinogen oxidase (protox) activity comprising transforming the host cell with a recombinant vector molecule according to the invention. Further preferred is a method of producing a plant cell comprising an isolated DNA molecule encoding a protein from a eukaryote having protoporphyrinogen oxidase (protox) activity comprising transforming the plant cell with a recombinant vector molecule according to the invention. Preferred is a method of producing transgenic progeny of a transgenic parent plant comprising an isolated DNA molecule encoding a protein from a eukaryote having protoporphyrinogen oxidase (protox) activity comprising transforming the parent plant with a recombinant vector molecule according to the invention and transferring the herbicide tolerant trait to the progeny of the transgenic parent plant involving known plant breeding techniques.

Preferred is a method for the production of plants, plant tissues, plant seeds and plant parts, which produce an inhibitor-resistant form of the plant protox enzyme, wherein the plants, plant tissues, plant seeds and plant parts have been stably transformed with a structural gene encoding the resistant protox enzyme. Particularly preferred is a method for the production of plants, plant tissues, plant seeds and plant parts, wherein the plants, plant tissues, plant seeds and plant parts have been stably transformed with the DNA according to the invention. Especially preferred is a method for the production of the plants, plant tissues, plant seeds and plant parts, which produce an inhibitor-resistant form of the plant protox enzyme, wherein the plants, plant tissues, plant seeds and plant parts have been prepared by direct selection techniques whereby herbicide resistant lines are isolated, characterized and developed.

The genetic properties engineered into the transgenic seeds and plants described above are passed on by sexual reproduction or vegetative growth and can thus be maintained and propagated in progeny plants. Generally the maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding that aims at the development of plants with improved properties such as tolerance of pests, herbicide tolerance, or stress tolerance, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines that for example increase the effectiveness of conventional methods such as herbicide or pesticide treatment or allow to dispense with the methods due to their modified genetic properties. Alternatively new crops with improved stress tolerance can be obtained that, due to their optimized genetic "equipment", yield harvested product of better quality than products that were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof.

Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is thus a further object of the present invention to provide plant propagation material for cultivated plants, but especially plant seed that is treated with an seed protectant coating customarily used in seed treatment.

It is a further aspect of the present invention to provide new agricultural methods such as the methods exemplified above, which are characterized by the use of transgenic plants, transgenic plant material, or transgenic seed according to the present invention. Comprised by the present invention is an agricultural method, wherein a transgenic plant or the progeny thereof is used comprising a chimeric gene according to the invention in an amount sufficient to express herbicide resistant forms of herbicide target proteins in a plant to confer tolerance to the herbicide.

To breed progeny from plants transformed according to the method of the present invention, a method such as that which follows may be used: maize plants produced as described in the examples set forth below are grown in pots in a greenhouse or in soil, as is known in the art, and permitted to flower. Pollen is obtained from the mature tassel and used to pollinate the ears of the same plant, sibling plants, or any desirable maize plant. Similarly, the ear developing on the transformed plant may be pollinated by pollen obtained from the same plant, sibling plants, or any desirable maize plant. Transformed progeny obtained by this method may be distinguished from non-transformed progeny by the presence of the introduced gene(s) and/or accompanying DNA (genotype), or the phenotype conferred. The transformed progeny may similarly be selfed or crossed to other plants, as is normally done with any plant carrying a desirable trait. Similarly, tobacco or other transformed plants produced by this method may be selfed or crossed as is known in the art in order to produce progeny with desired characteristics. Similarly, other transgenic organisms produced by a combination of the methods known in the art and this invention may be bred as is known in the art in order to produce progeny with desired characteristics.

The modified inhibitor-resistant protox enzymes of the invention have at least one amino acid substitution, addition or deletion relative to their naturally occurring counterpart (i.e. inhibitor-sensitive forms that occur naturally in a plant without being manipulated, either directly via recombinant DNA methodology or indirectly via selective breeding, etc., by man). Amino acid positions that may be modified to yield an inhibitor-resistant form of the protox enzyme, or enhance inhibitor resistance, are indicated in bold type in Table 1A in the context of plant protox-1 sequences from Arabidopsis, maize, soybean, cotton, sugar beet, oilseed rape, rice, sorghum, wheat, and sugar cane. The skilled artisan will appreciate that equivalent changes may be made to any plant protox gene having a structure sufficiently similar to the protox enzyme sequences shown herein to allow alignment and identification of those amino acids that are modified according to the invention to generate inhibitor-resistant forms:of the enzyme. Such additional plant protox genes may be obtained using standard techniques as described in International application no. PCT/IB95/00452 filed Jun. 8, 1995, published Dec. 21, 1995 as WO 95/34659 whose relevant parts are herein incorporated by reference.

DNA molecules encoding the herbicide resistant protox coding sequences taught herein may be genetically engineered for optimal expression in a crop plant. This may include altering the coding sequence of the resistance allele for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol.* 11: 194 (1993)).

Genetically engineering a protox coding sequence for optimal expression may also include operatively linking the appropriate regulatory sequences (i.e. promoter, signal sequence, transcriptional terminators). Examples of promoters capable of functioning in plants or plant cells (i.e., those capable of driving expression of the associated structural genes such as protox in plant cells) include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, heat shock protein promoter from Brassica with reference to EPA 0 559 603 (hsp80 promoter), Arabidopsis actin promoter and the SuperMas promoter with reference to WO 95/14098 and the like. Preferred promoters will be those that confer high level constitutive expression or, more preferably, those that confer specific high level expression in the tissues susceptible to damage by the herbicide. Preferred promoters are the rice actin promoter (McElroy et al., *Mol. Gen. Genet.* 231: 150 (1991)), maize ubiquitin promoter (EP 0 342 926; Taylor et al., *Plant Cell Rep.* 12: 491 (1993)), and the PR-1 promoter from tobacco, Arabidopsis, or maize (see U.S. Pat. No. 5,614,395 to Ryals et al., incorporated by reference herein in its entirety). The promoters themselves may be modified to manipulate promoter strength to increase protox expression, in accordance with art-recognized procedures.

The inventors have also discovered that another preferred promoter for use with the inhibitor-resistant protox coding sequences is the promoter associated with the native protox gene (i.e. the protox promoter; see copending, co-owned U.S. patent application Ser. No. 08/808,323, entitled "Promoters from Protoporphyrinogen Oxidase Genes", incorporated by reference herein in its entirety.) The promoter sequence from an Arabidopsis protox-1 gene is set forth in SEQ ID NO:13, the promoter sequence from a maize protox-1 gene is set forth in SEQ ID NO:14, and the promoter sequence from a sugar beet protox-1 gene is set forth in SEQ ID NO:26.

Since the protox promoter itself is suitable for expression of inhibitor-resistant protox coding sequences, the modifications taught herein may be made directly on the native protox gene present in the plant cell genome without the need to construct a chimeric gene with heterologous regulatory sequences. Such modifications can be made via directed mutagenesis techniques such as homologous recombination and selected for based on the resulting herbicide-resistance phenotype (see, e.g. Example 10, Pazkowski et al., *EMBO J.* 7. 4021–4026 (1988), and U.S. Pat. No. 5,487,992, particularly columns 18–19 and Example 8). An added advantage of this approach is that besides containing the native protox promoter, the resulting modified gene will also include any other regulatory elements, such as signal or transit peptide coding sequences, which are part of the native gene.

In the event of transformation of the nuclear genome, signal or transit peptides may be fused to the protox coding sequence in chimeric DNA constructs of the invention to direct transport of the expressed protox enzyme to the desired site of action. Examples of signal peptides include those natively linked to the plant pathogenesis-related proteins, e.g. PR-1, PR-2, and the like. See, e.g., Payne et al., *Plant Mol. Biol.* 11:89–94 (1988). Examples of transit peptides include the chloroplast transit peptides such as those described in Von Heijne et al., *Plant Mol. Biol. Rep.* 9:104–126(1991); Mazur et al., *Plant Physiol.* 85: 1110 (1987); Vorst et al., *Gene* 65: 59 (1988), and mitochondrial transit peptides such as those described in Boutry et al., *Nature* 328:340–342 (1987). Chloroplast and mitochondrial transit peptides are contemplated to be particularly useful with the present invention as protox enzymatic activity typically occurs within the mitochondria and chloroplast. Most preferred for use are chloroplast transit peptides, as inhibition of the protox enzymatic activity in the chloroplasts is contemplated to be the primary basis for the action of protox-inhibiting herbicides (Witkowski and Halling, *Plant Physiol.* 87: 632 (1988); Lehnen et al., *Pestic. Biochem. Physiol.* 37: 239 (1990); Duke et al., *Weed Sci.* 39: 465 (1991)). Also included are sequences that result in localization of the encoded protein to various cellular compartments such as the vacuole. See, for example, Neuhaus et al., *Proc. Natl. Acad. Sci. USA* 88: 10362–10366 (1991) and Chrispeels, *Ann. Rev. Plant Physiol. Plant Mol. Biol.* 42: 21–53 (1991). The relevant disclosures of these publications are incorporated herein by reference in their entirety.

Chimeric genes of the invention may contain multiple copies of a promoter or multiple copies of the protox structural genes. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes that can be easily detected by a visible reaction, for example a color reaction, for example luciferase, β-glucuronidase, or β-galactosidase.

The method of positive selection of genetically transformed cells into which a desired nucleotide sequence can be incorporated by providing the transformed cells with a selective advantage is herein incorporated by reference as WO 94/20627.

Where a herbicide resistant protox allele is obtained via directed mutation of the native gene in a crop plant or plant cell culture from which a crop plant can be regenerated, it may be moved into commercial varieties using traditional breeding techniques to develop a herbicide tolerant crop without the need for genetically engineering the modified coding sequence and transforming it into the plant. Alternatively, the herbicide resistant gene may be isolated, genetically engineered for optimal expression and then transformed into the desired variety.

Genes encoding altered protox resistant to a protox inhibitor can also be used as selectable markers in plant cell transformation methods. For example, plants, plant tissue or plant cells transformed with a transgene can also be transformed with a gene encoding an altered protox capable of being expressed by the plant. The thus-transformed cells are transferred to medium containing the protox inhibitor wherein only the transformed cells will survive. Protox inhibitors contemplated to be particularly useful as selective agents are the diphenylethers {e.g. acifluorfen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82–556), and phenopylate and its O-phenylpyrrolidino- and piperidinocarbamate analogs and bicyclic triazolones as disclosed in the International patent application WO 92/04827; EP 532146).

The method is applicable to any plant cell capable of being transformed with an altered protox-encoding gene, and can be used with any transgene of interest. Expression of the transgene and the protox gene can be driven by the same promoter functional on plant cells, or by separate promoters.

Modified inhibitor-resistant protox enzymes of the present invention are resistant to herbicides that inhibit the naturally occurring protox activity. The herbicides that inhibit protox include many different structural classes of molecules (Duke et al., *Weed Sci.* 39: 465 (1991); Nandihalli et al., *Pesticide Biochem. Physiol.* 43: 193 (1992); Matringe et al., *FEBS Lett.* 245: 35 (1989); Yanase and Andoh, *Pesticide Biochem. Physiol.* 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. INPP-ethyl, ethyl 2-[1-(2,3,4-trichlorophenyl)-4-nitropyrazolyl-5-oxy] propionate; M&B 39279), pyridine derivatives (e.g. LS 82–556), and phenopylate and its O-phenylpyrrolidino- and piperidinocarbamate analogs.

The diphenylethers of particular significance are those having the general formula

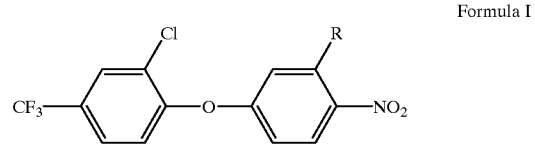

Formula I wherein R equals —COONa (Formula II), —CONHSO$_2$CH$_3$ (Formula III) or —COOCH$_2$COOC$_2$H$_5$ (Formula IV; see Maigrot et al., *Brighton Crop Protection Conference-Weeds*: 47–51 (1989)).

Additional diphenylethers of interest are those where R equals:

$$\underset{\underset{CCH_2OCH_3}{\|}}{NOCH_2COOCH_3}$$

(Formula IVa; see Hayashi et al., *Brighton Crop Protection Conference-Weeds*: 53–58 (1989)).

An additional diphenylether of interest is one having the formula:

(Formula IVb; bifenox, see Dest et al., *Proc. Northeast Weed Sci. Conf.* 27: 31(1973)).

A further diphenylether of interest is one having the formula:

(Formula IVc; oxyfluorfen; see Yih and Swithenbank, *J. Agric. Food Chem.*, 23: 592(1975))

Yet another diphenylether of interest is one having the formula:

(Formula IVd; lactofen, see page 623 of "The Pesticide Manual", 10$^{th}$ ed., ed. by C. Tomlin, British Crop Protection Council, Surrey (1994))

Also of significance are the class of herbicides known as imides, having the general formula (Formula V)

-continued wherein Q equals (Formula VI)

or (Formula VII)

or (Formula VIII)

or (Formula IX)

or (Formula IXa)

or (Formula IXb)

(see Hemper et al. (1995) in "Proceedings of the Eighth International Congress of Pesticide Chemistry", Ragdale et al., eds., Amer. Chem. Soc, Washington, D.C., pp. 42–48 (1994)); and $R_1$ equals H, Cl or F, $R_2$ equals Cl and $R_3$ is an optimally substituted ether, thioether, ester, amino or alkyl group. Alternatively, $R_2$ and $R_3$ together may form a 5 or 6 membered heterocyclic ring. Examples of imide herbicides of particular interest are

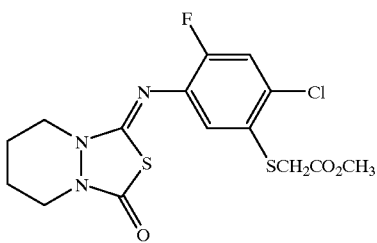

(Formula VIIa; fluthiacet-methyl, see Miyazawa et al., *Brighton Crop Protection Conference-Weeds*, pp. 23–28 (1993))

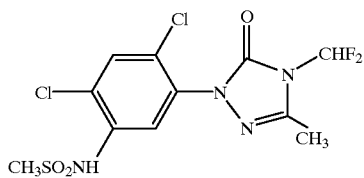

(Formula X sulfentrazone, see Van Saun et al., *Brighton Crop Protection Conference-Weeds*, pp. 77–82 (1991)).

(Formula XI)

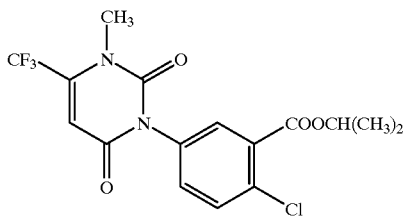

(Formula XII)

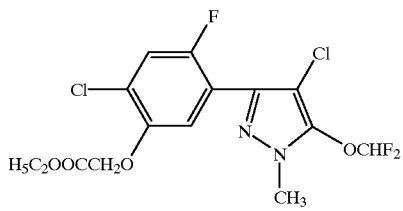

(see Miura et al., Brighton Crop Protection Conference-Weeds: 35–40 (1993))

(Formula XIII)

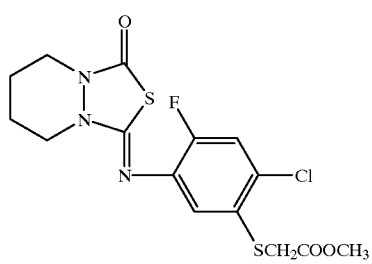

(Formula XIV)

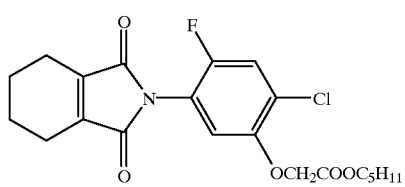

(Formula XV)

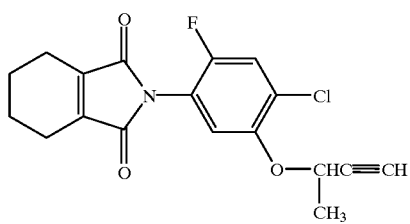

(Formula XVI)

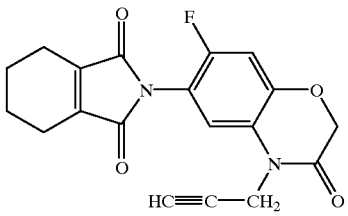

The herbicidal activity of the above compounds is described in the *Proceedings of the 1991 Brighton Crop Protection Conference, Weeds* (British Crop Protection Council) (Formulae X and XVI), *Proceedings of the 1993 Brighton Crop Protection Conference, Weeds* (British Crop Protection Council) (Formulae XII and XIII), U.S. Pat. No. 4,746,352 Formula XI) and *Abstracts of the Weed Science Society of America* vol. 33, pg. 9 (1993)(Formula XIV).

The most preferred imide herbicides are those classified as aryluracils and having the general formula (Formula XVII)

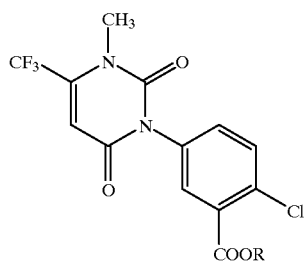

wherein R signifies the group ($C_{2-6}$-alkenyloxy)carbonyl-$C_{1-4}$-alkyl, as disclosed in U.S. Pat. No. 5,183,492, herein incorporated by reference.

Also of significance are herbicides having the general formula:

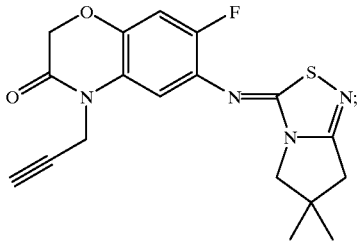

(Formula XVIII; thiadiazimin)
(see Weiler et al., Brighton Crop Protection Conference-Weeds, pp. 29–34 (1993))

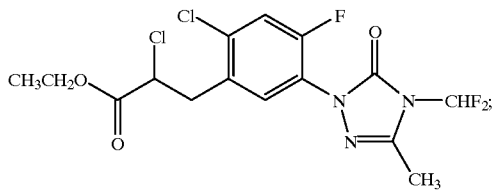

(Formula XIX; carfentrazone)
(see Van Saun et al., Brighton Crop Protection Conference-
Weeds: pp. 19–22 (1993))

N-substituted pyrazoles of the general formula:

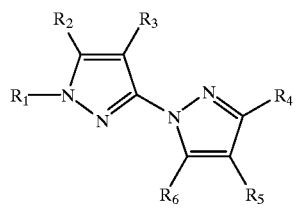

(Formula XX)

wherein $R_1$ is $C_1$–$C_4$-alkyl, optionally substituted by one or more halogen atoms;

$R_2$ is hydrogen, or a $C_1$–$C_4$-alkoxy, each of which is optionally substituted by one or more halogen atoms, or $R_1$ and $R_2$ together from the group —$(CH_2)_n$—X—, where X is bound at $R_2$;

$R_3$ is hydrogen or halogen, $R_4$ is hydrogen or $C_1$–$C_4$-alkyl, $R_5$ is hydrogen, nitro, cyano or the group —$COOR_6$ or —$CONR_7R_8$, and $R_6$ is hydrogen, $C_1$–$C_6$-alkyl, $C_2$–$C_6$-alkenyl or $C_2$–$C_6$-alkynyl;

(see international patent publications WO 94/08999, WO 93/10100, and U.S. Pat. No. 5,405,829 assigned to Schering);

N-phenylpyrazoles, such as:

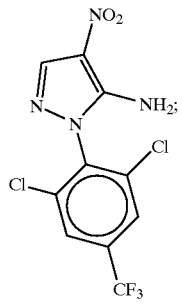

(Formula XXI; nipyraclofen)
(see page 621 of "The Pesticide Manual", 9th ed., by C.R. Worthing, British Crop Protection Council, Surrey (1991))

(Formula XXI; nipyraclofen)
(see page 621 of "The Pesticide Manual", 9th ed., ed. by C. R. Worthing, British Crop Protection Council, Surrey (1991));

and 3-substituted-2-aryl-4,5,6,7-tetrahydroindazoles (Lyga et al. *Pesticide Sci.* 42:29–36 (1994)).

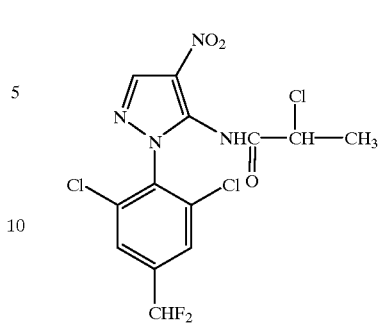

(Fomula XXIa; BAY 11340)

Also of significance are phenylpyrazoles of the type described in WO 96/01254 and WO 97/00246, both of which are hereby incorporated by reference. (Formula XXII).

Also of significance are pyridyl pyrazoles such as the following:

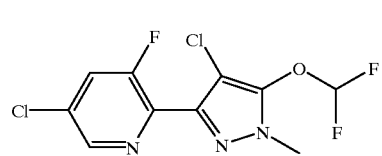

(Formula XXIIIa)

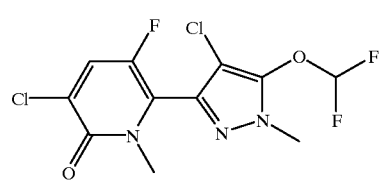

(Formula XXIIIb)

Levels of herbicide that normally are inhibitory to the activity of protox include application rates known in the art, and that depend partly on external factors such as environment, time and method of application. For example, in the case of the imide herbicides represented by Formulae V through IX, and more particularly those represented by Formulae X through XVII, the application rates range from 0.0001 to 10 kg/ha, preferably from 0.005 to 2 kg/ha. This dosage rate or concentration of herbicide may be different, depending on the desired action and particular. compound used, and can be determined by methods known in the art.

A further object of the invention is a method for controlling the growth of undesired vegetation that comprises applying to a population of the plant selected from a group consisting of Arabidopsis, sugar cane, soybean, barley, cotton, tobacco, sugar beet, oilseed rape, maize, wheat, sorghum, rye, oats, turf and forage grasses, millet, forage and rice and the like an effective amount of a protox-inhibiting herbicide. Preferred is a method for controlling the growth of undesired vegetation, which comprises applying to a population of the selected from the group consisting of selected from the group consisting of soybean, cotton, tobacco, sugar beet, oilseed rape, maize, wheat, sorghum, rye, oats, turf grasses and rice an effective amount of a protox-inhibiting herbicide. Particularly preferred is a method for controlling the growth of undesired vegetation, which comprises applying to a population of the selected from the group consisting of Arabidopsis, soybean, cotton, sugar beet, oilseed rape, maize, wheat, sorghum, and rice.

III. Plastid Transformation and Expression

The present invention further encompasses a chimeric gene comprising a promoter capable of expression in a plant plastid operatively linked to a DNA molecule of the present invention. A preferred promoter capable of expression in a plant plastid is a promoter isolated from the 5' flanking region upstream of the coding region of a plastid gene, which may come from the same or a different species, and the native product of which is typically found in a majority of plastid types including those present in non-green tissues. Examples of such promoters are promoters of clpP genes, such as the tobacco clpP gene promoter (WO 97/06250, incorporated herein by reference) and the Arabidopsis clpP gene promoter (U.S. application Ser. No. 09/038,878, incorporated herein by reference). Other promoters that are capable of expressing a DNA molecule in plant plastids are promoters recognized by viral RNA polymerases. Preferred promoters of this type are promoters recognized by a single sub-unit RNA polymerase, such as the T7 gene 10 promoter, which is recognized by the bacteriophage T7 DNA-dependent RNA polymerase. Yet another promoter that is capable of expressing a DNA molecule in plant plastids comes from the regulatory region of the plastid 16S ribosomal RNA operon (Harris et al., *Microbiol. Rev.* 58:700–754 (1994), Shinozaki et al., *EMBO J.* 5:2043–2049 (1986), both of which are incorporated herein by reference). The gene encoding the T7 polymerase is preferably transformed into the nuclear genome and the T7 polymerase is targeted to the plastids using a plastid transit peptide. Expression of the DNA molecules in the plastids can be constitutive or can be inducible. These different embodiment are extensively described in WO 98/11235, incorporated herein by reference. The chimeric gene preferably further comprises a 5' untranslated sequence (5' UTR) functional in plant plastids and a plastid gene 3' untranslated sequence (3' UTR) operatively linked to a DNA molecule of the present invention. Preferably, the 3' UTR is a plastid rps16 gene 3' untranslated sequence. In a further embodiment, the chimeric gene comprises a poly-G tract instead of a 3' untranslated sequence.

The present invention also encompasses a plastid transformation vector comprising the chimeric gene described above and flanking regions for integration into the plastid genome by homologous recombination. The plastid transformation vector may optionally comprise at least one chloroplast origin of replication. The present invention also encompasses a plant plastid transformed with such a plastid transformation vector, wherein the DNA molecule is expressible in the plant plastid. The invention also encompasses a plant or plant cell, including the progeny thereof, comprising this plant plastid. In a preferred embodiment, the plant is homoplasmic for transgenic plastids. The plants transformed in the present invention may be monocots or dicots. A preferred monocot is maize and a preferred dicot is tobacco. Other preferred dicots are tomato and potato.

In a preferred embodiment, the present invention encompasses a chimeric gene comprising a promoter capable of expression in a plant plastid operatively linked to a DNA molecule isolated from a prokaryote or a eukaryote that encodes a native or modified protox enzyme, such as a DNA molecule that encodes a native or modified wheat, soybean, cotton, sugar beet, oilseed rape, rice, sorghum, or sugar cane protox enzyme. Such a DNA molecule is comprised in a plastid transformation vector as described above and plants homoplasmic for transgenic plastid genomes are produced. Expression in plant plastids of a DNA molecule that encodes a modified protox enzyme preferably confers upon the plant tolerance to a herbicide in amounts that inhibit naturally occurring protox activity.

In a further preferred embodiment, the present invention encompasses a chimeric gene comprising (a) a DNA molecule isolated from a plant, which in its native state encodes a polypeptide that comprises a plastid transit peptide, and a mature enzyme that is natively targeted to a plastid of the plant by the plastid transit peptide, wherein the DNA molecule is modified such that it does not encode a functional plastid transit peptide; and (b) a promoter capable of expressing the DNA molecule in a plastid, wherein the promoter is operatively linked to the DNA molecule. In one preferred embodiment, the transit peptide is mutated and thus does not allow the proper transport of the enzyme encoded by the DNA molecule to the desired cell compartment, such as the plastid. In another preferred embodiment, a portion of the transit peptide coding sequence or the entire transit peptide coding sequence is removed from the DNA molecule, preventing the enzyme from being properly targeted to the desired cell compartment.

The chimeric genes described above are inserted in plastid transformation vectors, and the present invention is therefore also directed to plants having their plastid genome transformed with such vectors, whereby the DNA molecule is expressible in plant plastids. Such plants are preferably homoplasmic for transgenic plastids.

In a preferred embodiment, a DNA molecule described immediately above encodes an enzyme that in its wild-type form is inhibited by a herbicide. In a further preferred embodiment, the DNA molecule encodes an enzyme that in its wild-type form is inhibited by a herbicide, but that comprises at least one amino acid change compared to the wild-type enzyme. Such an amino acid change makes the enzyme resistant to compounds that naturally inhibit the wild-type enzyme. In a further preferred embodiment, the DNA molecule encodes an enzyme having protoporphyrinogen oxidase (protox) activity. In a further preferred embodiment, the transit peptide is removed from the DNA molecule as further illustrated in Examples 37–42. Plants homoplasmic for transgenic plastids of the invention are resistant to high amounts of herbicides such as Formula XVII that inhibit the naturally occurring protox activity (as further illustrated in Example 44).

In another preferred embodiment, the transit peptide of a DNA molecule encoding a 5-enolpyruvyl-3-phosphoshikimate synthase (EPSP synthase) is mutated or removed. The resulting DNA molecule is fused to a promoter capable of expression in plant plastids and homoplasmic plants harboring such constructs in their plastid genomes are obtained. These plants are resistant to herbicidal compounds that naturally inhibit EPSP synthase, in particular glyphosate. In another preferred embodiment, the transit peptide of a DNA molecule encoding a acetolactate synthase (ALS) is mutated or removed. The resulting DNA molecule is fused to a promoter capable of expression in plant plastids and homoplasmic plants harboring such constructs in their plastid genome are obtained. These plants are resistant to herbicidal compounds that naturally inhibit ALS, in particular sulfonylureas. In another preferred embodiment, the transit peptide of a DNA molecule encoding a acetoxyhydroxy acid synthase (AHAS) is mutated or removed. The resulting DNA molecule is fused to a promoter capable of expression in plant plastids and homoplasmic plants harboring such constructs in their plastid genome are obtained. These plants are resistant to herbicidal compounds that naturally inhibit AHAS, in particular, imidazolinone and sulfonamide herbicides. In another preferred embodiment, the transit peptide of a DNA molecule encoding an acetylcoenzyme A carboxylase (ACCase) is mutated or removed. The resulting DNA molecule is fused to a promoter capable of expression in plant plastids and homoplasmic plants harboring such constructs in their plastid genome are obtained. These plants are resistant to herbicidal compounds that naturally inhibit ACCase, in particular cyclohexanedione and arylphenoxypropanoic acid herbicides. In another preferred embodiment, the transit peptide of a DNA molecule encoding a glutamine synthase (GS) is mutated or removed. The resulting DNA molecule is fused to a promoter capable of expression in plant plastids and homoplasmic plants harboring such constructs in their plastid genome are obtained. These plants are resistant to herbicidal compounds that naturally inhibit GS, in particular phosphinothricin and methionine sulfoximine.

The present invention is also further directed to a method of obtaining herbicide-resistant plants by transforming their plastid genome with a chimeric gene comprising (a) a DNA molecule isolated from a plant, which in its native state encodes a polypeptide that comprises a plastid transit peptide, and a mature enzyme that is natively targeted to a plastid of the plant by the plastid transit peptide, wherein the DNA molecule is modified such that it does not encode a functional plastid transit peptide; and (b) a promoter capable of expressing the DNA molecule in a plastid, wherein the promoter is operatively linked to the DNA molecule. Examples of enzymes that are used in the present invention are cited immediately above, but the applicability of such a method is not limited to the cited examples.

The present invention is still further directed to a novel method for selecting a transplastomic plant cell, comprising the steps of: introducing the above-described chimeric gene into the plastome of a plant cell; expressing the encoded enzyme in the plastids of the plant cell; and selecting a cell that is resistant to a herbicidal compound that naturally inhibits the activity of the enzyme, whereby the resistant cell comprises transformed plastids. In a preferred embodiment, the enzyme is naturally inhibited by a herbicidal compound and the transgenic plant is able to grow on an amount of the herbicidal compound that naturally inhibits the activity of the enzyme. In a further preferred embodiment, the enzyme has protoporphyrinogen oxidase (protox) activity and is modified so that it that confers resistance to protox inhibitors.

A further aspect of the present invention is a novel method for plastid transformation of recalcitrant plants. The methods pioneered for plastid transformation of tobacco and lower plant species rely on non-lethal selection for resistance to antibiotics that preferentially affect the plastid translational apparatus and hence allow photo-heterotrophic transformants to outgrow heterotrophic, non-transformed tissue.

Several factors have likely contributed to the difficulties encountered with plastid transformation of monocots and other dicots. For example, the maize chloroplast 16S ribosomal RNA (rRNA) is naturally resistant to spectinomycin because of the presence of a G at position 1138 in the *Zea mays* 16S rDNA gene (Harris et al., 1994). Thus, utilization of 16s rRNA point mutations that confer spectinomycin and/or streptomycin resistance which have been used successfully as selectable chloroplast markers in Chlamydomonas and tobacco (Boynton and Gillham (1993) In Wu, R. [Ed.] *Methods in Enzymology* Vol. 217. Academic Press, San Diego, pp. 510–536; Svab et al. (1990) Proc. Natl. Acad. Sci. U.S.A. 87: 8526–8530) is not feasible for maize. Natural spectinomycin and streptomycin resistance in maize also obviates the use of the bacterial aadA gene encoding aminoglycoside 3"-adenyltransferase, which results in dominant spectinomycin and streptomycin resistance and allows a 100-fold increase in tobacco chloroplast transformation efficiency (Svab and Maliga (1993) *Proc. Natl. Acad. Sci. U.S.A.* 90: 913–917). Use of kanamycin (the only other antibiotic proven to be useful for chloroplast transformation) is also problematic due to a large excess (ca. 50:1) of nuclear vs. chloroplast-encoded resistance in tobacco following bombardment of the bacterial nptII gene encoding neomycin phosphotransferase (Carrer et al. (1993) *Mol. Gen. Genet.* 241: 49–56). This has been shown to result from both a high frequency of spontaneous nuclear resistance mutants as well as integration of nptII into the nuclear genome. Since nptII is also a highly effective selectable marker for maize nuclear transformation it is reasonable to expect similar background levels to that observed in tobacco. Spontaneous resistance and a significant excess of selectable marker integration by random, illegitimate recombination into the nuclear genome, rather than homologous integration into the chloroplast genome, would make recovery of bona fide chloroplast transformants difficult if not impossible.

A more fundamental reason for the difficulties encountered with plastid transformation in plant species other than tobacco may have to do with the non-photosynthetic nature of many regenerable cultured plant tissues, especially in maize and Arabidopsis. Tobacco is an exception in that cultured vegetative tissues are regenerable and contain mature differentiated chloroplasts that are photosynthetically competent in the presence of sucrose. Consequently, the current system for selecting tobacco plastid transformants relies on the faster growth rate of transformed cells that can use both reduced and inorganic carbon sources. Moreover; transformed cells do not suffer the chloroplast membrane damage that results from inhibition of plastid protein synthesis in the light. This expression of selectable markers that act preferentially on photosynthetic cells, driven by promoters that have high activity in differentiated chloroplasts, is unlikely to work in non-green tissues containing proplastids (e.g. dark-grown maize Type I callus, somatic embryos) or amyloplasts/leucoplasts (e.g. Arabidopsis root cultures). Plastid transformation in these plants requires a selectable marker that gives strong selection in all plastid types.

A preferred selectable marker for generalized plastid transformation: (1) is active only in the plastid to eliminate nuclear-transformed "escapes"; (2) has a mode of action that does not depend on photosynthetic competence or the presence of fully differentiated chloroplasts; and (3) has a level of resistance that is co-dependent on an adjustable external parameter (e.g. light), rather than being determined solely by the bulk concentration of a selective agent, so that selection pressure can vary during selection to facilitate segregation of the many-thousand plastid genome copies.

In a preferred embodiment, such a selectable marker gene involves the use of a chimeric gene comprising an isolated DNA molecule encoding a plastid-targeted enzyme having in its natural state a plastid transit peptide, wherein the DNA molecule is modified such that the transit peptide either is absent or does not function to target the enzyme to the plastid, wherein the DNA molecule is operatively linked to a promoter capable of expression in plant plastids. In a preferred embodiment, a DNA molecule of the present invention encodes an enzyme that is naturally inhibited by a herbicide. In another preferred embodiment, the DNA molecule encodes a protoporphyrinogen IX oxidase ("protox").

In a preferred embodiment, the protoporphyrinogen IX oxidase gene is from *Arabidopsis thaliana* and in a more preferred embodiment, the protoporphyrinogen IX oxidase gene is from *Arabidopsis thaliana* and comprises at least one amino acid substitution. Preferably, an amino acid substitution results in tolerance of the enzyme against inhibition by an herbicide which naturally inhibits the activity of the enzyme. Low concentrations of herbicide are thought to kill wildtype plants due to light-sensitive intermediates which build up when the plastid-localized protox enzyme is inhibited. Production of these photosensitizing compounds does not require differentiated chloroplasts or active photosynthesis, which is a key factor for successful plastid transformation of plants whose regenerable cultured tissues are of non-photosynthetic nature.

Another key feature is to have expression of the selectable marker gene in non-green plastids. In a preferred embodiment, the invention encompasses the use of promoters that are capable of expression of operatively linked DNA molecules in plastids of both green and non-green tissue. In particular, one such promoter comes from the regulatory region of the plastid 16S ribosomal RNA operon. Another candidate is the promoter and 5' UTR from the plastid clpP gene. The clpP gene product is expressed constitutively in plastids from all plant tissues, including those that do not contain chloroplasts (Shanklin (1995) *Plant Cell* 7: 1713–22).

Other DNA molecules may be co-introduced in plant plastids using the method described above. In a preferred embodiment, a plastid transformation vector of the present invention contains a chimeric gene allowing for selection of transformants as described above and at least one other gene fused to a promoter capable of expression in plant plastids. The other such gene may, for example, confer resistance to insect pests, or to fungal or bacterial pathogens, or may encode one or more value-added traits.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), *Current Protocols in Molecular Biology*, John Wiley and Sons, Inc. (1994); T. Maniatis, E. F. Fritsch and J. Sambrook, *Molecular Cloning: A Laboratory Manual*, Cold Spring Harbor laboratory, Cold Spring Harbor, N.Y. (1989); and by T. J. Silhavy, M. L. Berman, and L. W. Enquist, *Experiments with Gene Fusions*, Cold Spring Harbor Laboratory, Cold Spring Harbor, N.Y. (1984).

Section A. Isolation And Characterization Of Plant Protoporphyrinogen Oxidase (Protox) Genes Example 1

Isolation of a Wheat Protox-1 cDNA Based on Sequence Homology to a Maize Protox-1 Coding Sequence Total RNA prepared from *Triticum aestivum* (cv Kanzler) was submitted to Clontech for custom cDNA library construction in the Lambda Uni-Zap vector. Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize protox-1 cDNA (SEQ ID NO:5; see Example 2 of International application no. PCT/IB95/00452, filed Jun. 8, 1995, published Dec. 21, 1995 as WO 95/34659) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert, *Proc. Natl. Acad. Sci USA* 81: 1991–1995 (1984), hereby incorporated by reference in its entirety.) Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest wheat protox-1 cDNA obtained from initial screening efforts, designated "wheat protox-1", was 1489-bp in length. Wheat protox-1 lacks coding sequence for the transit peptide plus approximately 126 amino acids of the mature coding sequence based on comparison with the other known plant protox peptide sequences.

A second screen was performed to obtain a longer wheat protox cDNA. For this screen, a *Triticum aestivum* (cv Kanzler) cDNA library was prepared internally using the lambda Uni-Zap vector. Approximately 200,000 pfu of the cDNA library was screened as indicated above, except that the wheat protox-1 cDNA was used as a probe and hybridization and wash conditions were at 65° C. instead of 50° C. The longest wheat cDNA obtained from this screening effort, designated "wheat protox-1a", was 1811-bp in length. The nucleotide sequence of this cDNA and the amino acid sequence it encodes are set forth in SEQ ID NOs:9 and 10, respectively. Based on comparison with the other known plant protox peptide sequences and with corresponding genomic sequence, this cDNA is either full-length or missing only a few transit peptide codons (Table 1A). This wheat protein sequence is 91% identical (95% similar) to the maize protox-1 protein sequence set forth in SEQ ID NO:6.

Wheat protox-1a, in the pBluescript SK vector, was deposited Mar. 19, 1996, as pWDC-13 (NRRL #B21545).

Example 2

Isolation of a Soybean Protox-1 cDNA Based on Sequence Homology to an Arabidopsis Protox-1 Coding Sequence A Lambda Uni-Zap cDNA library prepared from soybean (v Williams 82, epicotyls) was purchased from Stratagene. Approximately 50,000 pfu of the library was plated at a density of approximately 5,000 pfu per 10 cm Petri dish and duplicate filter lifts were made onto Colony/Plaque Screen membranes (NEN Dupont). The plaque lifts were probed with the Arabidopsis protox-1 cDNA (SEQ ID NO:1; see Example 1 of International application no. PCT/IB95/00452, filed Jun. 8, 1995, published Dec. 21, 1995 as WO 95/34659)) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequence of the cDNA inserts was determined by the chain termination method using dideoxy terminators labeled with fluorescent dyes (Applied Biosystems, Inc.). The longest soybean cDNA obtained, designated "soybean protox-1", is full-length based on comparison with the other known plant protox peptide sequences (Table 1A). Soybean protox-1 is 1847-bp in length and encodes a protein of 58.8 kDa. The nucleotide sequence of this cDNA and the amino acid sequence it encodes are set forth in SEQ ID NOs:11 and 12, respectively. The soybean protein is 78% identical (87% similar) to the Arabidopsis protox-1 protein.

Soybean protox-1, in the pBluescript SK vector, was deposited Dec. 15, 1995 as pWDC-12 (NRRL #B-21516).

Example 3

Isolation of a Cotton Protox-1 cDNA Based on Sequence Homology to a Maize Protox-1 Coding Sequence A Lambda Uni-Zap cDNA library prepared from *Gossypium hirsutum* L. (72 hr. dark grown cotyledons) was obtained from Dr. Dick Trelease, Dept. of Botany, Arizona State University (Ni W. and Trelease R. N., *Arch. Biochem. Biophys*. 289: 237–243 (1991)). Approximately 50,000 pfu of the library was plated at a density of approximately 5,000 pfu per 10 cm Petri dish and duplicate filter lifts were made onto Colony/Plaque Screen membranes (NEN Dupont). The plaque lifts were probed with the maize protox-1 cDNA (SEQ ID NO:5) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequence of the cDNA inserts was determined by the chain termination method using dideoxy terminators labeled with fluorescent dyes (Applied Biosystems, Inc.). The longest cotton cDNA obtained, designated "cotton protox-1", appears to be full-length based on comparison with the other known plant protox peptide sequences (Table 1A). Cotton protox-1 is 1826-bp in length and encodes a protein of 58.2 kDa. The nucleotide sequence of this cDNA and the amino acid sequence it encodes are set forth in SEQ ID NOs:13 and 14, respectively. The cotton protein is 77% identical (86% similar) to the maize protox-1 protein.

Cotton protox-1, in the pBluescript SK vector, was deposited Jul. 1, 1996 as pWDC-15 (NRRL #B-21594).

Example 4

Isolation of a Sugar Beet Protox-1 cDNA Based on Sequence Homology to an Arabidopsis Protox-1 Coding Sequence A Lambda-Zap cDNA library prepared from *Beta vulgaris* was obtained from Dr. Philip Rea, Dept. of Botany, Plant Science Institute, Philadelphia, Pa. (Yongcheol Kim, Eugene J. Kim, and Philip A. Rea, *Plant Physiol*. 106: 375–382 (1994)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the Arabidopsis protox-1 cDNA (SEQ ID NO:1) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest sugar beet protox-1 cDNA obtained, designated "sugar beet protox-1", is full-length based on comparison with the other known plant protox peptide sequences Table 1A). Sugar beet protox-1 is 1910-bp in length and encodes a protein of 60 kDa. The nucleotide sequence of this cDNA and the amino acid sequence it encodes are set forth in SEQ ID NOs:15 and 16, respectively. The sugar beet protein is 73% identical (82% similar) to the Arabidopsis protox-1 protein.

Sugar beet protox-1, in the pBluescript SK vector, was deposited Jul. 29, 1996, as pWDC-16 (NRRL #B-21595N).

Example 5

Isolation of an Oilseed Rape Protox-1 cDNA Based on Sequence Homology to an Arabidopsis Protox-1 Coding Sequence A Lambda Uni-Zap II cDNA library prepared from *Brassica napus* (3–4 wk. mature green leaves) was obtained from Dr. Guenther Ochs, Institut Fuer Allgemeine Botanik, Johannes Gutenberg-Universitaet Mainz, Germany (GUnther Ochs, Gerald Schock, and Aloysius Wild, *Plant Physiol*. 103: 303–304 (1993)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the Arabidopsis protox-1 cDNA (SEQ ID NO:1) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest oilseed rape protox-1 cDNA obtained, designated "rape protox-1", is full-length based on comparison with the other known plant protox peptide sequences (Table 1A). Rape protox-1 is 1784-bp in length and encodes a protein of 57.3 kD. The nucleotide sequence of this cDNA and the amino acid sequence it encodes are set forth in SEQ ID NOs: 17 and 18, respectively. The oilseed rape protein is 87% identical (92% similar) to the Arabidopsis protox-1 protein.

Rape protox-1, in the pBluescript SK vector, was deposited Aug. 23, 1996, as pWDC-17 (NRRL #B-21615).

Example 6

Isolation of a Rice Protox-1 cDNA Based on Sequence Homology to a Maize Protox-1 Coding Sequence A Lambda gt11 cDNA library prepared from *Oryza sativa* (5 day etiolated shoots) was purchased from Clontech. Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize protox-1 cDNA (SEQ ID NO:5) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified, and lambda DNA was prepared using the Wizard Lambda-Prep kit (Promega). The cDNA inserts were subcloned as EcoRI fragments into the pBluescript SK vector using standard techniques. The sequences of the cDNA inserts were determined by the chain termination method using dideoxy terminators labeled with fluorescent dyes (Applied Biosystems, Inc.). The longest rice protox-1 cDNA obtained, designated "rice protox-1", was 1224-bp in length. Rice protox-1 lacks coding sequence for the transit peptide plus approximately 172 amino acids of the mature coding sequence based on comparison with the other known plant protox peptide sequences (Table 1A). The nucleotide sequence of this partial cDNA and the amino acid sequence it encodes are set forth in SEQ ID NOs:19 and 20, respectively.

Rice protox-1, in the pBluescript SK vector, was deposited Dec. 6, 1996, as pWDC-18 (NRRL #B-21648).

Example 7

Isolation of a Sorghum Protox-1 cDNA Based on Sequence Homology to a Maize Protox-1 Coding Sequence A Lambda-Zap II cDNA library prepared from Sorghum bicolor (3–6 day green seedlings) was obtained from Dr. Klaus Pfizenmaier, Institute of Cell Biology and Immunology, University of Stuttgart, Germany (Harald Wajant, Karl-Wolfgang Mundry, and Klaus Pfizenmaier, *Plant Mol. Biol.* 26: 735–746 (1994)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize protox-1 cDNA (SEQ ID NO:5) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest sorghum protox-1 cDNA obtained, designated "sorghum protox-1", was 1590-bp in length. Sorghum protox-1 lacks coding sequence for the transit peptide plus approximately 44 amino acids of the mature coding sequence based on comparison with the other known plant protox peptide sequences (Table 1A). The nucleotide sequence of this partial cDNA and the amino acid sequence it encodes are set forth in SEQ ID NOs:21 and 22, respectively.

Sorghum protox-1, in the pBluescript SK vector, was deposited Dec. 6, 1996, as pWDC-19 (NRRL #B-21649).

Example 8

Isolation of a Sugar Cane Protox-1 cDNA Based on Sequence Homology to a Maize Protox-1 Coding Sequence A Lambda-Zap II cDNA library prepared from sugar cane was obtained from Henrik Albert of USDA/ARS at the Hawaii Agricultural Research Center. Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize protox-1 cDNA (SEQ ID NO:5) labeled with 32P-dCTP by the random priming method (Life Technologies). Hybridization conditions were 7% sodium dodecyl sulfate (SDS), 0.5 M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest sugar cane protox-1 cDNA obtained, designated "sugar cane protox-1", was 633-bp in length. Sugar cane protox-1 lacks coding sequence for the transit peptide plus approximately 382 amino acids of the mature coding sequence based on comparison with the other known plant protox peptide sequences Table 1A). The nucleotide sequence of this partial cDNA and the amino acid sequence it encodes are set forth in SEQ ID NOs:36 and 37, respectively.

Example 9

Demonstration of Plant Protox Clone Sensitivity to Protox Inhibitory Herbicides in a Bacterial System Liquid cultures of protox-1/SASX38, protox-2/SASX38 and pBluescript/XL1-Blue were grown in L amp$^{100}$. One hundred microliter aliquots of each culture were plated on L amp$^{100}$ media containing various concentrations (1.0 nM–10 mM) of a protox inhibitory aryluracil herbicide of formula XVII. Duplicate sets of plates were incubated for 18 hours at 37° C.

The protox$^+$ *E. coli* strain XL1-Blue showed no sensitivity to the herbicide at any concentration, consistent with reported resistance of the native bacterial enzyme to similar herbicides. The protox-1/SASX38 was clearly sensitive, with the lawn of bacteria almost entirely eliminated by inhibitor concentrations as low as 10 nM. The protox-2/SASX38 was also sensitive, but only at a higher concentration (10 μM) of the herbicide. The herbicide was effective even on plates maintained almost entirely in the dark. The toxicity of the herbicide was entirely eliminated by the addition of 20 μg/ml hematin to the plates.

The different herbicide tolerance between the two plant protox strains is likely the result of differential expression from these two plasmids, rather than any inherent difference in enzyme sensitivity. Protox-1/SASX38 grows much more slowly than protox-2/SASX38 in any heme-deficient media. In addition, the Mzprotox-2/SASX38 strain, with a growth rate comparable to Arab protox-1/SASX38, is also very sensitive to herbicide at the lower (10–100 nM) concentrations.

Section B: Identification and Characterization of Plant Protox Genes Resistant to Protox-Inhibitory Herbicides Example 10

Selecting for Plant Protox Genes Resistant to Protox-Inhibitory Herbicides in the *E. coli* Expression System An *Arabidopsis thaliana* (Landsberg) cDNA library in the plasmid vector pFL61 (Minet et al., *Plant J.* 2:417–422 (1992) was obtained and amplified. The *E. coli* hemG mutant SASX38 (Sasarman et al., *J. Gen. Microbiol.* 113:297(1979)) was obtained and maintained on L media containing 20 ug/ml hematin (United States Biochemicals). The plasmid library was transformed into SASX38 by electroporation using the Bio-Rad Gene Pulser and the manufacturer's conditions. The electroporated cells were plated on L agar containing 100 ug/ml ampicillin at a density of approximately 500,000 transformants/10 cm plate. The cells were then incubated at 37° C. for 40 hours in low light and selected for the ability to grow without the addition of exogenous heme. Heme prototrophs were recovered at a frequency of 400/10$^7$; from the pFL61 library. Sequence analysis of twenty-two complementing clones showed that nine are of the type designated "protox-1," the protox gene expected to express a chloroplastic protox enzyme.

The pFL61 library is a yeast expression library, with the Arabidopsis cDNAs inserted bidirectionally. These cDNAs can also be expressed in bacteria. The protox cDNAs apparently initiate at an in-frame ATG in the yeast PGK 3' sequence approximately 10 amino acids 5'. to the NotI cloning site in the vector and are expressed either from the lacZ promoter 300 bp further upstream or from an undefined cryptic bacterial promoter. Because protox-1 cDNAs that included significant portions of a chloroplast transit sequence inhibited the growth of the *E. coli* SASX38 strain, the clone with the least amount of chloroplast transit sequence attached was chosen for mutagenesis/herbicide selection experiments. This clone, pSLV19, contains only 17 amino acids of the putative chloroplast transit peptide, with the DNA sequence beginning at bp-151 of the Arabidopsis protox-1 cDNA (SEQ ID NO:1).

The plasmid pSLV19 was transformed into the random mutagenesis strain XL1-Red (Stratagene, La Jolla, Calif.). The transformation was plated on L media containing 50 ug/ml ampicillin and incubated for 48 hours at 37° C. Lawns of transformed cells were scraped from the plates and plasmid DNA prepared using the Wizard Megaprep kit (Promega, Madison, Wis.). Plasmid DNA isolated from this mutator strain is predicted to contain approximately one random base change per 2000 nucleotides (see Greener et al., *Strategies* 7(2):32–34 (1994).

The mutated plasmid DNA was transformed into the hemG mutant SASX38 (Sasarman et al., *J. Gen. Microbiol.* 113:297 (1979) and plated on L media containing various concentrations of protox-inhibiting herbicide (formula XVII). The plates were incubated for 2 days at 37° C. Plasmid DNA was isolated from all colonies that grew in the presence of herbicide concentrations that effectively killed the wild type strain. The isolated DNA was then transformed into SASX38 and plated again on herbicide to ensure that the resistance observed was plasmid-borne. The protox coding sequence from plasmids passing this screen was excised by NotI digestion, recloned into an unmutagenized vector, and tested again for the ability to confer herbicide tolerance. The DNA sequence of protox cDNAs that conferred herbicide resistance was then determined and mutations identified by comparison with the wild type Arabidopsis protox-1 sequence (SEQ ID NO:1).

A single coding sequence mutant was recovered from the first mutagenesis experiment. This mutant leads to enhanced herbicide "resistance" only by increasing growth rate. It contains a C to A mutation at nucleotide 197 in SEQ ID NO:1 in the truncated chloroplast transit sequence of pSLV19, converting an ACG codon for threonine to an AAG codon for lysine at amino acid 56 of SEQ ID NO:2, and resulting in better complementation of the bacterial mutant. This plasmid also contains a silent coding sequence mutation at nucleotide 1059, with AGT (Ser) changing to AGC (Ser). This plasmid was designated pMut-1.

The pMut-1 plasmid was then transformed into the mutator XL1-Red strain as described above and the mutated DNA was isolated and plated on an herbicide concentration that is lethal to the unmutagenized pMut-1 protox gene. Herbicide tolerant colonies were isolated after two days at 37° C. and analyzed as described above. Multiple plasmids were shown to contain herbicide resistant protox coding sequences. Sequence analysis indicated that the resistant genes fell into two classes. One resistance mutation identified was a C to T change at nucleotide 689 in the Arabidopsis protox-1 sequence set forth in SEQ ID NO:1. This change converts a GCT codon for alanine at amino acid 220 of SEQ ID NO:2 to a GTT codon for valine, and was designated pAraC-1Val (see, Table 1B; sub-sequence 3).

A second class of herbicide resistant mutant contains an A to G change at nucleotide 1307 in the Arabidopsis protox-1 sequence. This change converts. a TAC codon for tyrosine at amino acid 426 to a TGC codon for cysteine, and was designated pAraC-2Cys (see, Table 1B; sub-sequence 7).

A third resistant mutant has a G to A change at nucleotide 691 in the Arabidopsis protox-1 sequence. This mutation converts a GGT codon for glycine at amino acid 221 to an AGT codon for serine at the codon position adjacent to the mutation in pAraC-1. This plasmid was designated pAraC-3Ser (see, Table 1B; sub-sequence 4).

Resistant mutant pAraC-2Cys, in the pMut-1 plasmid, was deposited on Nov. 14, 1994 under the designation pWDC-7 with the Agricultural Research Culture Collection and given the deposit designation NRRL #21339N.

Example 11

Additional Herbicide-Resistant Codon Substitutions at Positions Identified in the Random Screen The amino acids identified as herbicide resistance sites in the random screen are replaced by other amino acids and tested for function and for herbicide tolerance in the bacterial system. Oligonucleotide-directed mutagenesis of the Arabidopsis protox-1 sequence is performed using the Transformer Site-Directed Mutagenesis Kit (Clontech, Palo Alto, Calif.). After amino acid changes are confirmed by sequence analysis, the mutated plasmids are transformed into SASX38 and plated on L-amp$^{100}$ media to test for function and on various concentrations of protox-inhibiting herbicide to test for tolerance.

This procedure is applied to the alanine codon at nucleotides 688–690 and to the tyrosine codon at nucleotides 1306–1308 of the Arabidopsis protox-1 sequence (SEQ ID NO:1). The results demonstrate that the alanine codon at nucleotides 688–690 can be changed to a codon for valine (pAraC-1Val), threonine (pAraC-1Thr), leucine (pAraC-1Leu), cysteine (pAraC-1Cys), or isoleucine (pAraC-1Ile) to yield an herbicide-resistant protox enzyme that retains function (see, Table 1B; sub-sequence 3). The results further demonstrate that the tyrosine codon at nucleotides 1306–1308 can be changed to a codon for cysteine (pAraC-2Cys), isoleucine (pAraC-2Ile), leucine (pAraC-2Leu), threonine (pAraC-2Thr), methionine (pAraC-2Met), valine (pAraC-2Val), or alanine (pAraC-2Ala) to yield an herbicide-resistant protox enzyme that retains function (see, Table 1B; sub-sequence 7).

Example 12

Isolation of Additional Mutations that Increase Enzyme Function and/or Herbicide Tolerance of Previously Identified Resistant Mutants Plasmids containing herbicide resistant protox genes are transformed into the mutator strain XL1-Red and mutated DNA is isolated as described above. The mutated plasmids are transformed into SASX38 and the transformants are screened on herbicide concentrations (formula XVII) sufficient to inhibit growth of the original "resistant" mutant. Tolerant colonies are isolated and the higher tolerance phenotype is verified as being coding sequence dependent as described above. The sequence of these mutants is determined and mutations identified by comparison to the progenitor sequence.

This procedure was applied to the pAraC-1Val mutant described above. The results demonstrate that the serine codon at amino acid 305 (SEQ ID NO:2) can be changed to a codon for leucine to yield an enzyme with higher tolerance to protox-inhibiting herbicides than the pAraC-1Val mutant alone. This second site mutation is designated AraC305Leu (see, Table 1B; sub-sequence 13). The same results are demonstrated for the threonine codon at amino acid 249, where a change to either isoleucine or to alanine leads to a more tolerant enzyme (see, Table 1B; sub-sequence 12). These changes are designated AraC249Ile and AraC249Ala, respectively.

The procedure was also applied to the pAraC-2Cys mutant described above. The results demonstrate that the proline codon at amino acid 118 (SEQ ID NO:2) can be changed to a codon for leucine to yield an enzyme with higher tolerance to protox-inhibiting herbicides than the pAraC-1Cys mutant alone. This mutation is designated AraC118Leu (see, Table 1B; sub-sequence 11). The same results are demonstrated for the serine codon at amino acid 305, where a change to leucine leads to a more tolerant pAraC-2Cys enzyme (see, Table 1B; sub-sequence 13). This change was also isolated with the pAraC-1Val mutant as described above and is designated AraC305Leu. Additional mutations that enhance the herbicide resistance of the pAraC-2Cys mutant include an asparagine to serine change at amino acid 425, designated AraC425Ser (Table 1B; sub-sequence 14), and a tyrosine to cysteine at amino acid 498, designated AraC498Cys (Table 1B; sub-sequence 15).

These changes (Table 1B; sub-sequences 11–15) are referred to as "second site" mutations, because they are not sufficient to confer herbicide tolerance alone, but rather enhance the function and/or the herbicide tolerance of an already mutant enzyme. This does not preclude the possibility that other amino acid substitutions at these sites could suffice to produce an herbicide tolerant enzyme since exhaustive testing of all possible replacements has not been performed.

Example 13

Combining Identified Resistance Mutations with Identified Second Site Mutations to Create Highly Functional/Highly Tolerant Protox Enzymes The AraC305Leu mutation described above was found to enhance the function/herbicide resistance of both the AraC-1Val and the AraC-2Cys mutant plasmids. In an effort to test the general usefulness of this second site mutation, it was combined with the AraC-2Leu, AraC-2Val, and AraC-2Ile mutations and tested for herbicide tolerance. In each case, the AraC305Leu change significantly increased the growth rate of the resistant protox mutant on protox-inhibiting herbicide. Combinations of the AraC-2Ile resistant mutant with either the second site mutant AraC249Ile or AraC118Leu also produced more highly tolerant mutant protox enzymes. The AraC249Ile mutation demonstrates that a second site mutation identified as enhancing an AraC-1 (sub-sequence 3) mutant may also increase the resistance of an AraC-2 (sub-sequence 7) mutant. A three mutation plasmid containing AraC-2Ile, AraC305Leu, and AraC249Ile (Table 1B; sub-sequences 7, 13, and 12) has also been shown to produce a highly functional, highly herbicide tolerant protox-1 enzyme.

Example 14

Identification of Sites in the Maize Protox-1 Gene that Can Be Mutated to Give Herbicide Tolerance The pMut-1 Arabidopsis protox-1 plasmid described above is very effective when used in mutagenesis/screening experiments in that it gives a high frequency of genuine coding sequence mutants, as opposed to the frequent up-promoter mutants that are isolated when other plasmids are used. In an effort to create an efficient plasmid screening system for maize protox-1, the maize cDNA was engineered into the pMut-1 vector in approximately the same sequence context as the Arabidopsis cDNA. Using standard methods of overlapping PCR fusion, the 5' end of the pMut-1 Arabidopsis clone (including 17 amino acids of chloroplast transit peptide with one mis-sense mutation as described above) was fused to the maize protox-1 cDNA sequence starting at amino acid number 14 of the maize sequence (SEQ ID NO:6). The 3' end of the maize cDNA was unchanged. NotI restriction sites were placed on both ends of this fusion, and the chimeric gene was cloned into the pFL61 plasmid backbone from pMut-1. Sequence analysis revealed a single nucleotide PCR-derived silent mutation that converts the ACG codon at nucleotides 745–747 (SEQ ID NO:5) to an ACT codon, both of which encode threonine. This chimeric Arab-maize protox-1 plasmid was designated pMut-3.

The pMut-3 plasmid was transformed into the mutator XL1-Red strain as described above and the mutated DNA was isolated and plated on a herbicide concentration (formula XVII) that was lethal to the unmutagenized pMut-3 maize protox gene. Herbicide tolerant colonies were isolated after two days at 37° C. and analyzed as described above. This analysis revealed multiple plasmids containing herbicide resistant protox coding sequences. Sequence analysis showed 5 single base changes that individually result in an herbicide tolerant maize protox-1 enzyme. Three of these mutations correspond to amino acid changes previously shown to confer tolerance at the homologous position in the Arabidopsis protox-1 gene. Two of the three are pMzC-1Val and pMzC-1Thr, converting the alanine (GCT) at amino acid 164 (SEQ ID NO:6) to either valine (GAT) or to threonine (ACT). This position corresponds to the pAraC-1 mutations described above (see, Table 1B; sub-sequence 3). The third analogous change, pMzC-3Ser, converts the glycine (GGT) at amino acid 165 to Serine (AGT), corresponding to the AraC-3Ser mutation described above (see, Table 1B; sub-sequence 4). These results serve to validate the expectation that herbicide-tolerant mutations identified in one plant protox gene may also confer herbicide tolerance in an equivalent plant protox gene from another species.

Two of the mutations isolated from the maize protox-1 screen result in amino acid changes at residues not previously identified as herbicide resistance sites. One change (Mz159Phe) converts cysteine (TGC) to phenylalanine (TTC) at amino acid 159 of the maize protox-1 sequence (SEQ ID NO:6) (see, Table 1B; sub-sequence 2). The second (Mz419Thr) converts isoleucine (ATA) to threonine (ACA) at amino acid 419 (see, Table 1B; sub-sequence 9).

Additional amino acid substitutions were made and tested at three of the maize mutant sites. Tolerance was demonstrated when glycine 165 was changed to leucine (pMzC-3Leu) or when cysteine 159 was changed to either leucine (Mz159Leu) or to lysine (Mz159Lys) (see, Table 1B; sub-sequences 4 and 2). Tolerant enzymes were also created by changing isoleucine 419 to histidine (Mz419His), glycine (Mz419Gly), or asparagine (Mz419Asn) (see, Table 1B; sub-sequence 9).

Individual amino acid changes that produced highly herbicide tolerant Arabidopsis protox-1 enzymes were engineered into the maize protox-1 gene by site-directed mutagenesis as described above. Bacterial testing demonstrated that changing the alanine (GCT) at amino acid 164 (SEQ ID NO:6) to leucine (CTT produced a highly tolerant maize enzyme (pMzC-1Leu) (see, Table 1B; sub-sequence 3). No mutation analogous to the AraC-2 site (Table 1B; sub-sequence 7) in Arabidopsis was isolated in the maize random screen. However, changing this site, tyrosine 370 in the maize enzyme (SEQ ID NO:6), to either isoleucine (pMzC-2Ile) or methionine (pMzC-2Met) did produce herbicide tolerant enzymes (see, Table 1B; sub-sequence 7).

Additional mutant screens performed as described earlier in this example, except using formulas XXIIIa and XXIIIb instead of XVII, identified three additional amino acid changes that confer tolerant protox enzymes. One, using formula XXIIIb, demonstrated that changing the arginine (CGT) at amino acid 88 (SEQ ID NO:6) to cysteine (TGT) produced a highly tolerant maize enzyme (Mz88Cys) (see, Table 1B; sub-sequence 1). Another, using formula XXIIIa, demonstrated that changing both the leucine (TTA) at amino acid 347 (SEQ ID NO:6) to serine (TCA) and the alanine (GCA) at amino acid 453 (SEQ ID NO:6) to threonine (ACA) produced a highly tolerant maize enzyme (Mz347Ser453Thr) (see, Table 1B; sub-sequences 16 and 17). Unlike the second site mutations described above, which increase enzyme function and/or herbicide tolerance of previously identified resistant mutants, Mz347Ser453Thr is a "double mutant" that requires that both mutations be present for herbicide tolerance.

Example 15

Identification of Sites in the Wheat Protox-1 Gene that can be Mutated to Give Herbicide Tolerance To create an efficient plasmid screening system for wheat protox-1, the wheat cDNA was engineered into the pMut-1 vector as described above for the maize cDNA. This chimeric Arab-wheat protox-1 plasmid is designated pMut-4. The pMut-4 DNA was mutated and screened for herbicide tolerance as described above. This analysis revealed multiple plasmids containing herbicide resistant protox coding sequences. Sequence analysis showed 7 single base changes that individually result in an herbicide tolerant wheat protox-1 enzyme. Four of these mutations correspond to amino acid changes previously shown to confer tolerance at the homologous position in the Arabidopsis and/or in the maize protox-1 gene. Two, pWhtC-1Val and pWhtC-1Thr, convert the alanine (GCI) at amino acid 211 (SEQ ID NO:10) to valine (GAT) and to threonine (ACT), respectively. This position corresponds to the pAraC-1 mutations described above (see, Table 1B; sub-sequence 3). The third analogous change, pWhtC-3Ser, converts the glycine (GGT) at amino acid 212 to serine (AGT), corresponding to the AraC-3Ser mutation described above (see, Table 1B; sub-sequence 4). The fourth, Wht466Thr, converts isoleucine (ATA) to threonine (ACA) at amino acid 466, corresponding to the Mz419Thr mutant from maize (see, Table 1B; sub-sequence 9).

Three of the mutations isolated from the wheat protox-1 screen result in amino acid changes at residues not previously identified as herbicide resistance sites. One change (Wht356Leu) converts valine (GTT) to leucine (CM) at amino acid 356 of the wheat protox-1 sequence (SEQ ID NO:10) (see, Table 1B; sub-sequence 6). A second (Wht421Pro) converts serine (TCT) to proline (CCT) at amino acid 421 (see, Table 1B; sub-sequence 8). The third (Wht502Ala) converts valine (GTT) to alanine (GCT) at amino acid 502 (see, Table 1B; sub-sequence 10).

Example 16

Identification of Sites in the Soybean Protox-1 Gene that can be Mutated to Give Herbicide Tolerance To create an efficient plasmid screening system for soybean protox-1, the soybean cDNA was engineered into the pMut-1 vector as described above for the maize cDNA. This chimeric Arab-soybean protox-1 plasmid is designated pMut-5. The pMut-5 DNA was mutated and screened for herbicide tolerance as described above. This analysis revealed multiple plasmids containing herbicide resistant protox coding sequences. Sequence analysis showed 4 single base changes that individually result in an herbicide tolerant soybean protox-1 enzyme. Two of these mutations correspond to amino acid changes previously shown to confer tolerance at the homologous position in the Arabidopsis and/or in the wheat protox-1 gene. One, pSoyC-1Thr, converts the alanine (GCA) at amino acid 226 (SEQ ID NO:12) to threonine (ACA). This position corresponds to the pAraC-1Thr mutation described above (see, Table 1B; sub-sequence 3). The second analogous change, Soy517Ala, converts the valine (GTT) at amino acid 517 to alanine (GCT), corresponding to the Wht502Ala mutation from wheat (see, Table 1B; sub-sequence 10).

Two of the mutations isolated from the soybean protox-1 screen result in amino acid changes at a residue not previously identified as an herbicide resistance site. One change (Soy369Ser) converts proline (CCT) to serine (TCT) at amino acid 369 of the soybean protox-1 sequence (SEQ ID NO:12) (see, Table 1B; sub-sequence 5). A second (Soy369His) converts this same proline369 to histidine (CAT) (see, Table 1B; sub-sequence 5).

Individual amino acid changes that produced highly herbicide tolerant Arabidopsis protox-1 enzymes were engineered into the soybean protox-1 gene by site directed mutagenesis as described above. Bacterial testing demonstrated that changing the alanine (GCA) at amino acid 226 (SEQ ID NO:12) to leucine (pSoyC-1Leu) produced a tolerant soybean enzyme (see, Table 1B; sub-sequence 3). Changing the tyrosine (TAC) at amino acid 432 (SEQ ID NO:12) to either leucine (pSoyC-2Leu) or isoleucine (pSoyC-2Ile) also produced herbicide tolerant enzymes (see, Table 1B; sub-sequence 7).

Example 17

Identification of Sites in the Sugar Beet Protox-1 Gene that can be Mutated to Give Herbicide Tolerance To create an efficient plasmid screening system for sugar beet protox-1, the sugar beet cDNA was engineered into the pMut-1 vector as described above for the maize cDNA. This chimeric Arab-sugar beet protox-1 plasmid is designated pMut-6. The pMut-6 DNA was mutated and screened for herbicide tolerance as described above. This analysis revealed multiple plasmids containing herbicide resistant protox coding sequences. Sequence analysis showed a single base change that results in an herbicide tolerant sugar beet protox-1 enzyme. This change (pSugC-2Cys) converts tyrosine (TAC) at amino acid 449 to cysteine (TGC) and is analogous to the AraC-2 mutations in Arabidopsis (see, Table 1B; sub-sequence 7).

Individual amino acid changes that produced highly herbicide tolerant Arabidopsis protox-1 enzymes were engineered into the sugar beet protox-1 gene by site directed mutagenesis as described above. Bacterial testing demonstrated that changing the tyrosine (TAC) at amino acid 449 to leucine (pSugC-2Leu), isoleucine (pSugC-2Ile), valine (pSugC-2Val), or methionine (pSugC-2Met) produced herbicide tolerant sugar beet enzymes (see, Table 1B; sub-sequence 7).

Example 18

Identification of Sites in the Cotton Protox-1 Gene that can be Mutated to Give Herbicide Tolerance In an effort to create an efficient plasmid screening system for cotton protox-1, the cotton cDNA was engineered into the pMut-1 vector as described above for the maize cDNA. This chimeric Arab-cotton protox-1 plasmid is designated pMut-7. The pMut-7 DNA was mutated and screened for herbicide tolerance as described above. This analysis revealed multiple plasmids containing herbicide resistant protox coding sequences. Sequence analysis showed 3 single base changes that individually result in an herbicide tolerant cotton protox-1 enzyme. Two mutants, pCotC-2Cys and pCotC-2Arg, change tyrosine (TAC) at amino acid 428 (SEQ ID NO:16) to cysteine (TGC) and to arginine (CGC), respectively (see, Table 1B; sub-sequence 7). Arginine is a novel substitution giving tolerance at this previously identified AraC-2 (sub-sequence 7) site. The third mutation (Cot365Ser) converts proline (CCC) to serine (TCC) at amino acid 365. This change corresponds to the soybean mutant Soy369Ser (see, Table 1B; sub-sequence 5).

Example 19

Demonstration of Resistant Mutations' Cross-Tolerance to Various Protox-Inhibiting Compounds Resistant mutant plasmids, originally identified based on resistance against a single protox inhibitory herbicide, were tested against a spectrum of other protox inhibiting compounds. For this test, the SASX38 strain containing the wild-type plasmid is plated on a range of concentrations of each compound to determiine the lethal concentration for each one. Resistant mutant plasmids in SASX38 are plated and scored for the ability to survive on a concentration of each compound at least 10 fold higher than the concentration that is lethal to the SASX38 strain containing the wild-type plasmid.

Results from bacterial cross-tolerance testing, illustrated in Tables 3A and 3B, show that each of the mutations identified confers tolerance to a variety of protox inhibiting compounds.

Section C: Expression of Herbicide-Resistant Protox Genes in Transgenic Plants

Example 20

Engineering of Plants Tolerant to Protox-Inhibiting Herbicides by Homologous Recombination or Gene Conversion Because the described mutant coding sequences effectively confer herbicide tolerance when expressed under the control of the native protox promoter, targeted changes to the protox coding sequence in its native chromosomal location represent an alternative means for generating herbicide tolerant plants and plant cells. A fragment of protox DNA containing the desired mutations, but lacking its own expression signals (either promoter or 3' untranslated region) can be introduced by any of several art-recognized methods (for instance, Agrobacterium transformation, direct gene transfer to protoplasts, microprojectile bombardment), and herbicide-tolerant transformants selected. The introduced DNA fragment also contains a diagnostic restriction enzyme site or other sequence polymorphism that is introduced by site-directed mutagenesis in vitro without changing the encoded amino acid sequence (i.e. a silent mutation). As has been previously reported for various selectable marker and herbicide tolerance genes (see, e.g., Paszkowski et al., *EMBO J*. 7: 4021–4026 (1988); Lee et al., *Plant Cell* 2: 415425 (1990); Risseeuw et al., *Plant J*. 7: 109–119 (1995)). some transformants are found to result from homologous integration of the mutant DNA into the protox chromosomal locus, or from conversion of the native protox chromosomal sequence to the introduced mutant sequence. These transformants are recognized by the combination of their herbicide-tolerant phenotype, and the presence of the diagnostic restriction enzyme site in their protox chromosomal locus.

Example 21

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, *Gene* 19: 259–268 (1982); Bevan et al., *Nature* 304:184–187 (1983)), the bar gene, which confers resistance to the herbicide phosphinothricin (White et al., *Nucl Acids Res* 18: 1062 (1990), Spencer et al. Theor Appl Genet 79: 625–631(1990)), the hph gene, which confers resistance to the antibiotic hygromycin (Blochinger & Diggelmann, *Mol Cell Biol* 4: 2929–2931), and the dhfr gene, which confers resistance to methotrexate (Bourouis et al., *EMBO J*. 2(7): 1099–1104 (1983)).

I. Construction of Vectors Suitable for Agrobacteriun Transformation

Many vectors are available for transformation using *Agrobacterium tumefaciens*. These typically carry at least one T-DNA border sequence and include vectors such as pBIN19 (Bevan, *Nucl. Acids Res*. (1984)) and pXYZ. Below the construction of two typical vectors is described.

Construction of pCIB200 and pCIB2001: The binary vectors pCIB200 and pCIB2001 are. used for the construction of recombinant vectors for use with Agrobacteriun and was constructed in the following manner. pTJS75kan was created by NarI digestion of pTJS75 (Schmidhauser & Helinski, *J Bacteriol*. 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et al., *Plant Molecular Biology* 14: 26&276 (1990)). XhoI linkers were ligated to the EcoRV fragment of pCIB7, which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200, which is created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives Thereof: The binary vector pCIB10 contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al., Gene 53: 153–161 (1987). Various derivatives of pCIB10 have been constructed that incorporate the gene for hygromycin B phosphotransferase described by Gritz et al., Gene 25: 179–188 (1983)). These derivatives enable selection of transgenic plant cells on hygromycin only (pCIB743), or hygromycin and kanamycin (pCIB715, pCIB717).

II. Construction of Vectors Suitable for non-Agrobacterinum Transformation.

Transformation without the use of *Agrobacterium tumefaciens* circumvents the requirement for T-DNA sequences in the chosen transformation vector and consequently vectors lacking these sequences can be utilized in addition to vectors such as the ones described above that contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATG's and generate the restriction sites SspI and PvuII. The new restriction sites were 96 and 37-bp away from the unique SalI site and 101 and 42-bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400-bp SmaI fragment containing the bar gene from *Streptomyces viridochromogenes* was excised and inserted into the HpaI site of pCIB3060 (Thompson et al. *EMBO J* 6: 2519–2523 (1987)). This generated pCIB3064, which comprises the bar gene under the control of the CaMV 35S promoter and terminator for herbicide selection, a gene for ampicillin resistance (for selection in E. coli) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector that utilizes the E. coli gene dihydrofolate reductase (DHFR) as a selectable marker conferring resistance to methotrexate. PCR was used to amplify the 35S promoter (~800-bp), intron 6 from the maize Adh1 gene (~550-bp) and 18-bp of the GUS untranslated leader sequence from pSOG10. A 250-bp fragment encoding the E. coli dihydrofolate reductase type II gene was also amplified by PCR and these two PCR fragments were assembled with a SacI-PstI fragment from pBI221 (Clontech), which comprised the pUC19 vector backbone and the nopaline synthase terminator. Assembly of these fragments generated pSOG19, which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 22

Construction of Plant Expression Cassettes

Gene sequences intended for expression in transgenic plants are firsly assembled in expression cassettes behind a suitable promoter and upstream of a suitable transcription terrminator. These expression cassettes can then be easily transferred to the plant transformation vectors described above in Example 21.

I. Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

II. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator, the pea rbcS E9 terminator, as well as terminators naturally associated with the plant protox gene (i.e. "protox terminators"). These can be used in both monocotyledons and dicotyledons.

III. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. Plant Molec. Biol. 15: 65–79 (1990))

IV. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence that is found at the amino terminal end of various proteins and that is cleaved during chloroplast import yielding the mature protein (e.g. Comai et al. *J. Biol. Chem.* 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins that are known to be chloroplast localized.

Other gene products are localized to other organelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition, sequences have been characterized that cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy terminal sequences are responsible for vacuolar targeting of gene products (Shinshi et al., *Plant Molec. Biol.* 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site that are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp. 1081–1091 (1982); Wasmann et al. *Mol. Gen. Genet.* 205: 446–453 (1986)). These construction techniques are well known in the art and are equally applicable to mitochondria and peroxisomes. The choice of targeting that may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter that has an expression pattern different to that of the promoter from which the targeting signal derives.

Example 23

Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species that are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 24

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (ie. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15:473497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics' helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" that contained half-strength MS, 2% sucrose, and the same concentration of selection agent. Patent application WO 94/13822 describes methods for wheat transformation and is hereby incorporated by reference.

Example 25

Isolation of the *Arabidopsis thaliana* Protox-1 Promoter Sequence

A Lambda Zap II genomic DNA library prepared from *Arabidopsis thaliana* (Columbia, whole plant) was purchased from Stratagene. Approximately 125,000 phage were plated at a density of 25,000 pfu per 15 cm Petri dish and duplicate lifts were made onto Colony/Plaque Screen membranes (NEN Dupont). The plaque lifts were probed with the Arabidopsis protox-1 cDNA (SEQ ID NO:1 labeled with 32P-dCTP by the random priming method (Life Technologies). Hybridization and wash conditions were at 65° C. as described in Church and Gilbert, *Proc. Natl. Acad. Sci. USA* 81: 1991–1995 (1984). Positively hybridizing plaques were purified and in vivo excised into pBluescript plasmids. Sequence from the genomic DNA inserts was determined by the chain termination method using dideoxy terminators labeled with fluorescent dyes (Applied Biosystems, Inc.). One clone, AraPT1Pro, was determined to contain 580-bp of Arabidopsis sequence upstream from the initiating methionine (ATG) of the protox-1 protein coding sequence. This clone also contains coding sequence and introns that extend to-bp 1241 of the protox-1 cDNA sequence. The 580-bp 5' noncoding fragment is the putative Arabidopsis protox-1 promoter, and the sequence is set forth in SEQ ID NO:13.

AraPT1Pro was deposited Dec. 15, 1995, as pWDC-11 (NRRL #B-21515)

Example 26

Construction of Plant Transformation Vectors Expressing Altered Protox-1 Genes Behind the Native Arabidopsis Protox-1 Promoter A full-length cDNA of the appropriate altered Arabidopsis protox-1 cDNA was isolated as an EcoRI-XhoI partial digest fragment and cloned into the plant expression vector pCGN1761ENX (see Example 9 of International application no. PCT/IB95/00452 filed Jun. 8, 1995, published Dec. 21, 1995 as WO 95/34659). This plasmid was digested with NcoI and BamHI to produce a fragment comprised of the complete protox-1 cDNA plus a transcription terminator from the 3' untranslated sequence of the tml gene of *Agrobacterium tumefaciens*. The AraPT1Pro plasmid described above was digested with NcoI and BamHI to produce a fragment comprised of pBluescript and the 580-bp putative Arabidopsis protox-1 promoter. Ligation of these two fragments produced a fusion of the altered protox cDNA to the native protox promoter. The expression cassette containing the protox-1 promoter/protox-1 cDNA/tml terminator fusion was excised by digestion with KpnI and cloned into the binary vector pCIB200. The binary plasmid was transformed by electroporation into Agrobacterium and then into Arabidopsis using the vacuum infiltration method (Bechtold et al., *C.R. Acad. Sci. Paris* 316: 1194–1199 (1993). Transformants expressing altered protox genes were selected on kanamycin or on various concentrations of protox inhibiting herbicide.

Example 27

Production of Herbicide Tolerant Plants by Expression of a Native Protox-1 Promoter/Altered Protox-1 Fusion Using the procedure described above, an Arabidopsis protox-1 cDNA containing a TAC to ATG (Tyrosine to Methionine) change at nucleotides 1306–1308 in the protox-1 sequence (SEQ ID NO:1) was fused to the native protox-1 promoter fragment and transformed into *Arabidopsis thaliana*. This altered protox-1 enzyme (AraC-2Met) has been shown to be >10-fold more tolerant to various protox-inhibiting herbicides than the naturally occurring enzyme when tested in the previously described bacterial expression system. Seed from the vacuum infiltrated plants was collected and plated on a range (10.0 nM–1.0 uM) of a protox inhibitory aryluracil herbicide of formula XVII. Multiple experiments with wild type Arabidopsis have shown that a 10.0 nM concentration of this compound is sufficient to prevent normal seedling germination. Transgenic seeds expressing the AraC-2Met altered enzyme fused to the native protox-1 promoter produced normal Arabidopsis seedlings at herbicide concentrations up to 500 nM, indicating at least 50-fold higher herbicide tolerance when compared to wild-type Arabidopsis. This promoter/altered protox enzyme fusion therefore functions as an effective selectable marker for plant transformation. Several of the plants that germinated on 100.0 nM of protox-inhibiting herbicide were transplanted to soil, grown 2–3 weeks, and tested in a spray assay with various concentrations of the protox-inhibiting herbicide. When compared to empty vector control transformants, the AraPT1Pro/AraC-2Met transgenics were >10-fold more tolerant to the herbicide spray.

Example 28

Demonstration of Resistant Mutations' Cross-tolerance to Various Protox-inhibiting Compounds in an Arabidopsis Germination Assay Using the procedure described above, an Arabidopsis protox-1 cDNA containing both a TAC to ATC (tyrosine to isoleucine) change at nucleotides 1306–1308 and a TCA to TTA (serine to leucine) change at nucleotides 945–947 in the protox-1 sequence (SEQ ID NO:1) was fused to the native protox-1 promoter fragment and transformed into *Arabidopsis thaliana*. This altered protox-1 enzyme (AraC-2Ile+AraC305Leu) has been shown to be >10-fold more tolerant to a protox inhibitory aryluracil herbicide of formula XVII than the naturally occurring enzyme when tested in a bacterial system (see Examples 9–13). Homozygous Arabidopsis lines containing this fusion were generated from transformants that showed high tolerance to a protox inhibiting herbicide in a seedling germination assay as described above. The seed from one line was tested for cross-tolerance to various protox-inhibitory compounds by repeating the germination assay on concentrations of the compounds that had been shown to inhibit germination of wild-type Arabidopsis. The results from these experiments are shown in Table 4.

Example 29

Isolation of a Maize Protox-1 Promoter Sequence

A *Zea Mays* (Missouri 17 inbred, etiolated seedlings) genomic DNA library in the Lambda FIX II vector was purchased from Stratagene. Approximately 250,000 pfu of the library was plated at a density of 50,000 phage per 15 cm plate and duplicate lifts were made onto Colony/Plaque screen membranes (NEN Dupont). The plaque lifts were probed with the maize protox-1 cDNA (SEQ ID NO:5) labeled with 32P-dCTP by the random priming method (Life Technologies). Hybridization and wash conditions were at 65° C. as described in Church and Gilbert, *Proc. Natl. Acad. Sci. USA* 81: 1991–1995 (1984). Lambda phage DNA was isolated from three positively hybridizing phage using the Wizard Lambda Preps DNA Purification System (Promega). Analysis by restriction digest, hybridization patterns, and DNA sequence analysis identified a lambda clone containing approximately 3.5 kb of maize genomic DNA located 5' to the maize protox-1 coding sequence previously isolated as a cDNA clone. This fragment includes the maize protox-1 promoter. The sequence of this fragment is set forth in SEQ ID NO:14. From nucleotide 1 to 3532, this sequence is comprised of 5' noncoding sequence. From nucleotide 3533 to 3848, this sequence encodes the 5' end of the maize protox-1 protein.

A plasmid containing the sequence of SEQ ID NO:14 fused to the remainder of the maize protox-1 coding sequence was deposited Mar. 19, 1996 as pWDC-14 (NRRL #B-21546).

Example 30

Construction of Plant Transformation Vectors Expressing Altered Protox-1 Genes Behind the Native Maize Protox-1 Promoter The 3848-bp maize genomic fragment (SEQ ID NO:14) was excised from the isolated lambda phage clone as a SalI-KpnI partial digest product and ligated to a KpnI-NotI fragment derived from an altered maize protox-1 cDNA that contained an alanine to leucine change at amino acid 164 (SEQ ID NO:6). This created a fusion of the native maize protox-1 promoter to a full length cDNA that had been shown to confer herbicide tolerance in a bacterial system (Examples 9–14). This fusion was cloned into a pUC18 derived vector containing the CaMV 35S terminator sequence to create a protox promoter/altered protox cDNA/terminator cassette. The plasmid containing this cassette was designated pWCo-1.

A second construct for maize transformation was created by engineering the first intron found in the coding sequence from the maize genomic clone back into the maize cDNA. The insertion was made using standard overlapping PCR fusion techniques. The intron (SEQ ID NO:25) was 93-bp long and was inserted between nucleotides 203 and 204 of SEQ ID NO:6, exactly as it appeared in natural context in the lambda clone described in Example 29. This intron-containing version of the expression cassette was designated pWCo-2.

Example 31

Demonstration of Maize Protox-1 Promoter Activity in Transgenic Maize Plants Maize plants transformed with maize protox promoter/altered protox fusions were identified using PCR analysis with primers specific for the transgene. Total RNA was prepared from the PCR positive plants and reverse-transcribed using Superscript M-MLV (Life Technologies) under recommended conditions. Two microliters of the reverse transcription reaction was used in a PCR reaction designed to be specific for the altered protox sequence. While untransformed controls give no product in this reaction, approximately 85% of plants transformed with pWCo-1 gave a positive result, indicating the presence of mRNA derived from the transgene. This demonstrates some level of activity for the maize protox promoter. The RNA's from the transgenic maize plants were also subjected to standard northern blot analysis using the radiolabeled maize protox cDNA fragment from SEQ ID NO:6 as a probe. Protox-1 mRNA levels significantly above those of untransformed controls were detected in some of the transgenic maize plants. This elevated mRNA level is presumed to be due to expression of altered protox-1 mRNA from the cloned maize protox promoter.

Example 32

Isolation of a Sugar Beet Protox-1 Promoter Sequence

A genomic sugar beet library was prepared by Stratagene in the Lambda Fix II vector. Approximately 300,000 pfu of the library was plated and probed with the sugar beet protox-1 cDNA sequence (SEQ ID NO:17) as described for maize in Example 29. Analysis by restriction digest, hybridization patterns and DNA sequence analysis identified a lambda clone containing approximately 7 kb of sugar beet genomic DNA located 5' to the sugar beet coding sequence previously isolated as a cDNA clone. A PstI-SalI fragment of 2606-bp was subcloned from the lambda clone into a pBluescript vector. This fragment contains 2068-bp of 5' noncoding sequence and includes the sugar beet protox-1 promoter sequence. It also includes the first 453-bp of the protox-1 coding sequence and the 85-bp first intron contained in the coding sequence. The sequence of this fragment is set forth in SEQ ID NO:26.

A plasmid containing the sequence of SEQ ID NO:26 was deposited Dec. 6, 1996 as pWDC-20 (NRRL #B-21650).

Example 33

Construction of Plant Transformation Vectors Expressing Altered Sugar Beet Protox-1 Genes Behind the Native Sugar Beet Protox-1 Promoter The sugar beet genomic fragment (SEQ ID NO:26) was excised from the genomic subclone described in Example 32 as a SacI-BsrGI fragment that includes 2068-bp of 5' noncoding sequence and the first 300-bp of the sugar beet protox-1 coding sequence. This fragment was ligated to a BsrGI-NotI fragment derived from an altered sugar beet protox-1 cDNA that contained a tyrosine to methionine change at amino acid 449 (SEQ 1D NO:18). This created a fusion of the native sugar beet protox-1 promoter to a full length cDNA that had been shown to confer herbicide tolerance in a bacterial system (Examples 9–14). This fusion was cloned into a pUC18 derived vector containing the CaMV 35S terminator sequence to create a protox promoter/altered protox cDNA/terminator cassette. The plasmid containing this cassette was designated pWCo-3.

Example 34

Production of Herbicide Tolerant Plants by Expression of a Native Sugar Beet Protox-1 Promoter/Altered Sugar Beet Protox-1 Fusion The expression cassette from pWCo-3 is transformed into sugar beet using any of the transformation methods applicable to dicot plants, including Agrobacterium, protoplast, and biolistic transformation techniques. Transgenic sugar beets expressing the altered protox-1 enzyme are identified by RNA-PCR and tested for tolerance to protox-inhibiting herbicides at concentrations that are lethal to untransformed sugar beets.

Section D: Expression of Protox Genes in Plant Plastids

Example 35

Preparation of a Chimeric Gene Containing the Tobacco Plastid clpP Gene Promoter and Native clpP 5' Untranslated Sequence Fused to a GUS Reporter Gene and Plastid rps16 Gene 3' Untranslated Sequence in a Plastid Transformation Vector I. Amplification of the Tobacco Plastid clpP Gene Promoter and Complete 5' Untranslated RNA (5' UTR).

Total DNA from *N. tabacum* c.v. "Xanthi NC" was used as the template for PCR with a left-to-right "top strand" primer comprising an introduced EcoRI restriction site at position –197 relative to the ATG start codon of the constitutively expressed plastid clpP gene (primer Pclp_P1a: 5'-GCGGAATTCATACTTATTTATCATTAGAAAG-3' (SEQ ID NO:27); EcoRI restriction site underlined) and a right-to-left "bottom strand" primer homologous to the region from –21 to –1 relative to the ATG start codon of the clpP promoter that incorporates an introduced NcoI restriction site at the start of translation (primer Pclp_P2b: 5'-GCG CCATGGTAAATGAAAGAAAGAACTAAA-3' (SEQ ID NO:28); NcoI restriction site underlined). This PCR reaction was undertaken with Pfu thermostable DNA polymerase (Stratagene, La Jolla Calif.) in a Perkin Elmer Thermal Cycler 480 according to the manufacturer's recommendations (Perkin Elmer/Roche, Branchburg, N.J.) as follows: 7 min 95° C., followed by 4 cycles of 1 min 95° C./2 min 43° C./1 min 72° C., then 25 cycles of 1 min 95° C./2 min 55° C./1 min 72° C. The 213-bp amplification product comprising the promoter and 5' untranslated region of the clpP gene containing an EcoRI site at its left end and an NcoI site at its right end and corresponding to nucleotides 74700 to 74505 of the *N. tabacum* plastid DNA sequence (Shinozaki et al., *EMBO J*. 5: 2043–2049 (1986)) was gel purified using standard procedures and digested with EcoRI and NcoI (all restriction enzymes were purchased from New England Biolabs, Beverly, Mass.).

II. Amplification of the Tobacco Plastid rps16 Gene 3' Untranslated RNA Sequence (3'UTR).

Total DNA from *N. tabacum* c.v. "Xanthi NC" was used as the template for PCR as described above with a left-to-right "top strand" primer comprising an introduced XbaI restriction site immediately following the TAA stop codon of the plastid rps16 gene encoding ribosomal protein S16 (primer rps16P_1a (5'-GCG TCTAGATCAACCGAAATTCAATTAAGG-3' (SEQ ID NO:30); XbaI restriction site underlined) and a right-to-left "bottom strand" primer homologous to the region from +134 to +151 relative to the TAA stop codon of rps16 that incorporates an introduced HindIII restriction site at the 3' end of the rps16 3' UTR (primer rps16P_1b (5'-CGC AAGCTTCAATGGAAGCAATGATAA-3' (SEQ ID NO:31); HindIII restriction site underlined). The 169-bp amplification product comprising the 3' untranslated region of the rps16 gene containing an XbaI site at its left end and a HindIII site at its right end and containing the region corresponding to nucleotides 4943 to 5093 of the *N. tabacum* plastid DNA sequence (Shinozaki et al., 1986) was gel purified and digested with XbaI and HindIII.

III. Ligation of a GUS Reporter Gene Fragment to the clpP Gene Promoter and 5' and 3' UTR's.

An 1864-bp β-glucuronidase (GUS) reporter gene fragment derived from plasmid pRAJ275 (Clontech) containing an NcoI restriction site at the ATG start codon and an XbaI site following the native 3' UTR was produced by digestion with NcoI and XbaI. This fragment was ligated in a four-way reaction to the 201-bp EcoRI/NcoI clpP promoter fragment, the 157-bp XbaI/HindIII rps16 3'UTR fragment, and a 3148-bp EcoRI/HindIII fragment from cloning vector pGEM3Zf(−) (Promega, Madison Wis.) to construct plasmid pPH138. Plastid transformation vector pPH140 was constructed by digesting plasmid pPRV111a (Zoubenko et al. 1994) with EcoRI and HindIII and ligating the resulting 7287-bp fragment to a 2222-bp EcoRI/HindIII fragment of pPH138.

Example 36

Preparation of a Chimeric Gene Containing the Tobacco Plastid clpP Gene Promoter Plus Tobacco Plastid psbA Gene Minimal 5' Untranslated Sequence Fused to a GUS Reporter Gene and Plastid rps16 Gene 3' Untranslated Sequence in a Plastid Transformation Vector Amplification of the tobacco plastid clpP gene promoter and truncated 5' untranslated RNA (5' UTR): Total DNA from *N. tabacum* c.v. "Xanthi NC" was used as the template for PCR as described above with the left-to-right "top strand" primer Pclp_P1a (SEQ ID NO:27) and a right-to-left "bottom strand" primer homologous to the region from −34 to −11 relative to the ATG start codon of the clpP promoter that incorporates an introduced XbaI restriction site in the clpP 5' UTR at position −11 (primer Pclp_P1b: 5'-GCGTCTAGAAAGAACTAAATACTATATTTCAC-3' (SEQ ID NO:29); XbaI restriction site underlined). The 202-bp amplification product comprising the promoter and truncated 5' UTR of the clpP gene containing an EcoRI site at its left end and an XbaI site at its right end was gel purified and digested with XbaI. The XbaI site was subsequendy filled in with Klenow DNA polymerase (New England Biolabs) and the fragment digested with EcoRI. This was ligated in a five-way reaction to a double stranded DNA fragment corresponding to the final 38 nucleotides and ATG start codon of the tobacco plastid psbA gene 5' UTR (with an NcoI restriction site overhang introduced into the ATG start codon) that was created by annealing the synthetic oligonucleotides minpsb_U (top strand: 5'-GGGAGTC-CCTGATGATTAAATAAACCAAGATTTTAC-3' (SEQ ID NO:32)) and minpsb_L (bottom strand: 5'-CATGGTA-AAATCTTGGTTTATTTAATCATCAGGGACTCCC-3' (SEQ ID NO:33); NcoI restriction site 5' overhang underlined), the NcoI/XbaI GUS reporter gene fragment described above, the XbaI/HindIII rps16 3'UTR fragment described above, and the EcoRI/HindIII pGEM3Zf(−) fragment described above to construct plasmid pPH139. Plastid transformation vector pPH144 was constructed by digesting plasmid pPRV111a (Zoubenko, et al., *Nucleic Acids Res* 22: 3819–3824 (1994)) with EcoRI and HindIII and ligating the resulting 7287-bp fragment to a 2251-bp EcoRI/HindIII fragment of pPH139.

Example 37

Preparation of a Chimeric Gene Containing the Tobacco Plastid clpP Gene Promoter and Complete 5' Untranslated Sequence Fused to the *Arabidopsis thaliana* Protox-1 Coding Sequence and Plastid rps16 Gene 3' Untranslated Sequence in a Vector for Tobacco Plastid Transformation Miniprep DNA from plasmid AraC-2Met carrying an *Arabidopsis thaliana* NotI insert that includes cDNA sequences from the Protoporphyrinogen IX Oxidase ("protox") gene encoding a portion of the amino terminal plastid transit peptide, the full-length cDNA and a portion of the 3' untranslated region was used as the template for PCR as described above using a left-to-right "top strand" primer (with homology to nucleotides +172 to +194 relative to the ATG start codon of the full length precursor protein) comprising an introduced NcoI restriction site and new ATG start codon at the deduced start of the mature protox protein coding sequence (primer APRTXP1a: 5'-GGGA CCATGGATTGTGTGATTGTCGGCGGAGG-3' (SEQ ID NO:34); NcoI restriction site underlined) and a right-to-left "bottom strand" primer homologous to nucleotides +917 to +940 relative to the native ATG start codon of the protox precursor protein (primer APRTXP1b: 5'-CTCCGCTCTCCAGCTTAGTGATAC-3' (SEQ ID NO:35)). The 778-bp product was digested with NcoI and SfuI and the resulting 682-bp fragment ligated to an 844-bp SfuI/NotI DNA fragment of AraC-2Met comprising the 3' portion of the protox coding sequence and a 2978-bp NcoI/NotI fragment of the cloning vector pGEM5Zf(+) (Promega, Madison Wis.) to construct plasmid pPH141. Plastid transformation vector pPH143 containing the clpP promoter driving the Formula XVII-resistant AraC-2Met protox gene with the rps16 3' UTR was constructed by digesting pPH141 with NcoI and SspI and isolating the 1491-bp fragment containing the complete protox coding sequence, digesting the rps16P_1a and rps16P_1b PCR product described above with HindIII, and ligating these to a 7436-bp NcoI/HindIII fragment of pPH140.

Example 38

Preparation of a Chimeric Gene Containing the Tobacco Plastid clpP Gene Promoter Plus Tobacco Plastid psbA Gene Minimal 5' Untranslated Sequence Fused to the *Arabidopsis thaliana* Protox-1 Coding Sequence and Plastid rps16 Gene 3' Untranslated Sequence in a Vector for Tobacco Plastid Transformation Plastid transformation vector pPH145 containing the clpP promoter/psbA 5' UTR fusion driving the Formula XVII-resistant AraC-2Met protox gene with the rps16 3' UTR was constructed by digesting pPH141 with NcoI and SspI and isolating the 1491-bp fragment containing the complete protox coding sequence, digesting the rps16P_1a and rps16P_1b PCR product described above with HindIII, and ligating these to a 7465-bp NcoI/HindIII fragment of pPH144.

Example 39

Preparation of a Chimeric Gene Containing the Tobacco Plastid clpP Gene Promoter and 5' Untranslated Sequence Fused to the EPSP Synthase Coding Sequence and Plastid rps16 Gene 3' Untranslated Sequence in a Vector for Tobacco Plastid Transformation

A cDNA library is screened for the 5-enolpyruvyl-3-phosphoshikimate synthase (EPSP synthase) gene (U.S. Pat. Nos. 5,310,667, 5,312,910, and 5,633,435, all incorporated herein by reference). A plasmid clone containing the full length EPSP synthase gene cDNA is isolated by standard techniques of molecular cloning. PCR primers are designed for amplification of the mature-size EPSP synthase coding sequence from this plasmid using a top strand primer having a 5' extension containing an NcoI restriction site inserted at amino acid −1 from the deduced mature protein start, thus creating an ATG start codon at this position, and a bottom strand primer having a 5' extension containing an XbaI restriction site downstream of the stop codon of the EPSP mature coding sequence in the amplified PCR product. The PCR amplification is performed using the designated primers and plasmid DNA template according to standard protocols. Amplified products are cloned and sequenced and a NcoI-XbaI DNA fragment containing the complete mature EPSP synthase coding sequence is isolated by restriction digest with NcoI and XbaI, electrophoresis on a 0.8% TAE agarose gel, and phenol extraction of the excised band.

A plastid transformation vector containing the clpP promoter directing transcription of the mature-sized EPSP synthase gene with the rps16 3' UTR is constructed by digesting pPH140 with NcoI and XbaI and purifying the fragment containing the vector backbone, 5' and 3' plastid integration targeting sequences, aadA selectable marker cassette, and clpP promoter/rps16 3' UTR expression sequences. This product is ligated in a two-way reaction with the NcoI-XbaI DNA fragment containing the mature-sized EPSP synthase coding-sequence isolated as described above.

Example 40

Preparation of a Chimeric Gene Containing the Tobacco Plastid clpP Gene Promoter and 5' Untranslated Sequence Fused to the ALS Coding Sequence and Plastid rps16 Gene 3' Untranslated Sequence in a Vector for Tobacco Plastid Transformation

A cDNA library is screened for the acetolactate synthase (ALS) gene (U.S. Pat. No. 5,013,659). A plasmid clone containing the full length ALS gene cDNA is isolated by standard techniques of molecular cloning. PCR primers are designed for amplification of the mature-size ALS coding sequence from this plasmid using a top strand primer having a 5' extension containing an NcoI restriction site inserted at amino acid −1 from the deduced mature protein start, thus creating an ATG start codon at this position, and a bottom strand primer having a 5' extension containing an XbaI restriction site downstream of the stop codon of the ALS mature coding sequence in the amplified PCR product. The PCR amplification is performed using the designated primers and plasmid DNA template according to standard protocols. Amplified products are cloned and sequenced and a NcoI-XbaI DNA fragment containing the complete mature ALS coding sequence is isolated by restriction digest with NcoI and XbaI, electrophoresis on a 0.8% TAE agarose gel, and phenol extraction of the excised band.

A plastid transformation vector containing the clpP promoter driving the mature-sized ALS gene with the rps16 3' UTR is constructed by digesting pPH140 with NcoI and XbaI and purifying the fragment containing the vector backbone, 5' and 3' plastid integration targeting sequences, aadA selectable marker cassette, and clpP promoter/rps16 3' UTR expression sequences. This product is ligated in a two-way reaction with the NcoI-XbaI DNA fragment containing the mature-sized ALS coding sequence isolated as described above.

Example 41

Preparation of a Chimeric Gene Containing the Tobacco Plastid clpP Gene Promoter and 5' Untranslated Sequence Fused to the AHAS Coding Sequence and Plastid rps16 Gene 3' Untranslated Sequence in a Vector for Tobacco Plastid Transformation

A cDNA library is screened for the acetohydroxyacid synthase (AHAS) gene (U.S. Pat. No. 4,761,373). A plasmid clone containing the full length AHAS gene cDNA is isolated by standard techniques of molecular cloning. PCR primers are designed for amplification of the mature-size AHAS coding sequence from this plasmid using a top strand primer having a 5' extension containing an NcoI restriction site inserted at amino acid -1 from the deduced mature protein start, thus creating an ATG start codon at this position, and a bottom strand primer having a 5' extension containing an XbaI restriction site downstream of the stop codon of the AHAS mature coding sequence in the amplified PCR product. The PCR amplification is performed using the designated primers and plasmid DNA template according to standard protocols. Amplified products are cloned and sequenced and a NcoI-XbaI DNA fragment containing the complete mature AHAS coding sequence is isolated by restriction digest with NcoI and XbaI, electrophoresis on a 0.8% TAE agarose gel, and phenol extraction of the excised band.

A plastid transformation vector containing the clpP promoter driving the mature-sized AHAS gene with the rps16 3' UTR is constructed by digesting pPH140 with NcoI and XbaI and purifying the fragment containing the vector backbone, 5' and 3' plastid integration targeting sequences, aadA selectable marker cassette, and clpP promoter/rps16 3' UTR expression sequences. This product is ligated in a two-way reaction with the NcoI-XbaI DNA fragment containing the mature-sized AHAS coding sequence isolated as described above.

Example 42

Preparation of a Chimeric Gene Containing the Tobacco Plastid clpP Gene Promoter and 5' Untranslated Sequence Fused to the ACCase Coding Sequence and Plastid rps16 Gene 3' Untranslated Sequence in a Vector for Tobacco Plastid Transformation

A cDNA library is screened for the acetylcoenzyme A carboxylase (ACCase) gene (U.S. Pat. No. 5,162,602). A plasmid clone containing the full length ACCase gene cDNA is isolated by standard techniques of molecular cloning. PCR primers are designed for amplification of the mature-size ACCase coding sequence from this plasmid using a top strand primer having a 5' extension containing an NcoI restriction site inserted at amino acid −1 from the deduced mature protein start, thus creating an ATG start codon at this position, and a bottom strand primer having a 5' extension containing an XbaI restriction site downstream of the stop codon of the ACCase mature coding sequence in the amplified PCR product. The PCR amplification is performed using the designated primers and plasmid DNA template according to standard protocols. Amplified products are cloned and sequenced and a NcoI-XbaI DNA fragment containing the complete mature ACCase coding sequence is isolated by restriction digest with NcoI and XbaI, electrophoresis on a 0.8% TAE agarose gel, and phenol extraction of the excised band.

A plastid transformation vector containing the clpP promoter driving the mature-sized ACCase gene with the rps16 3' UTR is constructed by digesting pPH140 with NcoI and XbaI and purifying the fragment containing the vector backbone, 5' and 3' plastid integration targeting sequences, aadA selectable marker cassette, and clpP promoter/rps16 3' UTR expression sequences. This product is ligated in a two-way reaction with the NcoI-XbaI DNA fragment containing the mature-sized ACCase coding sequence isolated as described above.

Example 43

Biolistic Transformation of the Tobacco Plastid Genome

Seeds of Nicotiana tabacum c.v. 'Xanthi nc' were germinated seven per plate in a 1" circular array on T agar medium and bombarded 12–14 days after sowing with 1 $\mu$m tungsten particles (M10, Biorad, Hercules, Calif.) coated with DNA from plasmids pPH143 and pPH145 essentially as described in Svab, Z. and Maliga, P. (1993) PNAS 90, 913–917. Bombarded seedlings were incubated on T medium for two days after which leaves were excised and placed abaxial side up in bright light (350–500 $\mu$mol photons/m$^2$/s) on plates of RMOP medium (Svab, Z., Hajdukiewicz, P. and Maliga, P. (1990) PNAS 87, 8526–8530) containing 500 $\mu$g/ml spectinomycin dihydrochloride (Sigma, St. Louis, Mo.). Resistant shoots appearing underneath the bleached leaves three to eight weeks after bombardment were subcloned onto the same selective medium, allowed to form callus, and secondary shoots isolated and subcloned. Complete segregation of transformed plastid genome copies (homoplasmicity) in independent subclones was assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346–349) was separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301–7305) and transferred to the greenhouse.

Example 44

Assessment of Herbicide Tolerance in Nt_pPH143 and Nt_pPH145 Plastid Transformant Lines Primary homoplasmic transformant lines transformed with pPH143 (line Nt_pPH143) or with pPH145 (line Nt_pPH145), which were obtained as described in Example 43, were grown to maturity in the greenhouse. Flowers were either: (a) self-pollinated, (b) pollinated with wildtype tobacco (c.v. Xanthi nc), or (c) used as pollen donors to fertilize emasculated flowers of wildtype Xanthi plants. Plastid segregation of the linked spectinomycin resistance marker was verified by uniparental female inheritance of the spectinomycin-resistance phenotype in each transformant line using a minimum of 50 seeds per selection pool derived from either selfed or backcross capsules. Additional self or wildtype backcross (Xanthi pollen parent) seeds were germinated in soil. 36 plants of each line (143 1B-1, 143 1B-4, 143 4A-2, 143 4A-5, 145 7A-5, 145 7A-6, 145 8A-3) plus 36 wildtype Xanthi plants as isogenic controls were grown in separate 6" clay pots in a controlled environment cubicle. In order to assess tolerance to the protox inhibitor Formula XVII, plants of Xanthi and the seven transformant lines were distributed into eight identical 16-pot flats (2 plants of each type per flat). The flats were sprayed with Formula XVII until runoff at concentrations of either 0, 0.5, 2.5, 5, 10, 25, 50, or 100 mg Formula XVII per liter. Solutions were made up in water using 4 g/liter or 40 g/liter stock solutions of Formula XVII dissolved in dimethylsulfoxide (DMSO) and used immediately after preparation. Twenty microliters of the wetting agent Silwett was added to each 200 ml volume of herbicide solution for a final concentration of 0.01%. Flats were sprayed in the late afternoon and allowed to dry overnight before transfer to the growth cubicle. Tolerance was assessed by comparing leaf damage and wilting to the untransformed Xanthi controls at 0, 18 hrs, 48 hrs, and 6 days post-application. Severe damage was apparent on the Xanthi plants at all concentrations above 0.5 mg/l, and complete wilting/burn down occurred above 2.5 mg/l. Only slight damage occurred on the Nt_pPH143 plants even at the highest concentration (100 mg/liter), and the plants soon outgrew the bleached spots (the appearance of Xanthi at 0.5 mg/liter was approximately equivalent to Nt_pPH143 1B-1 at 100 mg/liter, giving a tolerance of ca. 200-fold).

Example 45

Plastid Transformation of Maize

Type I embryogenic callus cultures (Green et al. (1983) in A. Fazelahmad, K. Downey, J. Schultz, R. W. Voellmy, eds. Advances in Gene Technology: Molecular Genetics of Plants and Animals. Miami Winter Symposium Series, Vol. 20. Academic Press, N.Y.) of the proprietary genotypes CG00526 and CG00714 are initiated from immature embryos, 1.5–2.5 mm in length, from greenhouse grown material. Embryos are aseptically excised from surface-sterilized ears approximately 14 days after pollination. Embryos of CG00526 are placed on D callus initiation media with 2% sucrose and 5 mg/L chloramben (Duncan et al. (1985) Planta 165: 322–332) while those of CG00714 are placed onto KM callus initiation media with 3% sucrose and 0.75 mg/L 2,4-d (Kao and Michayluk (1975) Planta 126, 105–110). Embryos and embryogenic cultures are subsequently cultured in the dark. Embryogenic responses are removed from the explants after ~14 days. CG00526 responses are placed onto D callus maintenance media with 2% sucrose and 0.5 mg/L 2,4-d while those of CG00714 are placed onto KM callus maintenance media with 2% sucrose and 5 mg/L Dicamba After 3 to 8 weeks of weekly selective subculture to fresh maintenance media, high quality compact embryogenic cultures are established. Actively growing embryogenic callus pieces are selected as target tissue for gene delivery. The callus pieces are plated onto target plates containing maintenance medium with 12% sucrose approximately 4 hours prior to gene delivery. The callus pieces are arranged in circles, with radii of 8 and 10 mm from the center of the target plate. Plasmid DNA is precipitated onto gold microcarriers as described in the DuPont Biolistics manual. Two to three μg of each plasmid is used in each 6 shot microcarrier preparation. Genes are delivered to the target tissue cells using the PDS-1000He Biolistics device. The settings on the Biolistics device are as follows: 8 mm between the rupture disc and the macrocarrier, 10 mm between the macrocarrier and the stopping screen and 7 cm between the stopping screen and the target. Each target plate is shot twice using 650 psi rupture discs. A 200×200 stainless steel mesh (McMaster-Carr, New Brunswick, N.J.) is placed between the stopping screen and the target tissue.

Five days later, the bombed callus pieces are transferred to maintenance medium with 2% sucrose and 0.5 mg/L 2,4-d, but without amino acids, and containing 750 or 1000 nM Formula XVII. The callus pieces are placed for 1 hour on the light shelf 4–5 hours after transfer or on the next day, and stored in the dark at 27° C. for 5–6 weeks. Following the 5–6 week primary selection stage, yellow to white tissue is transferred to fresh plates containing the same medium supplemented with 500 or 750 nM Formula XVII. 4–5 hours after transfer or on the next day, the tissues are placed for 1 hour on the light shelf and stored in the dark at 27° C. for 3–4 weeks. Following the 3–4 week secondary selection stage, the tissues are transferred to plates containing the same medium supplemented with 500 nM Formula XVII. Healthy growing tissue is placed for 1 hour on the light shelf and stored in the dark at 27° C. It is subcultured every two weeks until the colonies are large enough for regeneration.

At that point, colonies are transferred to a modified MS medium (Murashige and Skoog (1962) Physiol. Plant 15: 473497) containing 3% sucrose (MS3S) with no selection agent and placed in the light. For CG00526, 0.25 mg/L ancymidol and 0.5 mg/L kinetin are added to this medium to induce embryo germination, while for CG00714, 2 mg/L benzyl adenine is added. Regenerating colonies are transferred to MS3S media without ancymidol and kinetin, or benzyl adenine, for CG00526 or CG00714, respectively, after 2 weeks. Regenerating shoots with or without roots are transferred to boxes containing MS3S medium and small plants with roots are eventually recovered and transferred to soil in the greenhouse.

Table 1A

Alignment of the full-length and partial protox-1 amino acid sequences from Arabidopsis ("Arabpt-1"; SEQ ID NO:2), maize ("Mzpt-1"; SEQ ID NO:6), wheat ("Wtpt-1"; SEQ ID NO:10), soybean ("Soybeanpt-1"; SEQ ID NO:12), cotton ("Cottonpt-1"; SEQ ID NO:16), sugar beet ("Sugpt-1"; SEQ ID NO:18), oilseed rape ("Rapept-1"; SEQ ID NO:20), rice ("Ricept-1"; SEQ ID NO:22), sorghum ("Sorghumpt-1"; SEQ ID NO:24), and sugar cane ("Scpt-1"; SEQ ID NO:37). Alignment was performed using the PileUp program (GCG package, University of Wisconsin, Madison, Wis.). Positions that may be modified according to the teachings herein to confer or enhance inhibitor resistance are shown in bold type.

```
                 1                                                    50
     Rapept-1    ..........  ..........  MDLSLLRP..  QPFLSPFSNP  FPRSRPYKPL Arabpt-1    ..........  ..........  MELSLLRPTT  QSLLPSFSKP  NLRLMVYKPL Sorghumpt-1    ..........  ..........  ..........  ..........  ..........

Mzpt-1   ..........  ..........  ..........  ..........  ..........

Wtpt-1   ..........  ..........  ..........M  ATATVAAASP  LRGRVTGRPH

Ricept-1   ..........  ..........  ..........  ..........  ..........

Cottonpt-1    ..........  .......MTAL IDLSLLRSSP  SVSPFSIPHH  QHPPRFRKPF

Soybeanpt1   ........MV  SVFNEILFPP  NQTLLRPSLH  SPTSFFTSPT  RKFPRSRPNP

Sugpt-1   MKSMALSNCI  PQTQCMPLRS  SGHYRGNCIM  LSIPCSLIGR  RGYYSHKKRR

Scpt-1   ..........  ..........  ..........  ..........  ..........

51                                                   100
     Rapept-1    NLRCSVSGGS  VVGSSTIEGG  GGGKTVTADC  VIVGGGISGL  CIAQALVTKH Arabpt-1    RLRCSVAGGP  TVGSSKIEGG  GGT.TITTDC  VIVGGGISGL  CIAQALATKH Sorghumpt-1    ..........  ..........  ..........  ..........  ..........

Mzpt-1   ..........  ..........  ........ADC  VVVGGGISGL  CTAQALATRH

Wtpt-1   RVRPRCATAS  SATETPAAPG  VRL...SAEC  VIVGAGISGL  CTAQALATRY

Ricept-1   ..........  ..........  ..........  ..........  ..........

Cottonpt-1    KLRCSLAEGP  TISSSKIDGG  ESS...IADC  VIVGGGISGL  CIAQALATKH

Soybeanpt1   ILRCSIAEES  TASPPKTR..  DSA...PVDC  VVVGGGVSGL  CIAQALATKH
```

```
                     -continued
     Sugpt-1  MSMSCSTSSG SKSAVKEAGS GSGAGGLLDC VIVGGGISGL CIAQALCTKH Scpt-1  .......... .......... .......... .......... ..........

101                                              150
    Rapept-1  PDA..AKNVM VTEAKDRVGG NIIT..REEQ GFLWEEGPNS FQPSDPMLTM Arabpt-1  PDA..APNLI VTEAKDRVGG NIIT..REEN GFLWEEGPNS FQPSDPMLTM Sorghumpt-1  .......... .......... ..STVERPEE GYLWEEGPNS FQPSDPVLSM Mzpt-1  ..G..VGDVL VTEARARPGG NITTVERPEE GYLWEEGPNS FQPSDPVLTM Wtpt-1  ..G..VSDLL VTEARDRPGG NITTVERPDE GYLWEEGPNS FQPSDPVLTM Ricept-1  .......... .......... .......... .......... ..........

Cottonpt-1  RDV..ASNVI VTEARDRVGG NITTVER..D GYLWEEGPNS FQPSDPILTM

Soybeanpt1  ..A..NANVV VTEARDRVGG NITTMER..D GYLWEEGPNS FQPSDPMLTM

Sugpt-1  SSSSLSPNFI VTEAKDRVGG NIVVVE..AD GYIWEEGPNS FQPSDAVLTM

Scpt-1  .......... .......... .......... .......... ..........

151                                              200
    Rapept-1  VVDSGLKDDL VLGDPTAPRF VLWNGKLRPV PSKLTDLPFF DLMSIGGKIR Arabpt-1  VVDSGLKDDL VLGDPTAPRF VLWNGKLRPV PSKLTDLPFF DLMSIGGKIR Sorghumpt-1  AVDSGLKDDL VFGDPNAPRF VLWEGKLRPV PSKPADLPFF DLMSIPGKLR Mzpt-1  AVDSGLKDDL VFGDPNAPRF VLWEGKLRPV PSKPADLPFF DLMSIPGKLR Wtpt-1  AVDSGLKDDL VFGDPNAPRF VLWEGKLRPV PSKPGDLPFF SLMSIPGKLR Ricept-1  .......... .......... .......... .......... ..........

Cottonpt-1  AVDSGLKDDL VLGDPNAPRF VLWEGKLRPV PSKPTDLPFF DLMSIAGKLR

Soybeanpt1  VVDSGLKDEL VLGDPDAPRF VLWNRKLRPV PGKLTDLPFF DLMSIGGKIR

Sugpt-1  AVDSGLKDEL VLGDPNAPRF VLWNDKLRPV PSSLTDLPFF DLMTIPGKIR

Scpt-1  .......... .......... .......... .......... ..........

201                                              250
    Rapept-1  AGFGAIGIRP SPPGREESVE EFVNRRNLGDE VFERLIEPFC SGVYAGPAK Arabpt-1  AGFGALGIRP SPPGREESVE EFVRRNLGDE VFERLIEPFC SGVYAGPSK Sorghumpt-1  AGLGALGIRP PAPGREESVE EFVRRNLGAE VFERLIEPFC SGVYAGPSK Mzpt-1  AGLGALGIRP PPPGREESVE EFVRRNLGAE VFERLIEPFC SGVYAGPSK Wtpt-1  AGLGALGIRP PPPGREESVE EFVRRNLGAE VFERLIEPFC SGVYAGPSK Ricept-1  .......... .......... .......... .......... ..........

Cottonpt-1  AGFGAIGIRP PPPGYEESVE EFVRRNLGAE VFERFIEPFC SGVYAGPSK

Soybeanpt1  AGFGALGIRP PPPGHEESVE EFVRRNLGDE VFERLIEPFC SGVYAGPSK

Sugpt-1  AALGALGFRP SPPPHEESVE HFVRRNLGDE VFERLIEPFC SGVYAGPAK

Scpt-1  .......... .......... .......... .......... ..........

251                                              300
    Rapept-1  LSMKAAFGKV WKLEENGGSI IGGAFKAIQA KNKAPKTTRD PRLPKPKGQT Arabpt-1  LSMKAAFGKV WKLEQNGGSI IGGTFKAIQE RKNAPKAERD PRLPKPQGQT Sorghumpt-1  LSMAAAFGKV WRLEEAGGSI IGGTIKTIQE RGKNPKPPRD PRLPKPKGQT Mzpt-1  LSMAAAFGKV WRLEETGGSI IGGTIKTIQE RSKNPKPPRD ARLPKPKGQT Wtpt-1  LSMAAAFGKV WRLEEIGGSI IGGTIKAIQD KGKNPKPPRD PRLPAPKGQT Ricept-1  RALKAAFGKV WRLEDTGGSI IGGTIKTIQE RGKNPKPPRD PRLPTPKGQT
```

-continued

```
   Cottonpt-1 LSMAAAFGRV WKLEEIGGSI IGGTFKTIQE RNKTPKPPRD PRLPKPKGQT

Soybeanpt1 LSMKAAFGKV WKLEKNGGSI IGGTFKAIQE RNGASKPPRD PRLPKPKGQT

Sugpt-1 LSMKAAFGKV WKLEQKGGSI IGGTLKAIQE RGSNPKPPRD QRLPKPKGQT

Scpt-1 .......... .......... .......... .......... ..........

301                                                  350
    Rapept-1 VGSFRKGLTM LPEAISARLG DKVKVSWKLS SITKLASGEY SLTYETPEGI Arabpt-1 VGSFRKGLRM LPEAISARLG SKVKLSWKLS GITKLESGGY NLTYETPDGL Sorghumpt-1 VASFRKGLAM LPNAITSSLG SKVKLSWKLT SMTKSDGKGY VLEYETPEGV Mzpt-1 VASFRKGLAM LPNAITSSLG SKVKLSWKLT SITKSDDKGY VLEYETPEGV Wtpt-1 VASFRKGLAM LPNAIASRLG SKVKLSWKLT SITKADNQGY VLGYETPEGL Ricept-1 VASFRKGLTM LPDAITSRLG SKVKLSWKLT SITKSDNKGY ALVYETPEGV Cottonpt-1 VGSFRKGLTM LPEAIANSLG SNVKLSWKLS SITKLGNGGY NLTFETPEGM Soybeanpt1 VGSFRKGLTM LPDAISARLG NKVKLSWKLS SISKLDSGEY SLTYETPEGV Sugpt-1 VGSFRKGLVM LPTAISARLG SRVKLSWTLS SIVKSLNGEY SLTYDTPDGL Scpt-1 .......... .......... .......... .......... ..........

351                                                  400
    Rapept-1 VTVQSKSVVM TVPSHVASSL LRPLSDSAAE ALSKLYYPPV AAVSISYAKE Arabpt-1 VSVQSKSVVM TVPSHVASGL LRPLSESAAN ALSKLYYPPV AAVSISYPKE Sorghumpt-1 VLVQAKSVIM TIPSYVASDI LRPLSGDAAD VLSRFYYPPV AAVTVSYPKE Mzpt-1 VSVQAKSVIM TIPSYVASNI LRPLSSDAAD ALSRFYYPPV AAVTVSYPKE Wtpt-1 VSVQAKSVIM TIPSYVASDI LRPLSIDAAD ALSKFYYPPV AAVTVSYPKE Ricept-1 VSVQAKTVVM TIPSYVASDI LRPLSSDAAD ALSIFYYPPV AAVTVSYPKE Cottonpt-1 VSLQSRSVVM TIPSHVASNL LHPLSAAAAD ALSQFYYPPV ASVTVSYPKE Soybeanpt1 VSLQCKTVVL TIPSYVASTL LRPLSAAAAD ALSKFYYPPV AAVSISYPKE Sugpt-1 VSVRTKSVVM TVPSYVASRL LRPLSDSAAD SLSKFYYPPV AAVSLSYPKE Scpt-1 .......... .......... .......... .......... ..........

401                                                  450
    Rapept-1 AIRSECLIDG ELKGFGQLHP RTQKVETLGT IYSSSLFPNR APPGRVLLLN Arabpt-1 AIRTECLIDG ELKGFGQLHP RTQGVETLGT IYSSSLFPNR APPGRILLLN Sorghumpt-1 AIRKECLIDG ELQGFGQLHP RSQGVETLGT IYSSSLFPNR APAGRVLLLN Mzpt-1 AIRKECLIDG ELQGFGQLHP RSQGVETLGT IYSSSLFPNR APDGRVLLLN Wtpt-1 AIRKECLIDG ELQGFGQLHP RSQGVETLGT IYSSSLFPNR APAGRVLLLN Ricept-1 AIRKECLIDG ELQGFGQLHP RSQGVETLGT IYSSSLFPNR APAGRVLLLN Cottonpt-1 AIRKECLIDG ELKGFGQLHP RSQGIETLGT IYSSSLFPNR APSGRVLLLN Soybeanpt1 AIRSECLIDG ELKGFGQLHP RSQGVETLGT IYSSSLFPNR APPGRVLLLN Sugpt-1 AIRSECLING ELQGFGQLHP RSQGVETLGT IYSSSLFPGR APPGRILILS Scpt-1 .......... .......... .......... .......... ..........

451                                                  500
    Rapept-1 YIGGATNTGI LSKSEGELVE AVDRDLRKML IKPSSTDPLV LGVKLWPQAI Arabpt-1 YIGGSTNTGI LSKSEGELVE AVDRDLRKML IKPNSTDPLK LGVRVWPQAI Sorghumpt-1 YIGGATNTGI VSKTESELVE AVDRDLRKML INPTAVDPLV LGVRVWPQAI Mzpt-1 YIGGATNTGI VSKTESELVE AVDRDLRKML INSTAVDPLV LGVRVWPQAI
```

-continued

```
     Wtpt-1 YIGGSTNTGI VSKTESDLVG AVDRDLRKML INPRAADPLA LGVRVWPQAI

Ricept-1 YIGGSTNTGI VSKTESELVE AVDRDLRKML INPRAVDPLV LGVRVWPQAI

Cottonpt-1 YIGGATNTGI LSKTEGELVE AVDRDLRKML INPNAKDPLV LGVRVWPKAI

Soybeanpt1 YIGGATNTGI LSKTDSELVE TVDRDLRKIL INPNAQDPFV VGVRLWPQAI

Sugpt-1 YIGGAKNPGI LNKSKDELAK TVDKDLRRML INPDAKLPRV LGVRVWPQAI

Scpt-1 .......... .SKTESELVE AVDRDLRKML INPTAVDPLV LGVRVWPQAI 501                                           550
    Rapept-1 PQFLIGHIDL VDAAKASLSS SGHEGLFLGG NYVAGVALGR CVEGAYETAT Arabpt-1 PQFLVGHFDI LDTAKSSLTS SGYEGLFLGG NYVAGVALGR CVEGAYETAI Sorghumpt-1 PQFLVGHLDL LEAAKSALDQ GGYNGLFLGG NYVAGVALGR CIEGAYESAA Mzpt-1 PQFLVGHLDL LEAAKAALDR GGYDGLFLGG NYVAGVALGR CVEGAYESAS Wtpt-1 PQFLIGHLDR LAAAKSALGQ GGYDGLFLGG KYVAGVALGR CIEGAYESAS Ricept-1 PQFLIGHLDH LEAAKSALGK GGYDGLFLGG NYVAGVALGR CVEGAYESAS Cottonpt-1 PQFLVGHLDL LDSAKMALRD SGFHGLFLGG NYVSGVALGR CVEGAYEVAA Soybeanpt1 PQFLVGHLDL LDVAKASIRN TGFEGLFLGG NYVSGVALGR CVEGAYEVAA Sugpt-1 PQFSIGHFDL LDAAKAALTD TGVKGLFLGG NYVSGVALGR CIEGAYESAA Scpt-1 PQFLVGHLDL LEAAKSALDR GGYDGLFLGG NYVAGVALGR CVEGAYESAS 551       563
    Rapept-1 QVNDFMSRYA YK*

Arabpt-1 EVNNFMSRYA YK*

Sorghumpt-1 QIYDFLTKYA YK*

Mzpt-1 QISDFLTKYA YK*

Wtpt-1 QVSDFLTKYA YK*

Ricept-1 QISDYLTKYA YK*

Cottonpt-1 EVKEFLSQYA YK*

Soybeanpt1 EVNDFLTNRV YK*

Sugpt-1 EVVDFLSQYS DK*

Scpt-1 QIYDFLTKYA YK*
```

TABLE 1B

Sub-sequences of herbicide-tolerant protox enzymes comprising point mutations.

| # | Sub-sequence | $\Delta_n$ AA wild-type | $\Delta_n$ AA sub-stitutions | Corresponding AA position of $\Delta_n$ in Table 1A | Exemplary mutants |
|---|---|---|---|---|---|
| 1 | AP$\Delta_1$F | R | C | 169 | Mz88Cys |
| 2 | F$\Delta_2$S | C | F, L, K | 240 | Mz159Phe, Mz159Leu, Mz159Lys |
| 3 | Y$\Delta_3$G | A | V, T, L, C, I | 245 | pAraC-1Val, pAraC-1Thr, pAraC-1Leu, pAraC-1Cys, pAraC-1Ile, pMzC-1Val, pMzC-1Thr, pMzC-1Leu, pWhtC-1Val, pWhtC-1Thr, pSoyC-1Thr, pSoyC-1Leu |
| 4 | A$\Delta_4$D | G | S, L | 246 | pAraC-3Ser, pMzC-3Ser, pMzC-3Leu, pWhtC-3Ser |

TABLE 1B-continued

Sub-sequences of herbicide-tolerant protox enzymes comprising point mutations.

| # | Sub-sequence | $\Delta_n$ AA wild-type | $\Delta_n$ AA sub-stitutions | Corresponding AA position of $\Delta_n$ in Table 1A | Exemplary mutants |
|---|---|---|---|---|---|
| 5 | Y$\Delta_5$P | P | S, H | 388 | Soy369Ser |
|   |   |   |   |   | Soy369His |
|   |   |   |   |   | Cot365Ser |
| 6 | P$\Delta_6$A | V | L | 390 | Wht356Leu |
| 7 | $\Delta_7$IG | Y | C, I, L, T, M, V, A, R | 451 | pAraC-2Cys |
|   |   |   |   |   | pAraC-2Ile |
|   |   |   |   |   | pAraC-2Leu |
|   |   |   |   |   | pAraC-2Thr |
|   |   |   |   |   | pAraC-2Met |
|   |   |   |   |   | pAraC-2Val |
|   |   |   |   |   | pAraC-2Ala |
|   |   |   |   |   | pMzC-2Ile |
|   |   |   |   |   | pMzC-2Met |
|   |   |   |   |   | pSoyC-2Leu |
|   |   |   |   |   | pSoyC-2Ile |
|   |   |   |   |   | pSugC-2Cys |
|   |   |   |   |   | pSugC-2Leu |
|   |   |   |   |   | pSugC-2Ile |
|   |   |   |   |   | pSugC-2Val |
|   |   |   |   |   | pSugC-2Met |
|   |   |   |   |   | pCotC-2Cys |
|   |   |   |   |   | pCotC-2Arg |
| 8 | YIGG$\Delta_8$ | A, S | P | 455 | Wht421Pro |
| 9 | A$\Delta_9$P | I | T, H, G, N | 500 | Mz419Thr |
|   |   |   |   |   | Mz419His |
|   |   |   |   |   | Mz419Gly |
|   |   |   |   |   | Mz419Asn |
|   |   |   |   |   | Wht466Thr |
| 10 | G$\Delta_{10}$A | V | A | 536 | Wht502Ala |
|   |   |   |   |   | Soy517Ala |

Second-site mutations

| 11 | Q$\Delta_{11}$S | P | L | 143 | AraC118Leu |
| 12 | IGG$\Delta_{12}$ | T | I, A | 274 | AraC249Ile |
|   |   |   |   |   | AraC249Ala |
| 13 | SWXL$\Delta_{13}$ | S, T | L | 330 | AraC305Leu |
| 14 | L$\Delta_{14}$Y | N | S | 450 | AraC425Ser |
| 15 | G$\Delta_{15}$XGL | Y, H, F, V | C | 523 | AraC498Cys |

Double mutation

| 16 | T$\Delta_{16}$G | L | S | 428 | Mz347Ser453Thr |
| 17 | YV$\Delta_{17}$G | A, (S) | T | 534 |  |

TABLE 2

Comparison of the Arabidopsis (SEQ ID NO:4) and maize (SEQ ID NO:8) protox-2 amino acid sequences. Identical residues are denoted by the vertical bars between the two sequences. Alignment was performed using the GAP program described in Deveraux et al., Nucleic Acids Res. 12:387–395 (1984). Percent similarity: 75.889/ percent identity: 57.905.

```
1   ........................MASGAVAD.HQIEAVSGKRVAV   21
                            .||:|:..:|..::.|||
1   MLALTASASSAHPYRHASAHTTRRPRLRAVLAMAGSDDPRAAPARSVAV   50

22  VGAGVSGLAAAYKLKSRGLNVTVFEADGRVGGKLRSVMQNGLIWDEGANT  71
    ||||||||||||:|: .|:|||||||.:|.|||:. :.|::|||||
51  VGAGVSGLAAAYRLRQSGVNVTVFEAADRAGGKIRTNSEGGFVWDEGANT  100

72  MTEAEPEVGSLLDDLGLREKQQFPISQKKRYIVRNGVPVMLPTNPIELVT  121
    |||:| |.:.|:||||.:|||:| ||.||||||::|.|.::|.:||.|:.
101 MTEGEWEASRLIDDLGLQDKQQYPNSQHKRYIVKDGAPALIPSDPISLMK  150

122 SSVLSTQSKFQILLEPFLWKK....KSSKVSDASAEESVSEFFQRHFGQE  167
    ||||||.||:.:::||||:||    .|:|||:. .|||:.|:||||.|
151 SSVLSTKSKIALFFEPFLYKKANTRNSGKVSEEHLSESVGSFCERHFGRE  200
```

TABLE 2-continued

Comparison of the Arabidopsis (SEQ ID NO:4) and maize (SEQ ID NO:8) protox-2 amino acid sequences. Identical residues are denoted by the vertical bars between the two sequences. Alignment was performed using the GAP program described in Deveraux et al., Nucleic Acids Res. 12:387–395 (1984). Percent similarity: 75.889/ percent identity: 57.905.

```
168 VVDYLIDPFVGGTSAADPDSLSMKHSFPDLWNVEKSFGSIIVGAIRTKFA 217
    ||||::||||:||||:||:|||::|.||.|||:|:..:||:||||.|:|
201 VVDYFVDPFVAGTSAGDPESLSIRHAFPALWNLERKYGSVIVGAILSKLA 250

218 AKGGKSRDTKSSPGTKKGSRGSFSFKGGMQILPDTLCKSLSHDEINLDSK 267
    |||:..:...|.|.|.:::..|.||||.|||| |..|...:::.|::.|:..
251 AKGDPVKTRHDSSGKRRNRRVSFSFHGGMQSLINALHNEVGDDNVKLGTE 300

268 VLSLS..YNSGSRQENWSLSCVSHNETQRQ...NPHYDAVIMTAPLCNVK 312
    ||||. :::.. :.||:|. |.:..::: |. :|||||||||:||:
301 VLSLACTFDGVPALGRWSISVDSKDSGDKDLASNQTFDAVIMTAPLSNVR 350

313 EMKVMKGGQPFQLNFLPEINYMPLSVLITTFTKEKVKRPLEGFGVLIPSK 362
    ||. |||.|. |:|||.::|:|||:::|.|.|:.||:|||||||| |
351 RMKFTKGGAPVVLDFLPKMDYLPLSLMVTAFKKDDVKKPLEGFGVLIPYK 400

363 E.QKHGFKTLGTLFSSMMFPDRSPSDVHLYTTFIGGSRNQELAKASTDEL 411
    | ||||:||||||||||||||.|.| .|||||:|||:|.:|| .|.|. |
401 EQQKHGLKTLGTLFSSMMFPDRAPDDQYLYTTFVGGSRNRDLAGAPTSIL 450

412 KQVVTSDLQRLLGVEGEPVSVNHYYWRKAFPLYDSSYDSVMEAIDKMEND 461
    ||:|||||.:||||||:|. |.| || .|||||.|.||:|||:||.:
451 KQLVTSDLKKLLGVEGQPTFVKHVYWGNAFPLYGHDYSSVLEAIEKMEKN 500

462 LPGFFYAGNHRGGLSVGKSIASGCKAADLVISYLESCSNDKKPNDSL*   509
    ||||||||| ::||.||. ||||:||||.||||| ......
501 LPGFFYAGNSKDG#VGSVIASGS#LAISYLESHT#SH*...           545
```

TABLE 3A

Cross tolerance of plant protox mutants to various protox inhibitors.

| Formula | AraC-1Val | AraC-2Cys | AraC-1Thr | AraC-3Thr | MzC-1Val |
|---|---|---|---|---|---|
| XVII | + | + | + | + | + |
| VIIa | + | + | + | − | + |
| IV | ++ | − | ++ | ++ | − |
| XV | + | + | + | + | + |
| XI | − | + | + | ++ | + |
| XVI | − | − | − | − | + |
| XII | + | − | ++ | ++ | ++ |
| XIV | + | − | + | + | + |
| *X | | | | | |

+ = 10X or more tolerant than WT
++ = 100X or more tolerant than WT
− = no cross tolerance
* = this compound was tested but provided no information

TABLE 3B

Cross tolerance of plant protox mutants to various protox inhibitors.

| Formula | AraC-1Leu | AraC-2Ile | AraC-1Leu + AraC-2Met | AraC-1Leu + AraC-2Leu | AraC-2Ile + AraC-305Leu | AraC-2Cys + AraC-425Ser | AraC-2Leu + AraC-425Ser | AraC-2Met + AraC-425Ser |
|---|---|---|---|---|---|---|---|---|
| XVII | + | + | + | + | + | + | + | + |
| VIIa | ++ | ++ | ++ | ++ | ++ | ++ | ++ | ++ |
| IV | ++ | − | + | ++ | + | − | + | + |
| XV | ++ | +++ | +++ | +++ | +++ | ++ | +++ | ++ |
| XI | ++ | ++ | ++ | ++ | ++ | ++ | ++ | ++ |
| XVI | +++ | +++ | +++ | +++ | +++ | + | ++ | ++ |
| XII | | | | | | | | |
| XIV | ++ | ++ | ++ | ++ | ++ | − | ++ | ++ |

TABLE 4

Cross tolerance to various protox inhibitors in a seed germination assay.

| Formula | Common name | Tolerance |
|---|---|---|
| II | acifluorofen | + |
| III | fomasafen | + |
| IV | fluoroglycofen | ± |
| IVb | bifenox | + |
| IVc | oxyfluorofen | + |
| IVd | lactofen | ± |
| VIIa | fluthiacet-methyl | ++ |
| X | sulfentrazone | + |
| XI | flupropazil | ++ |
| XIV | flumiclorac | + |
| XVI | flumioxazin | +++ |
| XVII |  | ++ |
| XXIa | BAY 11340 | + |
| XXII |  | ++ |

± ≤ 10X more tolerant than wt
+ ≥ 10X more tolerant than wt
++ ≥ 100X more tolerant than wt
+++ ≥ 1000X more tolerant than wt Various modifications of the invention described herein will become apparent to those skilled in the art. Such modifications are intended to fall within the scope of the appended claims.

What is claimed is:

1. A method for controlling the growth of undesired vegetation comprising applying an effective amount of a protox-inhibiting herbicide to a population of transgenic plants or plant seeds or to the locus where a population of transgenic plants or plant seeds is cultivated, wherein each transgenic plant or plant seed comprises a modified plant DNA molecule that encodes a modified enzyme having protoporphyrinogen oxidase (protox) activity, wherein said modified enzyme comprises at least one amino acid substitution relative to the corresponding wild-type enzyme, wherein said DNA molecule is expressed in said transgenic plant or plant seed and confers tolerance thereupon to the protox-inhibiting herbicide.

2. The method according to claim 1, wherein said protox-inhibiting herbicide is selected from the group consisting of an aryluracil, a diphenylether, an oxidiazole, an imide, a phenyl pyrazole, a pyridine derivative, a 3-substituted-2-aryl-4,5,6,7-tetrahydroindazole, a phenopylate, a O-phenylpyrrolidinocarbamate analog of said phenopylate and a piperidinocarbamate analog of said phenopylate.

3. The method according to claim 1, wherein said protox-inhibiting herbicide is an imide having formula V, VI, VII, VIIa, VIII, IX, IXa, or IXb.

4. The method according to claim 1, wherein said protox-inhibiting herbicide is a pyridyl pyrazole having formula XXIIIa or XXIIIb.

5. A method for selectively suppressing the growth of weeds in a field containing planted crops or crop seeds, comprising the steps of:
   (a) planting transgenic herbicide tolerant crops or crop seeds in a field, wherein each transgenic crop or crop seed comprises a modified plant DNA molecule that encodes a modified enzyme having protoporphyrinogen oxidase (protox) activity, wherein said modified enzyme comprises at least one amino acid substitution relative to the corresponding wild-type enzyme, wherein said DNA molecule is expressed in said transgenic crop or crop seed and confers tolerance thereupon to an inhibitor of wild-type protox activity; and
   (b) applying to the crops or crop seeds and the weeds in the field or to the locus where the crops or crop seeds are cultivated a protox-inhibiting herbicide in amounts that inhibit naturally occurring protox activity, wherein the herbicide suppresses the growth of the weeds without suppressing the growth of the transgenic crops or crop seeds.

6. A method for controlling the growth of undesired vegetation comprising applying an effective amount of a protox-inhibiting herbicide to the locus where a population of transgenic plants or plant seeds is cultivated, wherein each transgenic plant or plant seed comprises a modified plant DNA molecule that encodes a modified enzyme having protoporphyrinogen oxidase (protox) activity, wherein said modified enzyme comprises at least one amino acid substitution relative to the corresponding wild-type enzyme, wherein said DNA molecule is expressed in said transgenic plant or plant seed and confers tolerance thereupon to the protox-inhibiting herbicide.

7. The method according to claim 6, wherein said protox-inhibiting herbicide is selected from the group consisting of an aryluracil, a diphenylether, an oxidiazole, an imide, a phenyl pyrazole, a pyridine derivative, a 3-substituted-2-aryl4,5,6,7-tetrahydroindazole, a phenopylate, a O-phenylpyrrolidinocarbamate analog of said phenopylate and a piperidinocarbamate analog of said phenopylate.

8. The method according to claim 6, wherein said protox-inhibiting herbicide is an imide having formula V, VI, VII, VIIa, VIII, IX, IXa, or IXb.

9. The method according to claim 6, wherein said protox-inhibiting herbicide is a pyridyl pyrazole having formula XXIIIa or XXIIIb.

10. A method for selectively suppressing the growth of weeds in a field containing planted crops or crop seeds, comprising the steps of:
   (a) planting transgenic herbicide tolerant crops or crop seeds, wherein each transgenic crop or crop seed comprises a modified plant DNA molecule that encodes a modified enzyme having protoporphyrinogen oxidase (protox) activity, wherein said modified enzyme comprises at least one amino acid substitution relative to the corresponding wild-type enzyme, wherein said DNA molecule is expressed in said transgenic crop or crop seed and confers tolerance thereupon to an inhibitor of wild-type protox activity; and
   (b) applying to the locus where the crops or crop seeds are cultivated a protox-inhibiting herbicide in amounts that inhibit naturally occurring protox activity, wherein the herbicide suppresses the growth of the weeds without suppressing the growth of the transgenic crops or crop seeds.

11. The method according to claim 1, wherein said modified protox enzyme comprises at least one amino acid sub-sequence selected from the group consisting of:
   (a) AP$\Delta_1$F (SEQ ID NO:38), wherein $\Delta_1$ is an amino acid other than arginine;
   (b) F$\Delta_2$S, wherein $\Delta_2$ is an amino acid other than cysteine;
   (c) Y$\Delta_3$G, wherein $\Delta_3$ is an amino acid other than alanine;
   (d) A$\Delta_4$D, wherein $\Delta_4$ is an amino acid other than glycine;

(e) Y$\Delta_5$P, wherein $\Delta_5$ is an amino acid other than proline;
(f) P$\Delta_6$A, wherein $\Delta_6$ is an amino acid other than valine;
(g) $\Delta_7$IG, wherein $\Delta_7$ is an amino acid other than tyrosine;
(h) YIGG$\Delta_8$ (SEQ ID NO:39), wherein $\Delta_8$ is an amino acid other than alanine or serine;
(i) A$\Delta_9$P, wherein $\Delta_9$ is an amino acid other than isoleucine; and
(j) G$\Delta_{10}$A, wherein $\Delta_{10}$ is an amino acid other than valine.

12. The method according to claim 11, wherein said modified enzyme comprises the amino acid sub-sequence AP$\Delta_1$F (SEQ ID NO:38), wherein $\Delta_1$ is an amino acid other than arginine.

13. The method according to claim 12, wherein $\Delta_1$ is cysteine.

14. The method according to claim 11, wherein said modified enzyme comprises the amino acid sub-sequence F$\Delta_2$S, wherein $\Delta_2$ is an amino acid other than cysteine.

15. The method according to claim 14, wherein $\Delta_2$ is phenylalanine, leucine, or lysine.

16. The method according to claim 11, wherein said modified enzyme comprises the amino acid sub-sequence Y$\Delta_3$G, wherein $\Delta_3$ is an amino acid other than alanine.

17. The method according to claim 16, wherein $\Delta_3$ is valine, threonine, leucine, cysteine, or isoleucine.

18. The method according to claim 11, wherein said modified enzyme comprises the amino acid sub-sequence A$\Delta_4$D, wherein $\Delta_4$ is an amino acid other than glycine.

19. The method according to claim 18, wherein $\Delta_4$ is serine or leucine.

20. The method according to claim 11, wherein said modified enzyme comprises the amino acid sub-sequence Y$\Delta_5$P, wherein $\Delta_5$ is an amino acid other than proline.

21. The method according to claim 20, wherein $\Delta_5$ is serine or histidine.

22. The method according to claim 11, wherein said modified enzyme comprises the amino acid sub-sequence P$\Delta_6$A, wherein $\Delta_6$ is an amino acid other than valine.

23. The method according to claim 22, wherein $\Delta_6$ is leucine.

24. The method according to claim 11, wherein said modified enzyme comprises the amino acid sub-sequence $\Delta_7$IG, wherein $\Delta_7$ is an amino acid other than tyrosine.

25. The method according to claim 24, wherein $\Delta_7$ is cysteine, isoleucine, leucine, threonine, methionine, valine, alanine, or arginine.

26. The method according to claim 11, wherein said modified enzyme comprises the amino acid sub-sequence YIGG$\Delta_8$ (SEQ ID NO:39), wherein $\Delta_8$ is an amino acid other than alanine or serine.

27. The method according to claim 26, wherein $\Delta_8$ is proline.

28. The method according to claim 11, wherein said modified enzyme comprises the amino acid sub-sequence A$\Delta_9$P, wherein $\Delta_9$ is an amino acid other than isoleucine.

29. The method according to claim 28, wherein $\Delta_9$ is threonine, histidine, glycine, or asparagine.

30. The method according to claim 11, wherein said modified enzyme comprises the amino acid sub-sequence G$\Delta_{10}$A, wherein $\Delta_{10}$ is an amino acid other than valine.

31. The method according to claim 30, wherein $\Delta_{10}$ is alanine.

32. The method according to claim 11, wherein said modified enzyme further comprises at least one additional amino acid sub-sequence selected from the group consisting of:
(k) Q$\Delta_{11}$S, wherein $\Delta_{11}$ is an amino acid other than proline;
(l) IGG$\Delta_{12}$ (SEQ ID NO:40), wherein $\Delta_{12}$ is an amino acid other than threonine;
(m) SWXL$\Delta_{13}$ (SEQ ID NO:41), wherein $\Delta_{13}$ is an amino acid other than serine;
(n) L$\Delta_{14}$Y, wherein $\Delta_{14}$ is an amino acid other than asparagine; and
(o) G$\Delta_{15}$XGL (SEQ ID NO:42), wherein $\Delta_{15}$ is an amino acid other than tyrosine.

33. The method according to claim 11, wherein said modified enzyme comprises the amino acid sub-sequence Y$\Delta_3$G, wherein $\Delta_3$ is an amino acid other than alanine, or the amino acid sub-sequence $\Delta_7$IG, wherein $\Delta_7$ is an amino acid other than tyrosine, and wherein said modified enzyme further comprises at least one additional amino acid sub-sequence selected from the group consisting of:
(k) Q$\Delta_{11}$S, wherein $\Delta_{11}$ is an amino acid other than proline;
(l) IGG$\Delta_{12}$ (SEQ ID NO:40), wherein $\Delta_{12}$ is an amino acid other than threonine;
(m) SWXL$\Delta_{13}$ (SEQ ID NO:41), wherein $\Delta_{13}$ is an amino acid other than serine;
(n) L$\Delta_{14}$Y, wherein $\Delta_{14}$ is an amino acid other than asparagine; and
(o) G$\Delta_{15}$XGL (SEQ ID NO:42), wherein $\Delta_{15}$ is an amino acid other than tyrosine.

34. The method according to claim 33, wherein said additional amino acid sub-sequence is Q$\Delta_{11}$S, wherein $\Delta_{11}$ is an amino acid other than proline.

35. The method according to claim 24, wherein $\Delta_{11}$ is leucine.

36. The method according to claim 33, wherein said additional amino acid sub-sequence is IGG$\Delta_{12}$ (SEQ ID NO:40), wherein $\Delta_{12}$ is an amino acid other than threonine.

37. The method according to claim 36, wherein $\Delta_{12}$ is isoleucine or alanine.

38. The method according to claim 33, wherein said additional amino acid sub-sequence is SWXL$\Delta_{13}$ (SEQ ID NO:41), wherein $\Delta_{13}$ is an amino acid other than serine.

39. The method according to claim 38, wherein $\Delta_{13}$ is leucine.

40. The method according to claim 33, wherein said additional amino acid sub-sequence is L$\Delta_{14}$Y, wherein $\Delta_{14}$ is an amino acid other than asparagine.

41. The method according to claim 40, wherein $\Delta_{14}$ is serine.

42. The method according to claim 33, wherein said additional amino acid sub-sequence is G$\Delta_{15}$XGL (SEQ ID NO:42), wherein $\Delta_{15}$ is an amino acid other than tyrosine.

43. The method according to claim 42, wherein $\Delta_{15}$ is cysteine.

44. The method according to claim 33, wherein said modified enzyme comprises: the amino acid sub-sequence $\Delta_7$IG, wherein $\Delta_7$ is an amino acid other than tyrosine; the amino acid sub-sequences IGG$\Delta_{12}$ (SEQ ID NO:40), wherein $\Delta_{12}$ is an amino acid other than threonine; and the amino acid sub-sequence SWXL$\Delta_{13}$ (SEQ ID NO:41), wherein $\Delta_{13}$ is an amino acid other than serine.

45. The method according to claim 44, wherein $\Delta_7$ is isoleucine, wherein $\Delta_{12}$ is isoleucine, and wherein $\Delta_{13}$ is leucine.

46. The method according to claim 1, wherein said modified plant DNA molecule is modified from a nucleotide sequence isolated from a plant selected from the group consisting of: Arabidopsis, maize, wheat, soybean, cotton, sugar beet, oilseed rape, rice, sorghum, and sugar cane.

47. The method according to claim 1, wherein said modified plant DNA molecule is operatively linked to a promoter that is active in a plant.

48. The method according to claim 1, wherein said modified plant DNA molecule is operatively linked to a promoter functional in a plant plastid.

49. The method according to claim 48, wherein said promoter functional in a plant plastid is a clpP gene promoter.

50. The method according to claim 1, wherein said transgenic plants or plant seeds are selected from the group consisting of Arabidopsis, sugar cane, soybean, barley, cotton, tobacco, sugar beet, oilseed rape, maize, wheat, sorghum, rye, oat, a turf grass, a forage grass, millet, a forage plant and rice.

51. The method according to claim 5, wherein said modified plant DNA molecule is further characterized in that at least one of the following conditions is met:
   (a) said modified plant DNA molecule has a sequence that encodes amino acid sub-sequence AP$\Delta_1$F (SEQ ID NO:38), wherein $\Delta_1$ is an amino acid other than arginine;
   (b) said modified plant DNA molecule has a sequence that encodes amino acid sub-sequence F$\Delta_2$S, wherein $\Delta_2$ is an amino acid other than cysteine;
   (c) said modified plant DNA molecule has a sequence that encodes amino acid sub-sequence Y$\Delta_3$G, wherein $\Delta_3$ is an amino acid other than alanine;
   (d) said modified plant DNA molecule has a sequence that encodes amino acid sub-sequence A$\Delta_4$D, wherein $\Delta_4$ is an amino acid other than glycine;
   (e) said modified plant DNA molecule has a sequence that encodes amino acid sub-sequence Y$\Delta_5$P, wherein $\Delta_5$ is an amino acid other than proline;
   (f) said modified plant DNA molecule has a sequence that encodes amino acid sub-sequence P$\Delta_6$A, wherein $\Delta_6$ is an amino acid other than valine;
   (g) said modified plant DNA molecule has a sequence that encodes amino acid sub-sequence $\Delta_7$IG, wherein $\Delta_7$ is an amino acid other than tyrosine;
   (h) said modified plant DNA molecule has a sequence that encodes amino acid sub-sequence YIGG$\Delta_8$ (SEQ ID NO:39), wherein $\Delta_8$ is an amino acid other than alanine or serine;
   (i) said modified plant DNA molecule has a sequence that encodes amino acid sub-sequence A$\Delta_9$P, wherein $\Delta_9$ is an amino acid other than isoleucine;
   (j) said modified plant DNA molecule has a sequence that encodes amino acid sub-sequence G$\Delta_{10}$A, wherein $\Delta_{10}$ is an amino acid other than valine;
   (k) said modified plant DNA molecule has a sequence that encodes amino acid sub-sequence Y$\Delta_3$G, wherein $\Delta_3$ is an amino acid other than alanine, and said modified plant DNA molecule also has a sequence that encodes one of the group consisting of:
      (1) sub-sequence Q$\Delta_{11}$S, wherein $\Delta_{11}$ is an amino acid other than proline,
      (2) sub-sequence IGG$\Delta_{12}$ (SEQ ID NO:40), wherein $\Delta_{12}$ is an amino acid other than threonine,
      (3) sub-sequence SWXL$\Delta_{13}$ (SEQ ID NO:41), wherein $\Delta_{13}$ is an amino acid other than serine,
      (4) sub-sequence L$\Delta_{14}$Y, wherein $\Delta_{14}$ is an amino acid other than asparagine, and
      (5) sub-sequence G$\Delta_{15}$XGL (SEQ ID NO:42), wherein $\Delta_{15}$ is an amino acid other than tyrosine; or
   (l) said modified plant DNA molecule has a sequence that encodes amino acid sub-sequence $\Delta_7$IG, wherein $\Delta_7$ is an amino acid other than tyrosine, and said modified plant DNA molecule also has a sequence that encodes one of the group consisting of:
      (1) sub-sequence Q$\Delta_{11}$S, wherein $\Delta_{11}$ is an amino acid other than proline,
      (2) sub-sequence IGG$\Delta_{12}$ (SEQ ID NO:40), wherein $\Delta_{12}$ is an amino acid other than threonine,
      (3) sub-sequence SWXL$\Delta_{13}$ (SEQ ID NO:41), wherein $\Delta_{13}$ is an amino acid other than serine,
      (4) sub-sequence L$\Delta_{14}$Y, wherein $\Delta_{14}$ is an amino acid other than asparagine, and
      (5) sub-sequence G$\Delta_{15}$XGL (SEQ ID NO:42), wherein $\Delta_{15}$ is an amino acid other than tyrosine; and
   (m) said modified plant DNA molecule has a sequence that encodes amino acid sub-sequence T$\Delta_{16}$G, wherein $\Delta_{16}$ is an amino acid other than leucine, and said modified plant DNA molecule also has a sequence that encodes amino acid sub-sequence YV$\Delta_{17}$G (SEQ ID NO:43), wherein $\Delta_{17}$ is an amino acid other than alanine.

52. The method according to claim 51, wherein said modified plant DNA molecule has a sequence that encodes amino acid sub-sequence T$\Delta_{16}$G, wherein $\Delta_{16}$ is an amino acid other than leucine, and said modified plant DNA molecule also has a sequence that encodes amino acid sub-sequence YV$\Delta_{17}$G (SEQ ID NO:43), wherein $\Delta_{17}$ is an amino acid other than alanine.

* * * * *